(12) United States Patent
Ma et al.

(10) Patent No.: US 11,492,314 B2
(45) Date of Patent: Nov. 8, 2022

(54) ORGANIC COMPOUND, ORGANIC ELECTROLUMINESCENT DEVICE AND ELECTRONIC APPARATUS

(71) Applicant: Shaanxi Lighte Optoelectronics Material Co., Ltd., Xi'an (CN)

(72) Inventors: Linnan Ma, Xi'an (CN); Tiantian Ma, Xi'an (CN); Peng Nan, Xi'an (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 17/623,772

(22) PCT Filed: Jul. 24, 2020

(86) PCT No.: PCT/CN2020/104581
§ 371 (c)(1),
(2) Date: Dec. 29, 2021

(87) PCT Pub. No.: WO2021/135183
PCT Pub. Date: Jul. 8, 2021

(65) Prior Publication Data
US 2022/0220049 A1 Jul. 14, 2022

(30) Foreign Application Priority Data

Dec. 30, 2019 (CN) .......................... 201911404482.6
Jun. 9, 2020 (CN) .......................... 202010526332.9

(51) Int. Cl.
| | | |
|---|---|---|
| *C07C 13/72* | (2006.01) | |
| *C07C 25/22* | (2006.01) | |
| *H01L 51/00* | (2006.01) | |
| *H01L 51/50* | (2006.01) | |
| *C07D 209/08* | (2006.01) | |
| *C07D 209/86* | (2006.01) | |
| *C07D 213/16* | (2006.01) | |
| *C07D 215/06* | (2006.01) | |
| *C07D 217/02* | (2006.01) | |
| *C07D 239/26* | (2006.01) | |
| *C07D 241/42* | (2006.01) | |
| *C07D 307/91* | (2006.01) | |
| *C07D 327/08* | (2006.01) | |
| *C07D 333/76* | (2006.01) | |
| *C07D 405/10* | (2006.01) | |
| *C07D 409/10* | (2006.01) | |
| *C07D 413/10* | (2006.01) | |
| *C07D 471/04* | (2006.01) | |

(52) U.S. Cl.
CPC .............. *C07C 13/72* (2013.01); *C07C 25/22* (2013.01); *C07D 209/08* (2013.01); *C07D 209/86* (2013.01); *C07D 213/16* (2013.01); *C07D 215/06* (2013.01); *C07D 217/02* (2013.01); *C07D 239/26* (2013.01); *C07D 241/42* (2013.01); *C07D 307/91* (2013.01); *C07D 327/08* (2013.01); *C07D 333/76* (2013.01); *C07D 405/10* (2013.01); *C07D 409/10* (2013.01); *C07D 413/10* (2013.01); *C07D 471/04* (2013.01); *H01L 51/0054* (2013.01); *H01L 51/0056* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5004* (2013.01); *H01L 51/5016* (2013.01); *H01L 2251/552* (2013.01)

(58) Field of Classification Search
CPC ..... C07C 13/72; C07C 25/22; H01L 51/0052; H01L 51/0056; H01L 51/0058; H01L 51/0067; H01L 51/0073; H01L 51/0074
See application file for complete search history.

(56) References Cited

FOREIGN PATENT DOCUMENTS

| CN | 104710399 A | 6/2015 | |
| CN | 106008537 A | 10/2016 | |
| CN | 110128279 A | 8/2019 | |
| CN | 110467536 A | 11/2019 | |
| CN | 110615759 A | 12/2019 | |
| CN | 111039881 A | 4/2020 | |
| CN | 106206964 B | 5/2020 | |
| CN | 111377853 A | 7/2020 | |
| WO | 2011010843 A1 | 1/2011 | |
| WO | 2020046049 A1 | 3/2020 | |
| WO | WO-2021128764 A1 * | 7/2021 | ........... C07D 213/16 |
| WO | WO-2021135182 A1 * | 7/2021 | ........... C07D 209/86 |

OTHER PUBLICATIONS

English translation of WIPO Publication WO2021135182A1. (Year: 2022).*
English translation of WIPO Publication WO2021128764A1. (Year: 2022).*
International Search Report from corresponding International Application No. PCT/CN2020/104581, dated Sep. 24, 2020, 4 pages.

* cited by examiner

Primary Examiner — Joseph R Kosack
Assistant Examiner — Sagar Patel
(74) Attorney, Agent, or Firm — Tucker Ellis LLP

(57) ABSTRACT

The present disclosure belongs to the technical field of organic materials, and provides an organic compound. An adamantane spirofluorenyl and an anthryl are connected to obtain a novel compound for an organic electroluminescence device. In this compound, adamantane in the adamantane spirofluorene greatly increases the density of electron clouds on the fluorenyl through the hyperconjugation effect, which reduces the HOMO energy level of the compound and improves the hole migration ability. Both the adamantane spirofluorene and the anthryl have high hole mobility, so when the two are connected, the overall hole mobility of molecules is further improved, which is beneficial to reducing the working voltage of the device and improving the luminous efficiency. The present disclosure further provides an electronic component and an electronic apparatus including the compound. The organic compound can improve the performance of the electronic component.

19 Claims, 1 Drawing Sheet

ORGANIC COMPOUND, ORGANIC ELECTROLUMINESCENT DEVICE AND ELECTRONIC APPARATUS

CROSS REFERENCE TO RELATED APPLICATIONS

The application claims the priority to Chinese Patent Application CN201911404482.6 filed on Dec. 30, 2019 and Chinese Patent Application CN202010526332.9 filed on Jun. 9, 2020, the entirety of which is incorporated herein by reference.

TECHNICAL FIELD

The application relates to the technical field of organic materials, in particular to an organic compound, an organic electroluminescent device using the organic compound, and an electronic apparatus using the organic electroluminescent device.

BACKGROUND

An organic electroluminescent device, also known as an organic light-emitting diode, refers to a phenomenon that an organic light-emitting material is excited by current to emit light under the action of an electric field. It is a process of converting electrical energy into light energy. Compared with inorganic light-emitting materials, the organic electroluminescent device OLED has the advantages of active light emission, large optical path range, low driving voltage, high brightness, high efficiency, low energy consumption and simple manufacturing process. Just because of these advantages, organic light-emitting materials and devices have become one of the most popular scientific research topics in the scientific and industrial circles.

The organic electroluminescent device generally includes an anode, a hole transport layer, an electroluminescent layer as an energy conversion layer, an electron transport layer, and a cathode that are stacked in sequence. When voltage is applied to the cathode and the anode, the two electrodes generate an electric field. Under the action of the electric field, electrons on the cathode side move to the electroluminescent layer, and holes on the anode side also move to the electroluminescent layer. The electrons and the holes are combined in the electroluminescent layer to form excitons, and the excitons are in an excited state to release energy outward, which in turn enables the electroluminescent layer to emit light to the outside.

In the prior art, CN106206964, WO2011010843, etc. disclose electroluminescent layer materials that can be used in organic electroluminescent devices. However, it is still necessary to continue to develop new materials to further improve the performance of electronic components.

The above information in the background is only used to enhance the understanding of the background of the disclosure, so it may include information that does not constitute the prior art known to those of ordinary skill in the art.

SUMMARY

The objective of the disclosure is to provide an organic compound, an organic electroluminescent device, and an electronic apparatus, to improve the performance of the organic electroluminescent device and the electronic apparatus.

In order to achieve the above objective of the invention, the disclosure adopts the following technical solutions:

According to a first aspect of the disclosure, an organic compound is provided, and the structure of the organic compound is shown in chemical formula 1:

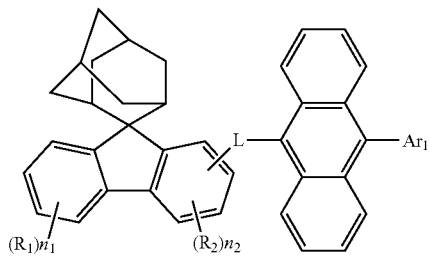

Formula 1 wherein L is selected from single bond, substituted or unsubstituted alkylene with 1 to 20 carbon atoms, substituted or unsubstituted arylene with 6 to 30 carbon atoms, substituted or unsubstituted heteroarylene with 3 to 30 carbon atoms, and substituted or unsubstituted cycloalkylene with 3 to 20 carbon atoms;

$Ar_1$ is selected from substituted or unsubstituted cycloalkyl with 3 to 20 carbon atoms, substituted or unsubstituted aryl with 6 to 40 carbon atoms, and substituted or unsubstituted heteroaryl with 3 to 30 carbon atoms;

Each $R_1$ and $R_2$ is the same or different from each other, and are independently selected from deuterium; fluorine; chlorine; bromine; cyano; aryl with 6 to 20 carbon atoms, which are optionally substituted by 0, 1, 2, 3, 4 or 5 substituents selected from deuterium, fluorine, cyano, methyl, ethyl, isopropyl, tert-butyl, and trimethylsilyl; heteroaryl with 3 to 18 carbon atoms; alkylsilyl with 3 to 18 carbon atoms; triarylsilyl with 6 to 18 carbon atoms; alkyl with 1 to 12 carbon atoms; alkoxy with 1 to 12 carbon atoms; haloalkyl with 1 to 12 carbon atoms; alkenyl with 2 to 12 carbon atoms; cycloalkyl with 3 to 10 carbon atoms; heterocycloalkyl with 2 to 12 carbon atoms; alkylamino with 1 to 10 carbon atoms; alkylthio with 1 to 10 carbon atoms; aryloxy with 6 to 18 carbon atoms; and arylthio with 6 to 18 carbon atoms;

$n_1$ is the number of substituents $R_1$, $n_1$ is selected from 0, 1, 2, 3 and 4, and when $n_1$ is greater than 1, any two $R_1$ are the same or different; or, $n_2$ is the number of substituents $R_2$, $n_2$ is selected from 0, 1, 2 and 3, and when $n_2$ is greater than 1, any two $R_2$ are the same or different;

the substituents in $Ar_1$ and L are the same or different from each other, and are each independently selected from deuterium; fluorine; chlorine; bromine; cyano; aryl with 6 to 20 carbon atoms, which are optionally substituted by 0, 1, 2 or 3 substituents selected from deuterium, fluorine, cyano, methyl, and trimethylsilyl; heteroaryl with 3 to 18 carbon atoms; alkylsilyl with 3 to 18 carbon atoms; arylsilyl with 6 to 18 carbon atoms; alkyl with 1 to 12 carbon atoms; alkoxy with 1 to 12 carbon atoms; haloalkyl with 1 to 12 carbon atoms; alkenyl with 2 to 12 carbon atoms; cycloalkyl with 3 to 10 carbon atoms; heterocycloalkyl with 2 to 12 carbon atoms; alkylamino with 1 to 10 carbon atoms; alkylthio with 1 to 10 carbon atoms; aryloxy with 6 to 18 carbon atoms; and arylthio with 6 to 18 carbon atoms.

In the disclosure, an adamantyl spirofluorenyl and an anthryl are linked and combined to obtain a novel compound for an organic electroluminescent device; in the compound, adamantyl in the adamantly-spirofluorenyl greatly increases the density of electron clouds on fluorenyl through the hyperconjugation effect, which reduces the HOMO energy level of the compound and improves the hole migration ability; both the adamantly-spirofluorenyl and the anthryl have high hole mobility, so when the two are linked, the overall hole mobility of molecules is further improved, which is beneficial to reducing the working voltage of the device and improving the luminous efficiency. In addition, in the compound of the disclosure, the adamantyl as a rigid polycyclic alkyl is combined with the rigid conjugated planar anthryl, which not only increases the overall electron density of molecules and the transmission rate of carriers, but also increases the triplet energy level ($T_1$), so that the compound is more suitable for light-emitting host materials. Moreover, the introduction of another aromatic group on the central anthryl enhances molecular asymmetry, which makes the material difficult to crystallize so as to improve the stability of the device. When this type of material is used as the host material of the organic electroluminescent device, the device can have relatively high luminous efficiency and long service life.

According to a second aspect of the disclosure, an organic electroluminescent device is provided, including an anode and a cathode arranged oppositely, and a functional layer arranged between the anode and the cathode; the functional layer includes the above-mentioned organic compound.

According to a third aspect of the disclosure, an electronic apparatus is provided, including the above-mentioned organic electroluminescent device.

BRIEF DESCRIPTION OF THE DRAWINGS

By describing exemplary embodiments in detail with reference to the accompanying drawings, the above and other features and advantages of the disclosure will become more apparent.

Figure 1:
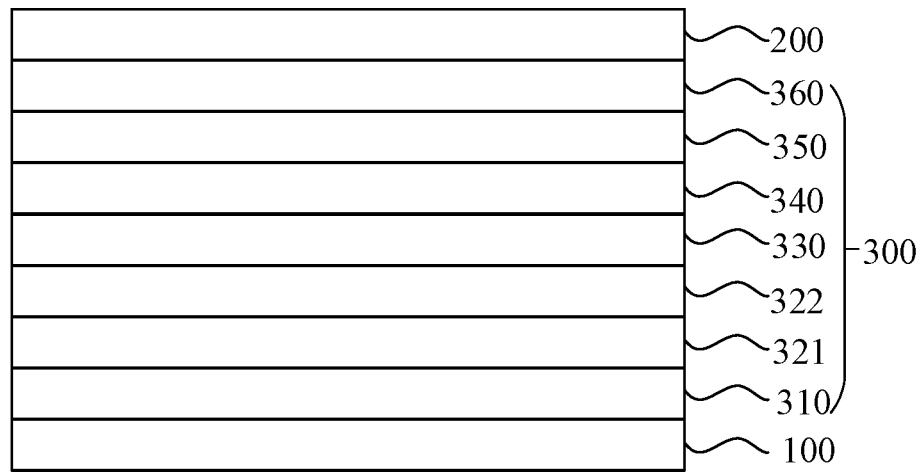
FIG. 1 is a schematic structural diagram of an organic electroluminescent device according to an embodiment of the disclosure.

Reference numerals of the main components in the figures are explained as follows:
100—anode; 200—cathode; 300—functional layer; 310—hole injection layer; 321—hole transport layer; 322—electron blocking layer; 330—organic electroluminescent layer; 340—hole blocking layer; 350—electron transport layer; 360—electron injection layer; 400—electronic apparatus.

DETAILED DESCRIPTION OF EMBODIMENTS

Exemplary embodiments will now be described more fully with reference to the accompanying drawings. However, the exemplary embodiments can be implemented in multiple forms, and should not be construed as being limited to the examples set forth here. Instead, the provision of these embodiments makes the disclosure more comprehensive and complete, and fully conveys the concept of the exemplary embodiments to those skilled in the art. The described features, structures or characteristics can be combined in one or more embodiments in any suitable way. In the following description, many specific details are provided to give a sufficient understanding of the embodiments of the disclosure.

In the figures, the thicknesses of regions and layers may be exaggerated for clarity. The same reference numerals in the figures represent the same or similar structures, and thus their detailed descriptions will be omitted.

The described features, structures, or characteristics are combined in one or more embodiments in any suitable way. In the following description, many specific details are provided to give a sufficient understanding of the embodiments of the disclosure. However, those skilled in the art will realize that the technical solutions of the disclosure can be practiced without one or more of the specific details, or other methods, components, materials, etc. can be used. In other cases, well-known structures, materials, or operations are not shown or described in detail to avoid obscuring the main technical ideas of the disclosure.

The disclosure provides an organic compound, the structure of which is shown in chemical formula 1:

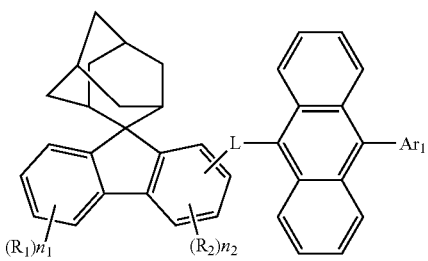

Formular 1

Wherein L is selected from single bond, substituted or unsubstituted alkylene with 1 to 20 carbon atoms, substituted or unsubstituted arylene with 6 to 30 carbon atoms, substituted or unsubstituted heteroarylene with 3 to 30 carbon atoms, and substituted or unsubstituted cycloalkylene with 3 to 20 carbon atoms;

$Ar_1$ is selected from a substituted or unsubstituted cycloalkyl with 3 to 20 carbon atoms, substituted or unsubstituted aryl with 6 to 40 carbon atoms, and substituted or unsubstituted heteroaryl with 3 to 30 carbon atoms;

each $R_1$ is the same or different, each $R_2$ is the same or different, and $R_1$ and $R_2$ are each independently selected from deuterium; fluorine; chlorine; bromine; cyano; aryl with 6 to 20 carbon atoms, which are optionally substituted by 0, 1, 2, 3, 4 or 5 substituents selected from deuterium, fluorine, cyano, methyl, ethyl, isopropyl, tert-butyl, and trimethylsilyl; heteroaryl with 3 to 18 carbon atoms; alkylsilyl with 3 to 18 carbon atoms; triarylsilyl with 6 to 18 carbon atoms; alkyl with 1 to 12 carbon atoms; alkoxy with 1 to 12 carbon atoms; haloalkyl with 1 to 12 carbon atoms; alkenyl with 2 to 12 carbon atoms; cycloalkyl with 3 to 10 carbon atoms; heterocycloalkyl with 2 to 12 carbon atoms; alkylamino with 1 to 10 carbon atoms; alkylthio with 1 to 10 carbon atoms; aryloxy with 6 to 18 carbon atoms; and arylthio with 6 to 18 carbon atoms;

$n_1$ is the number of substituents $R_1$, $n_1$ is selected from 0, 1, 2, 3 and 4, and when $n_1$ is greater than 1, any two $R_1$ are the same or different;

$n_2$ is the number of substituents $R_2$, $n_2$ is selected from 0, 1, 2 and 3, and when $n_2$ is greater than 1, any two $R_2$ are the same or different;

the substituents in $Ar_1$ and L are the same or different from each other, and are each independently selected from deuterium; fluorine; chlorine; bromine; cyano; aryl with 6 to 20 carbon atoms, which are optionally substituted by 0, 1, 2 or 3 substituents selected from deuterium, fluorine, cyano, methyl, and trimethylsilyl; heteroaryl with 3 to 18 carbon atoms; alkylsilyl with 3 to 18 carbon atoms; arylsilyl with 6 to 18 carbon atoms; alkyl with 1 to 12 carbon atoms; alkoxy with 1 to 12 carbon atoms; haloalkyl with 1 to 12 carbon atoms; alkenyl with 2 to 12 carbon atoms; cycloalkyl with 3 to 10 carbon atoms, heterocycloalkyl with 2 to 12 carbon atoms; alkylamino with 1 to 10 carbon atoms; alkylthio with 1 to 10 carbon atoms; aryloxy with 6 to 18 carbon atoms; and arylthio with 6 to 18 carbon atoms.

In the disclosure, an adamantly-spirofluorenyl and an anthryl are linked and combined to obtain a novel compound for an organic electroluminescent device; in the compound, adamantyl in the adamantly-spirofluorenyl greatly increases the density of electron clouds on fluorenyl through the hyperconjugation effect, which reduces the HOMO energy level of the compound and improves the hole migration ability; both the adamantly-spirofluorenyl and the anthryl have high hole mobility, so when the two are linked, the overall hole mobility of molecules is further improved, which is beneficial to reducing the working voltage of the device and improving the luminous efficiency. In addition, in the compound of the disclosure, the adamantyl as a rigid polycyclic alkyl is combined with the rigid conjugated planar anthryl, which not only increases the overall electron density of molecules and the transmission rate of carriers, but also increases the triplet energy level, so that the compound is more suitable for light-emitting host materials. Moreover, the introduction of another aromatic group on the central anthryl enhances molecular asymmetry, increases the rotation between groups, reduces molecular stacking, increases space complexity, and makes molecules difficult to crystallize in an amorphous state, so that the film-forming property of the material is improved, which in turn improves the stability of the device. When this type of material is used as the host material of the organic electroluminescent device, the device can have relatively high luminous efficiency and long service life.

In the disclosure, the number of carbon atoms of L and $Ar_1$ refers to the total number of carbon atoms. For example, if L is selected from substituted arylene with 10 carbon atoms, the number of all carbon atoms of the arylene and a substituent thereof is 10, and if $Ar_1$ is phenyl substituted by tert-butyl, the $Ar_1$ is substituted aryl with 9 carbon atoms.

In the disclosure, when no specific definition is provided otherwise, "hetero" indicates that a functional group includes at least one heteroatom selected from B, N, O, S, Se, Si or P. The unsubstituted alkyl is a "saturated alkyl" without any double or triple bonds.

In the disclosure, the term "substituted or unsubstituted" indicates that the functional group described after the term may or may not have a substituent. For example, the "substituted or unsubstituted alkyl" refers to alkyl with a substituent or an unsubstituted alkyl. The "substituted" indicates that a can be substituted by a substituent selected from the following groups: deuterium, halogen, heteroaryl, aryl, trialkylsilyl, alkyl, haloalkyl, alkenyl, cycloalkyl, heterocycloalkyl, cycloalkenyl, heterocycloalkenyl, alkoxy, alkylthio, aryloxy, arylthio, triarylsilyl, alkylboronyl, alkylphosphonyloxy, etc.

In the disclosure, the "alkyl" includes linear or branched alkyl. The alkyl has 1 to 20 carbon atoms. In the disclosure, a numerical range such as "1 to 20" refers to each integer in the given range; for example, "1 to 20 carbon atoms" indicates that the alkyl may include 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The alkyl may also be a medium-sized alkyl having 1 to 10 carbon atoms. The alkyl may also be lower alkyl with 1 to 6 carbon atoms. In still other embodiments, the alkyl includes 1 to 4 carbon atoms; in still other embodiments, the alkyl includes 1 to 3 carbon atoms. The alkyl is optionally substituted by one or more substituents described in the invention. Examples of the alkyl include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), etc. In addition, the alkyl is substituted or unsubstituted.

In the disclosure, the "alkenyl" refers to a hydrocarbon including one or more double bonds in a straight or branched hydrocarbon chain. The alkenyl is unsubstituted or substituted. The alkenyl may have 1 to 20 carbon atoms, and whenever appearing herein, a numerical range such as "1 to 20" refers to each integer in the given range; for example, "1 to 20 carbon atoms" indicates that the alkenyl includes 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. For example, the alkenyl is vinyl, bivinyl or propenyl.

In the disclosure, the cycloalkyl refers to a saturated hydrocarbon having an alicyclic structure, including monocyclic and condensed ring structures. The cycloalkyl may have 3 to 20 carbon atoms, and a numerical range such as "3 to 20" refers to each integer in the given range; for example, "3 to 20 carbon atoms" indicates that the cycloalkyl may include 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The cycloalkyl is a small ring, an ordinary ring, or a large ring having 3 to 20 carbon atoms. The cycloalkyl may also be classified as monocyclic-only one ring, bicyclic-two rings or polycyclic-three or more rings. The cycloalkyl may also be classified as two rings sharing one carbon atom-spiro ring, two rings sharing two carbon atoms-fused ring, and two rings sharing two or more carbon atoms-bridged ring. In addition, the cycloalkyl is substituted or unsubstituted. In some embodiments, the cycloalkyl is a 5- to 10-membered cycloalkyl. In other embodiments, the cycloalkyl is a 5- to 8-membered cycloalkyl. For example, examples of the cycloalkyl is, but are not limited to: five-membered cycloalkyl (i.e. cyclopentyl), six-membered cycloalkyl (i.e. cyclohexyl), 10-membered polycyclic alkyl such as an adamantyl, etc.

The "ring" in the disclosure includes saturated rings and unsaturated rings; the saturated rings include cycloalkyl and heterocycloalkyl, and the unsaturated rings include cycloalkenyl, heterocycloalkenyl, aryl and heteroaryl. In the disclosure, the "aliphatic ring" includes saturated cycloalkyl and partially unsaturated cycloalkyl, for example, the saturated cycloalkyl include cyclopentyl, cyclohexyl, adamantyl, etc., and the partially unsaturated cycloalkyl include cyclobutene and the like.

In the disclosure, the aryl refers to an optional functional group or substituent derived from an aromatic hydrocarbon ring. The aryl is monocyclic aryl or polycyclic aryl, that is, the aryl is a monocyclic aryl, condensed ring aryl, two or more monocyclic aryl conjugated by carbon-carbon bonds, monocyclic aryl and a fused ring aryl conjugated by carbon-carbon bonds, and two or more fused ring aryl conjugated by carbon-carbon bonds. That is, two or more aromatic conjugated by carbon-carbon bonds also are regarded as an aryl in the disclosure. The aryl does not include any heteroatom. For example, in the disclosure, the biphenyl, the terphenyl, etc. are aryl. Examples of the aryl includes phenyl, naphthyl, fluorenyl, anthryl, phenanthryl, biphenyl, terphenyl, tetraphenyl, pentaphenyl, hexaphenyl, benzo[9,10]phenanthryl, pyrenyl, benzofluoranthryl, chrysene, perylene, 9,9-dimethylfluorenyl, 9,9-diphenylfluorenyl, spirobifluorenyl, indenyl, but are not limited to these. The number of carbon atoms in the aryl is 6 to 25 in some embodiments, 6 to 18 in other embodiments, and 6 to 13 in other embodiments. For example, the number of carbon atoms is 6, 12, 13, 18, 20, 25 or 30. Of course, the number of carbon atoms may also be other numbers, which will not be listed here. In the disclosure, 9,9-dimethylfluorenyl, 9,9-diphenylfluorenyl, and spirobifluorenyl are all regarded as aryl.

The "aryl" in the disclosure may have one or more points of connection to the rest of a molecule.

In the disclosure, the explanation of aryl can be applied to arylene.

In the disclosure, the substituted aryl indicates that one or more hydrogen atoms in the aryl are substituted by other groups. For example, at least one hydrogen atom is substituted by deuterium atom, F, Cl, I, CN, hydroxyl, amino, a branched alkyl, linear alkyl, cycloalkyl, alkoxy, alkylamino, alkylthio or other groups. It is noted that the number of carbon atoms of the substituted aryl refers to the total number of carbon atoms of the aryl and the substituents on the aryl. For example, the substituted aryl with 18 carbon atoms indicates that the total number of carbon atoms of the aryl and the substituents on the aryl is 18. For example, the 2-tert-butylphenyl is a substituted aryl with 9 carbon atoms.

In the disclosure, the aryl with 6 to 25 ring-forming carbon atoms indicates that the number of carbon atoms on the main aromatic ring in the aryl is 6 to 25, and the number of carbon atoms in the substituents on the aryl is not counted. The number of ring-forming carbon atoms in the aryl may also be 6 to 20, 6 to 18, 6 to 14, or 6 to 10, but is not limited thereto. For example, the diphenylfluorenyl has 13 ring-forming carbon atoms, and the spirobifluorenyl is an aryl having 25 ring-forming carbon atoms.

In the disclosure, the heteroaryl is a heteroaryl including at least one of B, O, N, P, Se, Si and S as a heteroatom. The heteroaryl is monocyclic heteroaryl or polycyclic heteroaryl, that is, the heteroaryl is a single aromatic ring system or multiple aromatic ring systems conjugated by carbon-carbon bonds, any aromatic ring system is an aromatic monocyclic ring or an aromatic condensed ring, and any aromatic ring system includes the heteroatom. Exemplarily, the heteroaryl includes thienyl, furyl, pyrrolyl, imidazolyl, thiazolyl, oxazolyl, oxadiazolyl, triazolyl, pyridyl, bipyridy, pyrimidinyl, triazinyl, cridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, phenyl-substituted dibenzofuranyl, phenoxytheophyllinyl

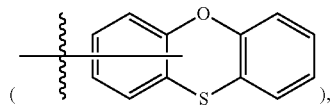

thioanthryl

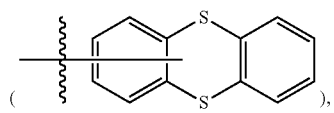

benzoxazinyl

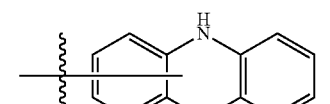

phenothiazinyl

etc., but are not limited thereto. Among them, the thienyl, the furanyl, the phenanthrolinyl, etc. are heteroaryl of a single aromatic ring system, and the N-arylcarbazolyl, the N-heteroarylcarbazolyl, the phenyl-substituted dibenzofuranyl, etc. are heteroaryl of multiple aromatic ring systems conjugated by carbon-carbon bonds.

It is noted that there may be one bond, two bonds or multiple bonds on the "heteroaryl" that are connect to other parts of a molecule.

It is noted that "the substituted heteroaryl with 3 to 30 carbon atoms" indicates that the total number of carbon atoms of the heteroaryl and the substituents on the heteroaryl is 3 to 30.

The heteroaryl with 4 to 18 ring-forming carbon atoms indicates that the number of carbon atoms on the heteroaromatic ring in the heteroaryl is 4 to 18, and the number of carbon atoms in the substituents on the heteroaryl is not counted. The number of carbon atoms on the heteroaryl is 3 to 18, 4 to 18, 3 to 12, or 3 to 8, but is not limited thereto. For example, the phenyl-substituted pyridyl has 5 ring-forming carbon atoms, and the N-phenylcarbazolyl has 12 ring-forming carbon atoms.

In the disclosure, the explanation of the heteroaryl can be applied to a heteroarylene.

In the disclosure, the ring system formed by n atoms is an n-membered ring. For example, the phenyl is 6-membered aryl. The 6- to 10-membered aromatic ring refers to benzene ring, indene ring, naphthalene ring, etc.

In the disclosure, the explanation of the aryl can be applied to arylene, the explanation of the heteroaryl can be applied to a heteroarylene, the explanation of the alkyl can be applied to alkylene, and the explanation of the cycloalkyl can be applied to cycloalkylene.

The descriptions "each . . . is independently", " . . . are independently", and " . . . are independently selected from" used in the disclosure are interchangeable, and should be understood in a broad sense. They indicate that the specific options expressed between the same symbols do not affect each other in different groups, and also indicate that the specific options expressed between the same symbols do not affect each other in the same group.

For example: in the description

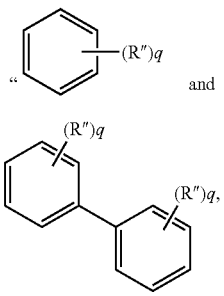

wherein each q is independently 0, 1, 2 or 3, and each R" is independently selected from hydrogen, fluorine, chlorine", formula Q-1 indicates q substituents R" on the benzene ring, each R" is the same or different, and the options of each R" do not affect each other; formula Q-2 indicates q substituents R" on each benzene ring of the biphenyl, the numbers q of R" substituents on the two benzene rings is the same or different, each R" is the same or different, and the options of each R" do not affect each other.

The non-localized bond in the disclosure refers to single bond

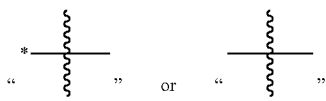

extending from the ring system, which indicates that one end of the bond can be linked to any position in the ring system through which the bond penetrates, and the other end is linked to the rest part of the compound molecule. For example, as shown in the following formula (f), the naphthyl represented by formula (f) is linked to other positions of the molecule through two non-localized bonds that penetrate the dual rings, including any possible connection shown in formulae (f-1) to (f-10).

formula (f)

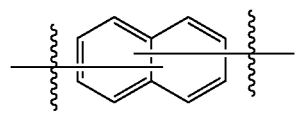

formula(f-1)

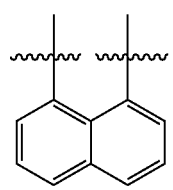

formula (f-2)

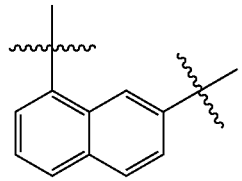

formula (f-3)

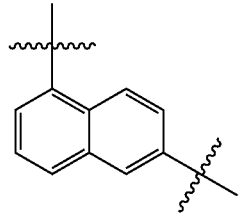

formula (f-4)

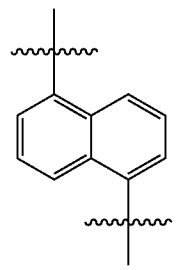

formula (f-5)

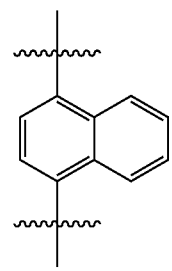

formula (f-6)

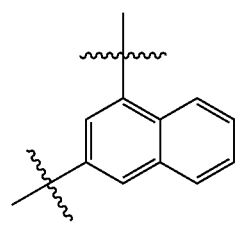

formula (f-7)

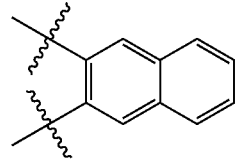

formula (f-8)

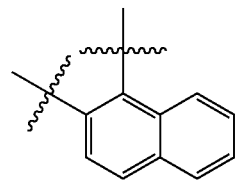

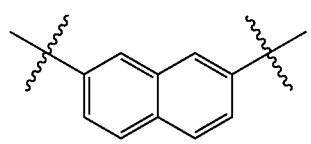

formula (f-9)

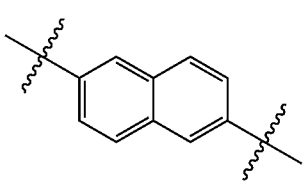

formula (f-10)

For example, as shown in the following formula (X'), the phenanthryl represented by the formula (X') is linked to other positions of the molecule through a non-localized bond extending from the middle of a benzene ring on one side, including any possible link shown in formulae (X'-1) to (X'-4).

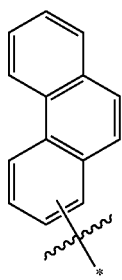

(X')

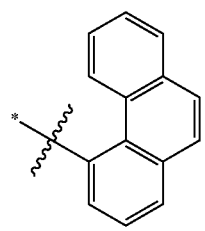

(X'-1)

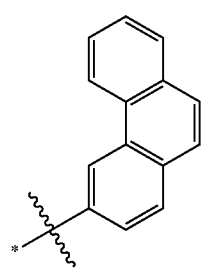

(X'-2)

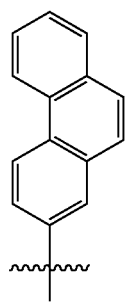

(X'-3)

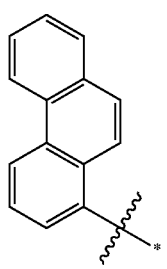

(X'-4)

The non-localized substituent in the disclosure refers to a substituent linked by single bond extending from the center of a ring system, which indicates that the substituent can be linked to any possible position in the ring system. For example, as shown in the following formula (Y), the substituent R represented by the formula (Y) is linked to a quinoline ring by a non-localized bond, including any possible link shown in formulae (Y-1) to (Y-7).

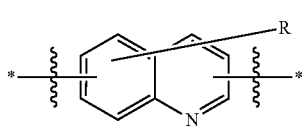

(Y)

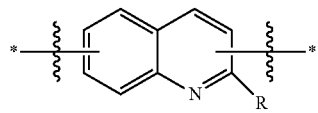

(Y-1)

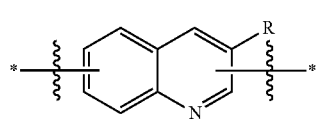

(Y-2)

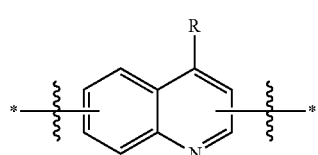

(Y-3)

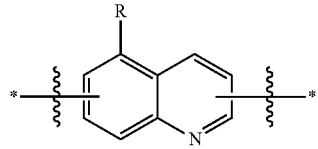

(Y-4)

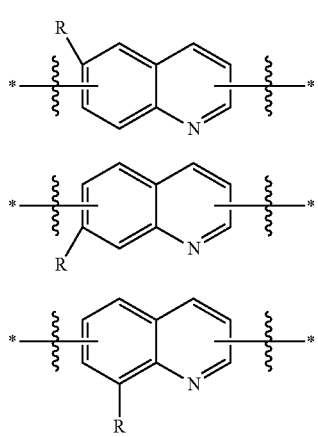

(Y-5)

(Y-6)

(Y-7)

In some embodiments, each $R_1$ is the same or different, each $R_2$ is the same or different, and $R_1$ and $R_2$ are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, triarylsilyl with 6 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylamino with 1 to 10 carbon atoms, alkylthio with 1 to 10 carbon atoms, aryloxy with 6 to 18 carbon atoms, and arylthio with 6 to 18 carbon atoms;

The substituents in $Ar_1$ and L are the same or different from each other, and are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, arylsilyl with 6 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylamino with 1 to 10 carbon atoms, alkylthio with 1 to 10 carbon atoms, aryloxy with 6 to 18 carbon atoms, and arylthio with 6 to 18 carbon atoms. In some embodiments, each $R_1$ is the same or different, each $R_2$ is the same or different, and $R_1$ and $R_2$ are each independently selected from deuterium, fluorine, chlorine, bromine, cyano, alkyl with 1 to 6 carbon atoms, haloalkyl with 1 to 4 carbon atoms, alkoxy with 1 to 4 carbon atoms, alkylamino with 1 to 4 carbon atoms, alkylthio with 1 to 4 carbon atoms, aryl with 6 to 15 carbon atoms, heteroaryl with 3 to 15 carbon atoms, trialkylsilyl with 3 to 8 carbon atoms, triphenylsilyl, cycloalkyl with 5 to 10 carbon atoms, an aryloxy with 6 to 12 carbon atoms, and arylthio with 6 to 12 carbon atoms.

In some embodiments, each $R_1$ and $R_2$ are the same or different, and are independently selected from deuterium; fluorine; chlorine; bromine; cyano; methyl; ethyl; isopropyl; tert-butyl; methoxy; ethoxy; isopropoxy; n-propoxy; cyclopentyl; cyclohexyl; trifluoromethyl; trimethylsilyl; triphenylsilyl; phenyl, which is optionally substituted by 0, 1, 2, 3, 4 or 5 substituents selected from deuterium, fluorine, chlorine, cyano, methyl, ethyl, isopropyl, tert-butyl, and trimethylsilyl; naphthyl; pyridyl; pyrimidyl; dibenzothienyl; dibenzofuryl or quinolyl; and when the numbers of $R_1$ and $R_2$ are more than 1, any two $R_1$ or $R_2$ are the same or different.

In some embodiments, in the compound of the disclosure, each $R_1$ is the same or different, each $R_2$ is the same or different, and $R_1$ and $R_2$ are each independently selected from deuterium, fluorine, cyano, cyclohexyl, cyclopentyl, trimethylsilyl, methoxy, ethoxy, isopropoxy, methyl, ethyl, isopropyl, tert-butyl, diisopropylsilyl, phenyl, naphthyl, pyridyl, and quinolyl.

In some embodiments, the compound of the disclosure has the structure shown in the following chemical formula 1-1 to chemical formula 1-3:

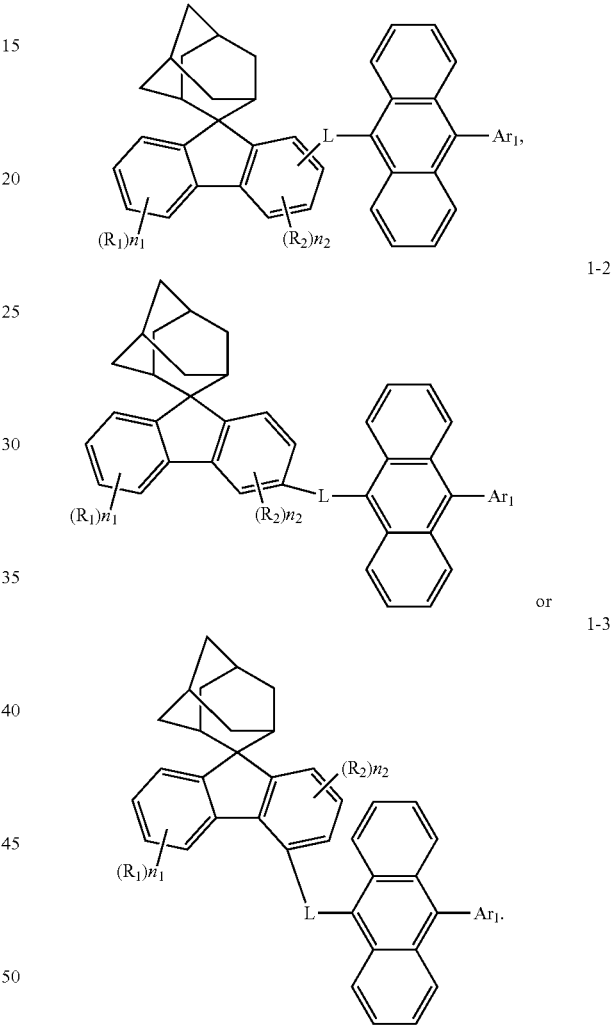

In some embodiments, in the compound of the disclosure, L is selected from a substituted or Unsubstituted arylene with 6 to 25 ring-forming carbon atoms, and substituted or unsubstituted heteroarylene with 3 to 18 ring-forming carbon atoms; the substituents in L are the same or different from each other, and are each independently selected from deuterium, fluorine, chlorine, bromine, cyano, alkyl with 1 to 6 carbon atoms, haloalkyl with 1 to 4 carbon atoms, alkoxy with 1 to 4 carbon atoms, alkylamino with 1 to 4 carbon atoms, alkylthio with 1 to 4 carbon atoms, aryl with 6 to 15 carbon atoms, heteroaryl with 3 to 15 carbon atoms, trialkylsilyl with 3 to 8 carbon atoms, triphenylsilyl, cycloalkyl with 5 to 10 carbon atoms, aryloxy with 6 to 12 carbon atoms, or arylthio with 6 to 12 carbon atoms.

In some embodiments, L is selected from single bond and the group consisting of groups represented by chemical formula j-1 to chemical formula j-13:

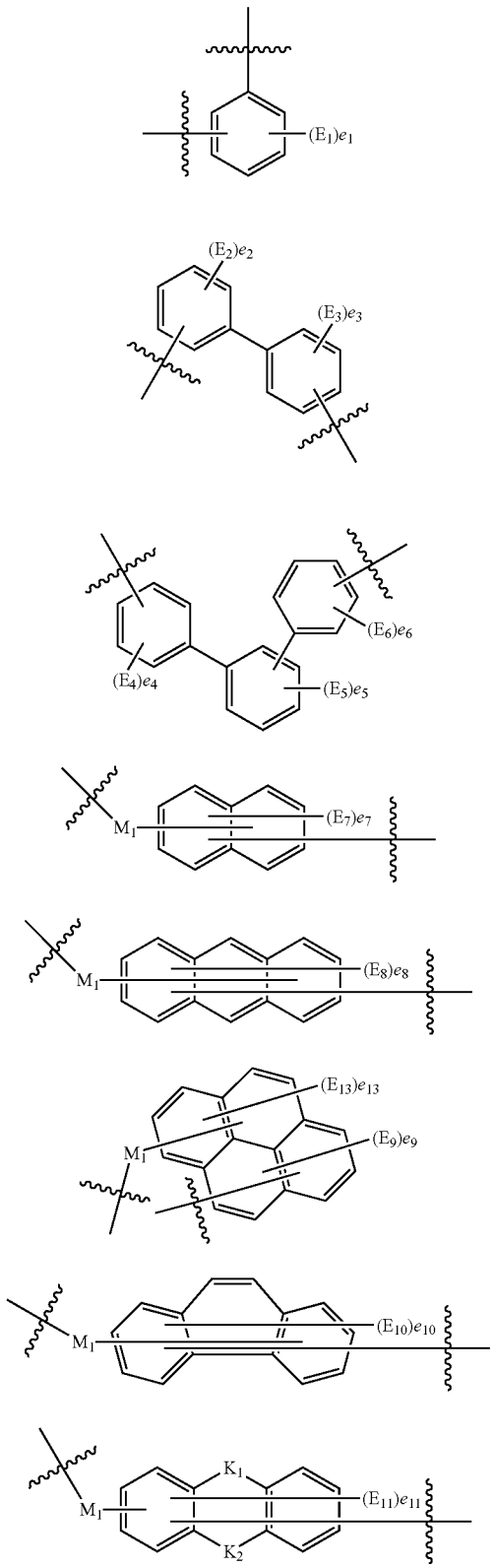

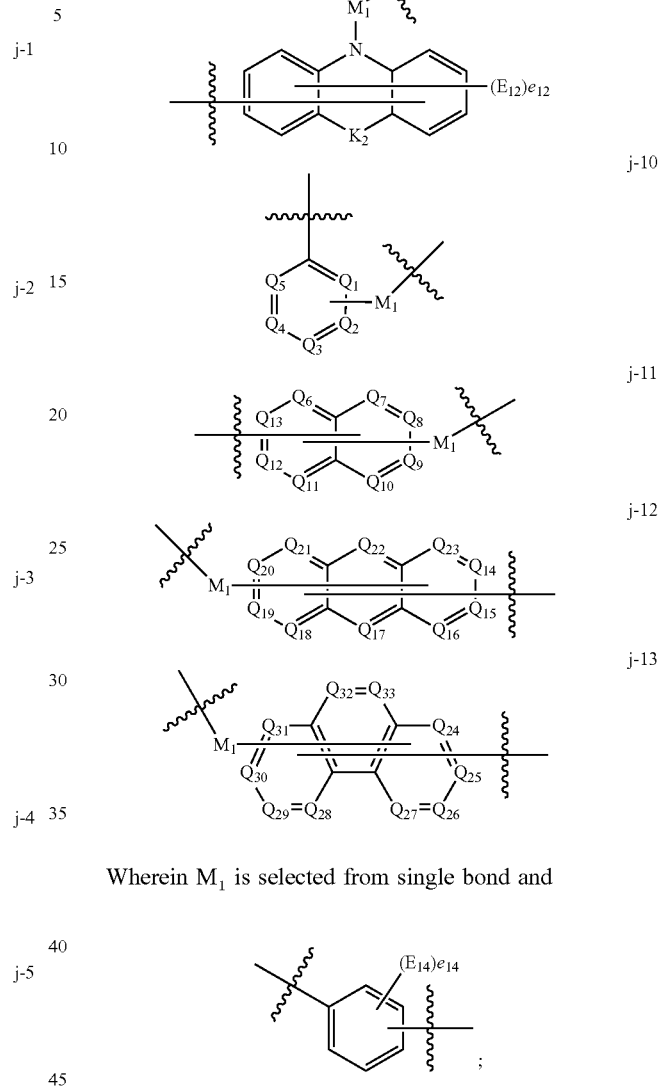

Wherein $M_1$ is selected from single bond and $Q_1$ to $Q_5$ are each independently selected from N and $C(F_1)$, and at least one of $Q_1$ to $Q_5$ is selected from N; when two or more of $Q_1$ to $Q_5$ are selected from $C(F_1)$, any two $F_1$ are the same or different; $Q_6$ to $Q_{13}$ are each independently selected from N and $C(F_2)$, and at least one of $Q_6$ to $Q_{13}$ is selected from N; when two or more of $Q_6$ to $Q_{13}$ are selected from $C(F_2)$, any two $F_2$ are the same or different;

$Q_{14}$ to $Q_{23}$ are each independently selected from N and $C(F_3)$, and at least one of $Q_{14}$ to $Q_{23}$ is selected from N; when two or more of $Q_{14}$ to $Q_{23}$ are selected from $C(F_3)$, any two $F_3$ are the same or different;

$Q_{24}$ to $Q_{33}$ are each independently selected from N and $C(F_4)$, and at least one of $Q_{24}$ to $Q_{33}$ is selected from N; when two or more of $Q_{24}$ to $Q_{33}$ are selected from $C(F_4)$, any two $F_4$ are the same or different;

$E_1$ to $E_{14}$ and $F_1$ to $F_4$ are each independently selected from: hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms; $e_r$ is the number of substituents $E_r$, and r is any integer from 1 to 14; when r is selected from 1, 2, 3, 4, 5, 6, 9, 13 and 14, $e_r$ is selected from 1, 2, 3 and 4; when r is selected from 7 and 11, $e_r$ is selected from 1, 2, 3, 4, 5 and 6; when r is 12, $e_r$ is selected from 1, 2, 3, 4, 5, 6 and 7; when r is selected from 8 and 10, $e_r$ is selected from 1, 2, 3, 4, 5, 6, 7 and 8; when $e_r$ is greater than 1, any two $E_r$ are the same or different;

$K_1$ is selected from O, S, Se, $N(E_{15})$, $C(E_{16}E_{17})$, and $Si(E_{16}E_{17})$; wherein $E_{15}$, $E_{16}$, and $E_{17}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms, and heterocycloalkyl with 2 to 10 carbon atoms, or $E_{16}$ and $E_{17}$ are linked to each other to form a saturated or unsaturated 5- to 13-membered aliphatic ring together with atoms linked to the both. For example, in formula j-8, when $K_2$ is single bond, $M_1$ is single bond, $K_1$ is a carbon atom and $E_{16}$ and $E_{17}$ are linked to each other to form a saturated or unsaturated ring together with atoms linked to the both, the ring is a 5-membered ring

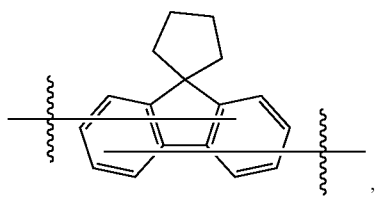

, a 6-membered ring

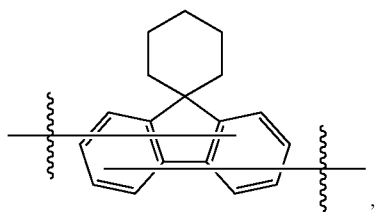

, or a 13-membered ring

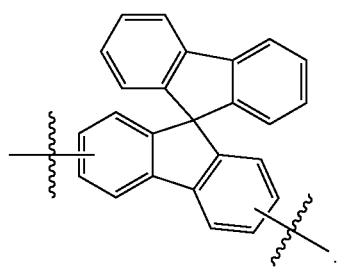

.

Of course, the number of atoms on the ring formed by the link between $E_{16}$ and $E_{17}$ may also be other values, which will not be listed here.

$K_2$ is selected from single bond, O, S, Se, $N(E_{18})$, $C(E_{19}E_{20})$, and $Si(E_{19}E_{20})$; wherein $E_{18}$, $E_{19}$, and $E_{20}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms, and heterocycloalkyl with 2 to 10 carbon atoms, or $E_{19}$ and $E_{20}$ are linked to each other to form a saturated or unsaturated 5- to 12-membered aliphatic ring together with atoms linked to the both. Here, the understanding of optional ring formation of $E_{19}$ and $E_{20}$ is consistent with the understanding in other technical solutions (when $E_{16}$ and $E_{17}$ are linked to each other to form a ring) of the disclosure.

In some embodiments, L is selected from single bond, and unsubstituted $W_1$ or substituted $W_1$, wherein the unsubstituted $W_1$ is selected from the group consisting of the following substituents:

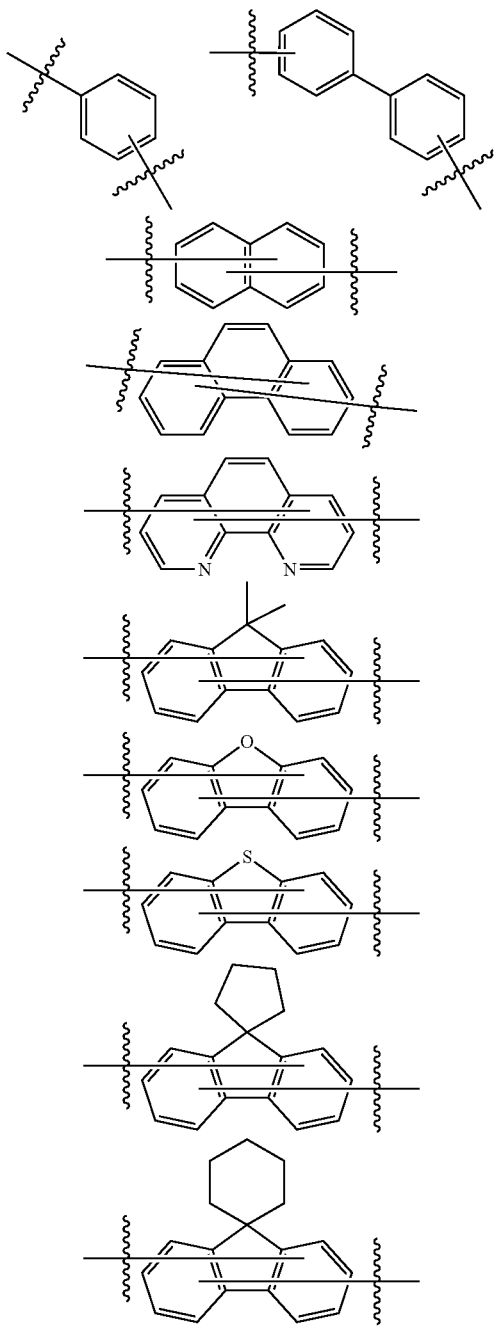

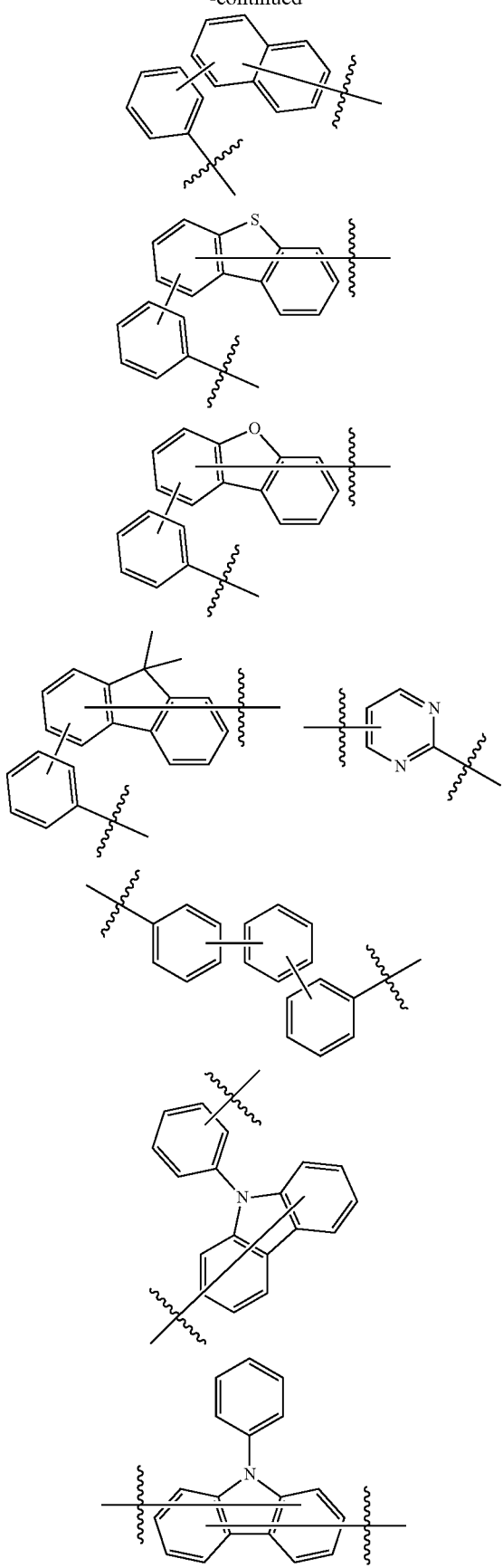
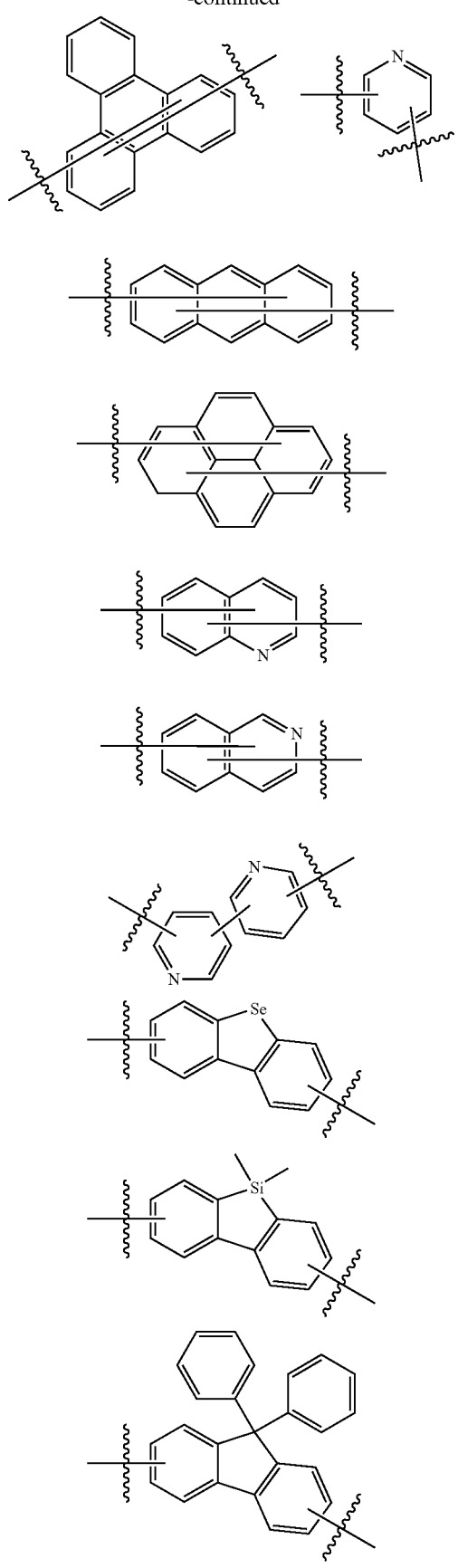

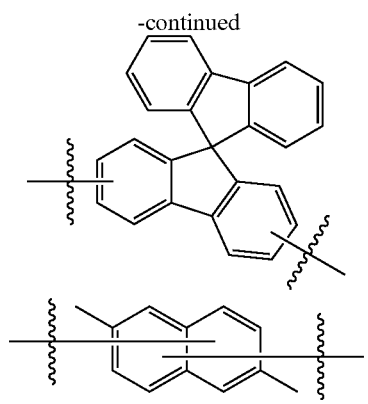

The substituted $W_1$ is a group formed by substituting unsubstituted $W_1$ by one or more substituents selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, triphenylsilyl, cycloalkyl with 3 to 10 carbon atoms, aryl with 6 to 12 carbon atoms, and heteroaryl with 3 to 12 carbon atoms, and when the substituted $W_1$ includes a plurality of substituents, any two substituents are the same or different. In still some embodiments, L is

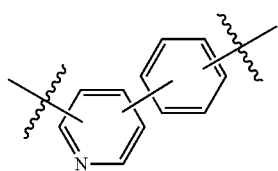

In other embodiments, in the compound of the disclosure, L is selected from single bond, substituted or unsubstituted phenylene, substituted or unsubstituted biphenylene, substituted or unsubstituted terphenylene, substituted or unsubstituted naphthylene, substituted or unsubstituted dibenzofurylene, substituted or unsubstituted dibenzothiophenylene, substituted or unsubstituted quinolinylene, substituted or unsubstituted carbazolylidene, substituted or unsubstituted naphthylene, substituted or unsubstituted fluorenylene, substituted or unsubstituted anthrylene, substituted or unsubstituted phenanthrylene, substituted or unsubstituted perylene, substituted or unsubstituted pyrylene, substituted or unsubstituted 9,9-diphenylfluorenyl, substituted or unsubstituted spirobifluorenylene, substituted or unsubstituted dibenzothienylene, substituted or unsubstituted dibenzofluorenylene, substituted or unsubstituted carbazolylidene, substituted or unsubstituted pyrimidinylene, substituted or unsubstituted pyridiylene, substituted or unsubstituted pyrazinylene, substituted or unsubstituted quinolinylene, substituted or unsubstituted isoquinolylene, substituted or unsubstituted quinazolinylene, and subunit formed by linking two or three of them through single bond; the substitution refers to optional substitution by 0, 1, 2, 3 or 4 substituents selected from deuterium, fluorine, chlorine, cyano, methyl, ethyl, isopropyl, tert-butyl, methoxy, ethoxy, isopropoxy, propoxy, trifluoromethyl, phenyl, naphthyl, trimethylsilyl, and triphenylsilyl.

In some embodiments, L is selected from single bond, and unsubstituted $W_2$ or substituted $W_2$, wherein the unsubstituted $W_2$ is selected from the group consisting of the following substituents:

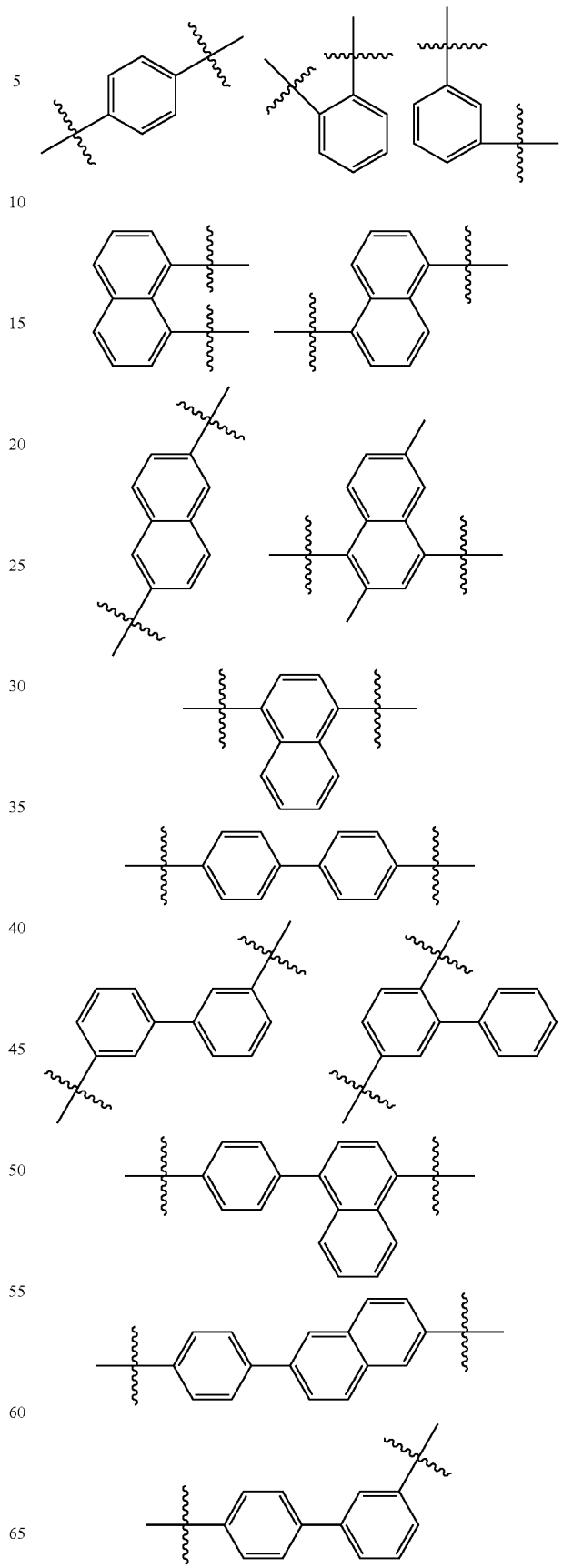

-continued
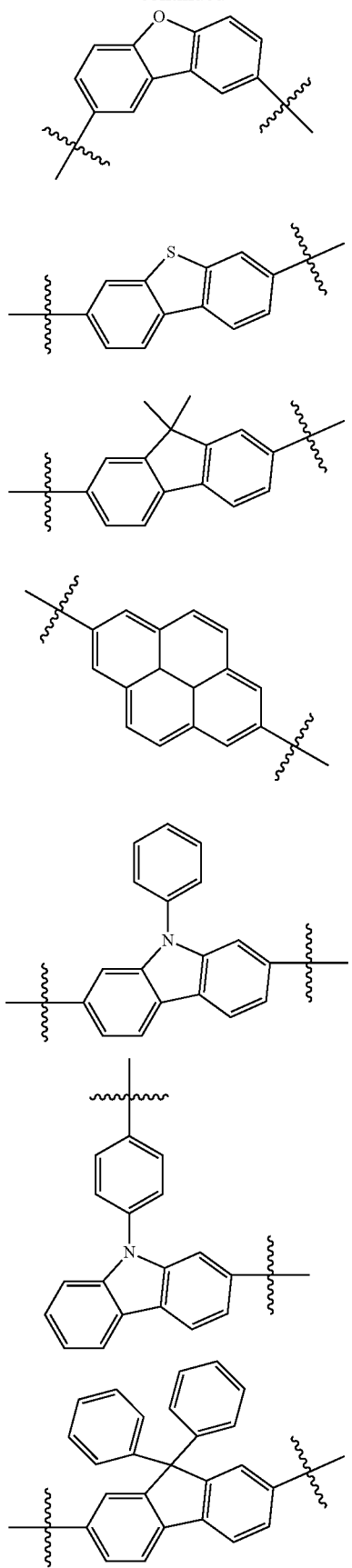
-continued
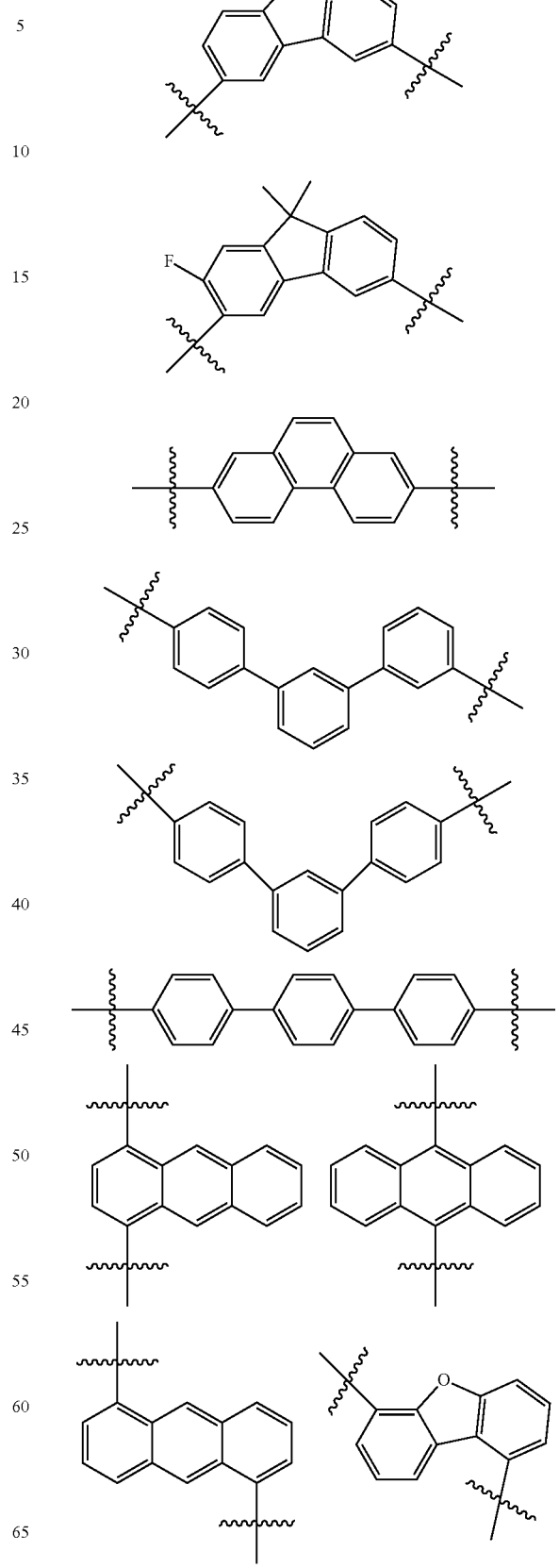

-continued

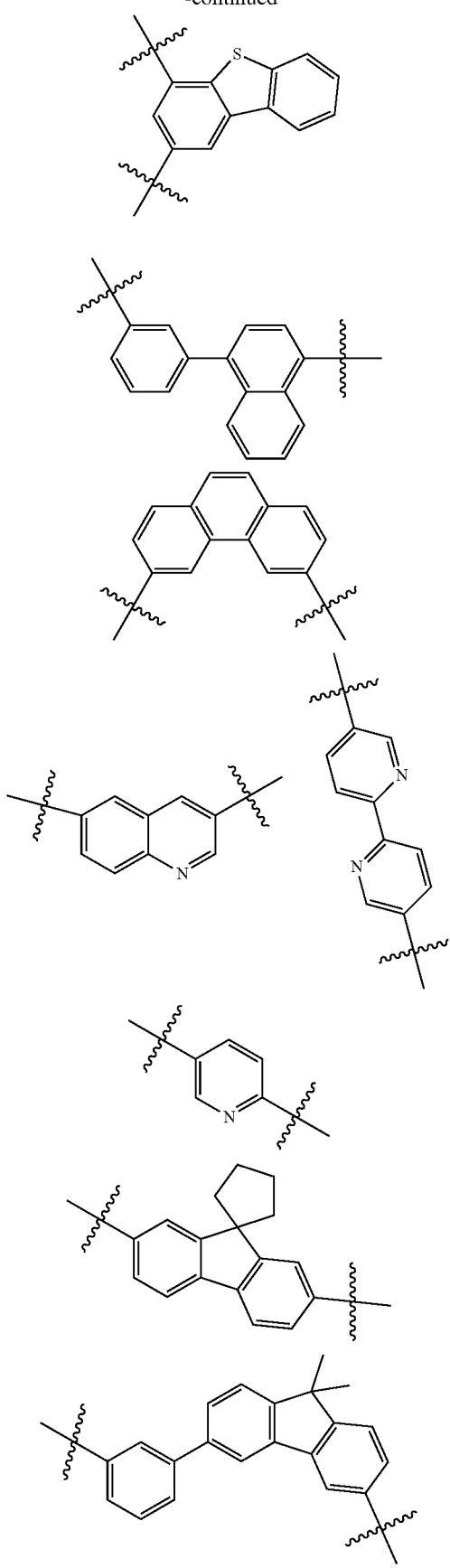

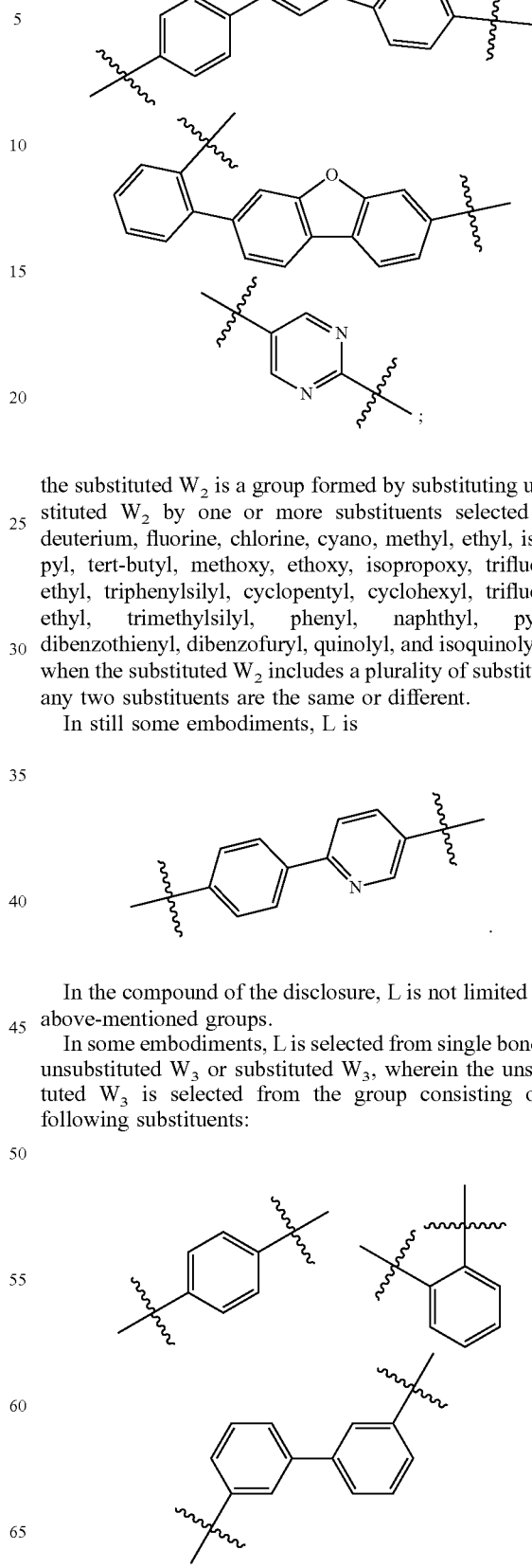

the substituted $W_2$ is a group formed by substituting unsubstituted $W_2$ by one or more substituents selected from deuterium, fluorine, chlorine, cyano, methyl, ethyl, isopropyl, tert-butyl, methoxy, ethoxy, isopropoxy, trifluoromethyl, triphenylsilyl, cyclopentyl, cyclohexyl, trifluoromethyl, trimethylsilyl, phenyl, naphthyl, pyridyl, dibenzothienyl, dibenzofuryl, quinolyl, and isoquinolyl, and when the substituted $W_2$ includes a plurality of substituents, any two substituents are the same or different.

In still some embodiments, L is

In the compound of the disclosure, L is not limited to the above-mentioned groups.

In some embodiments, L is selected from single bond, and unsubstituted $W_3$ or substituted $W_3$, wherein the unsubstituted $W_3$ is selected from the group consisting of the following substituents:

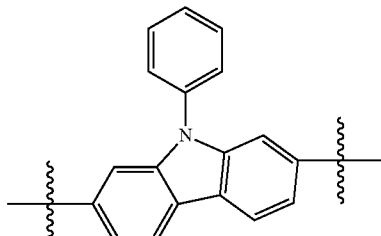
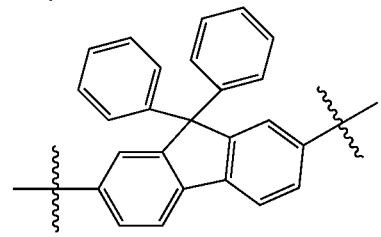
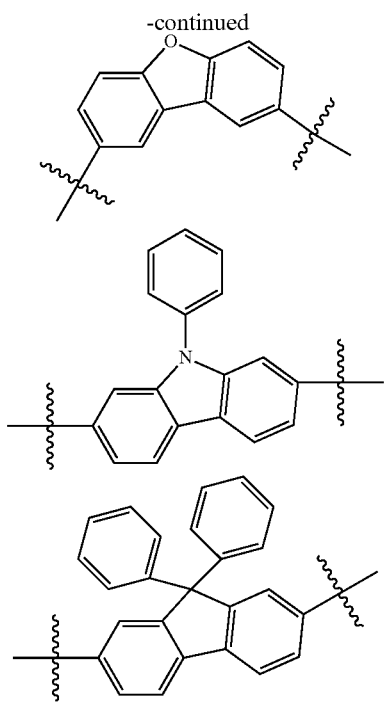

The substituted $W_3$ is a formed by substituting unsubstituted $W_3$ by one or more substituents selected from deuterium, fluorine, chlorine, cyano, methyl, ethyl, isopropyl, tert-butyl, methoxy, ethoxy, isopropoxy, trifluoromethyl, triphenylsilyl, cyclopentyl, cyclohexyl, trifluoromethyl, trimethylsilyl, phenyl, naphthyl, pyridyl, dibenzothienyl, dibenzofuryl, quinolyl, and isoquinolyl, and when the substituted $W_3$ includes a plurality of substituents, any two substituents are the same or different.

In some embodiments, $Ar_1$ is selected from substituted or unsubstituted aryl with 6 to 25 ring-forming carbon atoms, or a substituted or unsubstituted heteroaryl with 4 to 18 ring-forming carbon atoms.

In some embodiments, the aryl with 6 to 25 ring-forming carbon atoms and the heteroaryl with 4 to 18 ring-forming carbon atoms are optionally substituted by 0, 1, 2, 3, 4 or 5 substituents selected from: deuterium, fluorine, chlorine, bromine, cyano, alkyl with 1 to 6 carbon atoms, haloalkyl with 1 to 4 carbon atoms, alkoxy with 1 to 4 carbon atoms, alkylamino with 1 to 4 carbon atoms, alkylthio with 1 to 4 carbon atoms, aryl with 6 to 15 carbon atoms, heteroaryl with 3 to 15 carbon atoms, trialkylsilyl with 3 to 8 carbon atoms, triphenylsilyl, cycloalkyl with 5 to 10 carbon atoms, aryloxy with 6 to 12 carbon atoms, and arylthio with 6 to 12 carbon atoms, and any two substituents are the same or different.

In some embodiments, $Ar_1$ is selected from the group consisting of substituents represented by formula S-1 to formula S-11:

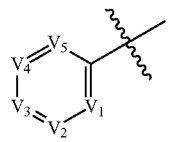

S-1

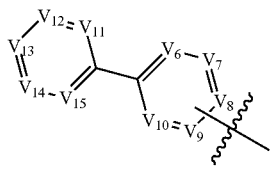

S-2

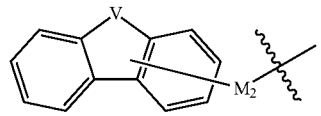

S-3

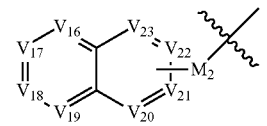

S-4

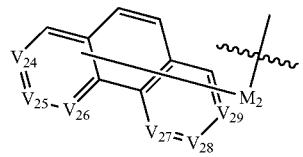

S-5

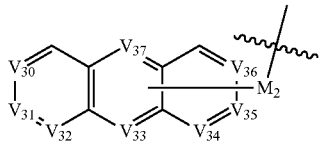

S-6

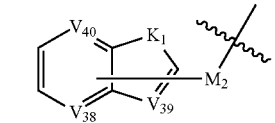

S-7

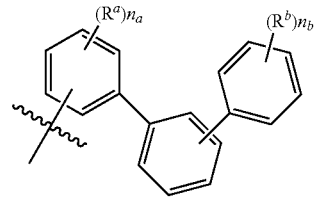

S-8

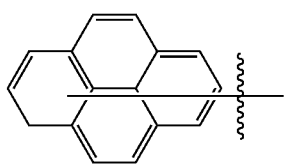

S-9

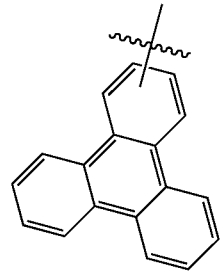

S-10

-continued

S-11

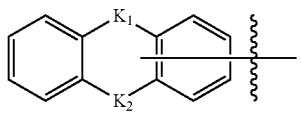

In the above groups, M₂ is selected from single bond and

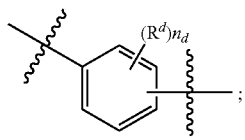

$n_a$ and $n_d$ are each independently 1, 2, 3 or 4; when a group includes two or more $R^d$, each $R^d$ is the same or different; when a group includes two or more $R^d$, each $R^d$ is the same or different; $n_b$ is selected from 1, 2, 3, 4 and 5; when a group includes two or more $R^b$, each $R^b$ is the same or different;

$V_1$ to $V_{40}$ are each independently selected from $C(R^v)$ and N, and when a group includes two or more $R^v$, any two $R^v$ are the same or different from each other;

V is selected from the group consisting of O, S, Se, $N(R^{v1})$, $C(R^{v2}R^3)$ and $Si(R^{v2}R^3)$;

$K_1$ and $K_2$ are each independently selected from O, S and $N(R^k)$;

$R^a$, $R^b$, $R^d$, $R^k$, $R^{v1}$, $R^{v2}$, and $R^{v3}$ are each independently hydrogen, aryl with 6 to 18 carbon atoms, heteroaryl with 3 to 18 carbon atoms, alkyl with 1 to 10 carbon atoms, cycloalkyl with 3 to 10 carbon atoms, or heterocycloalkyl with 2 to 10 carbon atoms; or, $R^{v2}$ and $R^{v3}$ linked to the same atom are linked to each other to form a saturated or unsaturated 5- to 13-membered aliphatic ring together with the atom linked to the both. For example, when $R^{v2}$ and $R^{v3}$ are linked to each other to form a ring, the ring is a 5-membered ring

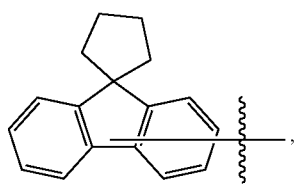

a 6-membered ring or a 13-membered ring

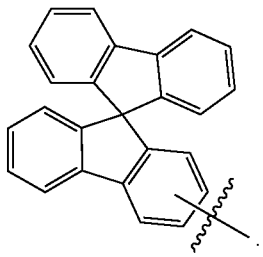

Of course, the number of atoms on the ring formed by the link between $R^{v2}$ and $R^{v3}$ may also be other values, which will not be listed here.

Each $R^v$ is independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 18 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms.

In some embodiments, in the organic compound of the disclosure, $Ar_1$ is unsubstituted $T_1$ or substituted $T_1$, wherein the unsubstituted $T_1$ is selected from the group consisting of the following substituents:

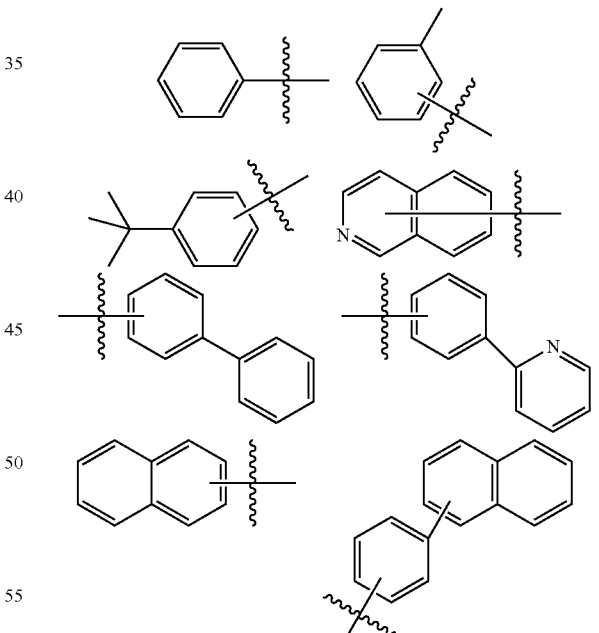

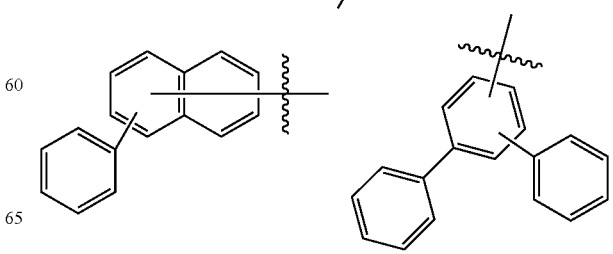

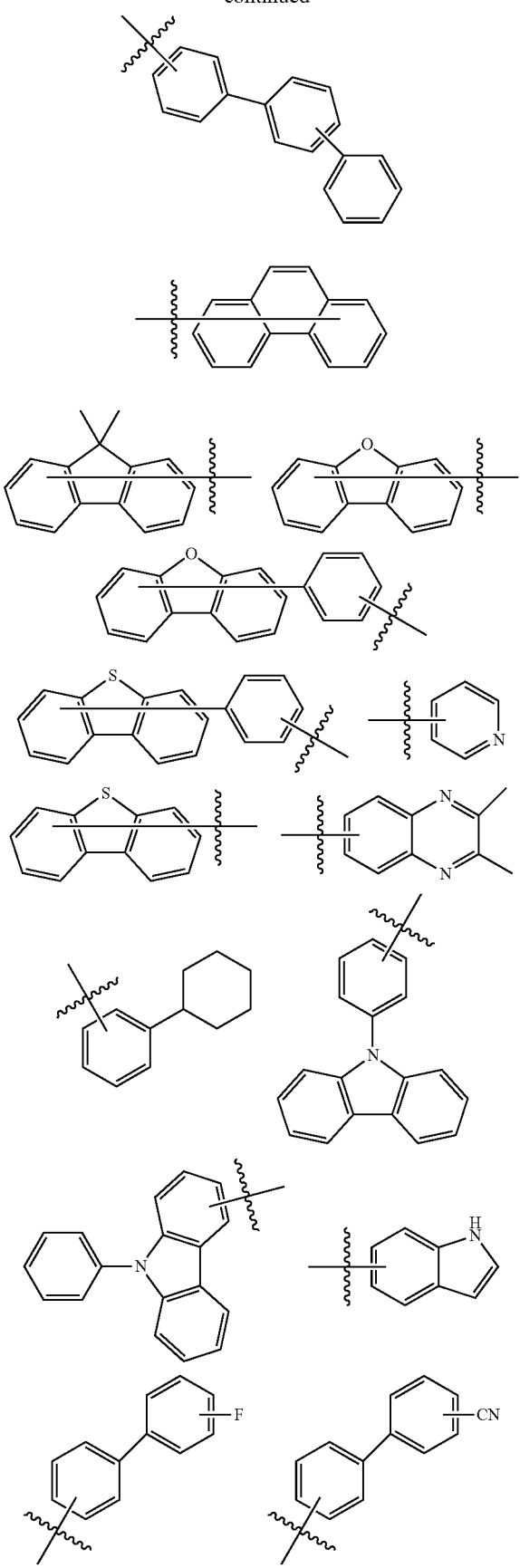
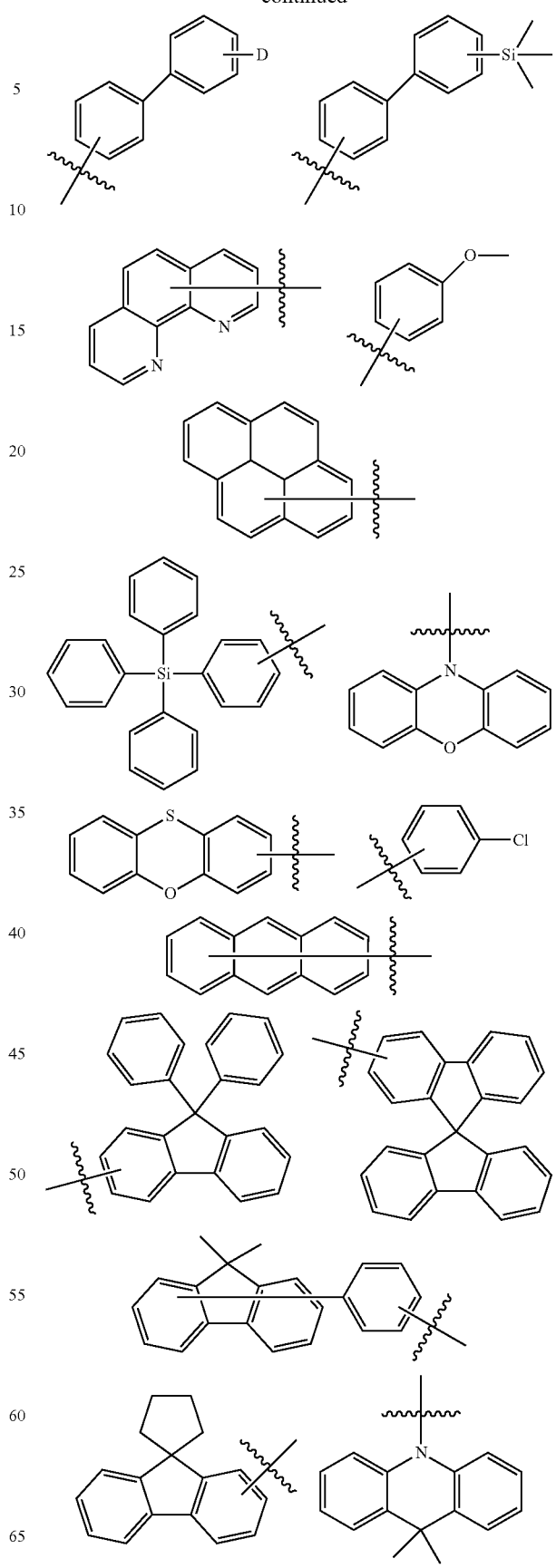

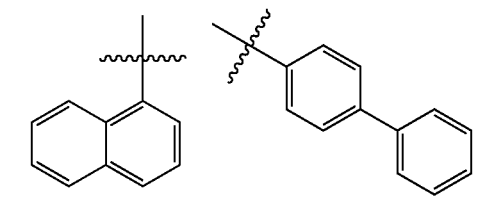

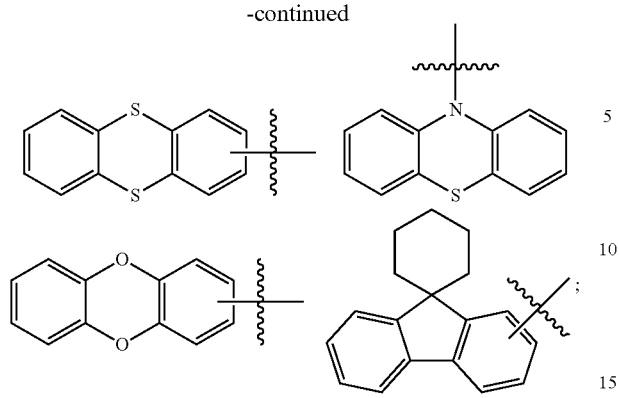

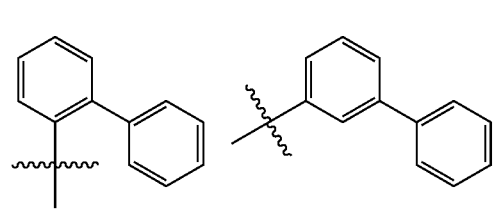

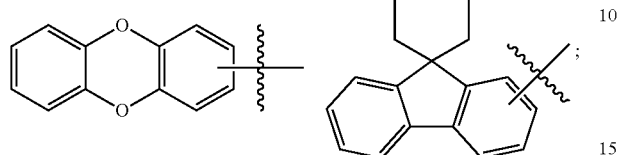

The substituted $T_1$ is a group formed by substituting unsubstituted $T_1$ by one or more substituents selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, triphenylsilyl, cycloalkyl with 5 to 10 carbon atoms, aryl with 6 to 15 carbon atoms, and heteroaryl with 3 to 12 carbon atoms, and when the substituted $T_1$ includes a plurality of substituents, any two substituents are the same or different.

In still some embodiments, $Ar_1$ is

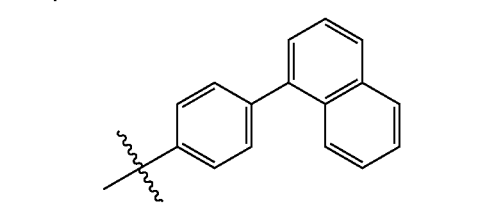

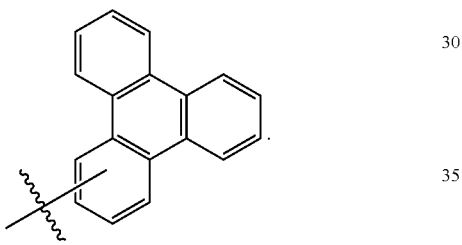

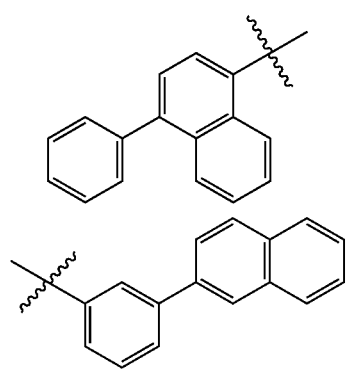

In still some embodiments, the substituted $T_1$ is a group formed by substituting unsubstituted $T_1$ by one or more substituents selected from deuterium, fluorine, chlorine, cyano, methyl, ethyl, isopropyl, tert-butyl, methoxy, ethoxy, isopropoxy, trifluoromethyl, triphenylsilyl, cyclopentyl, cyclohexyl, trifluoromethyl, trimethylsilyl, phenyl, naphthyl, pyridyl, pyridyl, 9,9-dimethylfluorenyl, dibenzothienyl, dibenzofuryl, quinolyl, and isoquinolyl, and when the substituted $T_1$ includes a plurality of substituents, any two substituents are the same or different. In some embodiments, in the organic compound of the disclosure, $Ar_1$ is selected from the group consisting of the following substituents:

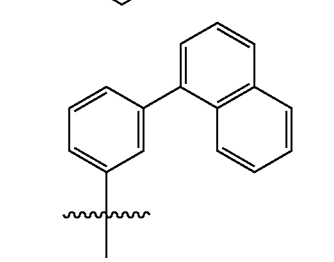

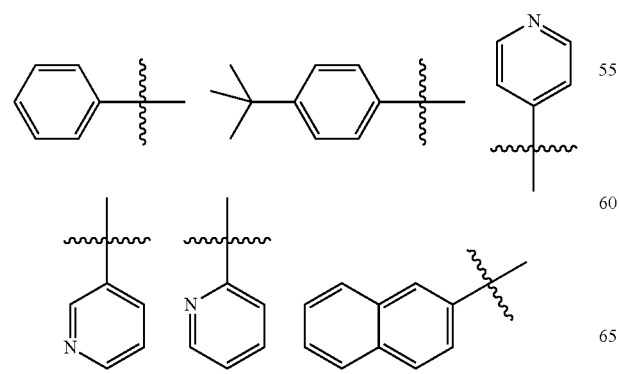

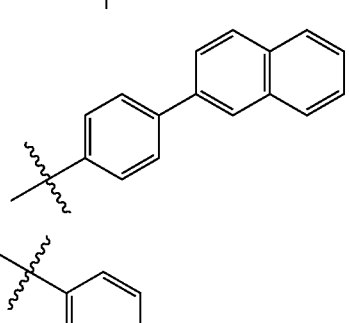

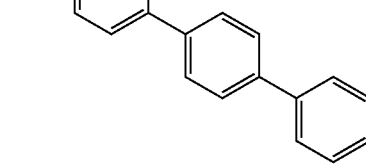

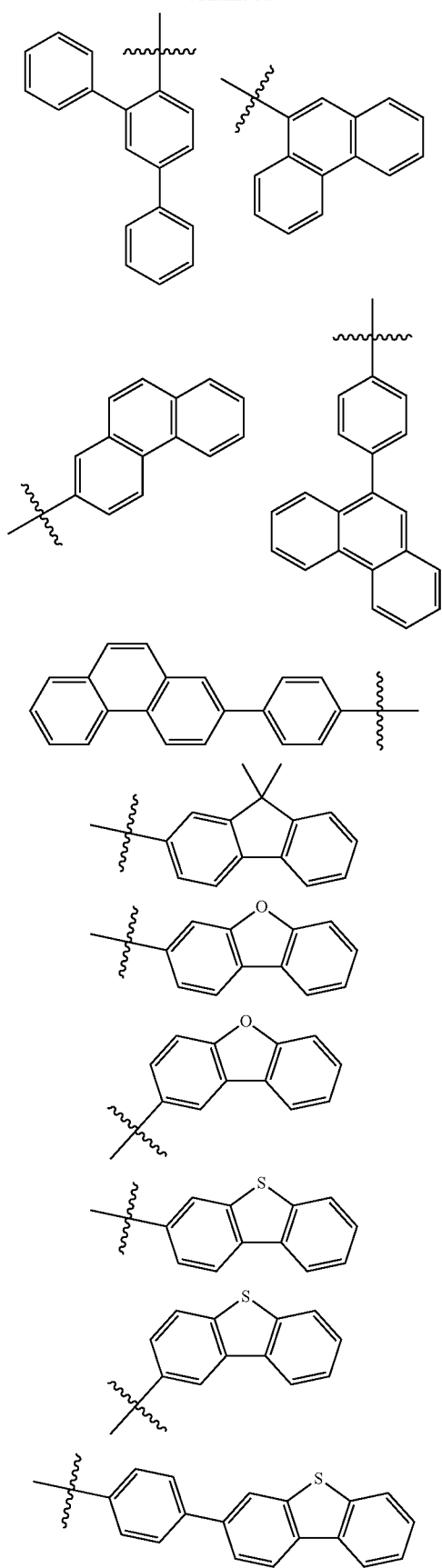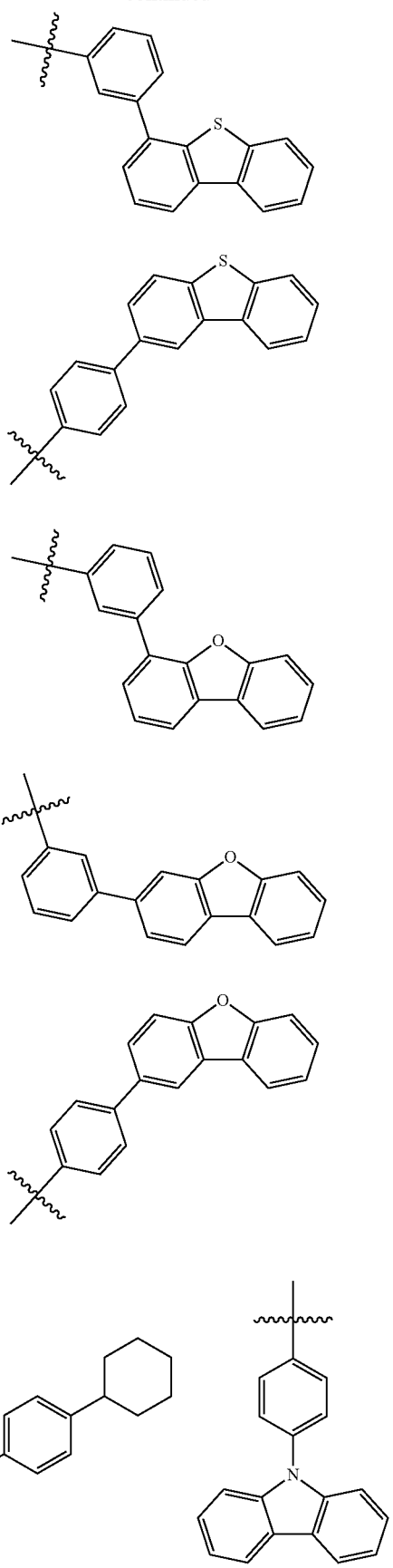

-continued
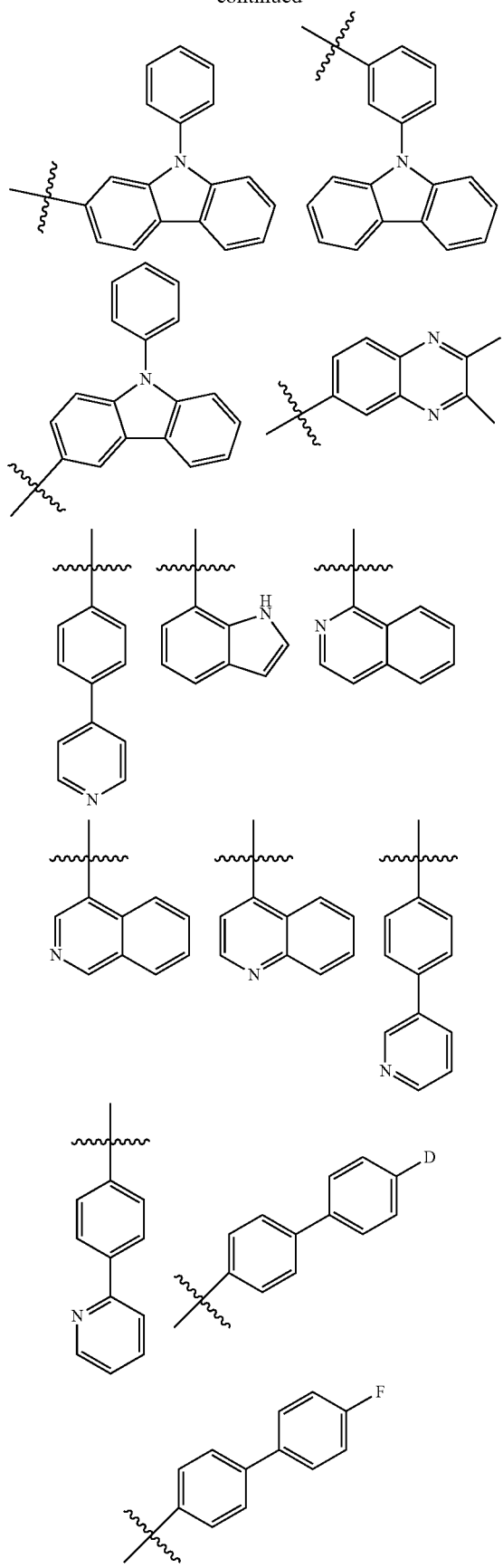
-continued
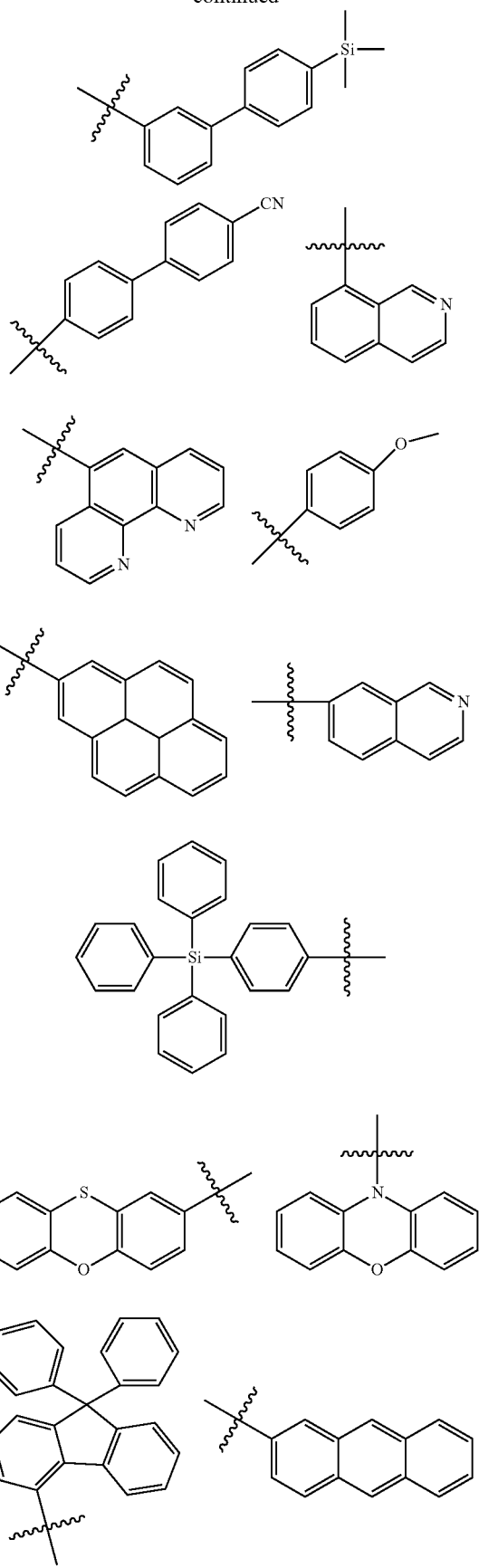

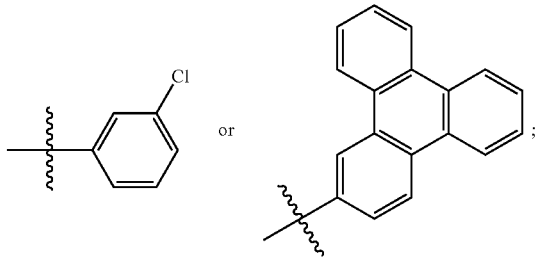 or 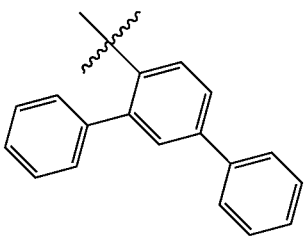
In the compound of the disclosure, Ar$_1$ is not limited to the above-mentioned groups.
In some embodiments, in the organic compound of the disclosure, Ar$_1$ is selected from the group consisting of the following substituents:
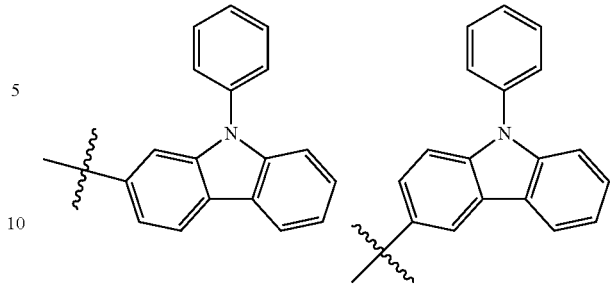
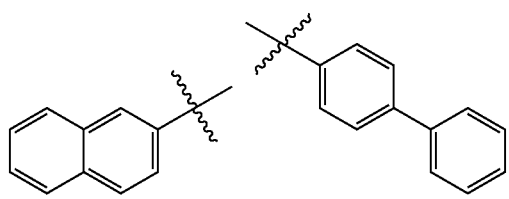
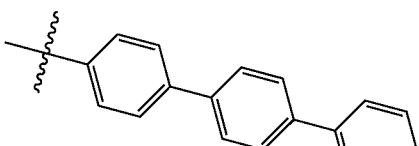
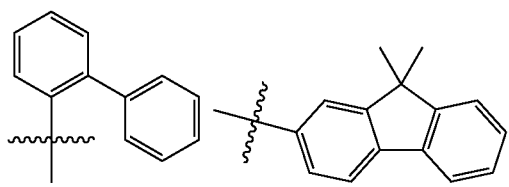
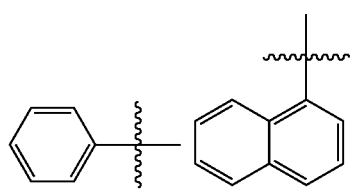
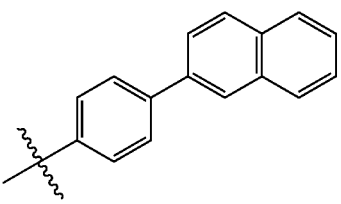
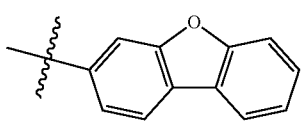
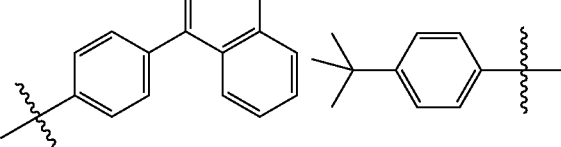
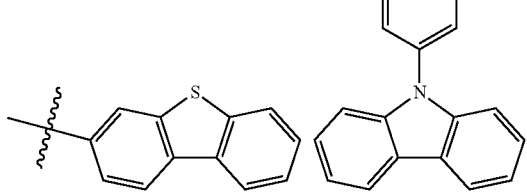
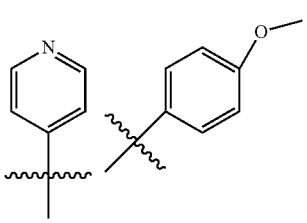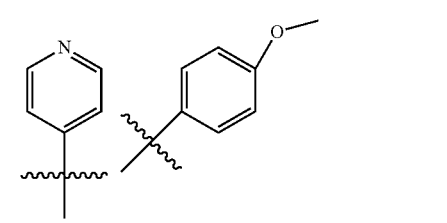

-continued

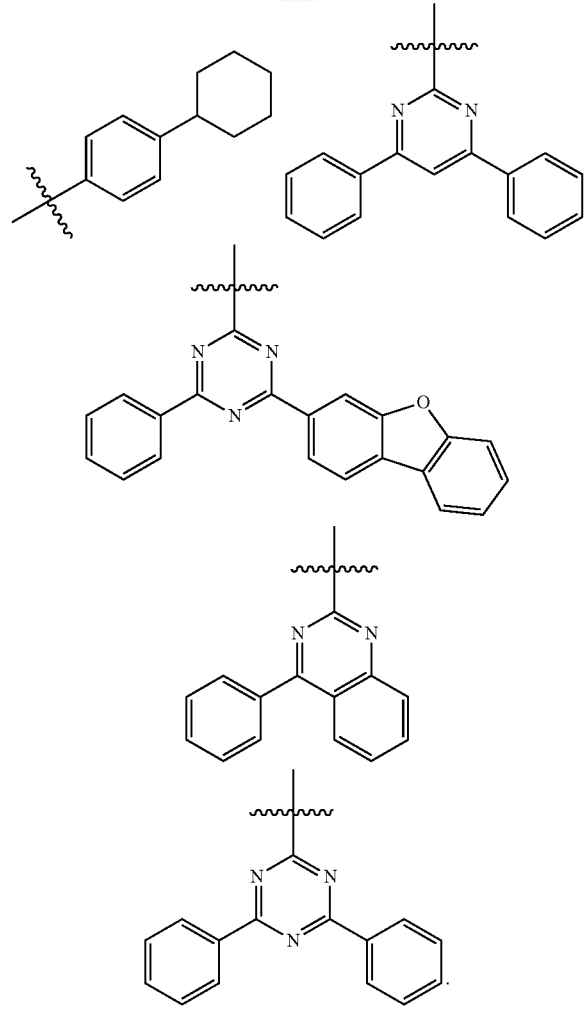

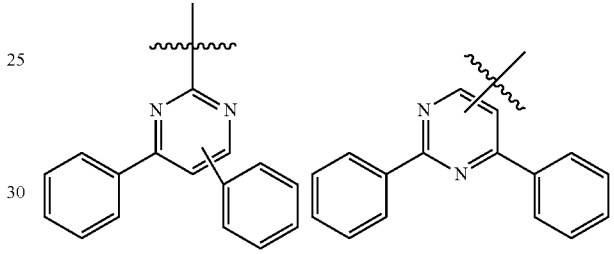

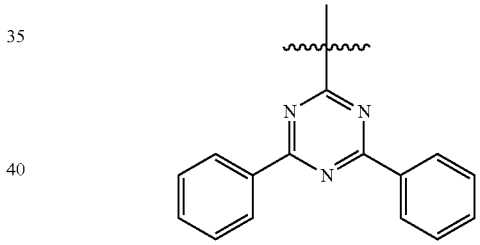

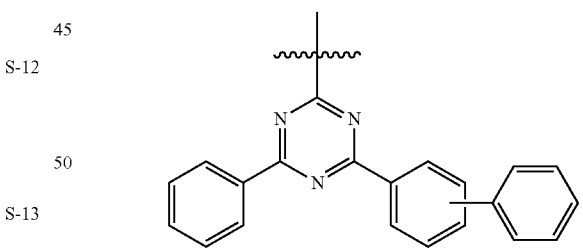

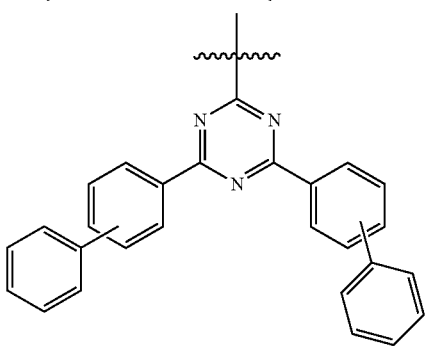

10 carbon atoms, or a heterocycloalkyl with 2 to 10 carbon atoms; or, $R^{12}$ and $R^{13}$ linked to the same atom are linked to each other to form a saturated or unsaturated 5- to 13-membered ring together with the atom linked to the both;

Each $R^{v4}$ is independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms, or any two adjacent $R^{v4}$ are linked to each other to form a 6- to 10-membered aromatic ring or a 6- to 10-membered heteroaromatic ring. In still some embodiments, $Ar_1$ is selected from substituted or unsubstituted $T_2$, wherein the unsubstituted $T_2$ is independently selected from the following groups:

In still some embodiments, $Ar_1$ is also selected from the group represented by the following formula S-12 and formula S-13:

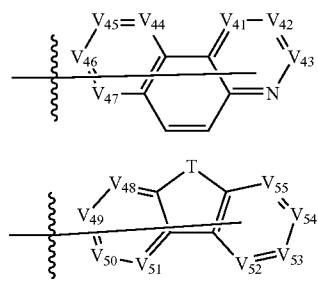

S-12

S-13

Wherein $V_{41}$ to $V_{55}$ are each independently selected from $C(R^{v4})$ and N, at least one of $V_{48}$ to $V_{55}$ is N, and when the same group includes a plurality of $R^{v4}$, any two $R^{v4}$ are the same or different from each other;

T is selected from the group consisting of O, S, Se, $N(R^{r1})$, $C(R^{r2}R^{r3})$ and $Si(R^{r2}R^{r3})$;

$R^{r1}$, $R^{r2}$, and $R^{r3}$ are each independently hydrogen, aryl with 6 to 18 carbon atoms, heteroaryl with 3 to 18 carbon atoms, alkyl with 1 to 10 carbon atoms, cycloalkyl with 3 to -continued
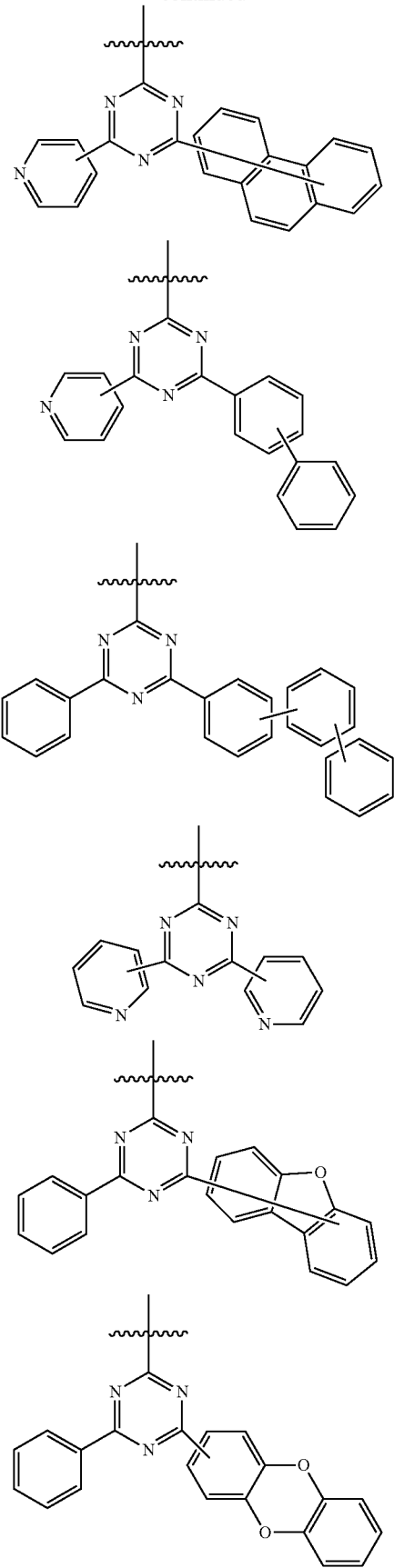
-continued
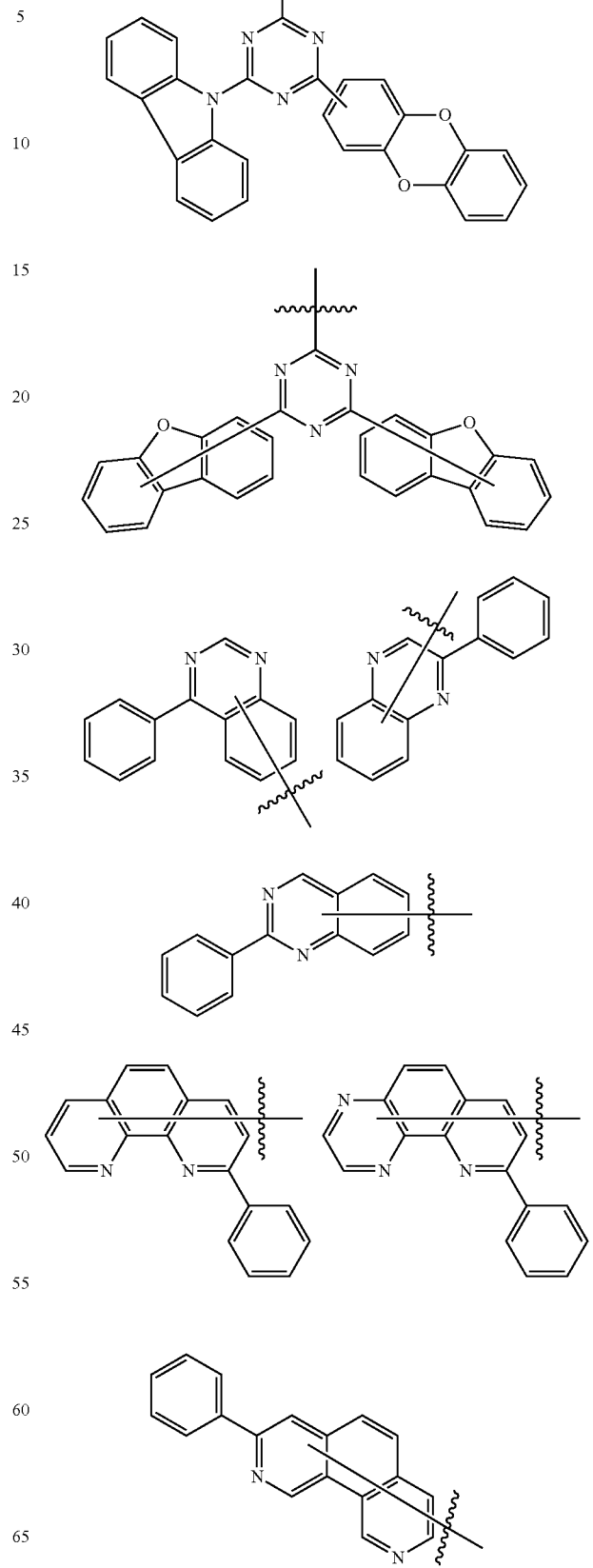

-continued

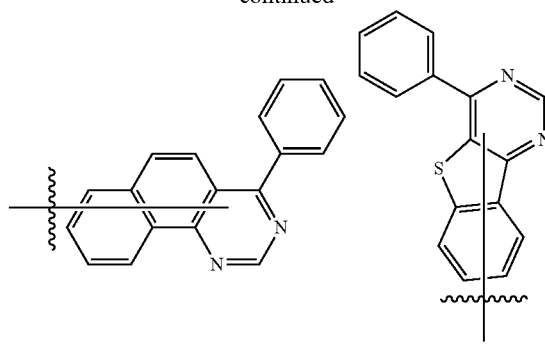

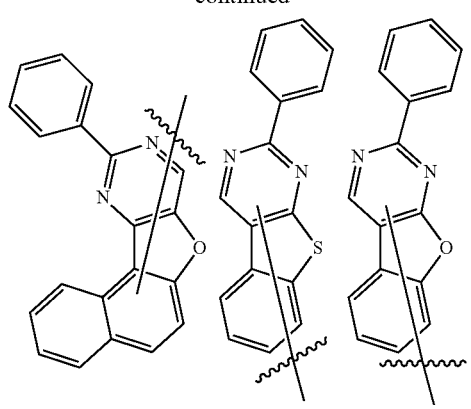

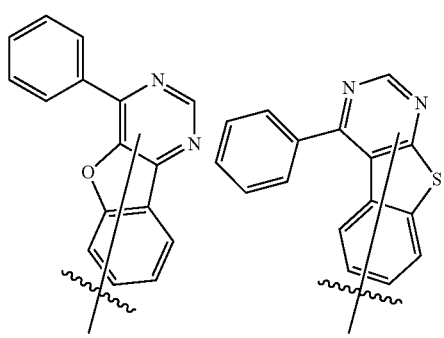

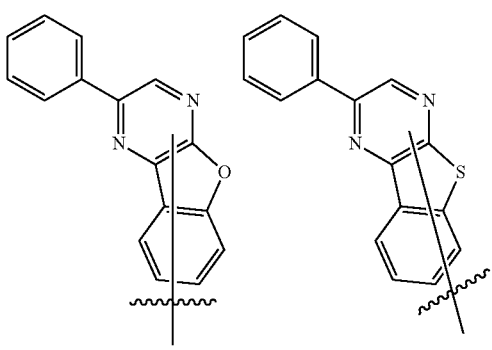

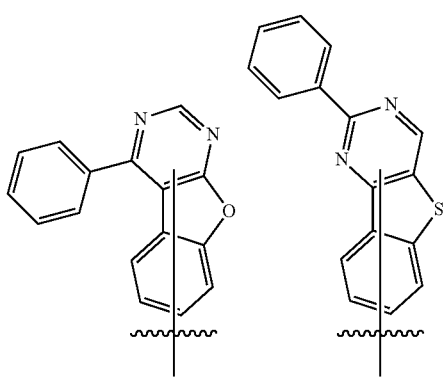

The substituted $T_2$ is a group formed by substituting unsubstituted $T_2$ by one or more substituents selected from deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, arylsilyl with 6 to 18 carbon atoms, cycloalkyl with 5 to 7 carbon atoms, aryl with 6 to 13 carbon atoms, and heteroaryl with 3 to 12 carbon atoms, and when the substituted $T_2$ includes a plurality of substituents, any two substituents are the same or different.

In still some embodiments, $Ar_1$ is independently selected from the following groups:

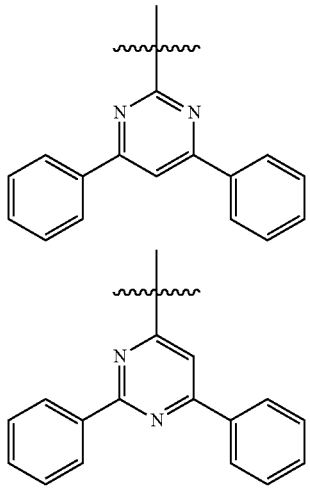

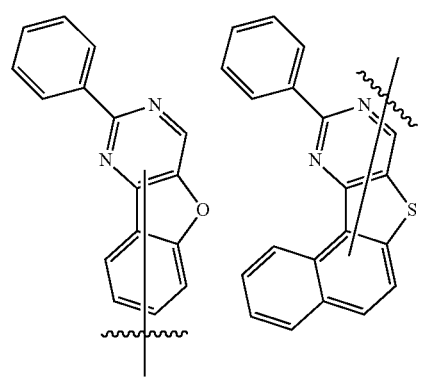

-continued
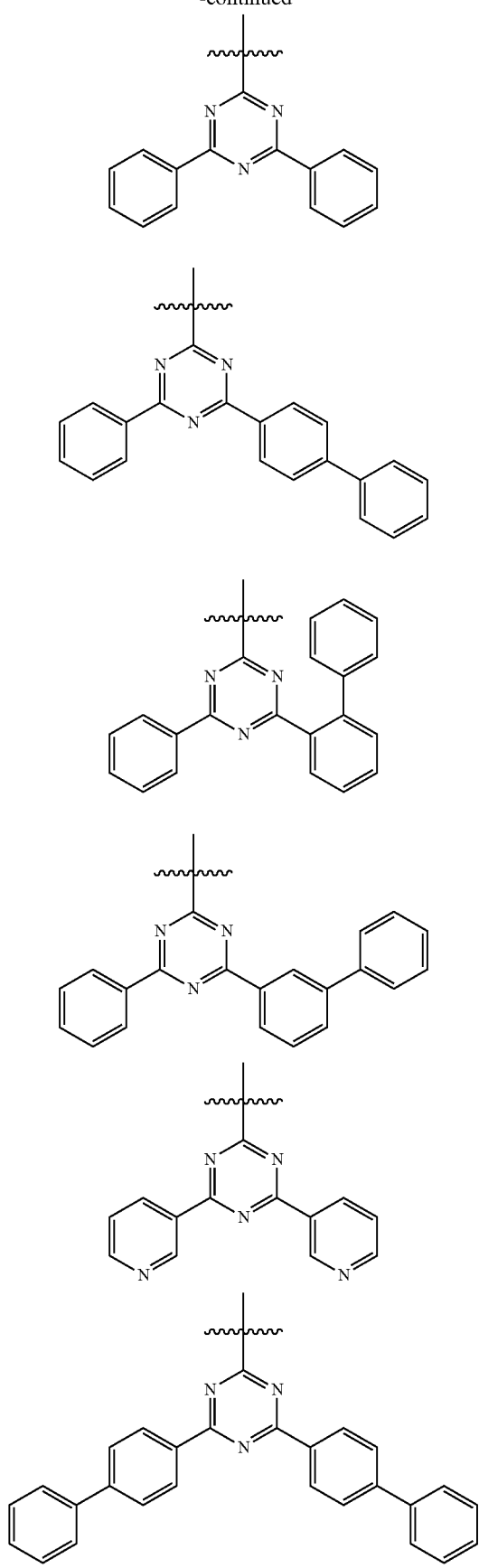
-continued
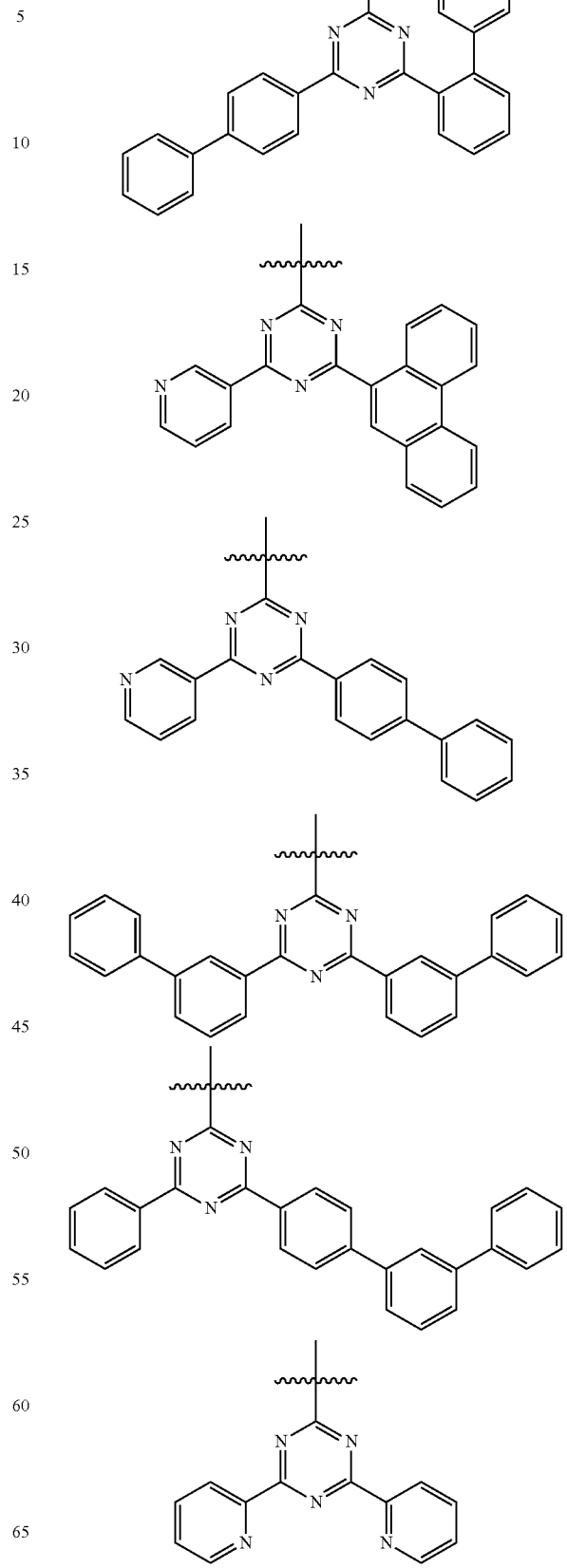

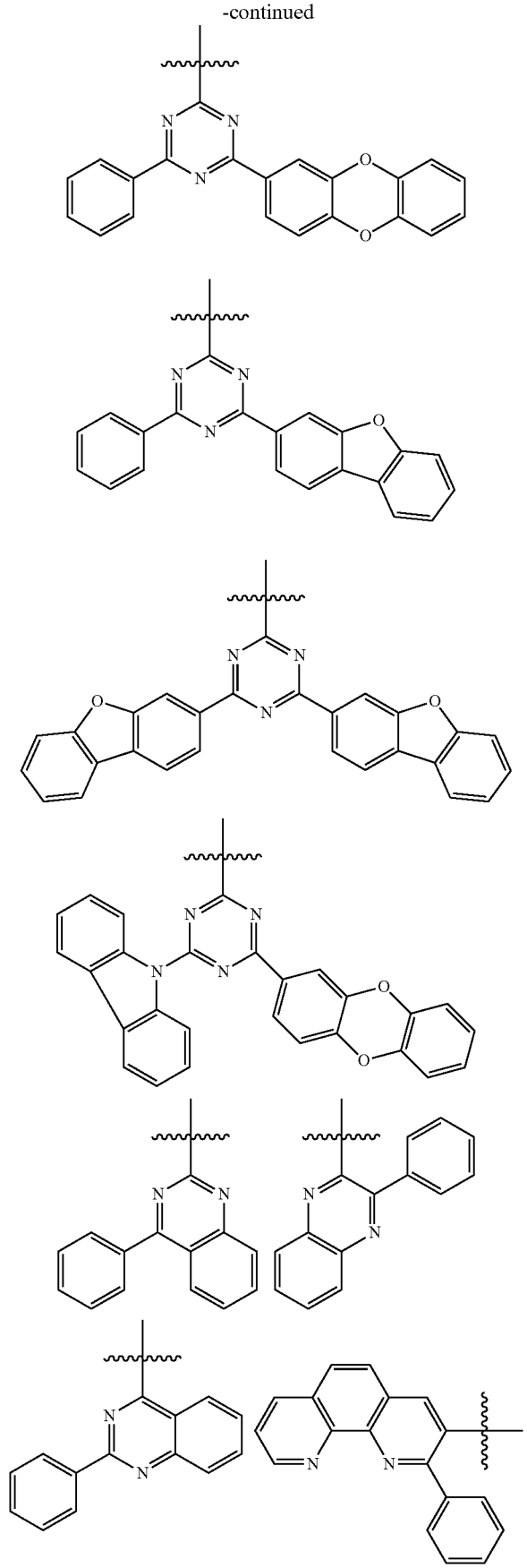
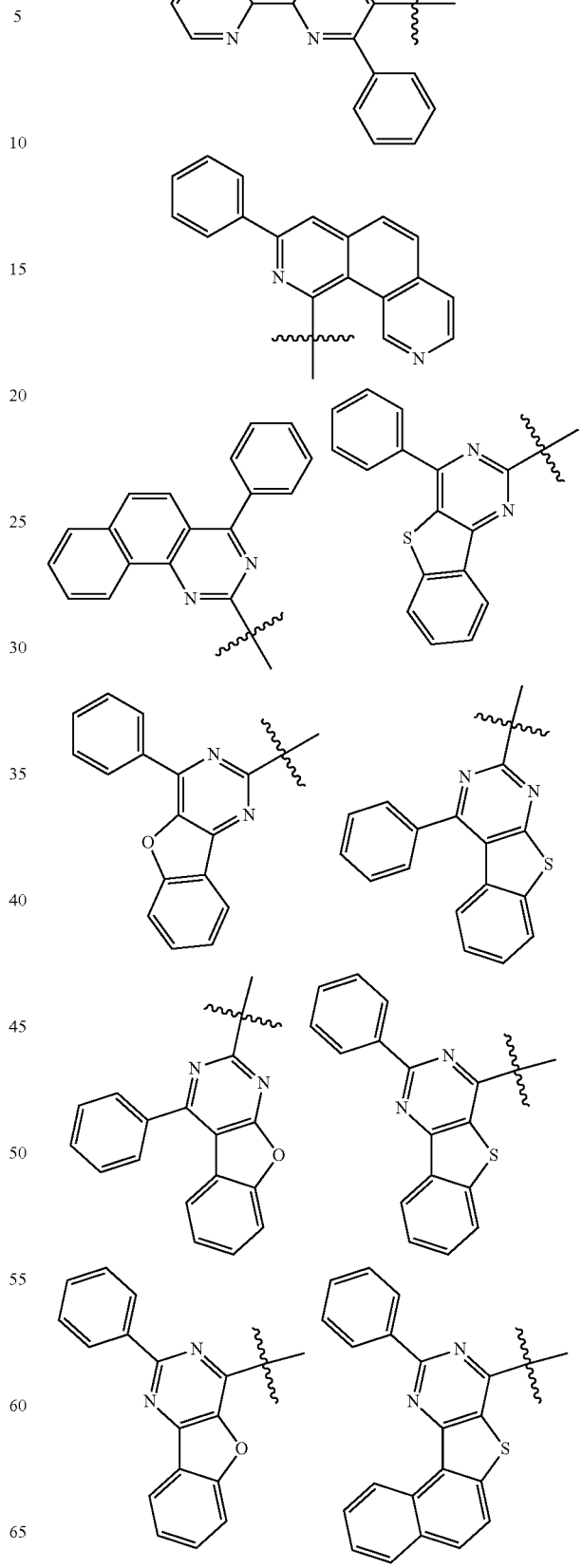

51
-continued
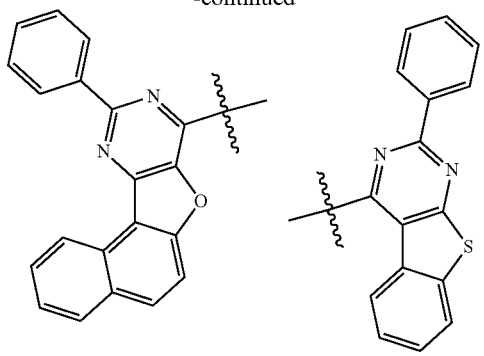
In some embodiments, the organic compound of the disclosure is selected from the group consisting of the following compounds:
1
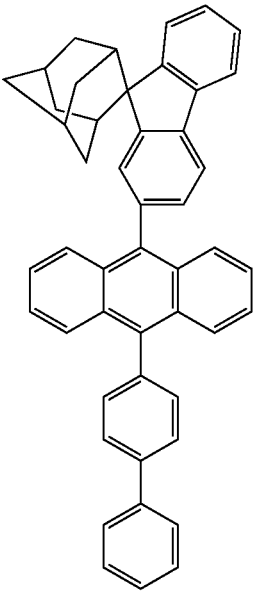
52
-continued
2
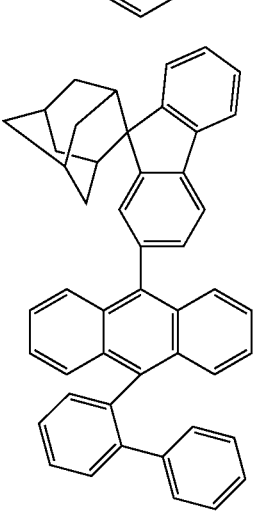
3
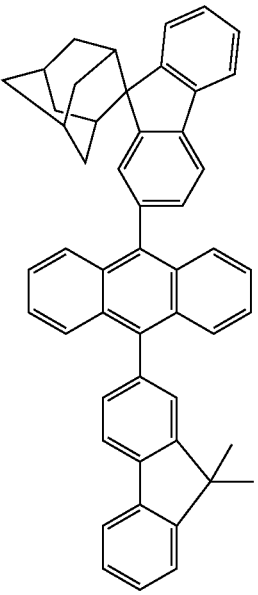
4

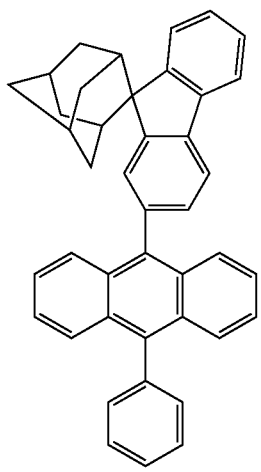
5
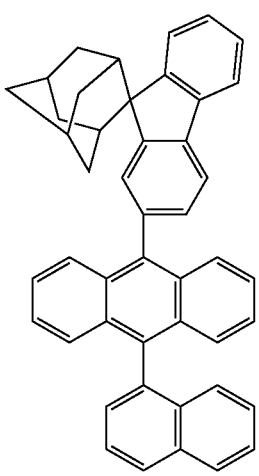
6
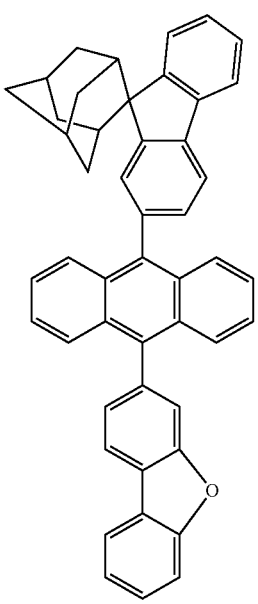
7
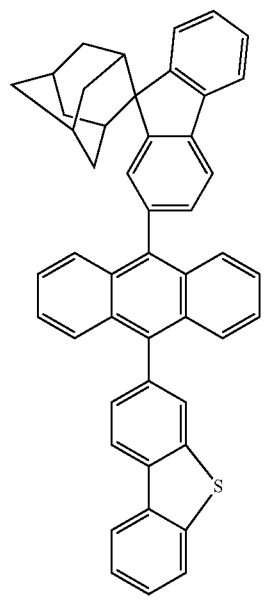
8
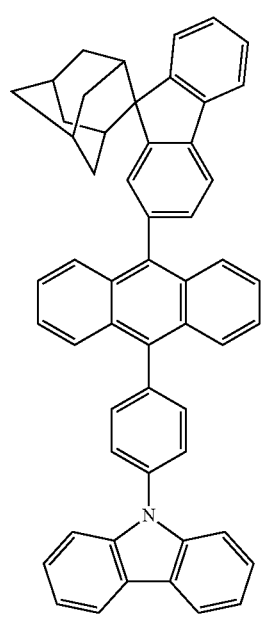
9

10
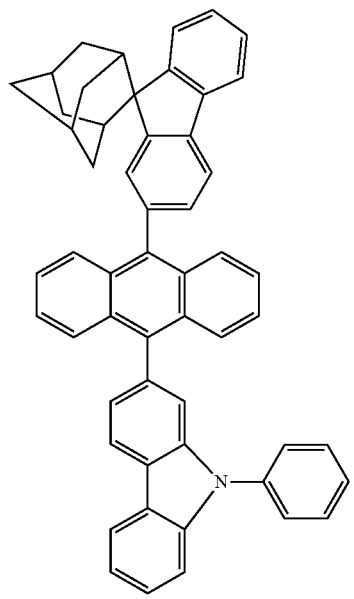
12
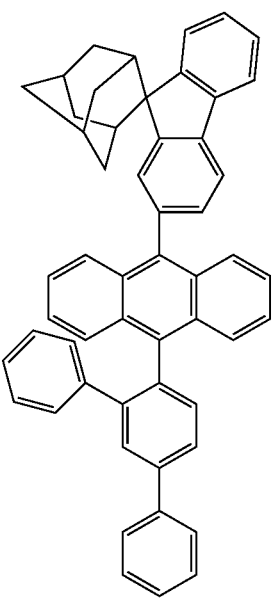
11
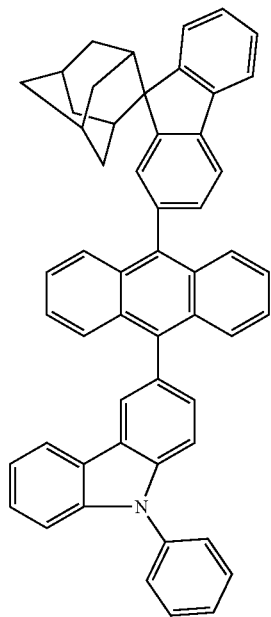
13
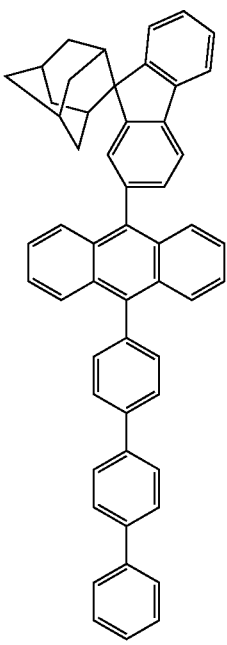

14
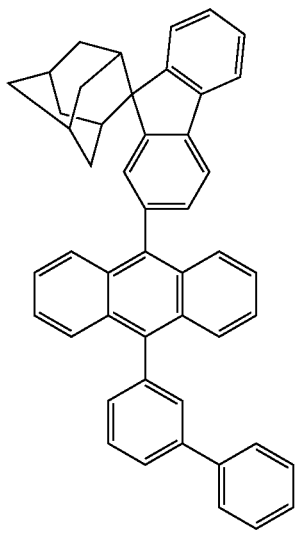
15
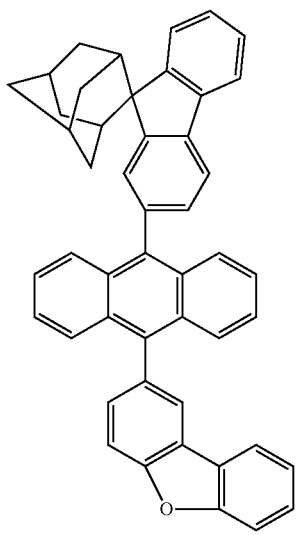
16
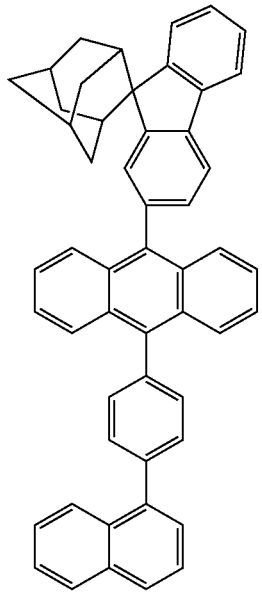
17
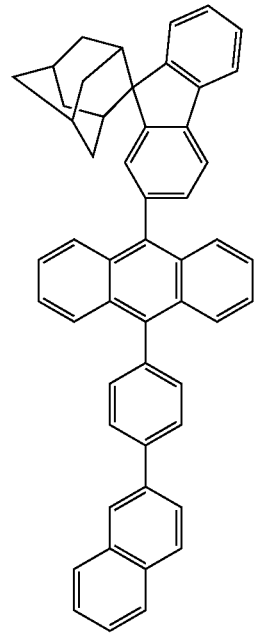
18
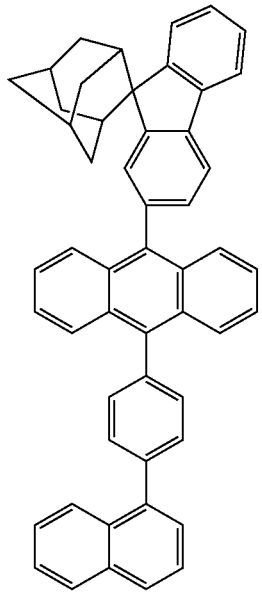

19
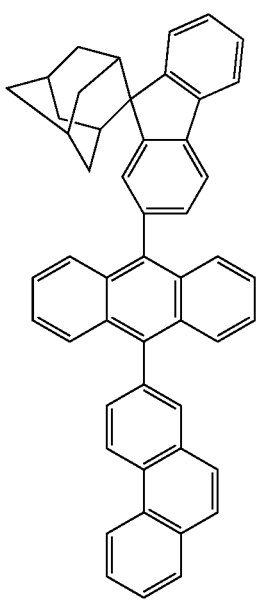
20
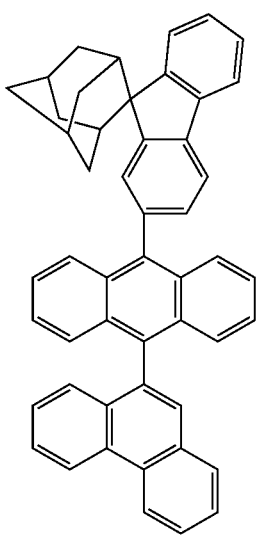
21
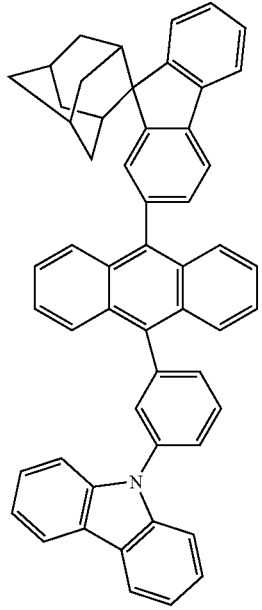
22
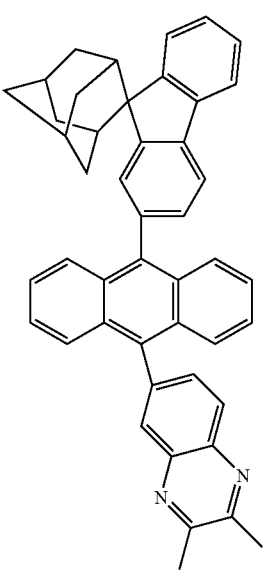

23
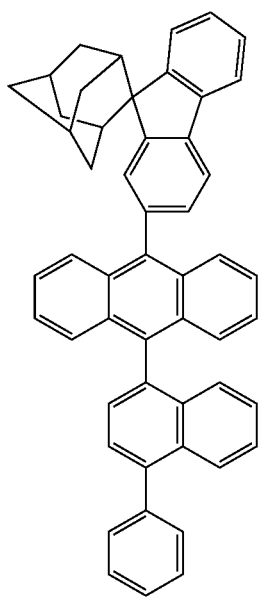
24
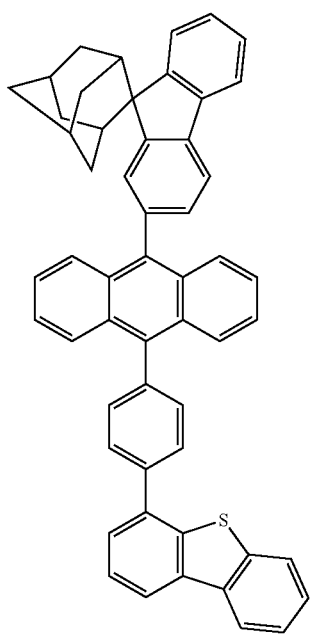
25
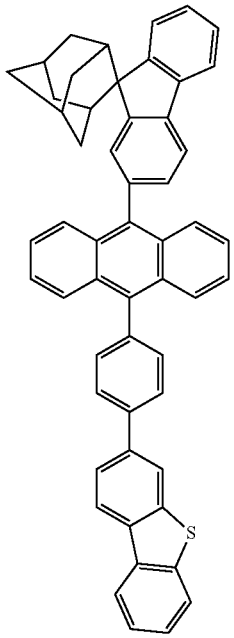
26
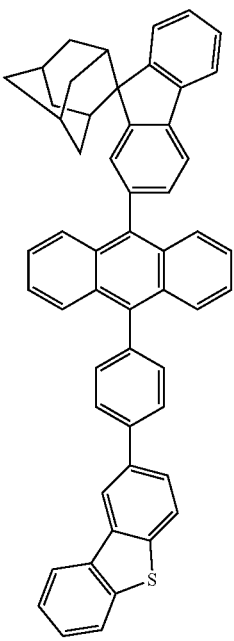

27
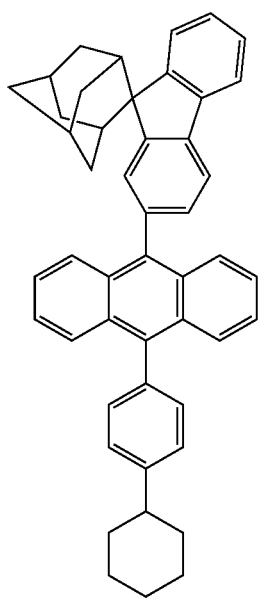
28
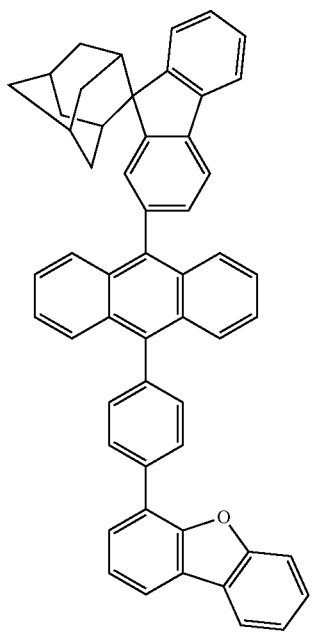
29
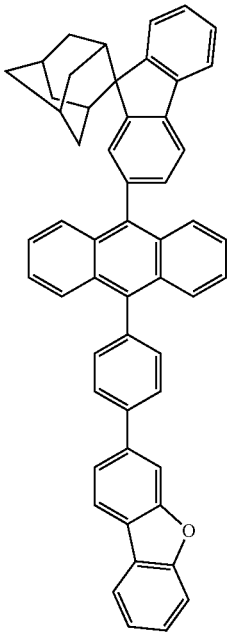
30
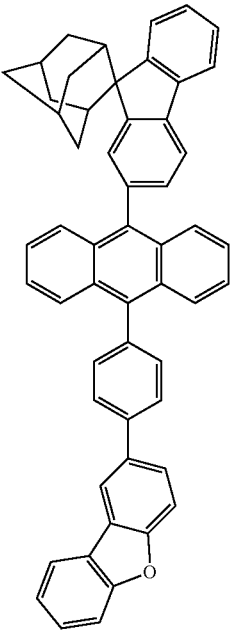

31
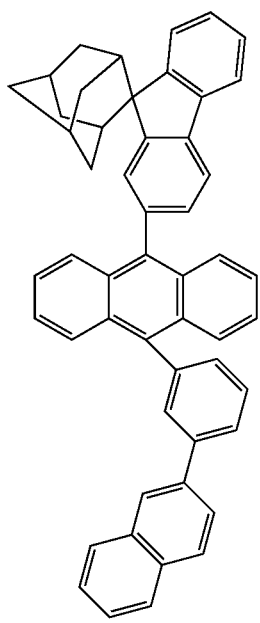
32
33
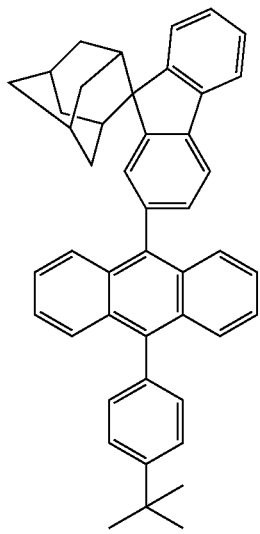
34
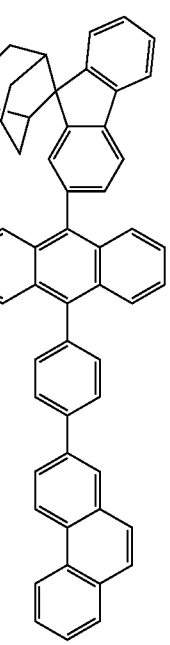

35
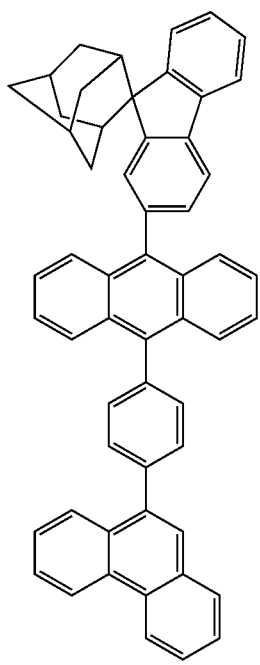
36
37
38
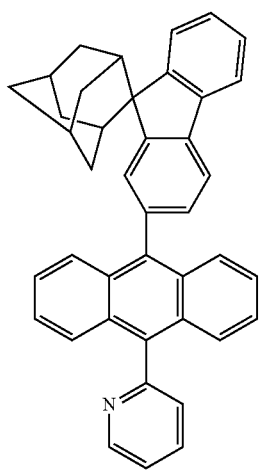
39
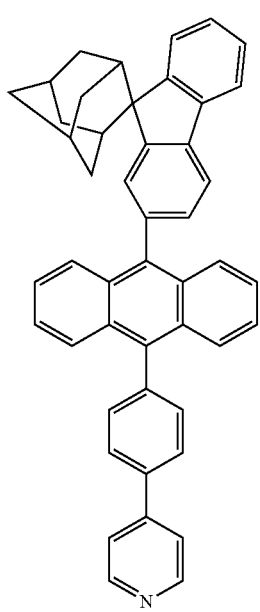
40
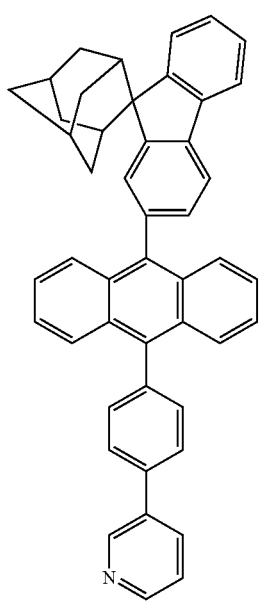

41
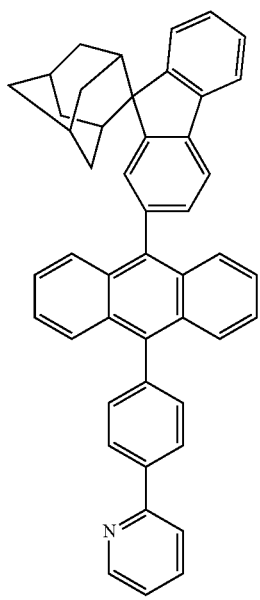
42
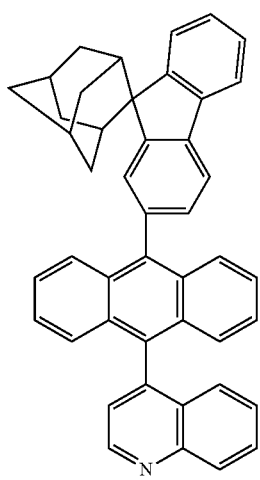
43
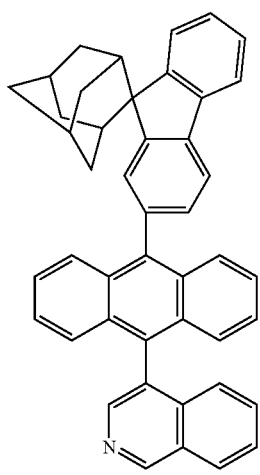
44
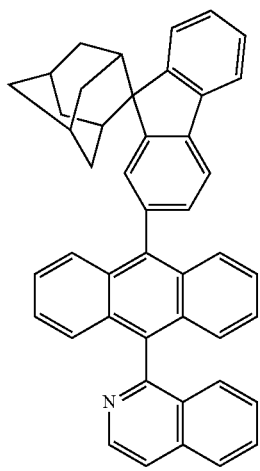
45
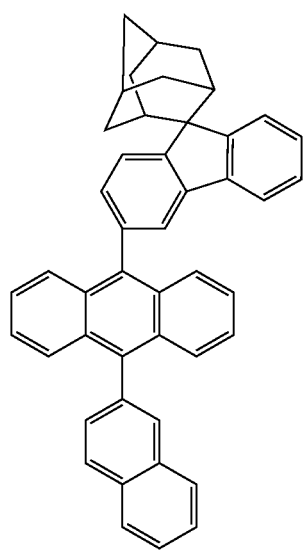
46
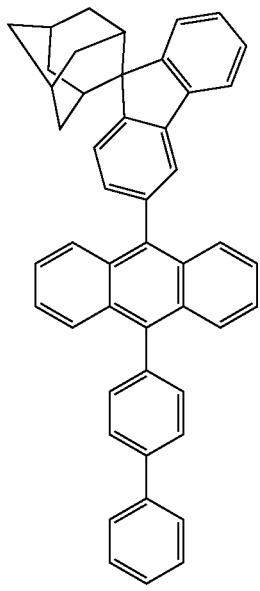

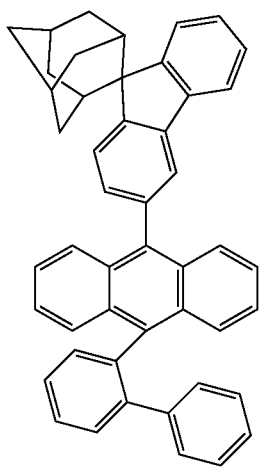
47
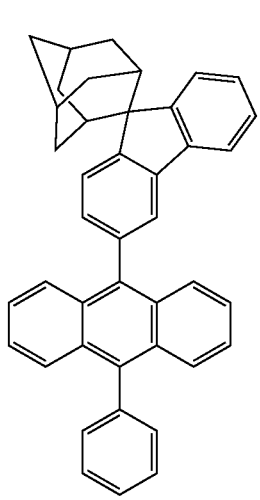
48
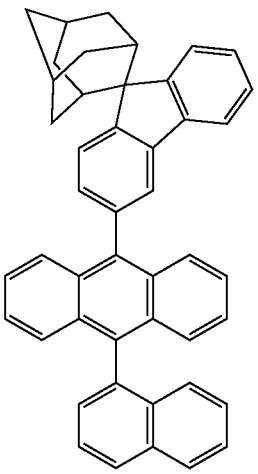
49
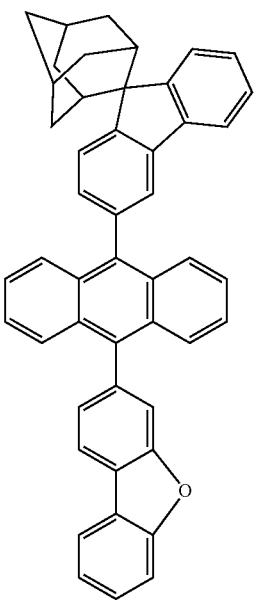
50
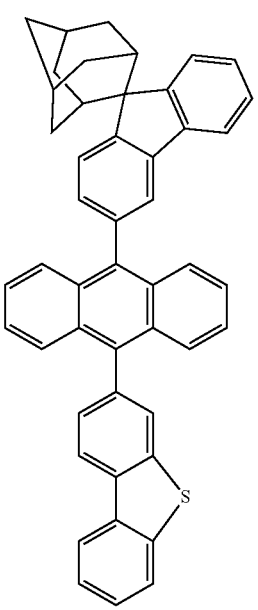
51
52

53
54
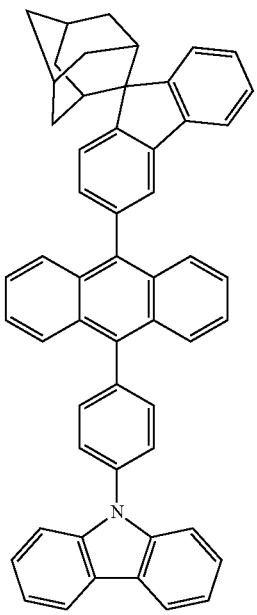
55
56
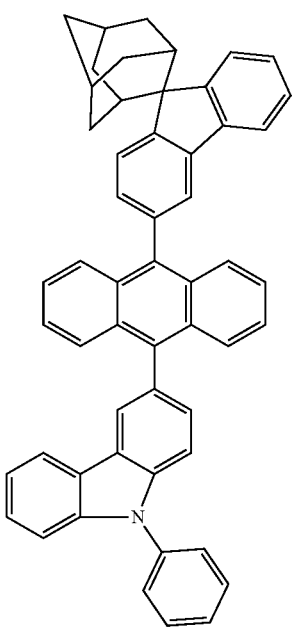
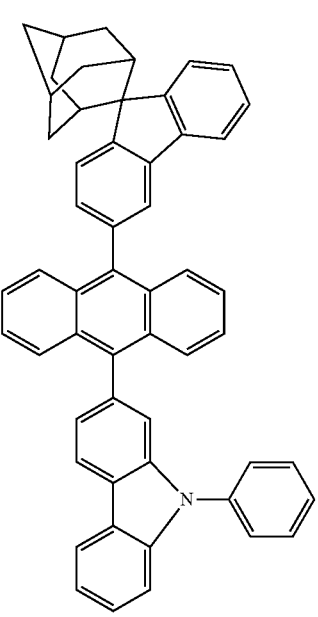
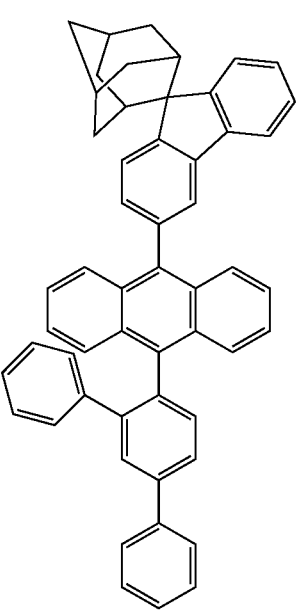

57
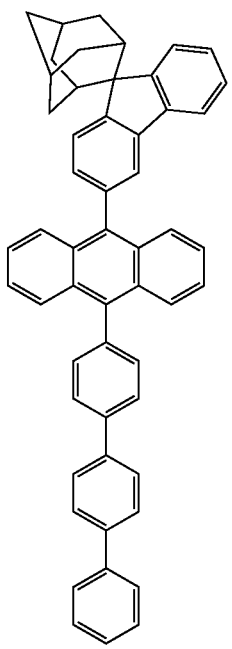
58
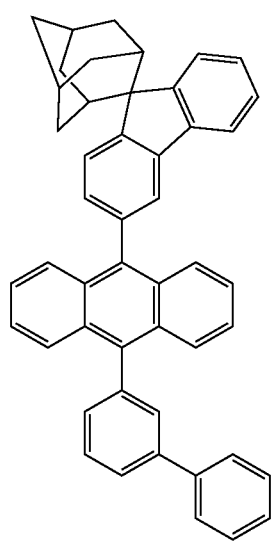
59
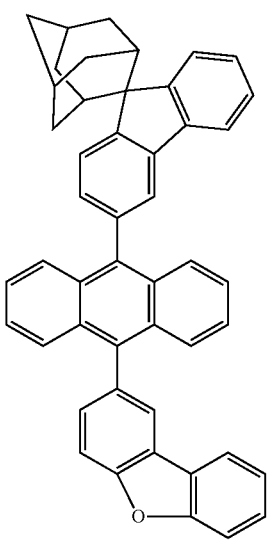
60
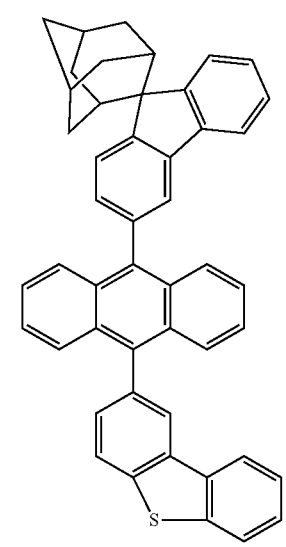

61
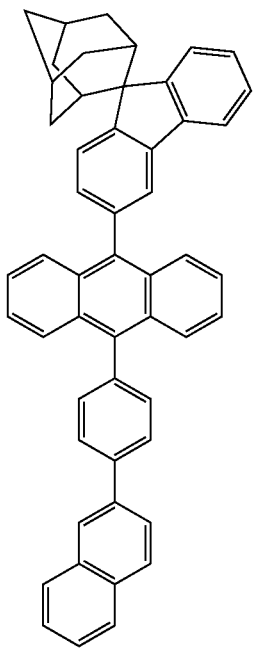
62
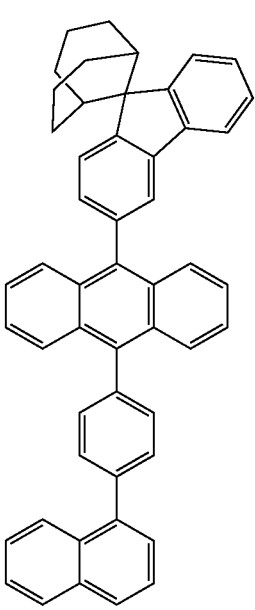
63
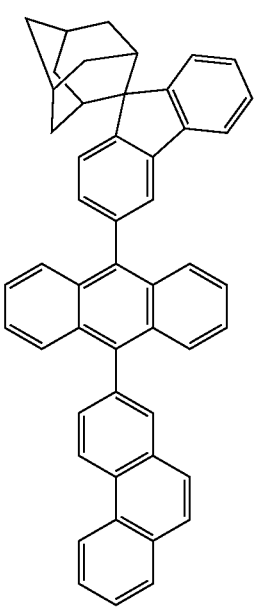
64
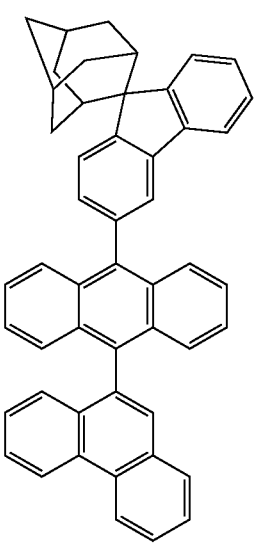

65
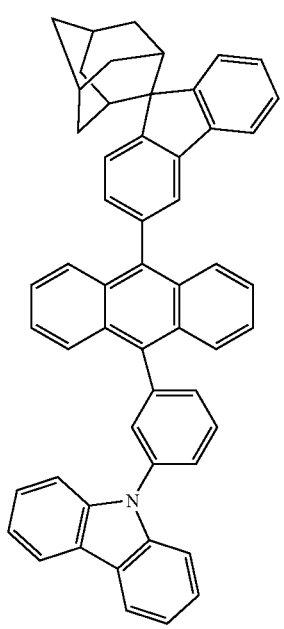
66
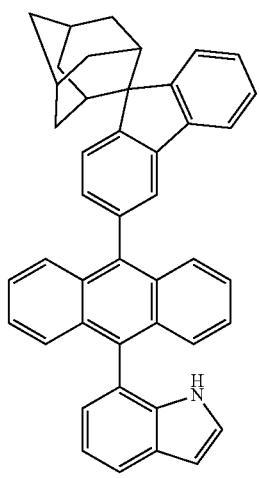
67
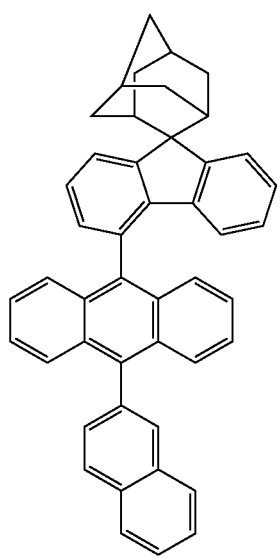
68
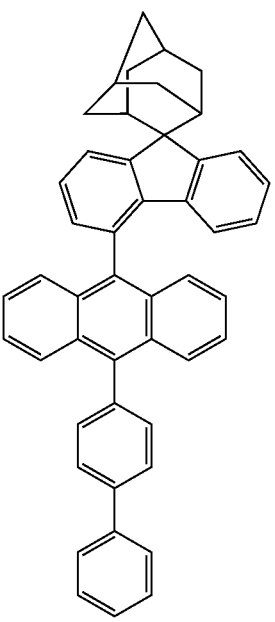
69
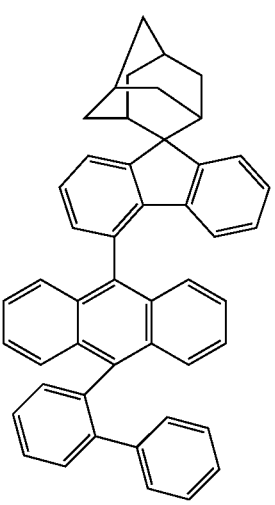

70
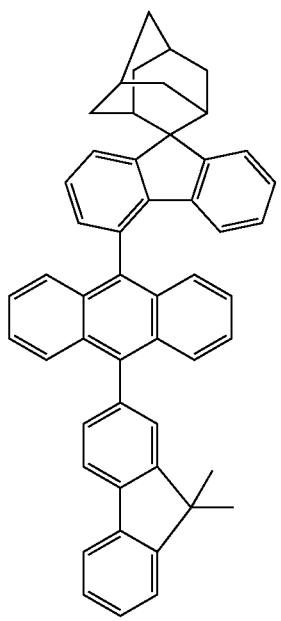
71
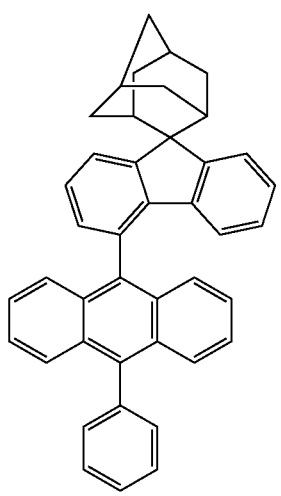
72
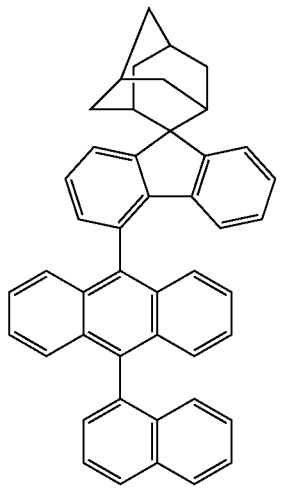
73
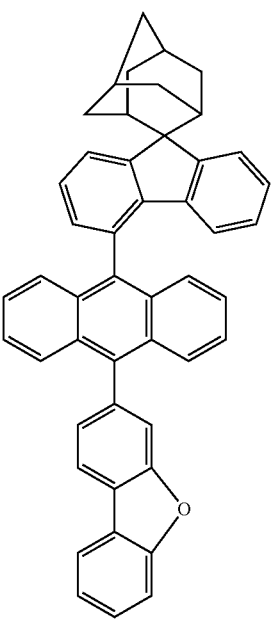
74
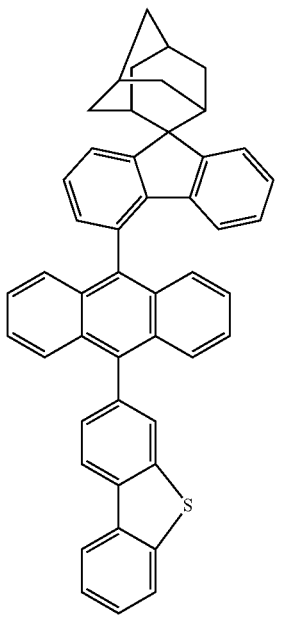

75
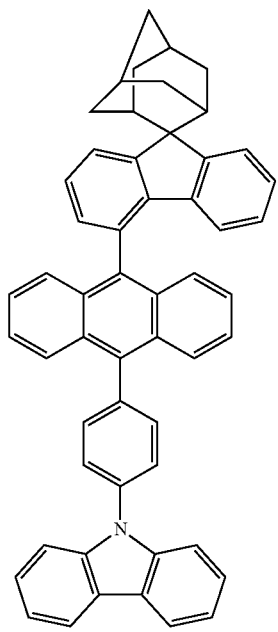
76
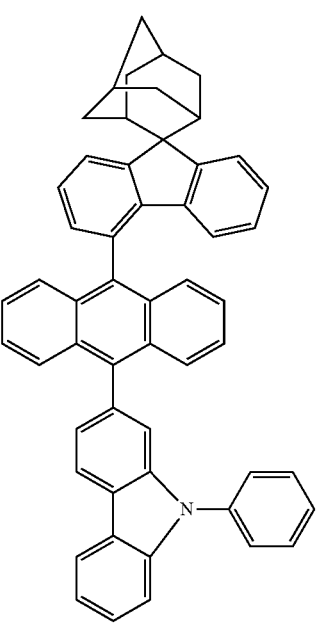
77
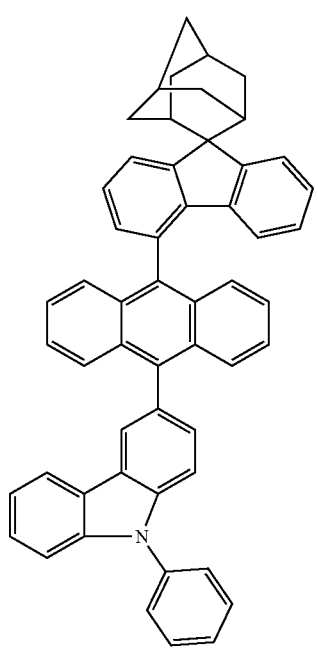
78
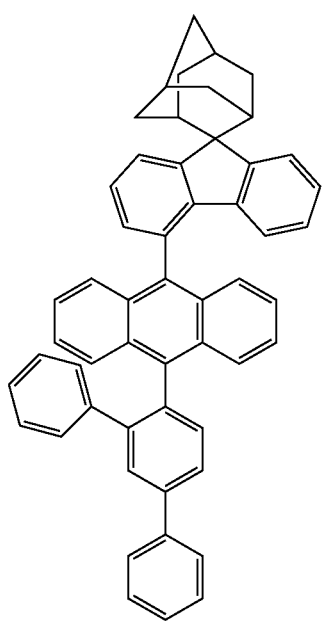

85
-continued
79
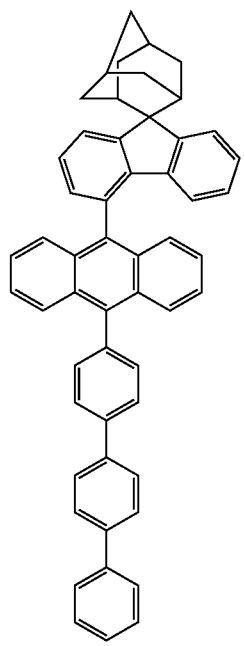
80
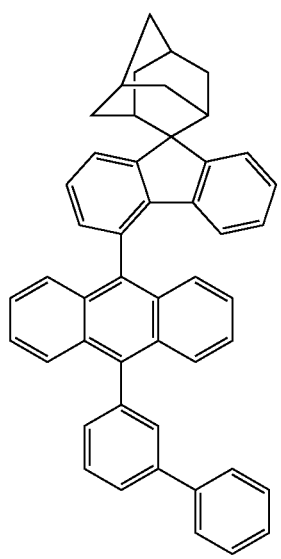
86
-continued
81
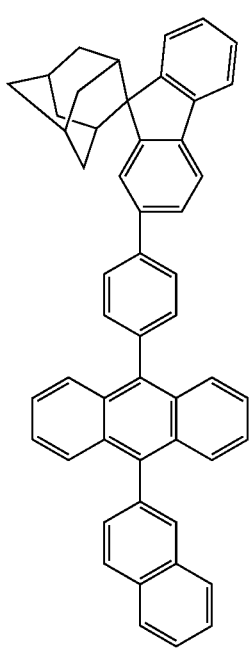
82
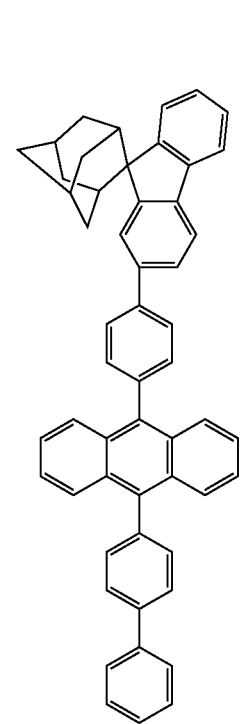

83
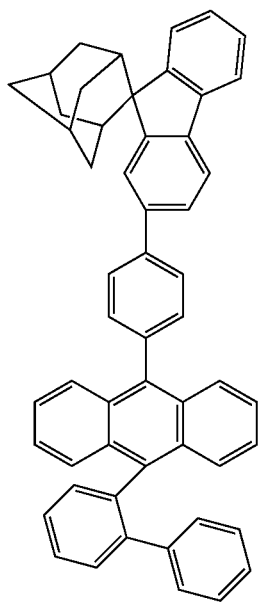
85
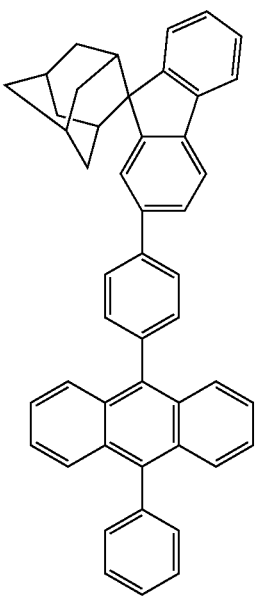
84
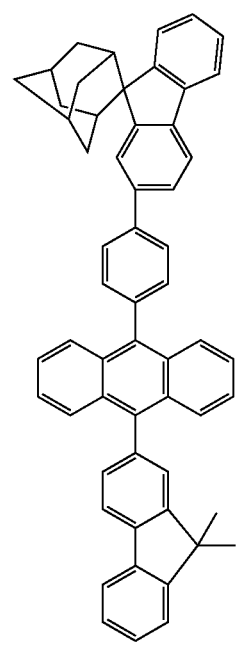
86
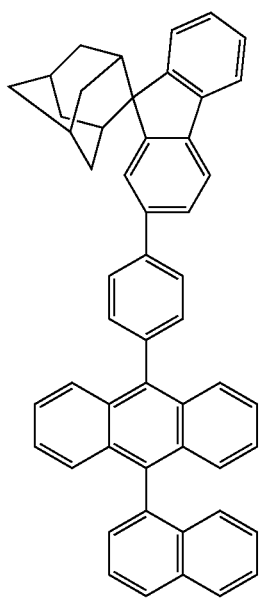

87
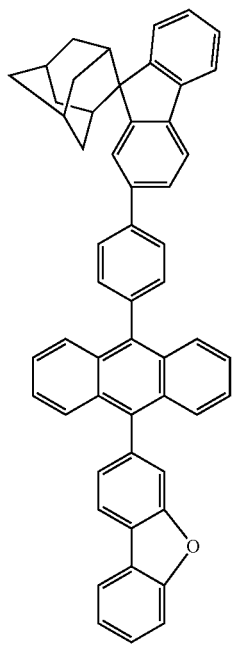
88
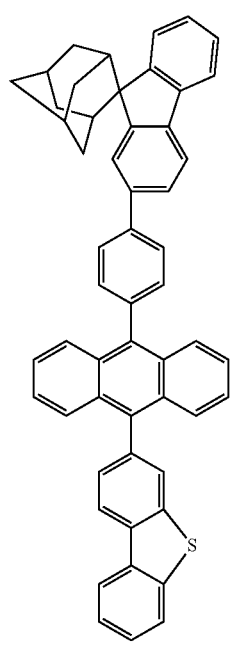
89
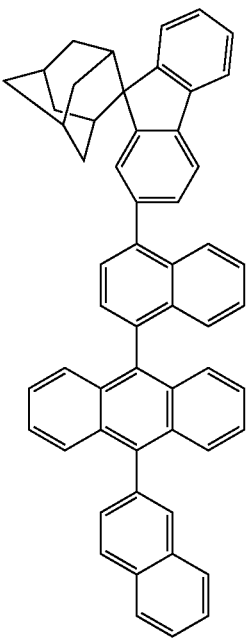
90
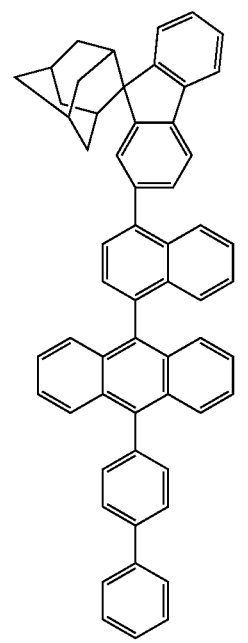

91
-continued
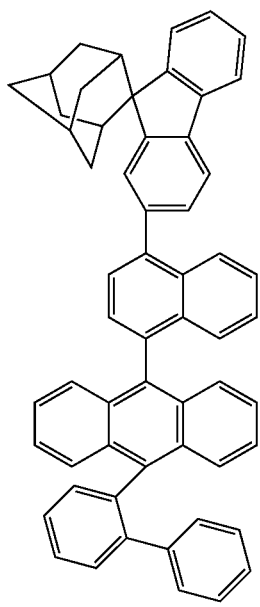
92
-continued
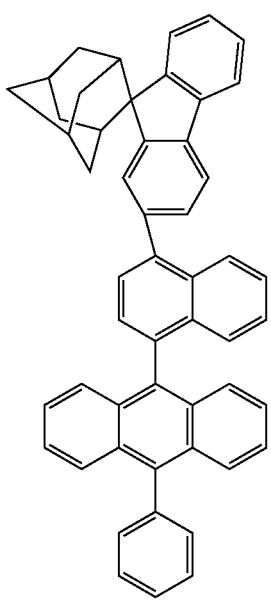
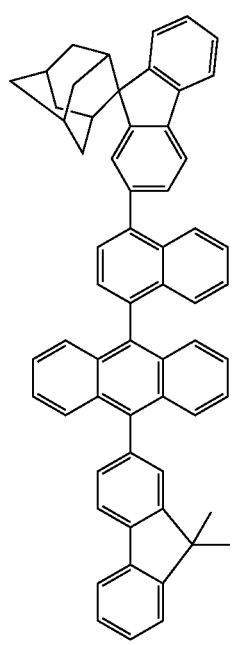
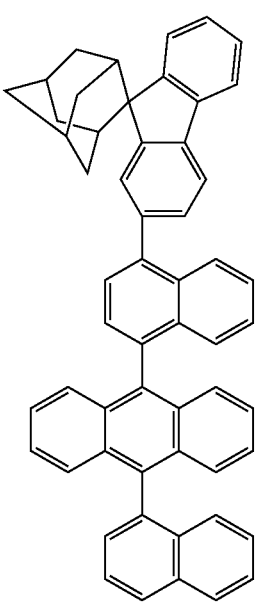

95
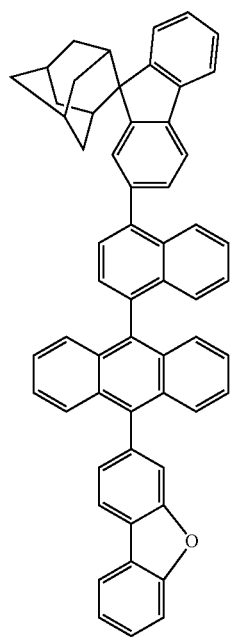
96
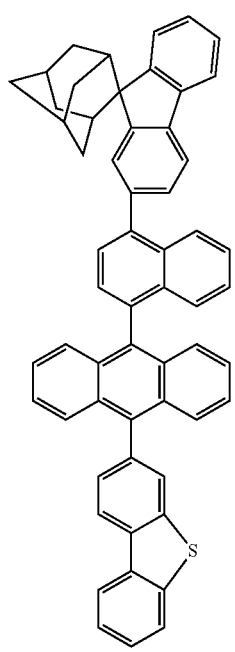
97
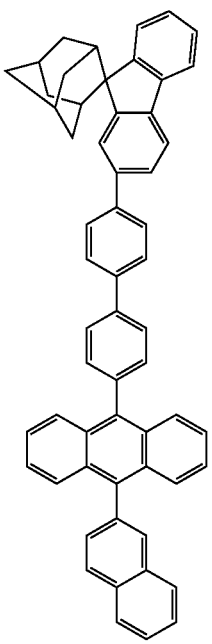
98
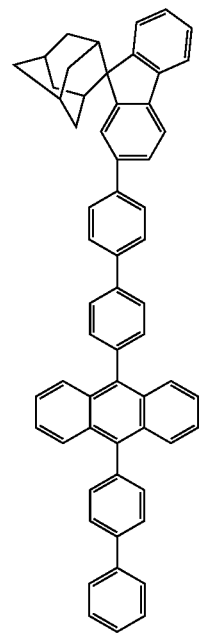

95 96
-continued -continued
99 101
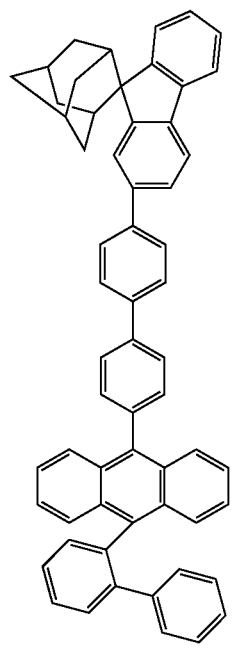 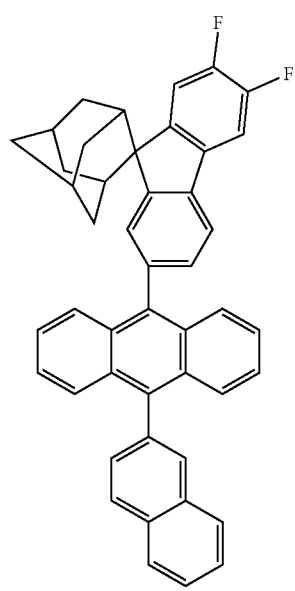
100 102
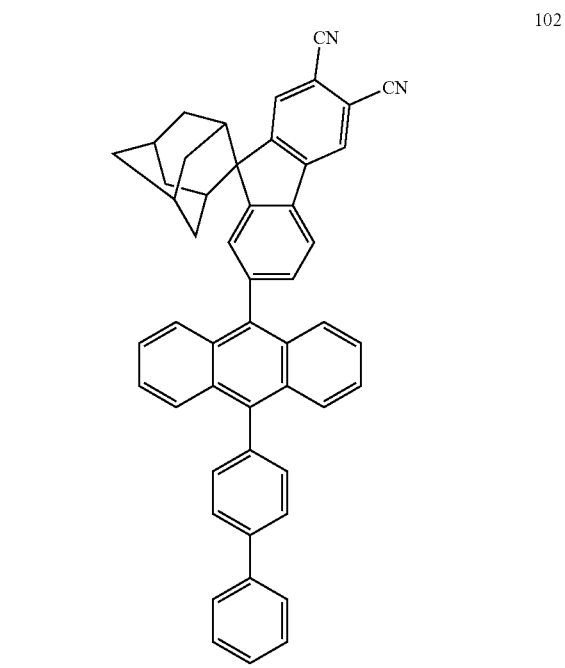

103
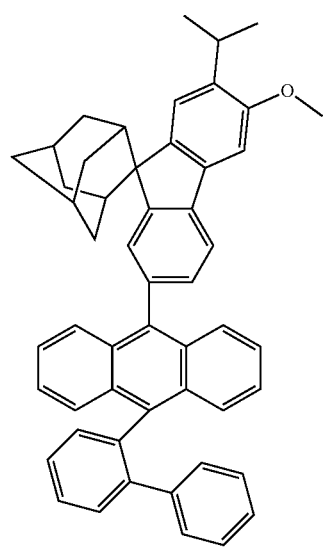
104
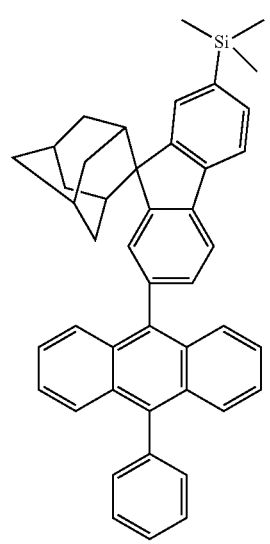
105
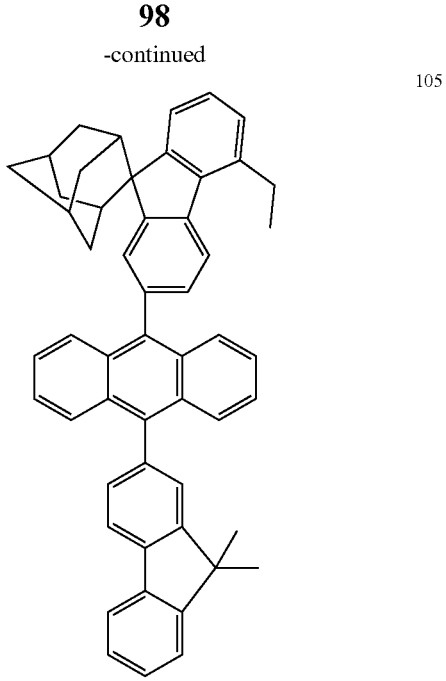
106
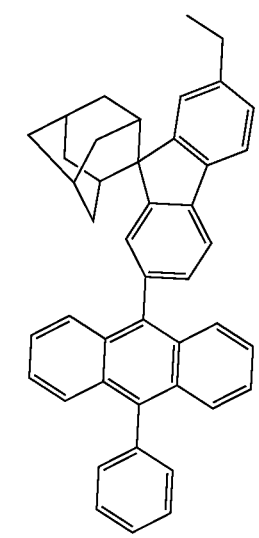

107
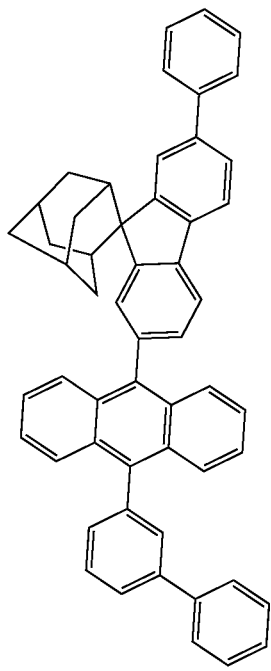
108
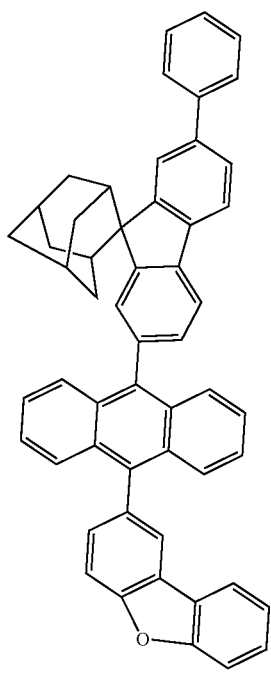
109
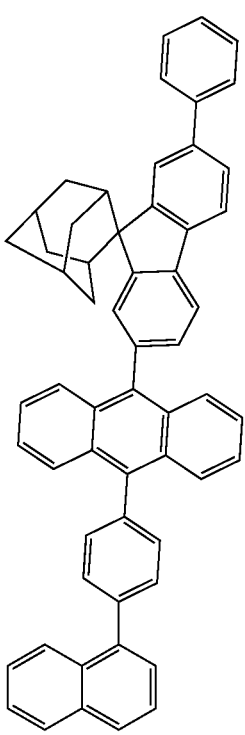
110
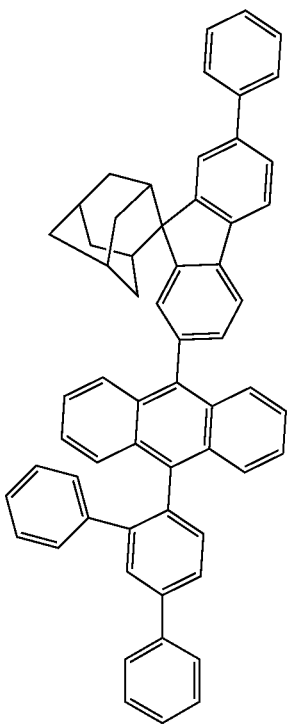

101
-continued
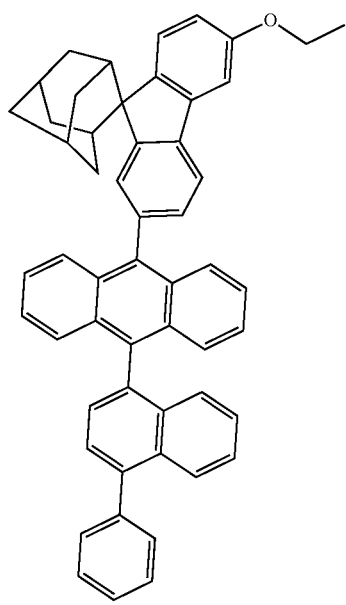
111
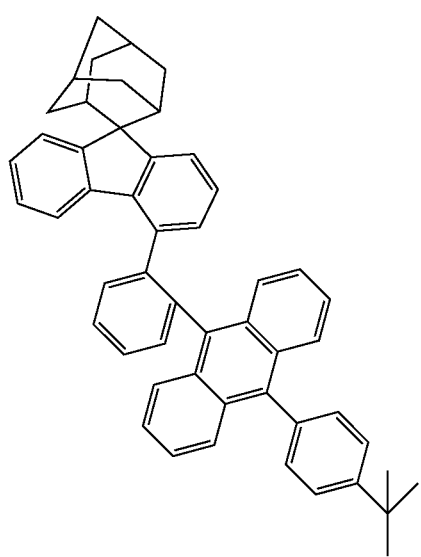
112
102
-continued
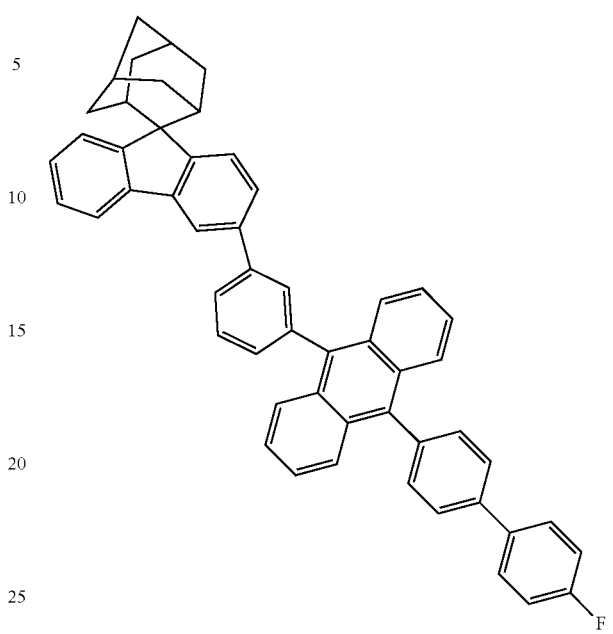
113
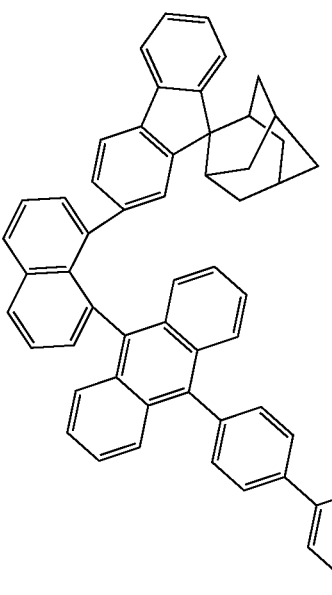
114

103
-continued
115
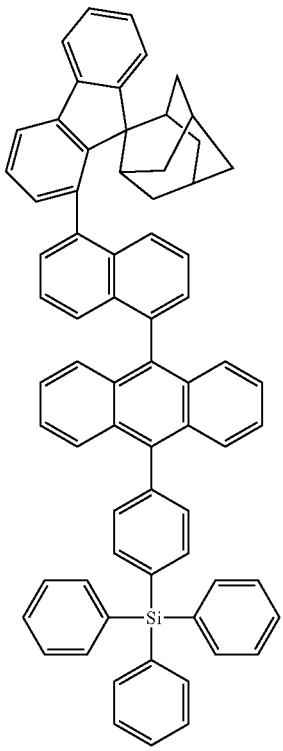
116
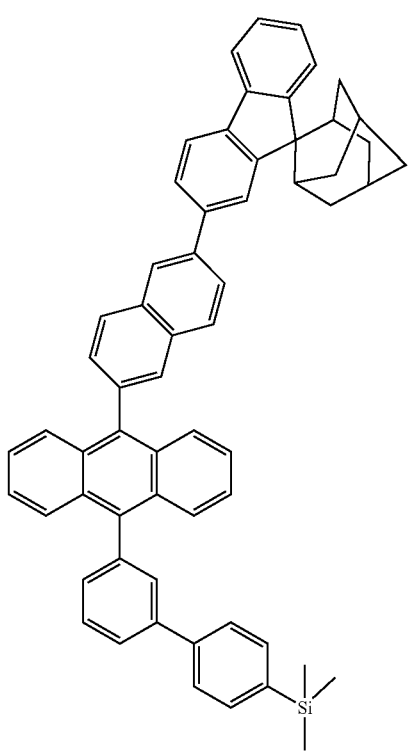
104
-continued
117
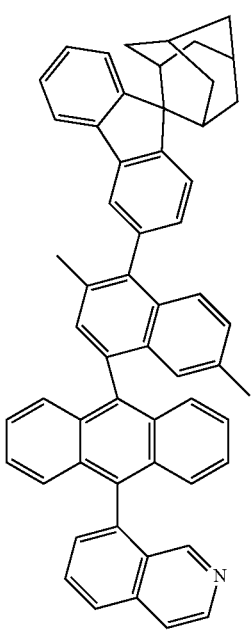
118
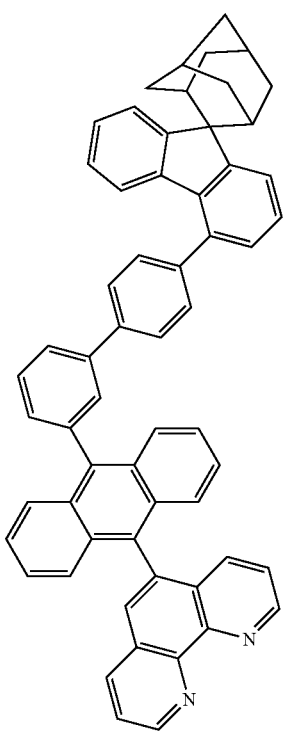

119
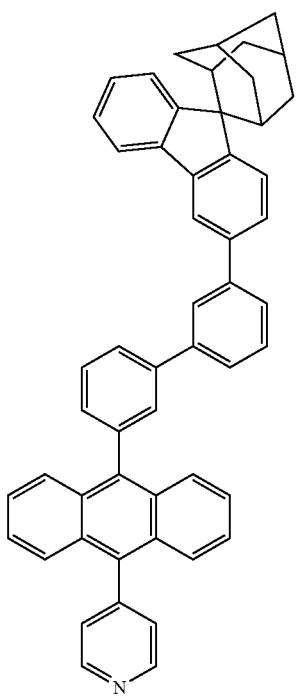
120
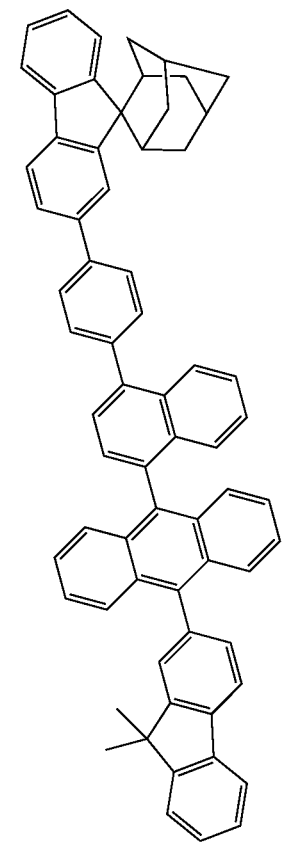
121
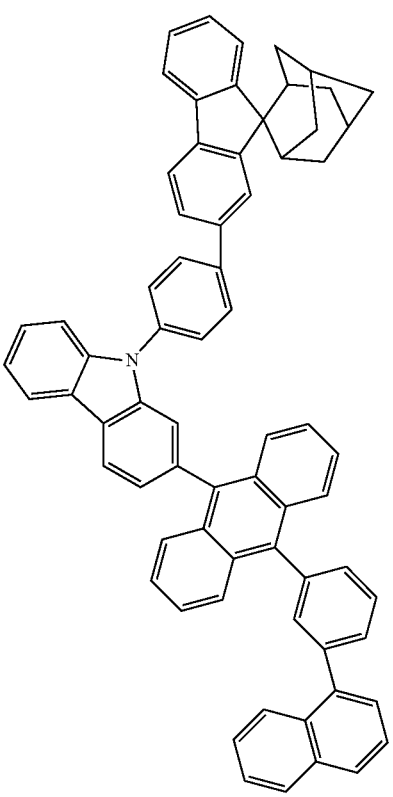
122
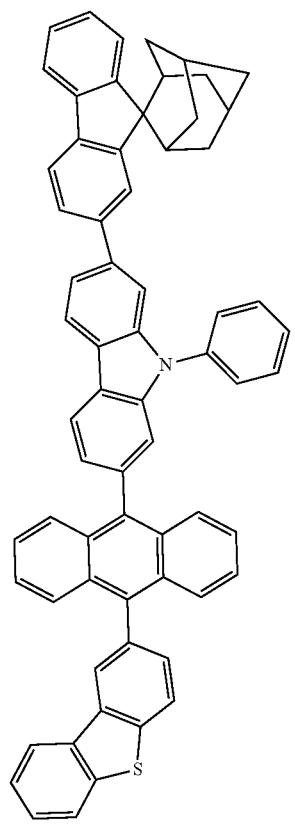

123
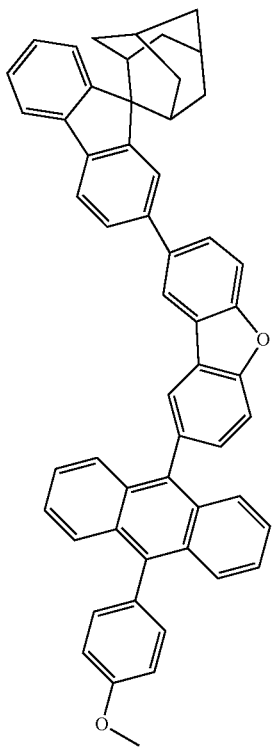
124
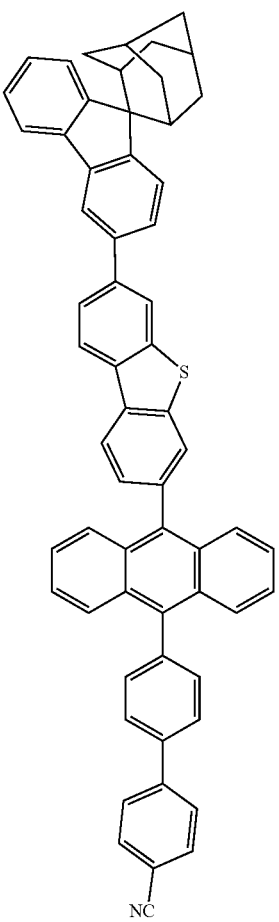
125
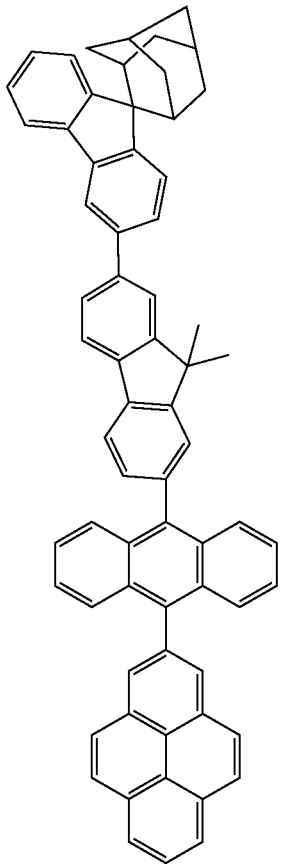
126
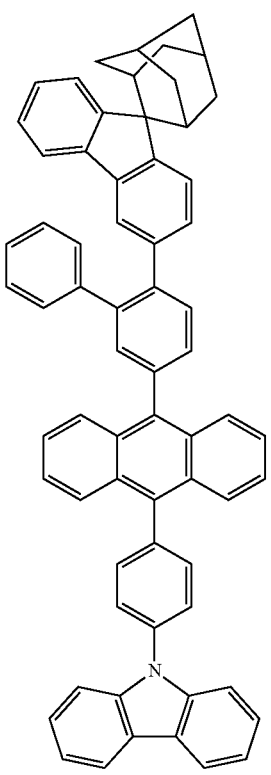

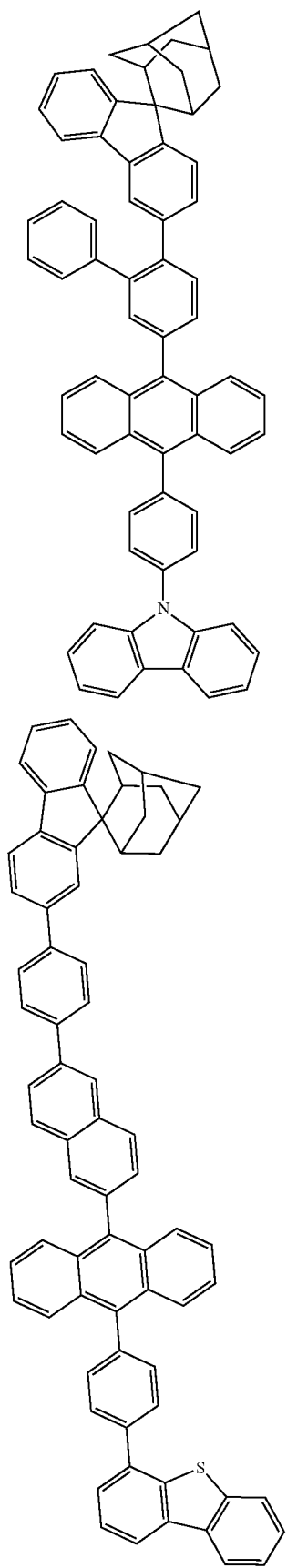
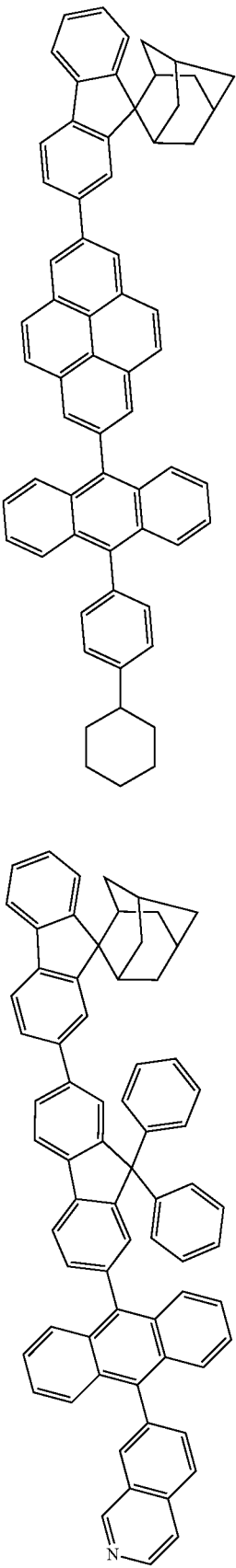

-continued
131
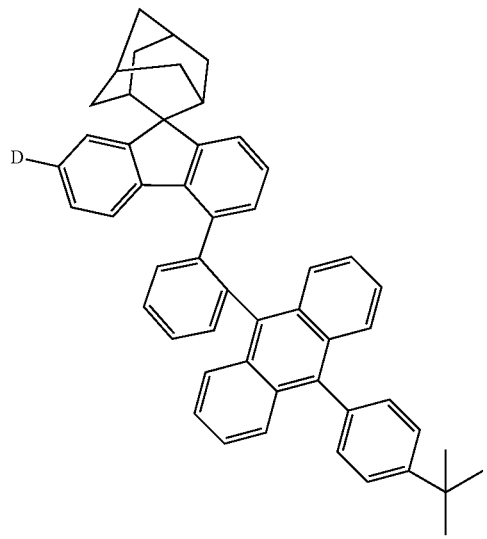
132
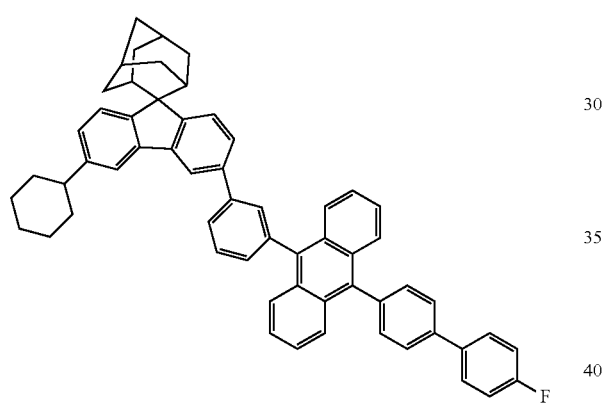
133
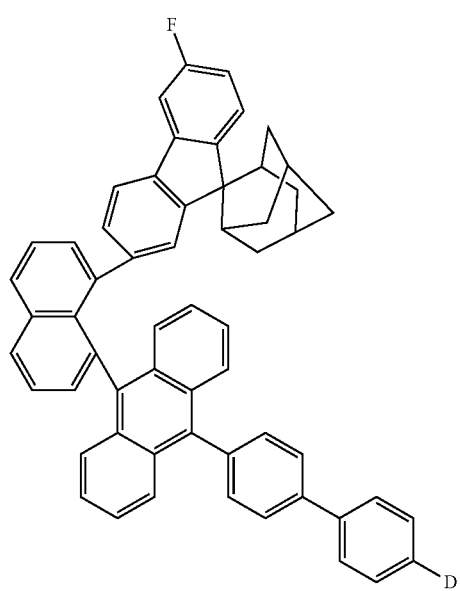
-continued
134
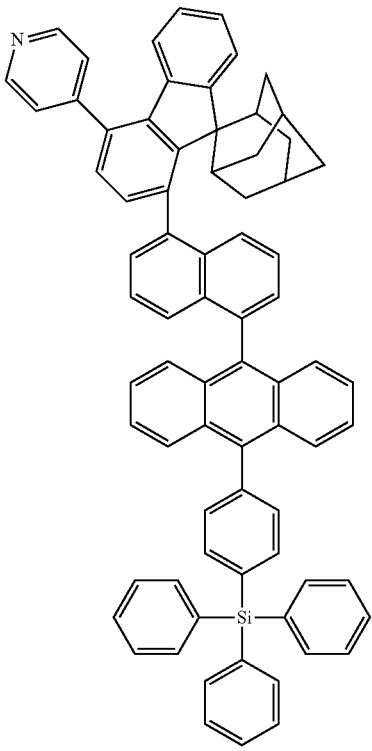
135
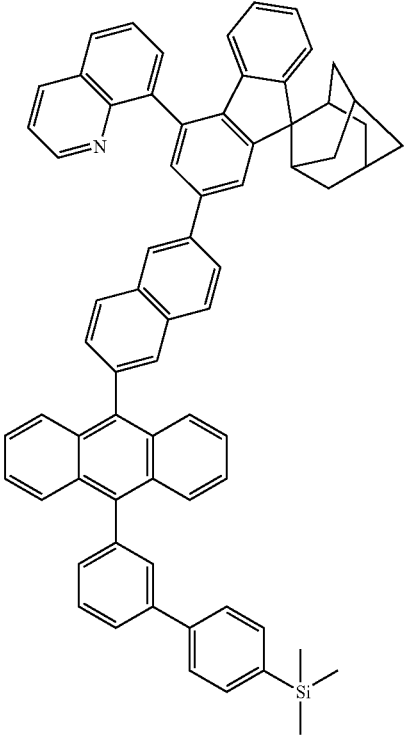

113
-continued
136
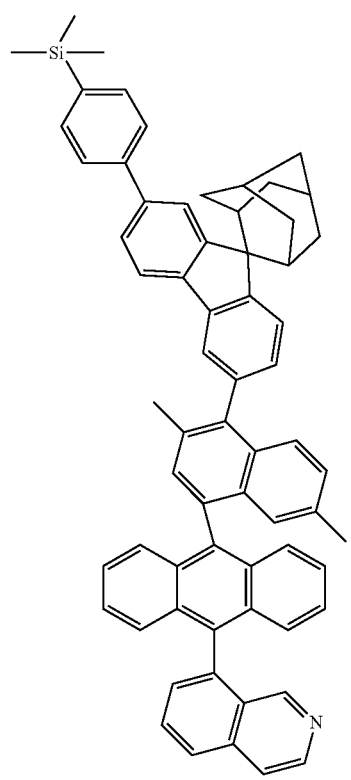
137
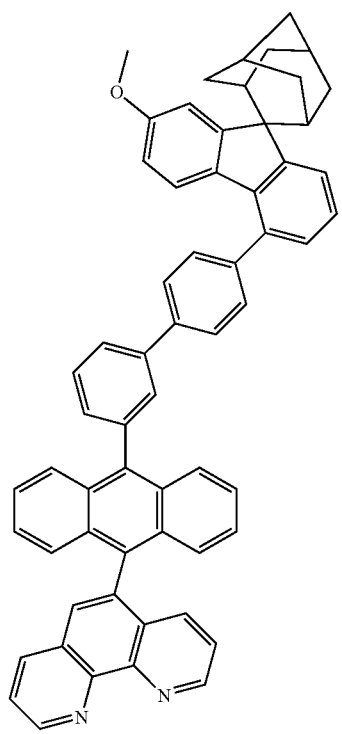
114
-continued
138
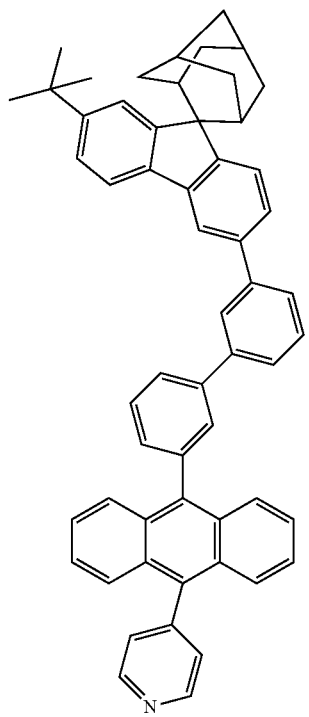
139
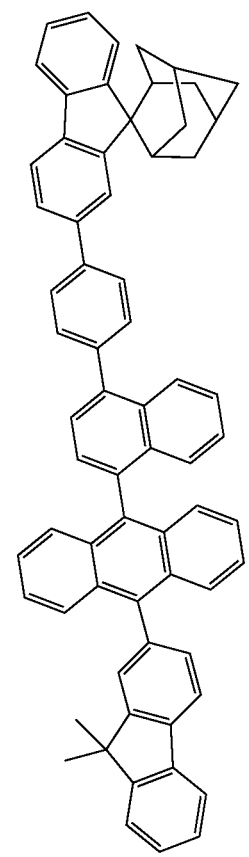

115
-continued
140
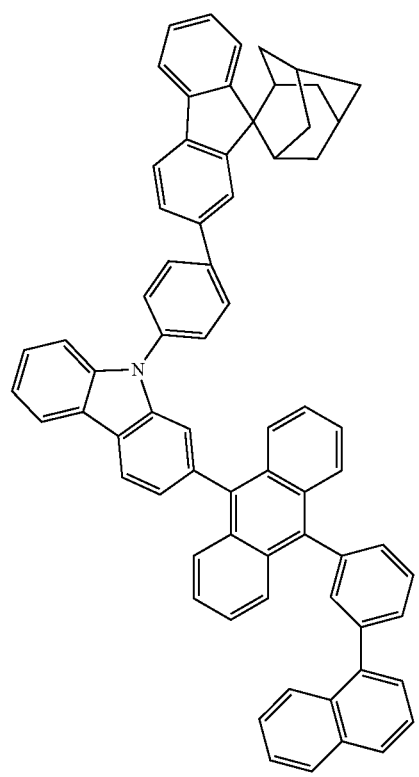
141
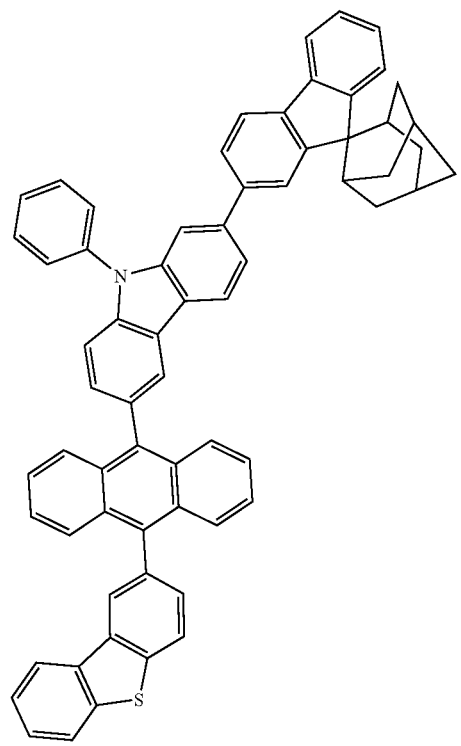
116
-continued
142
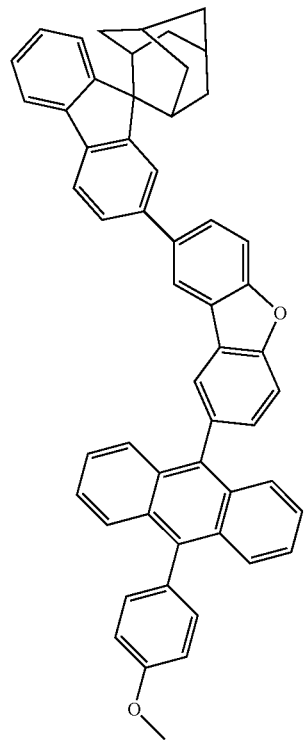
143
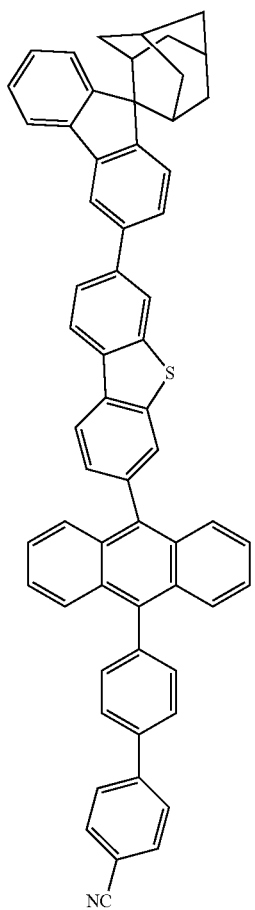

144
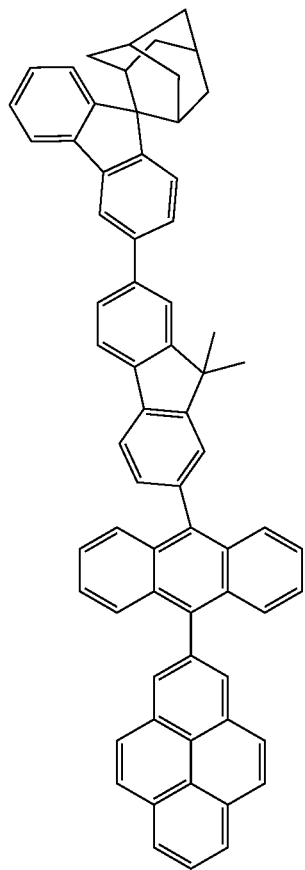
145
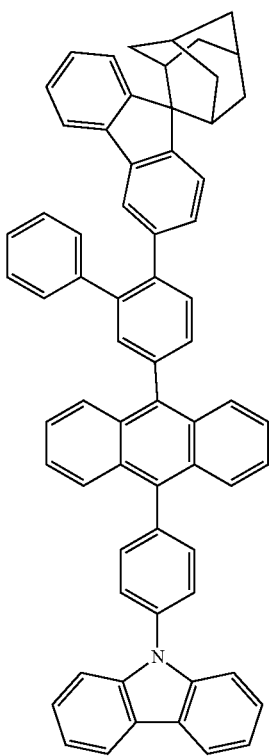
146
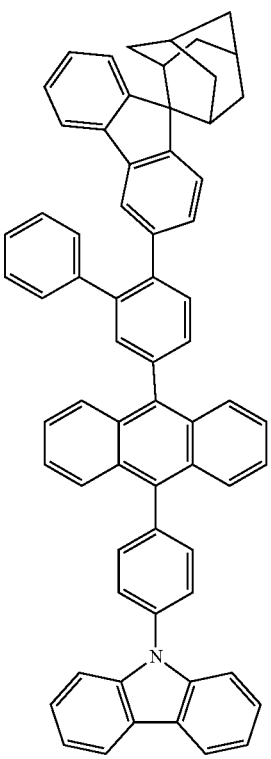
147
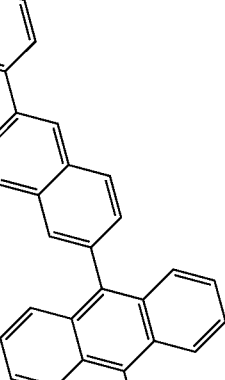

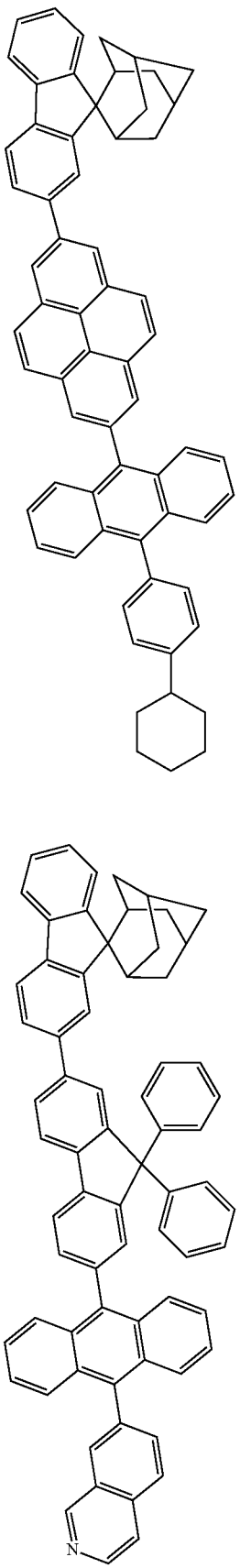
148
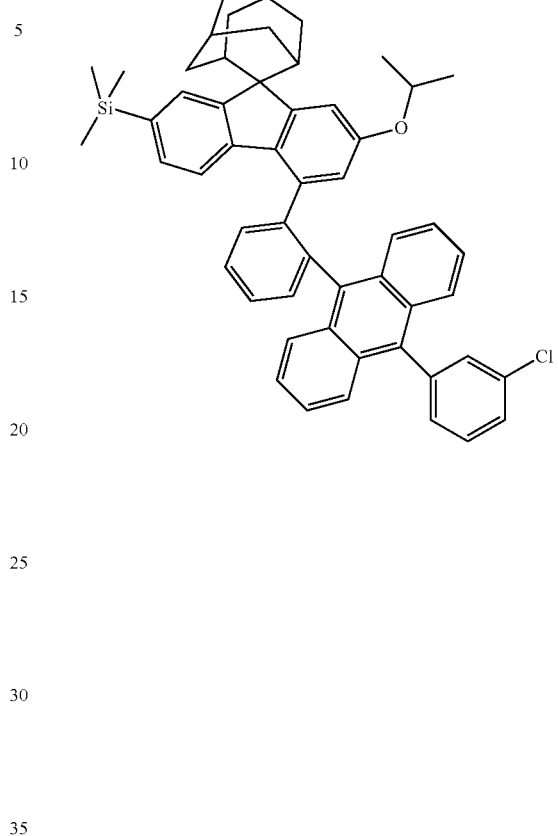
150
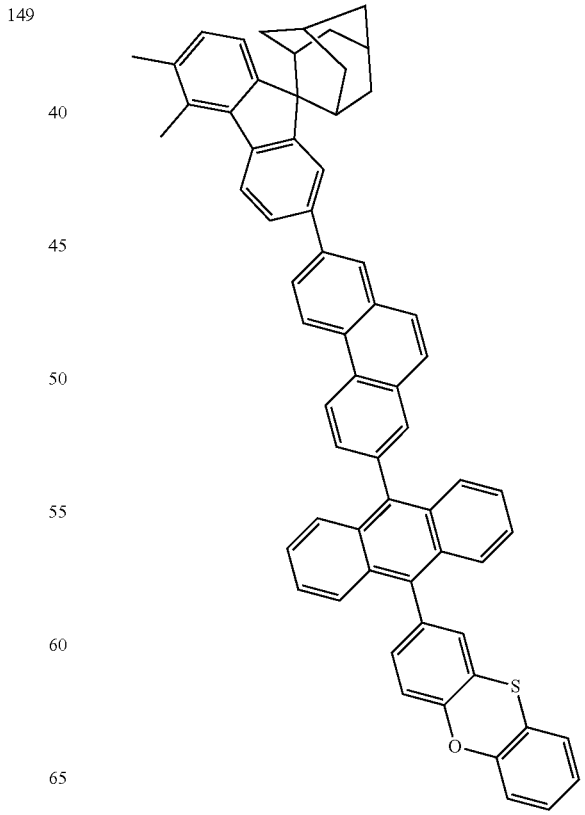
151

121
-continued
122
-continued
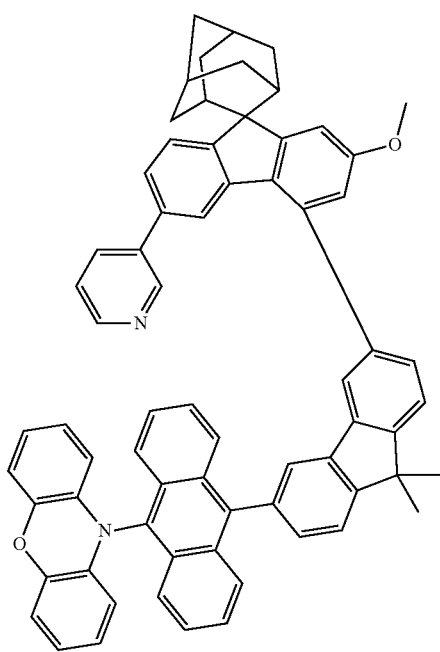
152
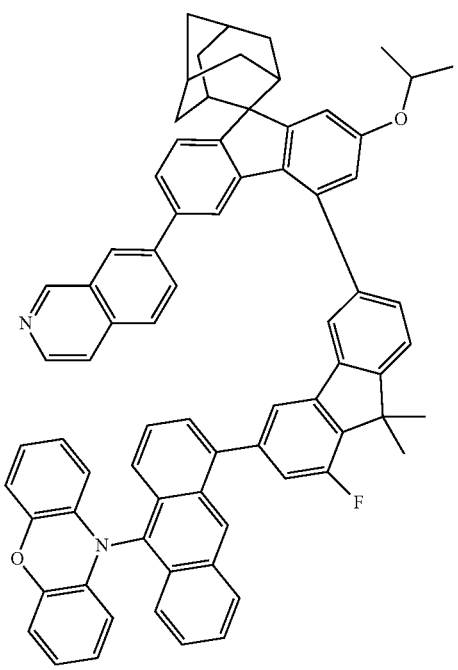
154
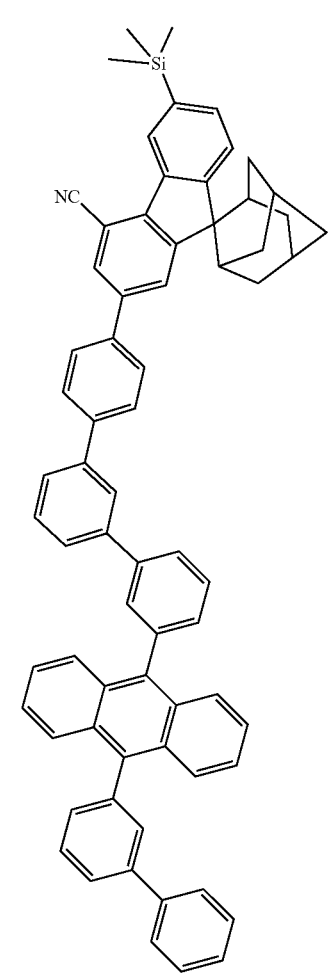
153
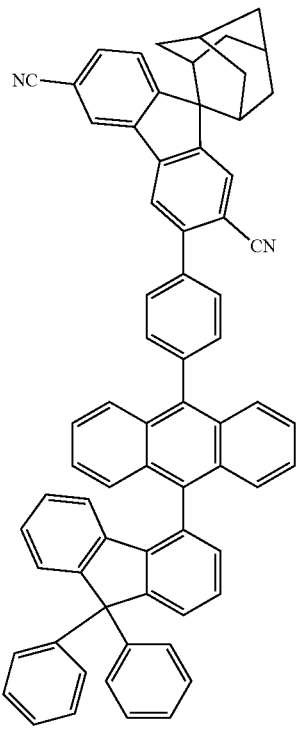
155

123
-continued
156
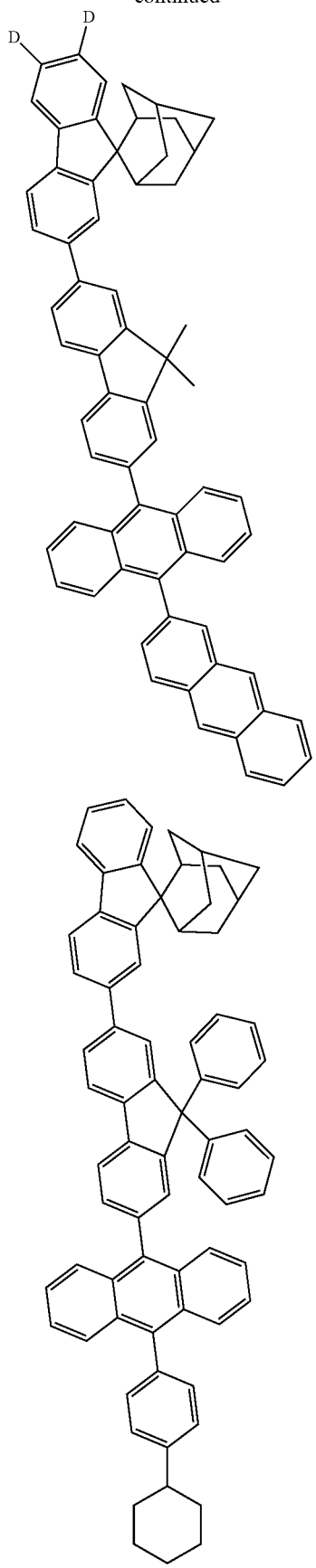
157
124
-continued
158
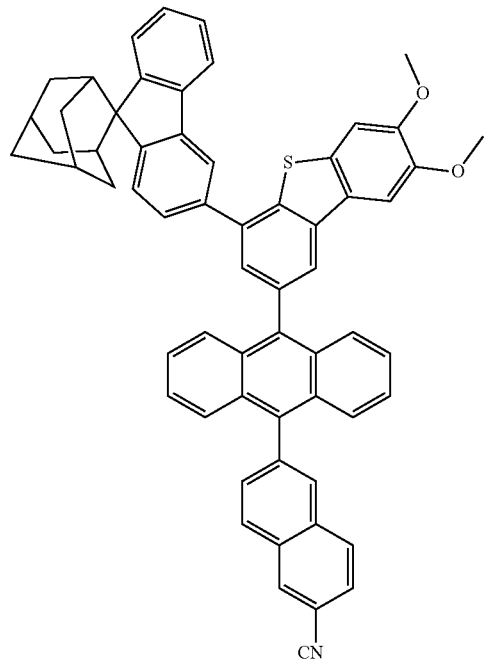
159
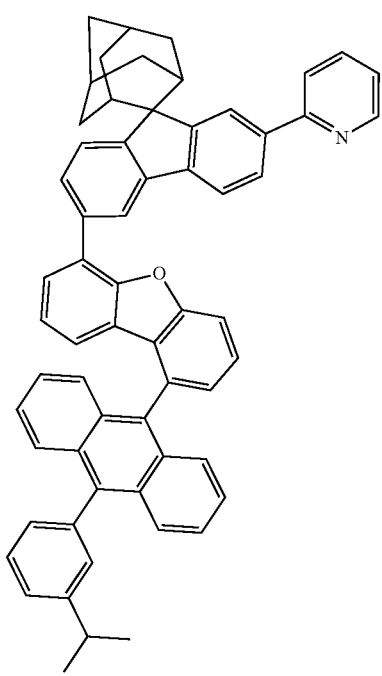

125 126
-continued
160
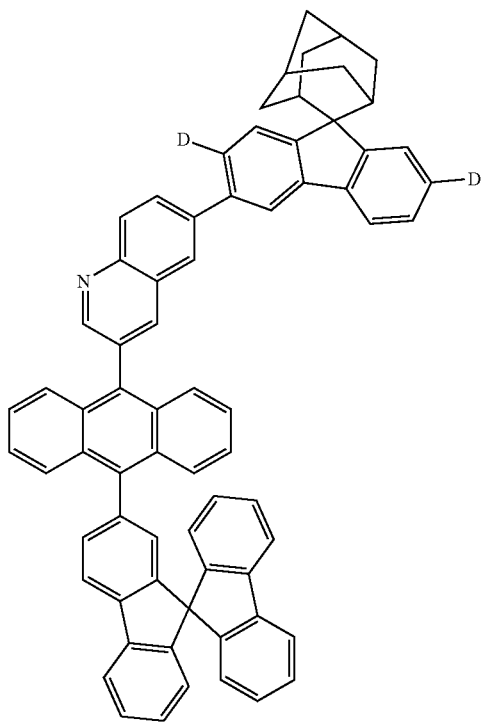
162
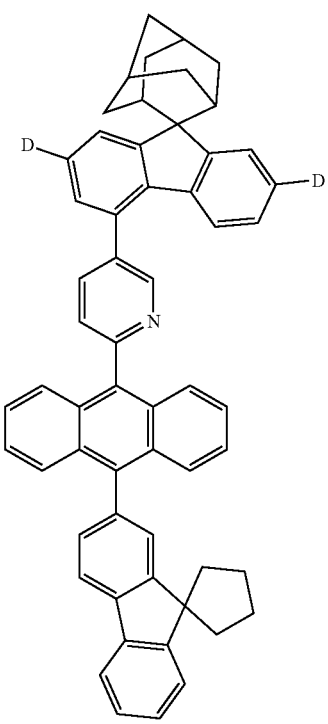
161
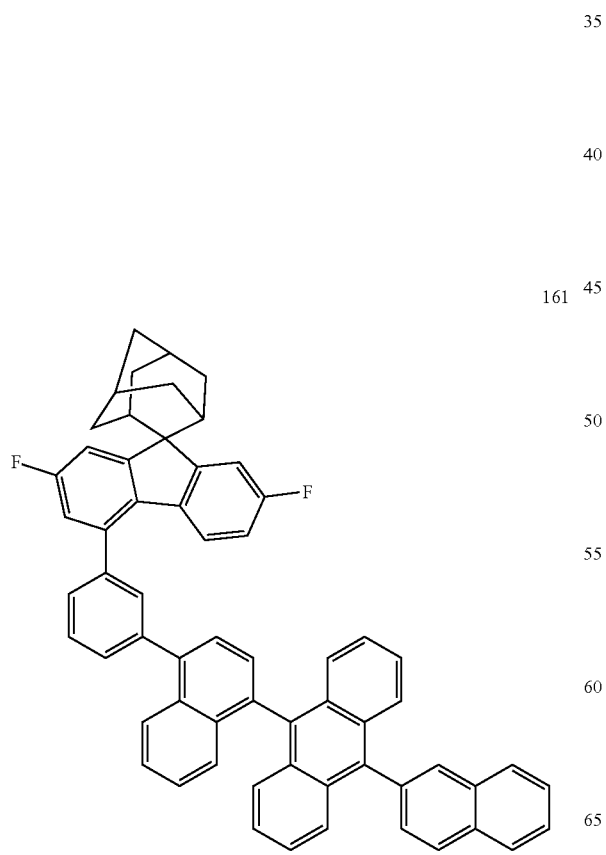
163
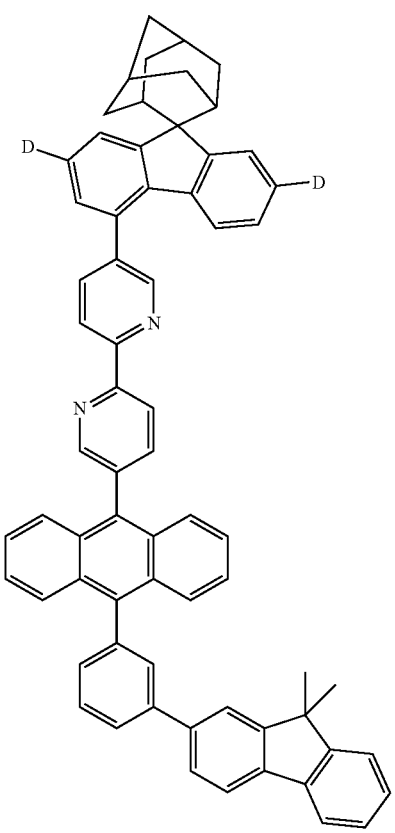

127
-continued
164
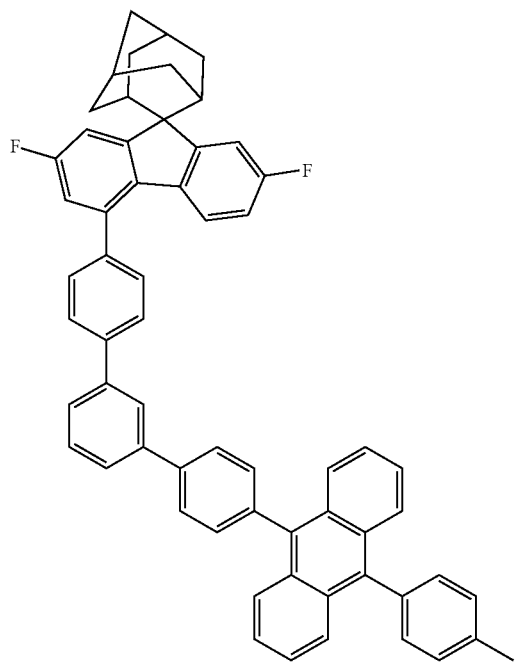
165
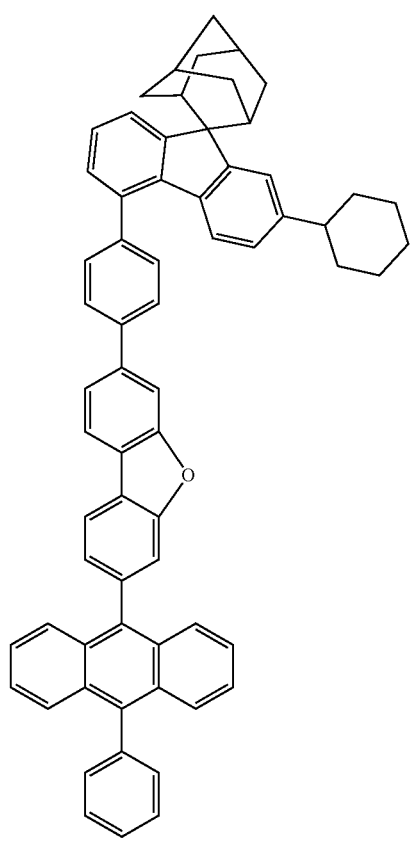
128
-continued
166
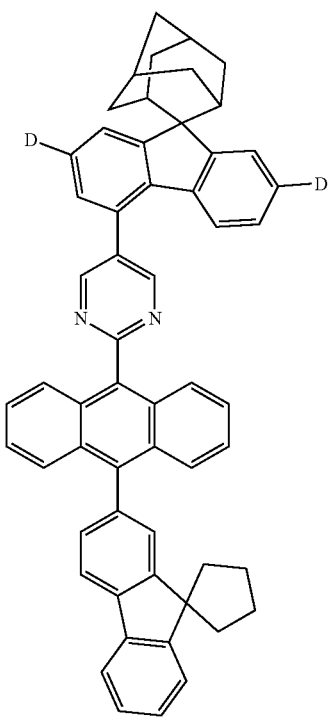
167
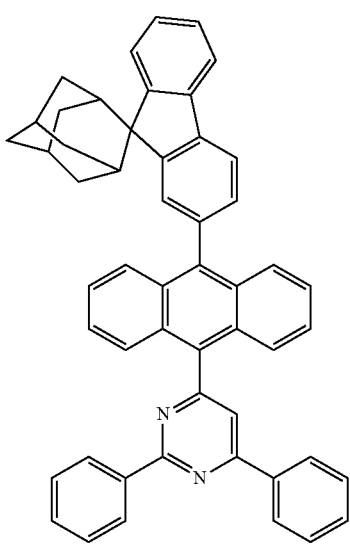

129
-continued
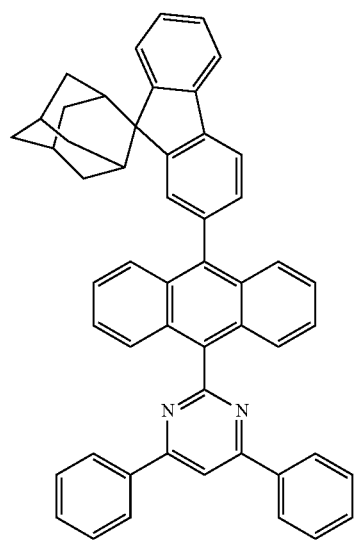
168
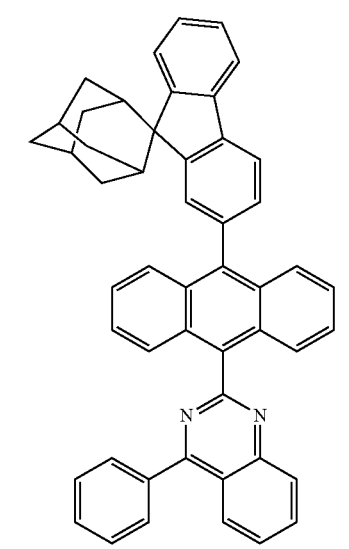
169
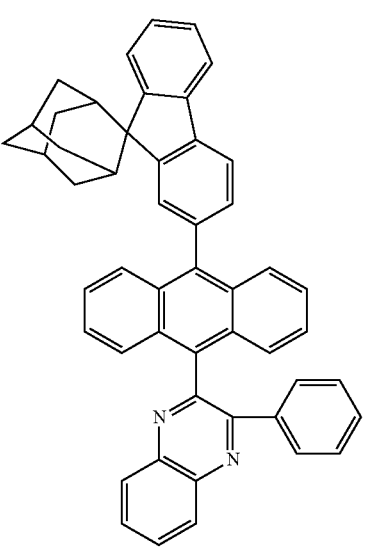
170
130
-continued
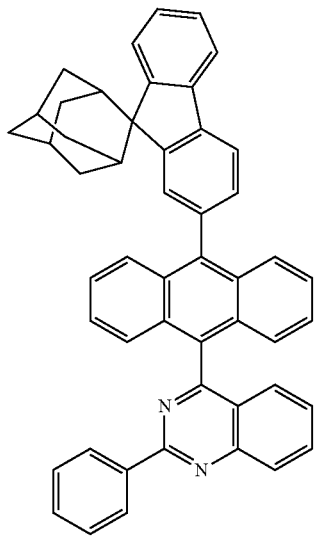
171
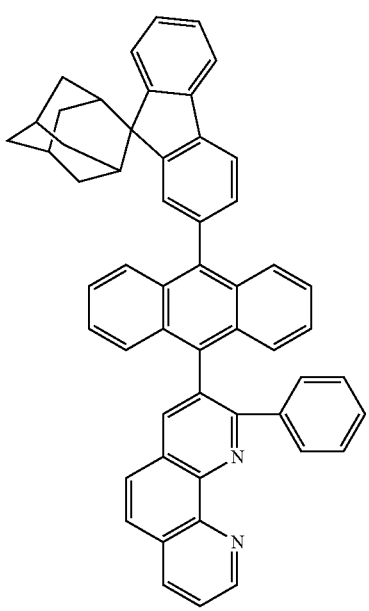
172

131
-continued
173
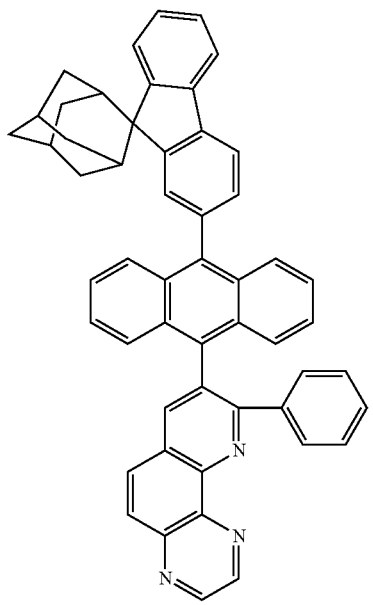
174
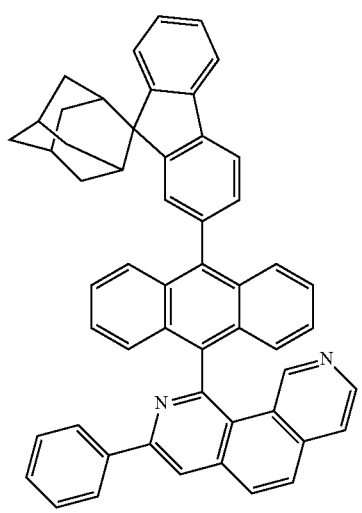
175
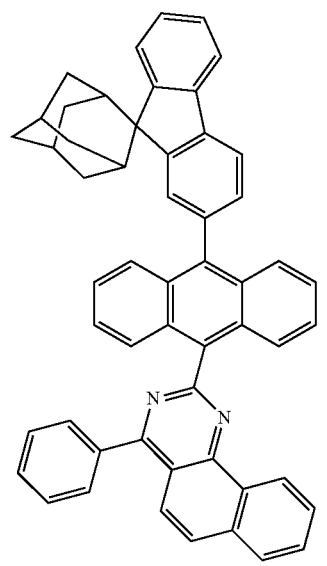
132
-continued
176
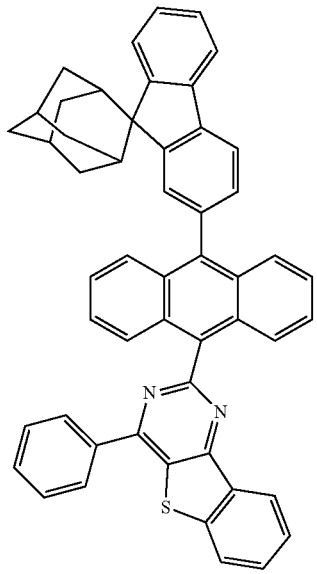
177
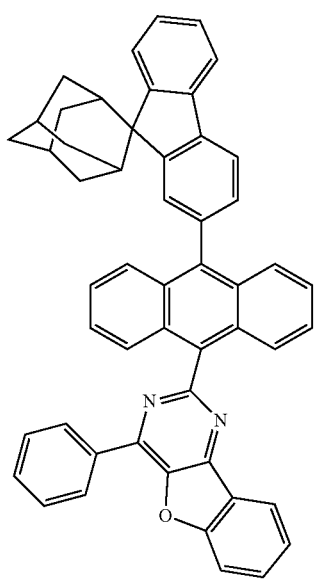

178
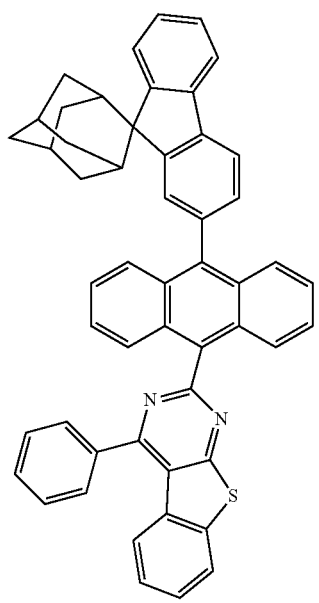
179
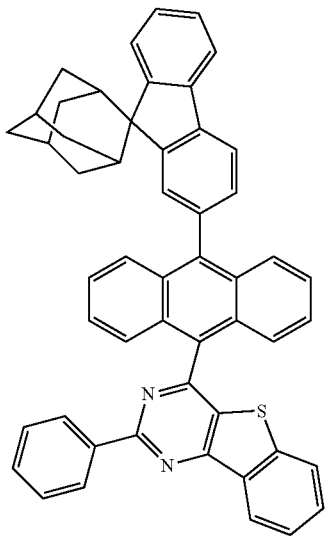
180
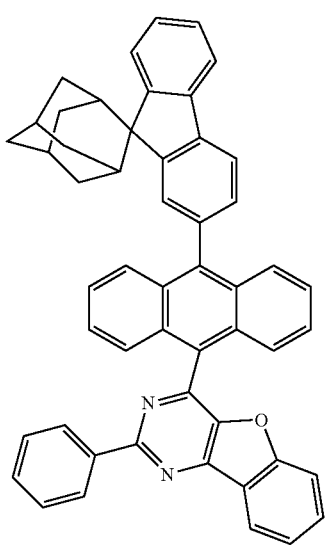
181

182
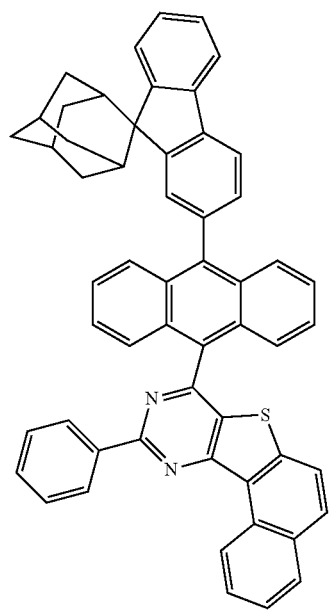
183
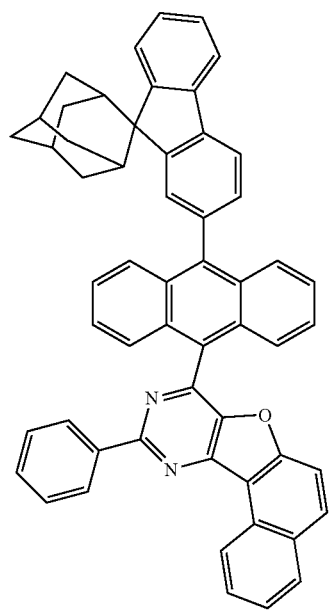
184
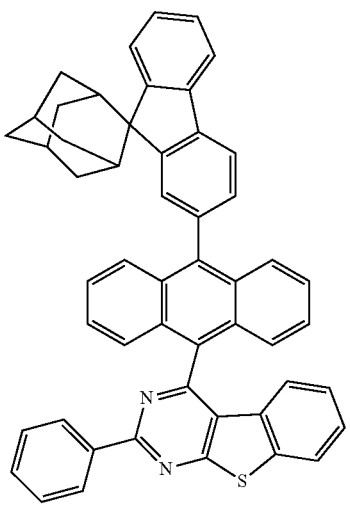
185
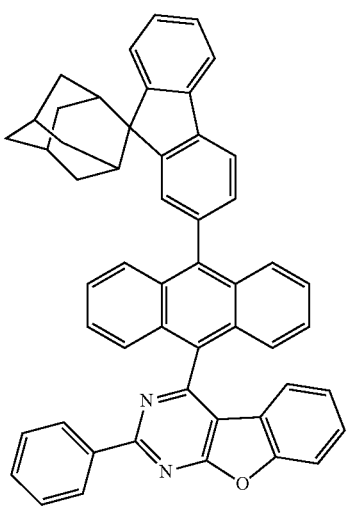
186
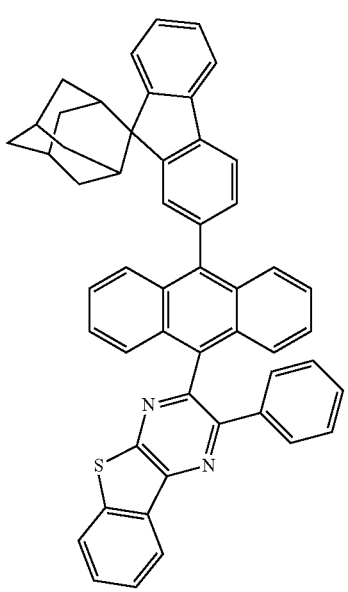

187
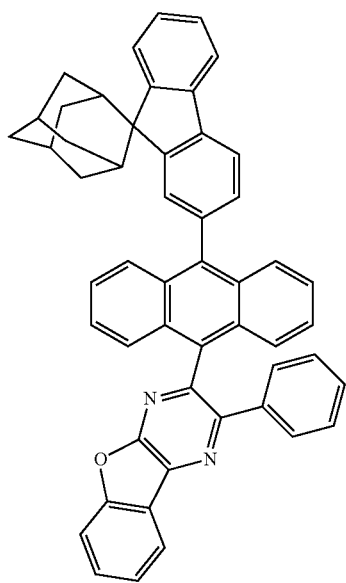
189
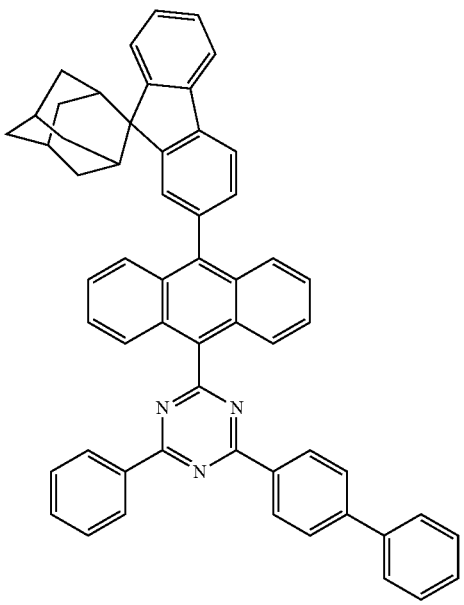
188
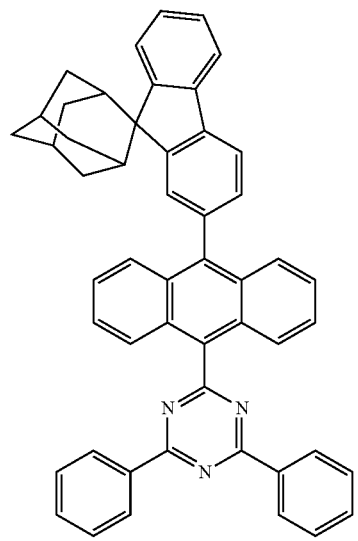
190
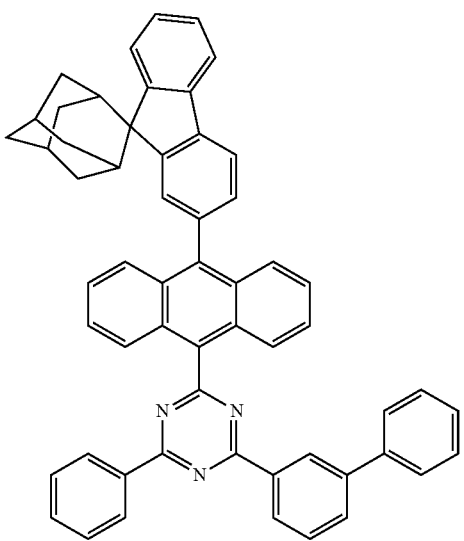

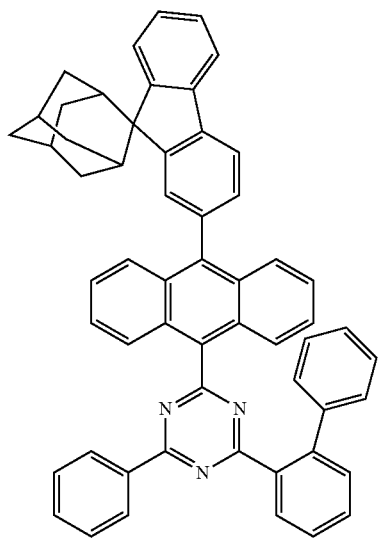
191
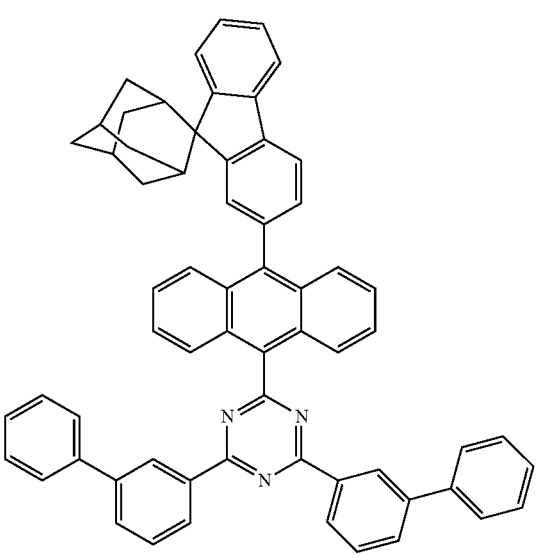
192
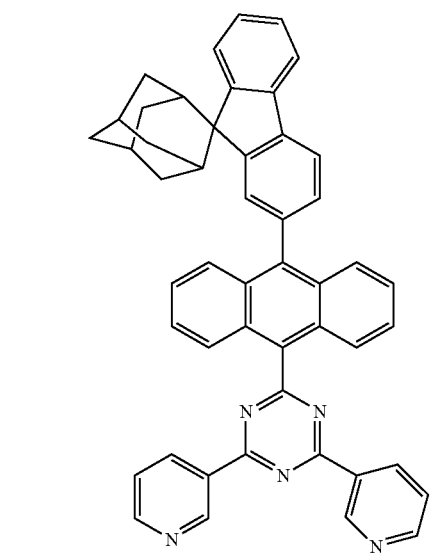
193
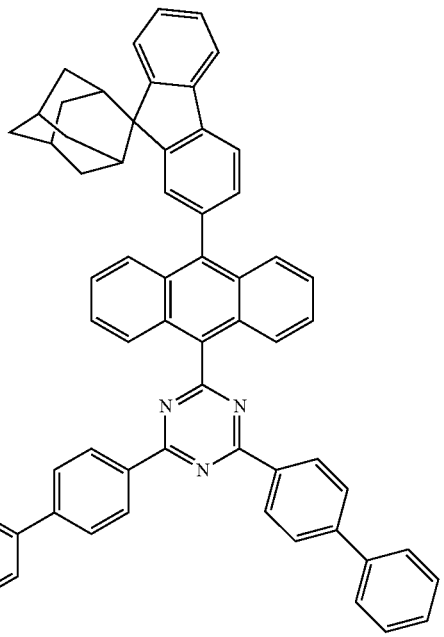
194
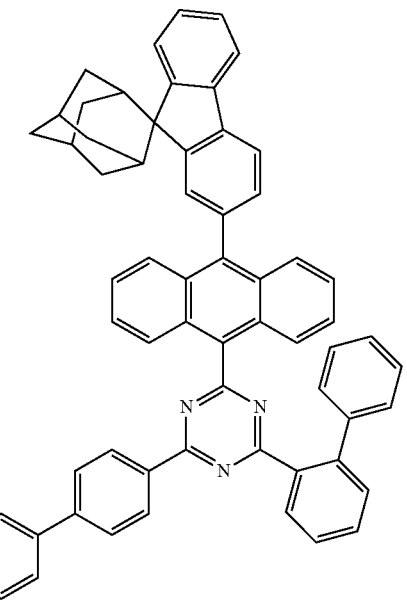
195

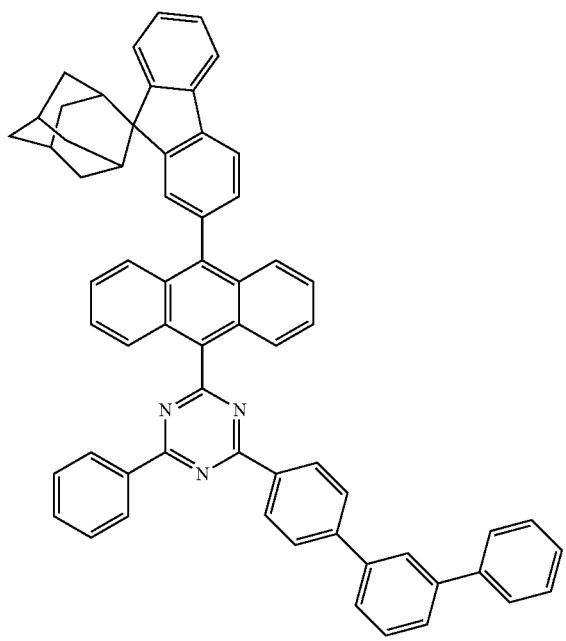
196
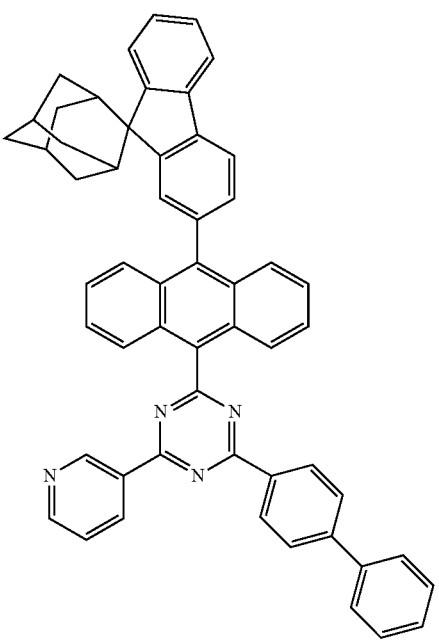
197
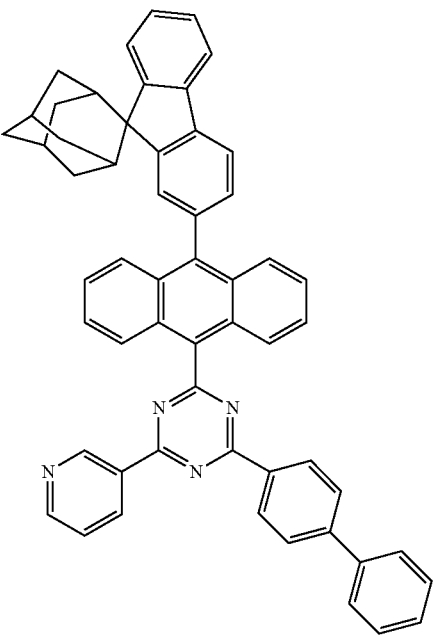
198
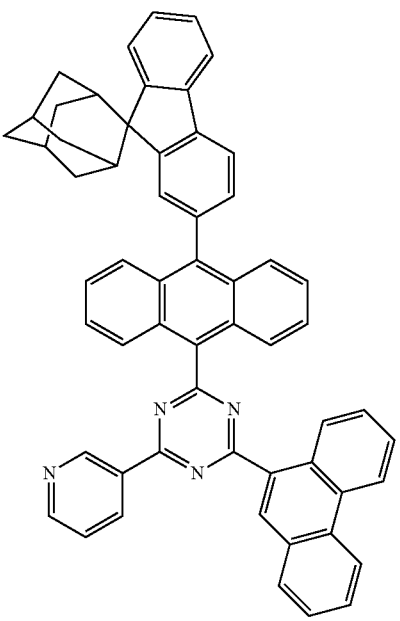
199

143
-continued
200
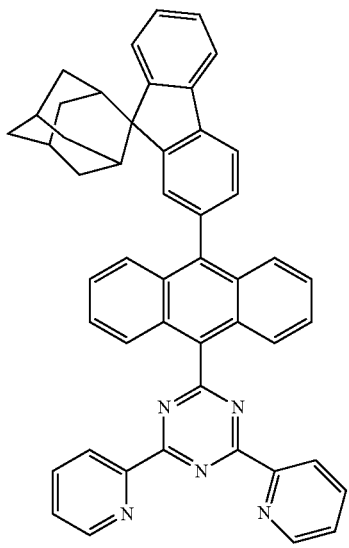
201
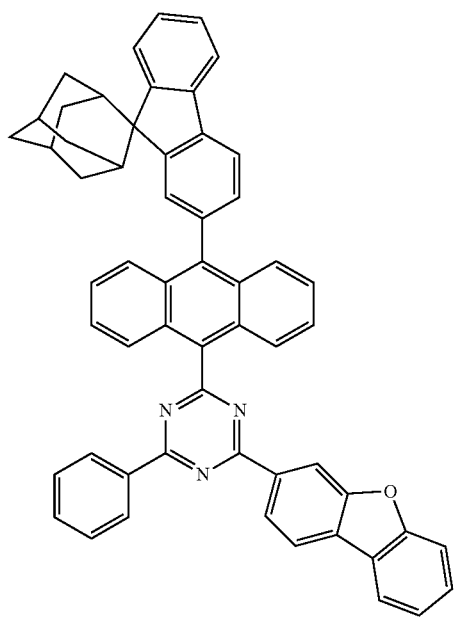
144
-continued
202
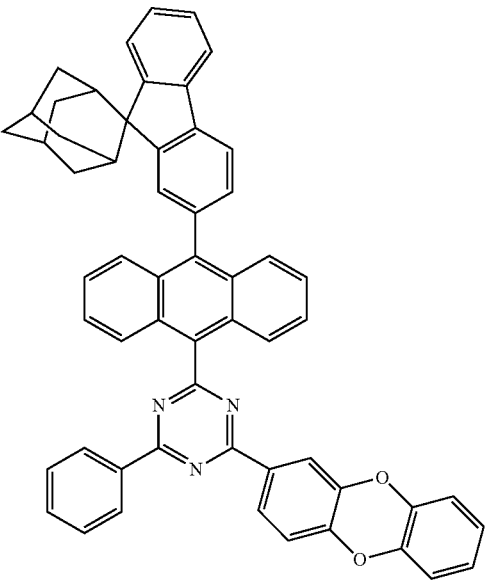
203
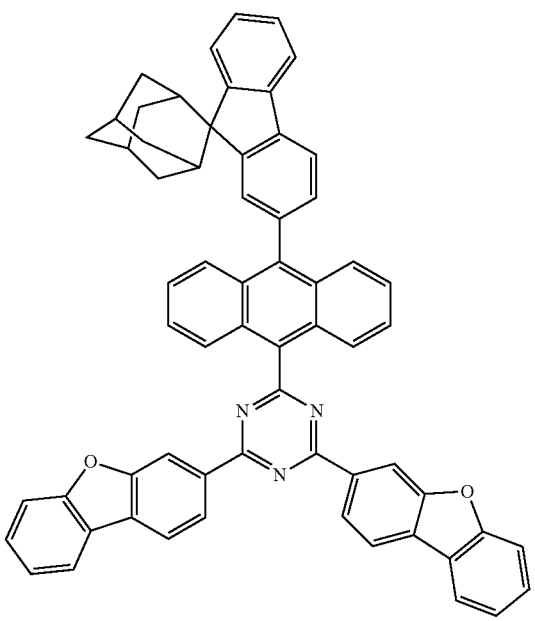

-continued

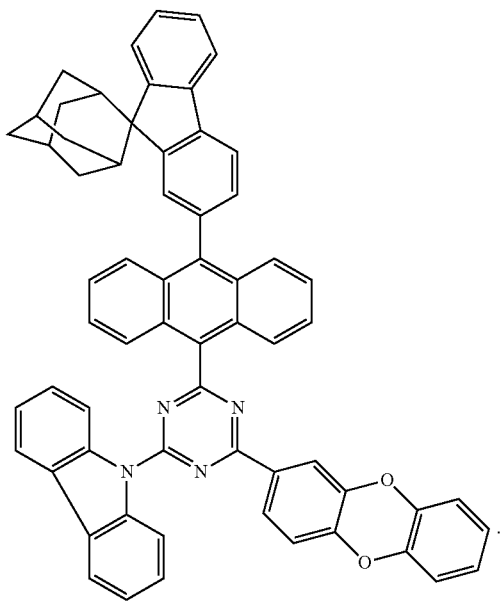

204

The disclosure further provides an organic electroluminescent device, including an anode and a cathode arranged oppositely, and a functional layer arranged between the anode and the cathode; the functional layer includes the organic compound of the disclosure.

For example, as shown in FIG. 1, the organic electroluminescent device includes an anode 100 and a cathode 200 arranged oppositely, and a functional layer 300 arranged between the anode 100 and the cathode 200; the functional layer 300 includes the organic compound provided by the disclosure.

In some embodiments, the functional layer 300 includes an organic electroluminescent layer 330, and the organic electroluminescent layer 330 includes the organic compound of the disclosure.

In some embodiments, the organic electroluminescent layer 330 is composed of a single light-emitting material, and may also include a host material and a guest material. In some embodiments, the organic electroluminescent layer 330 is composed of a host material and a guest material, holes injected into the organic electroluminescent layer 330 and electrons injected into the organic electroluminescent layer 330 can be combined in the organic electroluminescent layer 330 to form excitons, the excitons transfer energy to the host material, and the host material transfers energy to the guest material, thereby enabling the guest material to emit light.

The host material of the organic electroluminescent layer 330 is a metal chelate compound, a bisstyryl derivative, an aromatic amine derivative, a dibenzofuran derivative or other materials, which are not particularly limited in the disclosure. In an embodiment of the disclosure, the host material of the organic electroluminescent layer 330 is the organic compound of the disclosure and BH-n1.

The guest material of the organic electroluminescent layer 330 is a compound having a condensed aryl ring or a derivative thereof, a compound having a heteroaryl ring or a derivative thereof, an aromatic amine derivative, or other materials. In some embodiments of the disclosure, the guest material of the organic electroluminescent layer 330 is BD-1.

In an embodiment of the disclosure, the organic electroluminescent device includes an anode 100, a hole transport layer 321, an electron blocking layer 322, an organic electroluminescent layer 330 as an energy conversion layer, an electron transport layer 350 and a cathode 200, which are sequentially stacked. The organic compound provided in the disclosure can be applied to the organic electroluminescent layer 330 of the organic electroluminescent device, and can effectively improve the luminous efficiency and service life of the organic electroluminescent device and reduce the driving voltage of the organic electroluminescent device.

In some embodiments, the anode 100 includes the following anode material, which is preferably a material that facilitates injection of holes into functional layers and has a large work function.

Specific examples of the anode material include: metals such as nickel, platinum, vanadium, chromium, copper, zinc and gold, or alloys thereof; metal oxides such as zinc oxide, indium oxide, indium tin oxide (ITO), and indium zinc oxide (IZO); combined metals and oxides such as ZnO:Al or $SnO_2$:Sb; or conductive polymers such as poly(3-methylthiophene), poly[3,4-(ethylene-1,2-dioxy)thiophene] (PEDT), polypyrrole and polyaniline, but are not limited thereto. Preferably, a transparent electrode containing indium tin oxide (ITO) serves as the anode.

In some embodiments, the hole transport layer 321 includes one or more hole transport materials, and the hole transport materials is selected from carbazole polymers, carbazole-linked triarylamine compounds, or other compounds, which are not specifically limited in the disclosure. For example, in an embodiment of the disclosure, the hole transport layer 321 is composed of a compound NPB. In some embodiments, the electron blocking layer 322 includes one or more electron blocking materials, and the electron blocking materials is selected from carbazole polymers or other compounds, which are not specifically limited in the disclosure. For example, in some embodiments of the disclosure, the electron blocking layer 322 is composed of PAPB.

In some embodiments, the electron transport layer 350 is of a single-layer structure or a multilayer structure, and may include one or more electron transport materials, and the electron transport materials is selected from benzimidazole derivatives, oxadiazoles derivatives, quinoxaline derivatives or other electron transport materials, which are not specifically limited in the disclosure.

For example, in an embodiment of the disclosure, the electron transport layer 350 is composed of compounds ET-06 and LiQ.

In some embodiments, the cathode 200 includes the following cathode material, which is a material that facilitates injection of electrons into the functional layers and has a small work function. Specific examples of the cathode material include: metals such as magnesium, calcium, sodium, potassium, titanium, indium, yttrium, lithium, gadolinium, aluminum, silver, tin and lead, or alloys thereof; or multilayer materials such as LiF/Al, Liq/Al, $LiO_2$/Al, LiF/Ca, LiF/Al and $BaF_2$/Ca, but are not limited thereto. Preferably, a metal electrode containing magnesium and silver serves as the cathode.

In some embodiments, as shown in FIG. 1, a hole injection layer 310 is further arranged between the anode 100 and the hole transport layer 321 to enhance the ability to inject holes into the hole transport layer 321. The hole injection layer 310 is made of benzidine derivatives, starburst arylamine compounds, phthalocyanine derivatives or other materials, which are not particularly limited in the disclosure. In an embodiment of the disclosure, the hole injection layer 310 is composed of F4-TCNQ.

In some embodiments, as shown in FIG. 1, an electron injection layer 360 is further arranged between the cathode 200 and the electron transport layer 340 to enhance the ability to inject electrons into the electron transport layer 350. The electron injection layer 360 may include inorganic materials such as alkali metal sulfides and alkali metal halides, or may include complexes of alkali metals and organic substances. In an embodiment of the disclosure, the electron injection layer 360 is composed of metal Yb.

In some embodiments, a hole blocking layer 340 is further arranged between the organic electroluminescent layer 330 and the electron transport layer 350.

The organic electroluminescent device of the disclosure is optionally a blue light device.

An embodiment of the disclosure further provides an electronic apparatus, which includes the above-mentioned organic electroluminescent device. Since the electronic apparatus has the above-mentioned organic electroluminescent device, it has the same beneficial effects, which will not be repeated in the disclosure.

Figure 2:
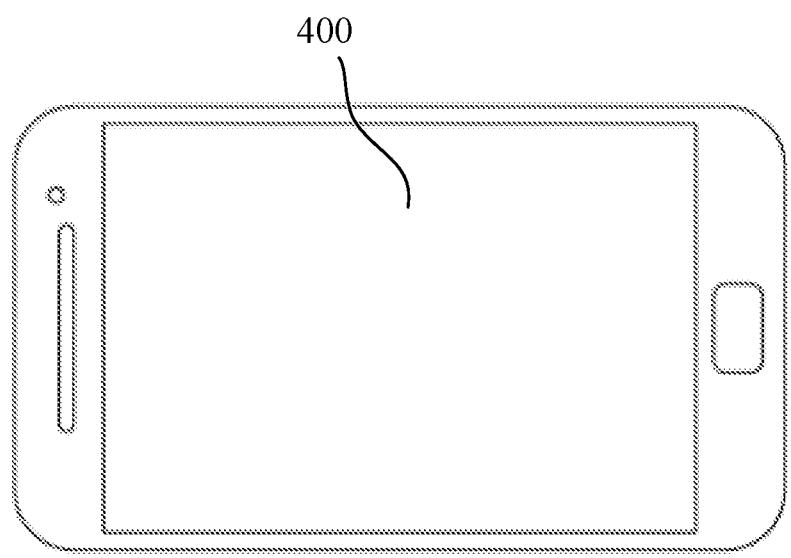
FIG. 2 is a schematic structural diagram of an electronic apparatus according to an embodiment of the disclosure.

For example, as shown in FIG. 2, the disclosure provides an electronic apparatus 400, including the above-mentioned organic electroluminescent apparatus. The electronic apparatus 400 is a display apparatus, a lighting apparatus, an optical communication apparatus or other electronic apparatuses, for example, may include but is not limited to a computer screen, a mobile phone screen, a television, electronic paper, an emergency lamp, an optical module, etc. Since the electronic apparatus 400 has the above-mentioned organic electroluminescent apparatus, it has the same beneficial effects, which will not be repeated in the disclosure.

Hereinafter, the disclosure will be further described in detail through examples. However, the following examples are only illustrations of the disclosure, and do not limit the disclosure.

Synthesis of Compound

Those skilled in the art will recognize that the chemical reactions described in the disclosure can be used to appropriately prepare many other compounds of the disclosure, and other methods used to prepare the compound of the disclosure are considered to fall within the scope of the disclosure. For example, the synthesis of non-exemplified compounds according to the disclosure can be successfully completed by those skilled in the art through modification methods, for example, appropriately protecting interfering groups, using other known reagents in addition to those described in the disclosure, or making some conventional modifications to the reaction conditions. In addition, the reactions or known reaction conditions applied in the disclosure are also recognized to be applicable to the preparation of other compounds in the disclosure.

In the examples described below, all temperatures are set to degrees Celsius unless otherwise indicated. The compounds of the synthesis methods not mentioned in the disclosure are all raw materials obtained through commercial channels. The reagents were purchased from commercial suppliers such as Aldrich Chemical Company, Arco Chemical Company and Alfa Chemical Company, and were used without further purification unless otherwise indicated. General reagents were purchased from Shantou Xilong Chemical Plant, Guangdong Guanghua Chemical Reagent Plant, Guangzhou Chemical Reagent Plant, Tianjin Haoyuyu Chemical Co., Ltd., Tianjin Fuchen Chemical Reagent Plant, Wuhan Xinhuayuan Technology Development Co., Ltd., Qingdao Tenglong Chemical Reagent Co., Ltd., and Qingdao Ocean Chemical Plant.

The following reactions were generally performed under positive pressure of nitrogen or argon or by covering an anhydrous solvent with a drying tube (unless otherwise indicated), reaction flasks were plugged with suitable rubber stoppers, and substrates were injected through syringes. A silica gel column was used as the chromatographic column. Silica gel (100-200 meshes) was purchased from Qingdao Ocean Chemical Plant.

Measurement conditions of low-resolution mass spectrometry (MS) data were: Agilent 6120 quadrupole HPLC-M (column model: Zorbax SB-C18, 2.1×30 mm, 3.5 microns, 6 min, flow rate 0.6 mL/min. Mobile phase: 5%-95% (ratio of ($CH_3CN$ containing 0.1% formic acid) in ($H_2O$ containing 0.1% formic acid)), electrospray ionization (ESI), and UV detection at 210 nm/254 nm. $^1H$ NMR spectra were recorded using the Bruker 400 MHz or 600 MHz nuclear magnetic resonance spectrometer. The $^1H$ NMR spectra took $CDCl_3$, $CD_2Cl_2$, $D_2O$, DMSO-$d_6$, $CD_3OD$ or acetone-$d_6$ as a solvent (in ppm), and TMS (0 ppm) or chloroform (7.26 ppm) as the reference standard. When multiple peaks appeared, the following abbreviations were used: s (singlet), d (doublet), t (triplet), m (multiplet), br (broadened), dd (doublet of doublets), ddd (doublet of doublet of doublets), dddd (doublet of doublet of doublet of doublets), dt (doublet of triplets), and tt (triplet of triplets). The coupling constant J was expressed in Hertz (Hz).

In the following general synthesis schemes (1) and (2), $R_1$ in intermediate compounds had the same meaning as described in other parts of the specification.

In the disclosure, the compounds having the structures shown in the following chemical formulae (Ia) and (Ib) can be synthesized according to the following general synthesis schemes (1) and (2), but were not limited thereto.

Synthesis Scheme (1)

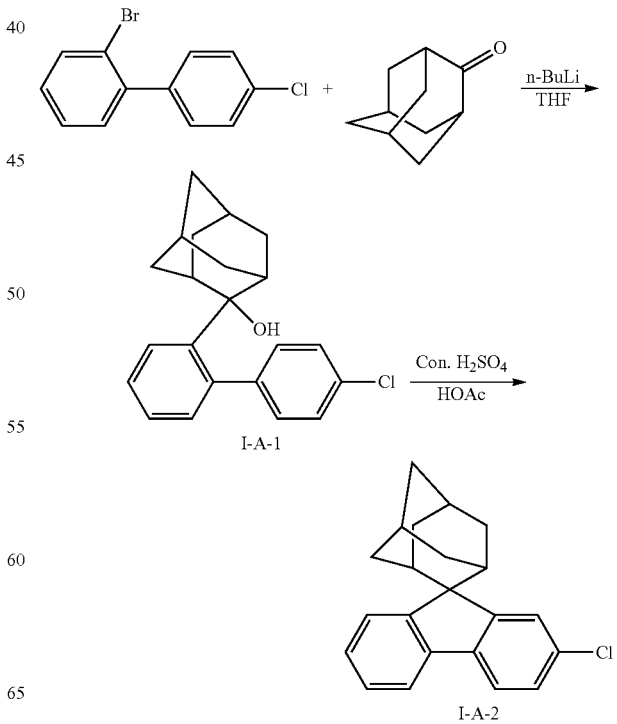

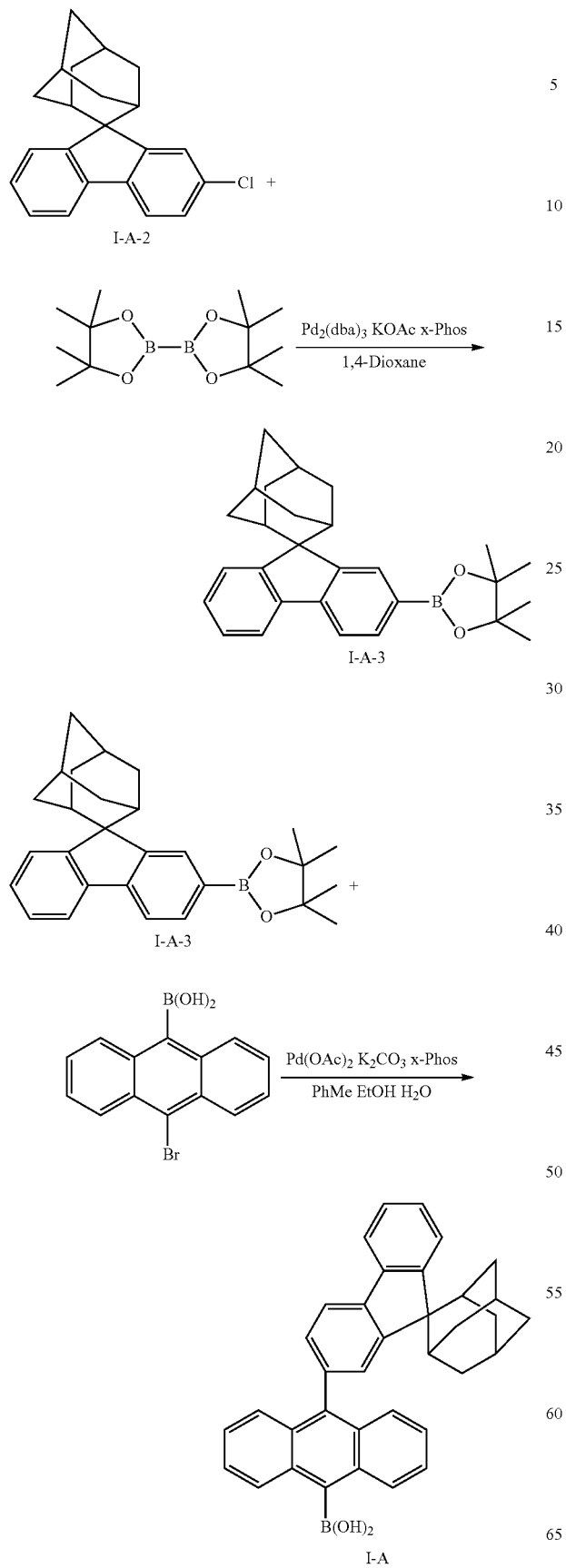

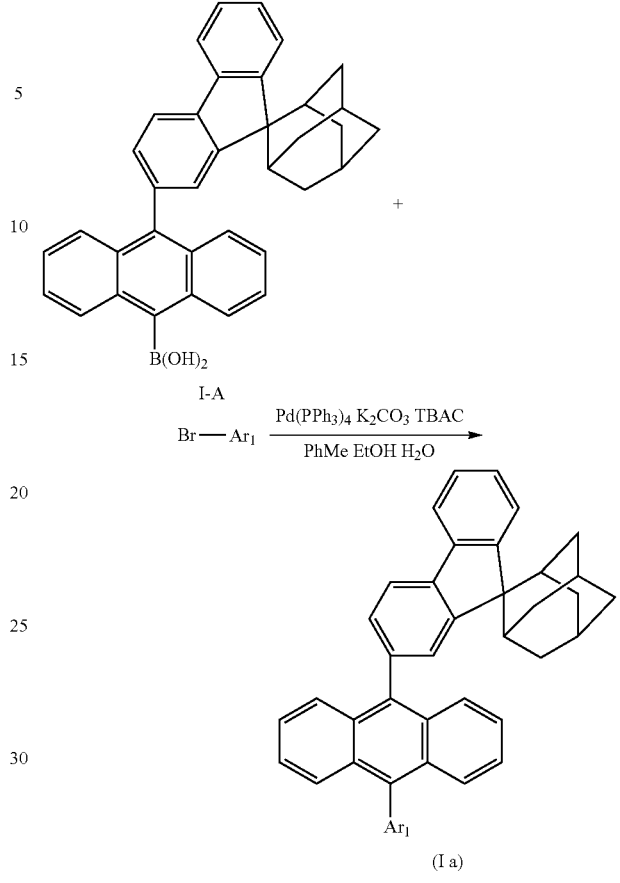

Wherein $Ar_1$ had the meaning as described in the disclosure.

Synthesis process: 2-bromo-4'-chlorobiphenyl and adamantanone generated an intermediate I-A-1 under the action of n-butyl lithium, the intermediate I-A-1 formed a ring under acidic conditions to generate an intermediate I-A-2, pinacol borate and the intermediate I-A-2 underwent Suzuki reaction under alkaline conditions to generate an intermediate I-A-3, 10-bromoanthracene-9-boronic acid and the intermediate I-A-3 underwent a coupling reaction in the presence of a palladium catalyst under alkaline conditions to generate an intermediate I-A, and an aryl bromide and the intermediate I-A underwent a coupling reaction in the presence of the palladium catalyst under alkaline conditions to generate a final product with the structure represented by formula (Ia). Compounds 1 to 18 of the disclosure can be prepared by the above general synthesis scheme (1). For ease of understanding, the synthesis process of some compounds of the disclosure was illustrated below, taking the preparation process of specific compound 1 as an example.

Synthesis of Intermediate I-A

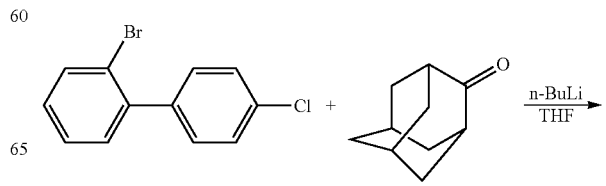

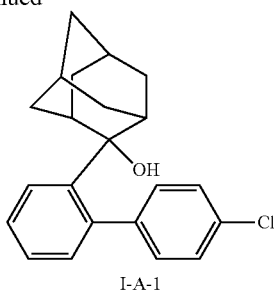

I-A-1

Under the nitrogen atmosphere, 2-bromo-4'-chlorobiphenyl (142 g, 530 mmol) and THF (852 mL) were added into a 2 L three-necked round bottom flask and dissolved at −80° C. to −90° C. until clarification, n-BuLi (254.75 mL, 2.5 mol/L) was added dropwise slowly to the reaction mixture, the mixture was stirred at the constant temperature of −80° C. to −90° C. for 50 min, then a solution of adamantanone (63.78 g, 42.45 mmol) in THF (260 mL) was added dropwise slowly to the reaction system, and the system was stirred at the constant temperature of −80° C. to −90° C. for 1 h. After the reaction was over, the temperature of reaction mixture was naturally raised to room temperature, 5% hydrochloric acid was poured into the reaction solution until pH<7, thorough stirring was carried out, then DCM was added for extraction. The combined organic phases were washed with water until neutral and dried with anhydrous magnesium sulfate, the solvent was removed under reduced pressure after filtration. The obtained oily substance was added to a flask with n-heptane and heated for reflux to obtain a clear solution, and the clear solution was placed at −20° C. for recrystallization to obtain intermediate I-A-1 as a white solid (122 g, yield 68%).

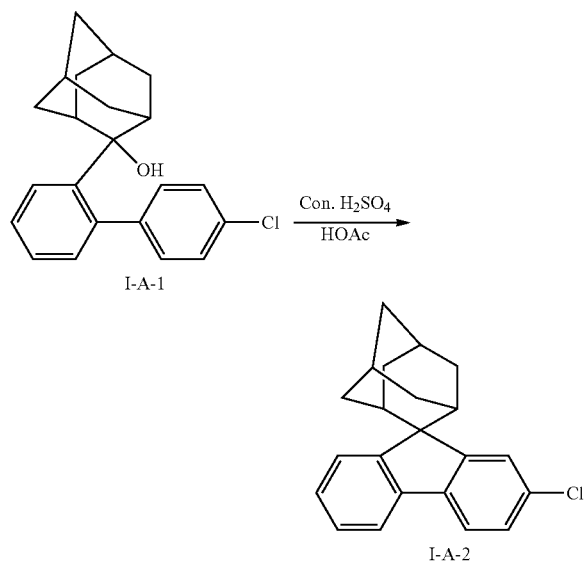

Under the nitrogen atmosphere, the intermediate I-A-1 (122 g, 360 mmol) was added to glacial acetic acid (1.5 L), and the mixture was stirred at 50° C. to 60° C. After the reaction solution was completely clear, concentrated sulfuric acid (3.08 mL) was added dropwise, the reaction solution was continuously heated to 70° C. to 80° C. and stirred for 30 min, then the reaction solution was naturally cooled to room temperature, deionized water (2 L) was added, thorough stirring and filtration were carried out. The filter cake was washed with deionized water to be neutral, put into a vacuum drying oven for baking for 1 h and dissolved in DCM, anhydrous sodium sulfate was added for drying for 30 min, filtration was carried out, the solvent was removed under reduced pressure to obtain the crude product. n-heptane and anhydrous DCM was added to dissolve the crude product, and then the solution of crude product was placed at −20° C. for recrystallization, and the crystal was filtered and then dried in the vacuum drying oven to obtain intermediate I-A-2 as a white solid (92.8 g, yield 80%).

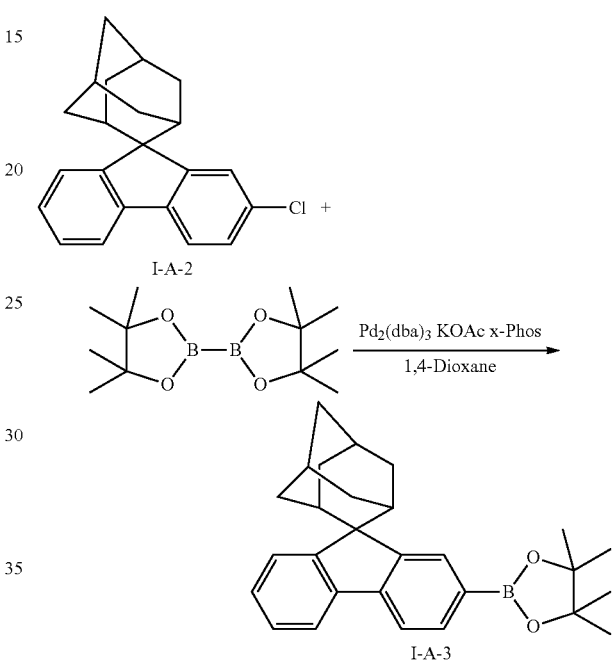

The intermediate I-A-2 (104.8 g, 327.5 mmol), pinacol diborate (83.2 g, 327.5 mmol), tris(dibenzylideneacetone)dipalladium (2.9 g, 3.28 mmol), 2-dicyclohexylphosphorus-2',4',6'-triisopropylbiphenyl (2.7 g, 6.6 mmol) and potassium acetate (62 g, 655 mmol) were added into 1,4-dioxane (800 mL), the reaction mixture was heated to 80° C. under nitrogen atmosphere, and stirred for 3 h; then the reaction solution was cooled to room temperature and washed with water, then anhydrous magnesium sulfate was added for drying, filtration was carried out, and the solvent was removed from the filtrate under reduced pressure; the crude product was purified by recrystallization using toluene to obtain intermediate I-A-3 as a white solid (108 g, yield 80%).

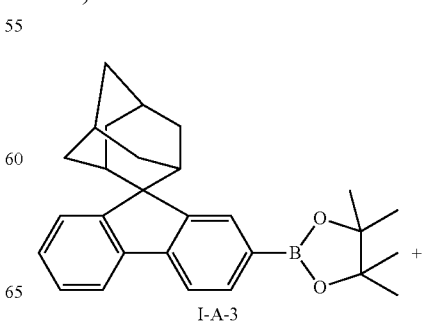

I-A-3

-continued

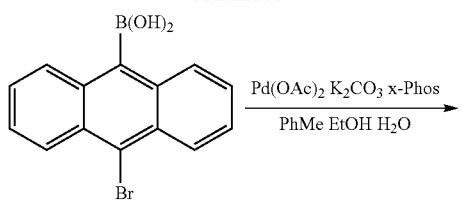

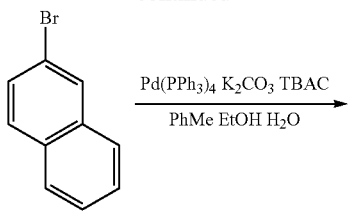

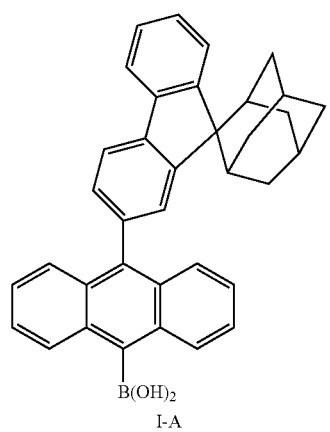

I-A

The intermediate I-A-3 (108 g, 262.3 mmol), 10-bromoanthracene-9-boronic acid (82.6 g, 275.2 mmol), palladium acetate (1.54 g, 2.62 mmol), 2-dicyclohexylphosphorus-2',4',6'-triisopropylbiphenyl (2.5 g, 5.2 mmol) and potassium carbonate (72.5 g, 524.6 mmol) were added into a mixture of toluene (400 mL), absolute ethanol (200 mL) and deionized water (100 mL), the resulting mixture was heated to 80° C. under nitrogen atmosphere, and stirred for 2 h; then the reaction solution was cooled to room temperature and washed with water, anhydrous magnesium sulfate was added for drying, filtration was carried out, and the solvent was removed from the filtrate under reduced pressure. The crude product was purified by recrystallization using a mixture of dichloromethane and n-heptane to obtain intermediate I-A as a white solid (99 g, yield 75%).

Synthesis of Compound 1

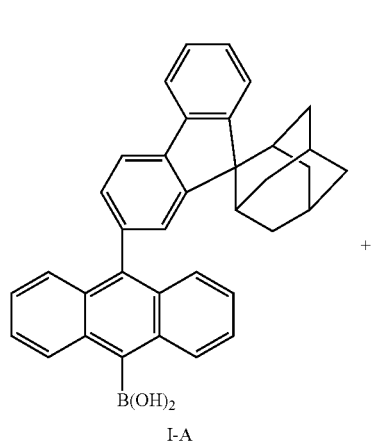

+

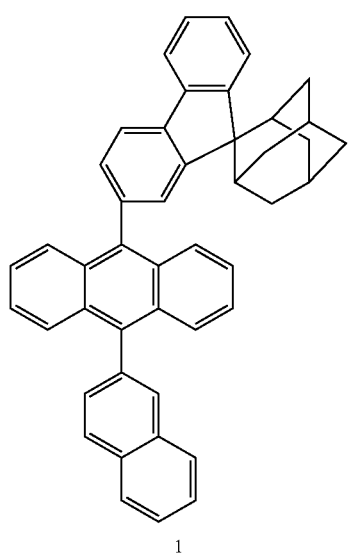

1

The intermediate I-A (8 g, 15.8 mmol), 2-bromonaphthalene (3.27 g, 15.8 mmol), tetrakis(triphenylphosphine)palladium (0.365 g, 0.316 mmol), potassium carbonate (4.8 g, 3.5 mmol) and tetrabutylammonium chloride (0.25 g, 0.79 mmol) were added into a three-necked flask respectively, toluene (40 mL), ethanol (20 mL) and water (10 mL) were added into the flask, the mixture was heated to reflux at 80° C. for 12 h. Extraction was carried out using $CH_2Cl_2$ and water when the reaction was completed, the organic phase was dried with anhydrous $MgSO_4$ and filtered, then the filtrate was concentrated in vacuo to obtain the crude product, and the crude product was purified by silica column chromatography to obtain compound 1 as a white solid (6 g, yield 65%). LC-MS(ESI, pos.ion) m/z: 588.98[M+H]$^+$ Compounds 2 to 18 were prepared by referring to the method of synthesizing compound 1 and using the raw material 2 in Table 1 instead of 2-bromonaphthalene to react with the intermediate I-A. Wherein the number, structure, raw material, synthesis yield of the last step, characterization data, etc. of compounds 2 to 18 were shown in Table 1:

TABLE 1

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 2 | (structure I-A with B(OH)$_2$) | 4-bromobiphenyl | (compound 2 structure) | 70% | 615.30 |
| 3 | | 2-bromobiphenyl | (compound 3 structure) | 68% | 615.30 |

TABLE 1-continued

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 4 | | Br-(9,9-dimethylfluorene) | (structure) | 65% | 655.03 |
| 5 | | Br-phenyl | (structure) | 71% | 538.97 |

TABLE 1-continued
Structure, preparation and characterization data of compounds
| Compound | Intermediate I-A | Raw material 2 | Structure of compound | Yield (%) | Mass spectrum (m/z) (M + H)+ |
|---|---|---|---|---|---|
| 6 |  | 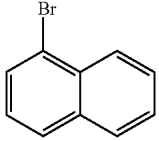 | 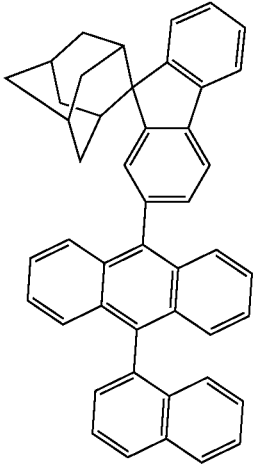 [SMILES: c1ccc2c(c1)-c1ccc(-c3c4ccccc4c(-c4cccc5ccccc45)c4ccccc34)cc1C21C2CC3CC(C2)CC1C3] | 70% | 588.98 |
| 7 |  | 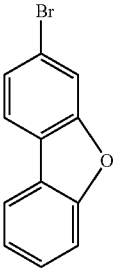 [SMILES: Brc1ccc2c(c1)oc1ccccc12] | 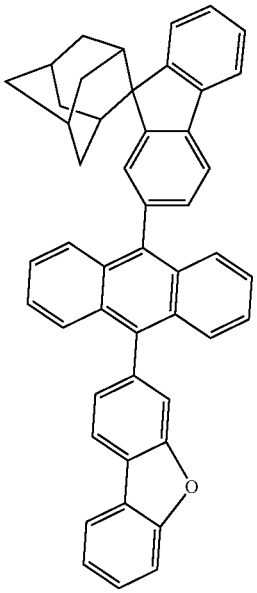 [SMILES: c1ccc2c(c1)-c1ccc(-c3c4ccccc4c(-c4ccc5c(c4)oc4ccccc45)c4ccccc34)cc1C21C2CC3CC(C2)CC1C3] | 65% | 628.98 |

TABLE 1-continued

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 8 | | (dibenzothiophene-Br) | | 63% | 644.95 |
| 9 | | (4-bromophenyl-carbazole) | | 59% | 704.02 |

TABLE 1-continued
Structure, preparation and characterization data of compounds
| Compound | Intermediate I-A | Raw material 2 | Structure of compound | Yield (%) | Mass spectrum (m/z) (M + H)+ |
|---|---|---|---|---|---|
| 10 | | 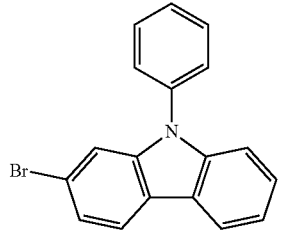 [SMILES: Brc1ccc2c3ccccc3n(-c3ccccc3)c2c1] | 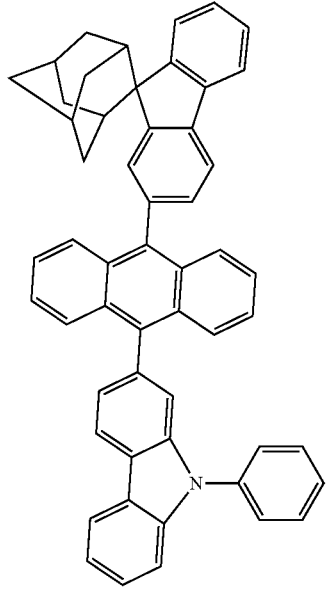 [SMILES: c1ccc(-n2c3ccccc3c3ccc(-c4c5ccccc5c(-c5ccc6c(c5)C5(c7ccccc7-6)C6CC7CC(C6)CC5C7)c5ccccc45)cc32)cc1] | 75% | 704.02 |
| 11 | | 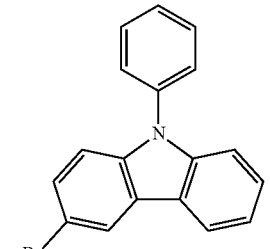 | 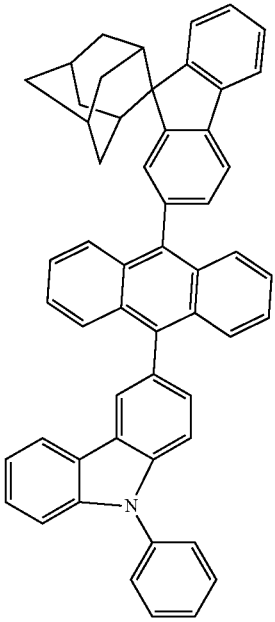 [SMILES: c1ccc(-n2c3ccccc3c3cc(-c4c5ccccc5c(-c5ccc6c(c5)C5(c7ccccc7-6)C6CC7CC(C6)CC5C7)c5ccccc45)ccc32)cc1] | 72% | 704.02 |

US 11,492,314 B2
165                                                                 166
TABLE 1-continued
Structure, preparation and characterization data of compounds
| Compound | Intermediate I-A | Raw material 2 | Structure of compound | Yield (%) | Mass spectrum (m/z) (M + H)+ |
|---|---|---|---|---|---|
| 12 | | 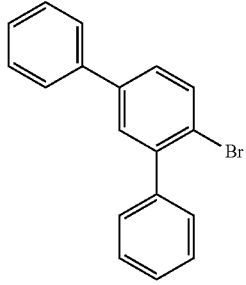 [SMILES: Brc1ccc(-c2ccccc2)cc1-c1ccccc1] | 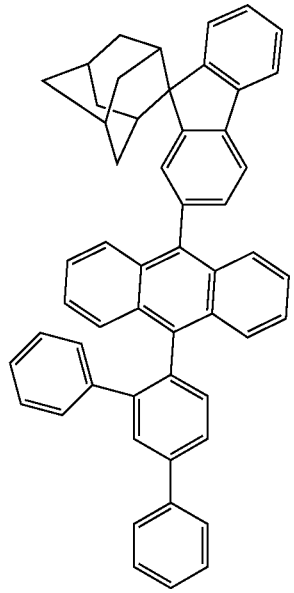 [SMILES: c1ccc(-c2ccc(-c3c4ccccc4c(-c4ccc5c(c4)C4(c6ccccc6-5)C5CC6CC(C5)CC4C6)c4ccccc34)c(-c3ccccc3)c2)cc1] | 48% | 691.03 |
| 13 | | 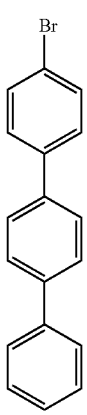 [SMILES: Brc1ccc(-c2ccc(-c3ccccc3)cc2)cc1] | 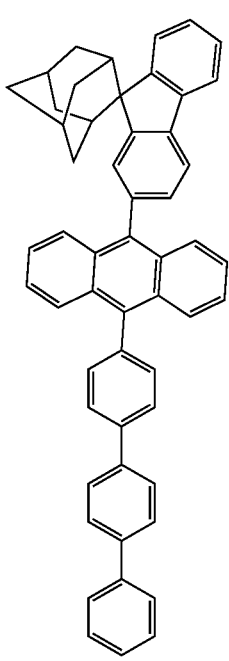 [SMILES: c1ccc(-c2ccc(-c3ccc(-c4c5ccccc5c(-c5ccc6c(c5)C5(c7ccccc7-6)C6CC7CC(C6)CC5C7)c5ccccc45)cc3)cc2)cc1] | 45% | 691.03 |

TABLE 1-continued

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 14 | | 3-bromobiphenyl | | 51% | 615.3 |
| 15 | | 2-bromodibenzofuran | | 53% | 628.98 |

TABLE 1-continued
Structure, preparation and characterization data of compounds
| Compound | Intermediate I-A | Raw material 2 | Structure of compound | Yield (%) | Mass spectrum (m/z) (M + H)+ |
|---|---|---|---|---|---|
| 16 | | 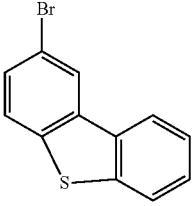 [SMILES: Brc1ccc2sc3ccccc3c2c1] | 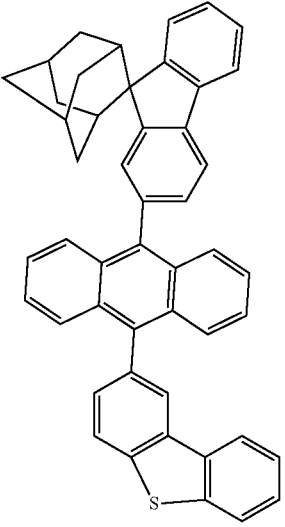 [SMILES: c1ccc2c(c1)-c1ccc(-c3c4ccccc4c(-c4ccc5sc6ccccc6c5c4)c4ccccc34)cc1C21C2CC3CC(C2)CC1C3] | 60% | 644.95 |
| 17 | |  | 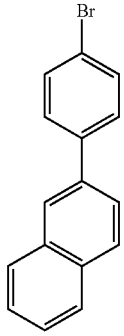 [SMILES: Brc1ccc(-c2ccc3ccccc3c2)cc1] | 75% | 665.01 |

TABLE 1-continued

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 18 | | 4-bromo-1-phenylnaphthalene | | 69% | 665.01 |
| 168 | I-A (anthracene-fluorene-adamantane boronic acid) | 2-bromo-4,6-diphenylpyrimidine | | 68% | 693.32 |
| 169 | | 2-chloro-4-phenylquinazoline | | 62% | 667.31 |

TABLE 1-continued

Structure, preparation and characterization data of compounds

| Compound | Intermediate I-A | Raw material 2 | Structure of compound | Yield (%) | Mass spectrum (m/z) (M + H)+ |
|---|---|---|---|---|---|
| 188 | | 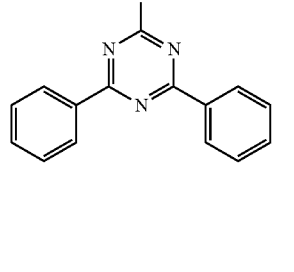 | 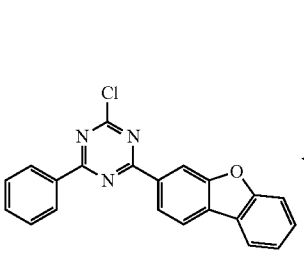 | 70% | 694.3 |
| 201 | | 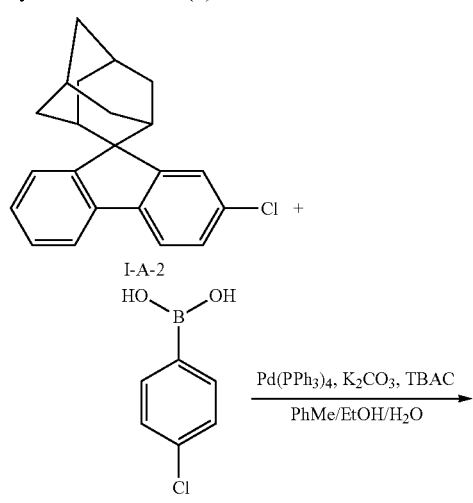 | | 65% | 784.32 |

¹H NMR

Compound 168

¹H NMR (CD₂Cl₂, 400 MHz) δ (ppm): 8.35 (d, 5H), 8.26 (d, 1H), 7.98 (m, 5H), 7.86 (d, 1H), 7.80-7.72 (m, 12H), 7.48 (L, 1H), 7.30 (L, 1H), 3.00 (d, 2H), 2.81 (d, 2H), 2.21 (s, 1H), 2.02 (s, 1H), 1.94 (s, 2H), 1.83 (d, 4H), 1.72 (s, 2H).

Compound 169

¹H NMR (CD₂Cl₂, 400 MHz) δ (ppm): 8.38 (m, 4H), 8.33-8.29 (m, 2H), 8.20-8.00 (m, 6H), 7.80-7.65 (m, 10H), 7.48 (t, 1H), 7.30 (L, 1H), 2.98 (d, 2H), 2.83 (d, 2H), 2.20 (s, 1H), 2.01 (s, 1H), 1.94 (s, 2H), 1.84 (d, 4H), 1.73 (s, 2H).

Compound 188

¹H NMR (CD₂Cl₂, 400 MHz) δ (ppm): 8.56 (m, 4H), 8.38 (m, 4H), 8.29-8.00 (m, 5H), 7.80-7.65 (m, 10H), 7.48 (L, 1H), 7.30 (L, 1H), 3.01 (d, 2H), 2.83 (d, 2H), 2.22 (s, 1H), 2.02 (s, 1H), 1.95 (s, 2H), 1.82 (d, 4H), 1.74 (s, 2H).

Compound 201

¹H NMR (CD₂Cl₂, 400 MHz) δ (ppm): 8.53 (m, 2H), 8.38 (m, 4H), 8.29-8.10 (m, 4H), 7.80-7.65 (m, 13H), 7.48 (t, 2H), 7.30 (t, 2H), 3.02 (d, 2H), 2.80 (d, 2H), 2.23 (s, 1H), 2.04 (s, 1H), 1.92 (s, 2H), 1.84 (d, 4H), 1.71 (s, 2H).

Synthesis Scheme (2)

Other compounds can be synthesized by the following synthesis scheme (2).

-continued

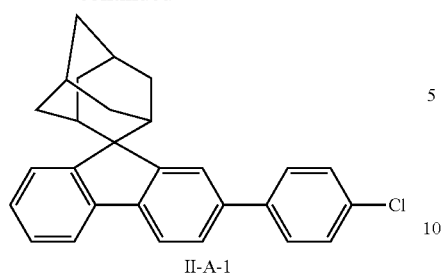

II-A-1

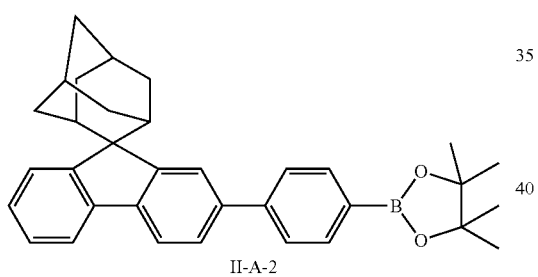

-continued

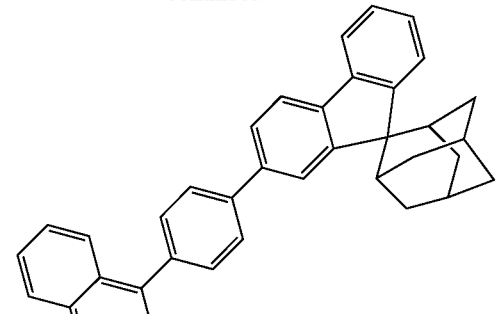

II-A

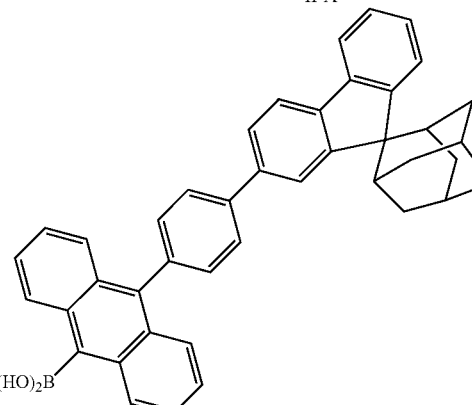

II-A

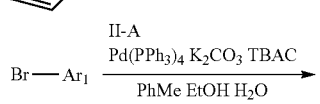

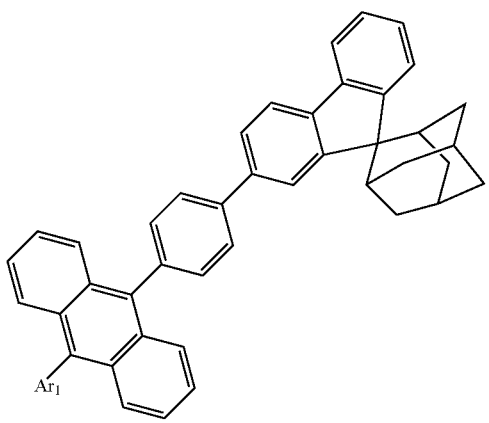

(Ib)

Wherein Ar₁ has the meaning described in the disclosure.

Synthesis process: the intermediate I-A-2 and p-chlorophenylboronic acid underwent Suzuki reaction under alkaline conditions to generate an intermediate II-A-1, bis(pinacolato)diboron and the intermediate II-A-1 underwent Suzuki reaction in the presence of a palladium catalyst under alkaline conditions to generate an intermediate II-A-2, 10-bromoanthracene-9-boronic acid and the intermediate II-A-2 underwent Suzuki reaction in the presence of the palladium catalyst under alkaline conditions to generate an intermediate II-A, an aryl bromide BrR₁ and the intermediate II-A underwent a coupling reaction in the presence of the palladium catalyst under alkaline conditions to generate a compound with the structure represented by formula (Ib).

Compounds 81 and 82 of the disclosure can be prepared by the above general synthesis scheme (2). For ease of understanding, the synthesis process of some compounds of the disclosure was illustrated below, taking the preparation process of specific compound 81 as an example.

Synthesis of Intermediate II-A

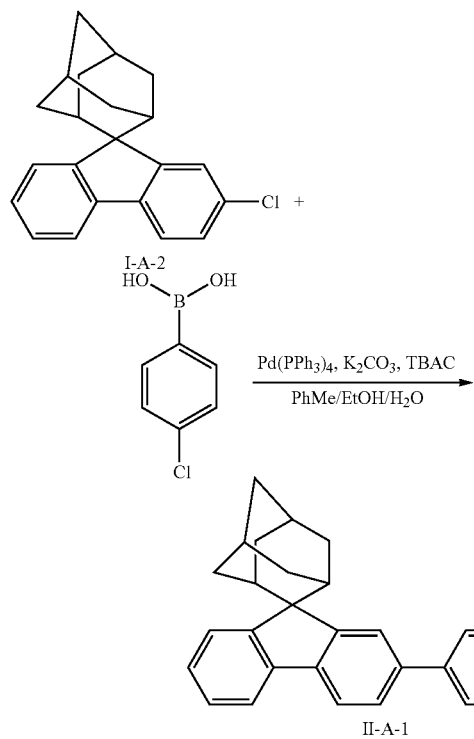

The intermediate I-A-2 (20 g, 62.34 mmol), p-chlorophenylboronic acid (9.75 g, 62.34 mmol), tetrakis(triphenylphosphine)palladium (0.72 g, 0.62 mmol), potassium carbonate (17.2 g, 124.6 mmol), tetrabutylammonium chloride (0.34 g, 1.25 mmol), toluene (160 mL), ethanol (40 mL) and deionized water (40 mL) were added into a round bottom flask, the mixture was heated to 78° C. under nitrogen atmosphere, and stirred for 8 hours. The reaction solution was cooled to room temperature, toluene (100 mL) was added for extraction, the combined organic phases were dried with anhydrous magnesium sulfate, filtration was carried out, and the solvent was removed from the filtrate under reduced pressure to obtain the crude product; the crude product was purified by silica column chromatography using n-heptane as a mobile phase, and then purified by recrystallization using a mixture of dichloromethane and n-heptane to obtain intermediate II-A-1 as a white solid (18.6 g, 75%).

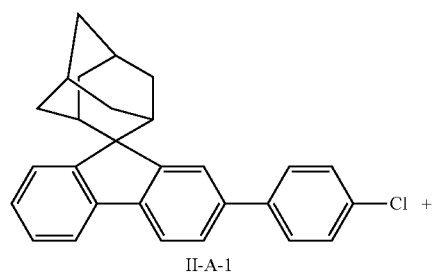

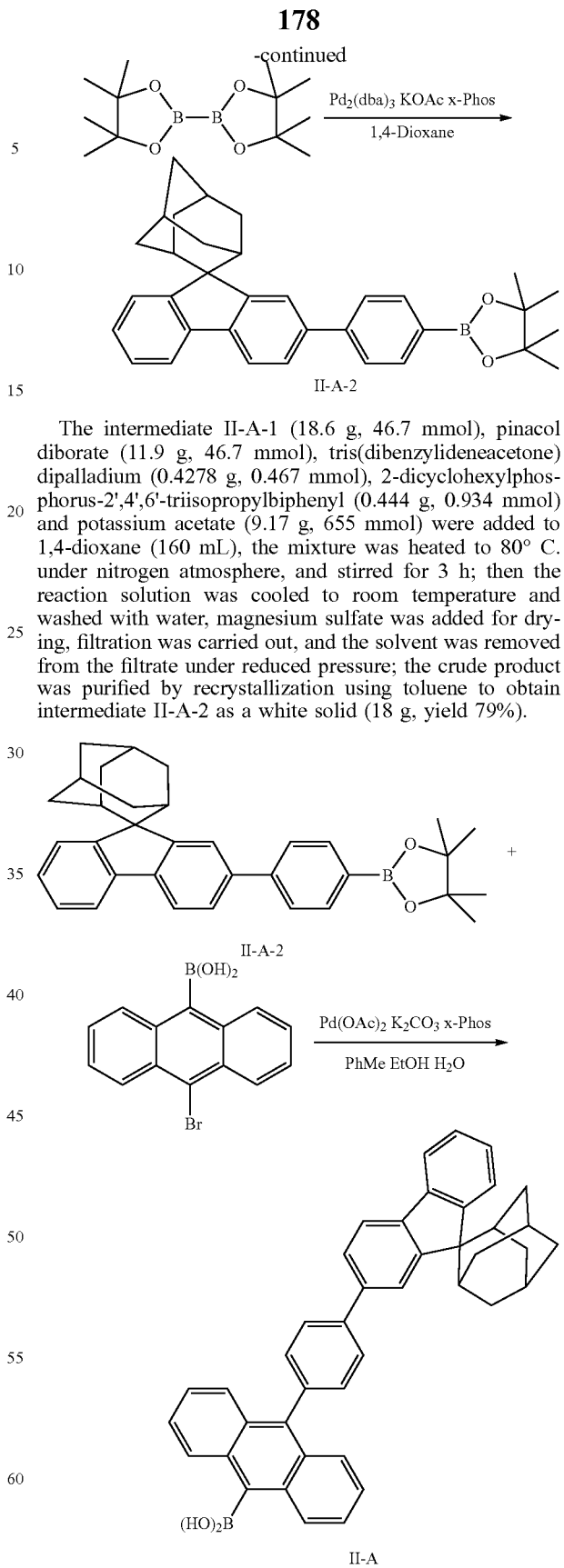

The intermediate II-A-1 (18.6 g, 46.7 mmol), pinacol diborate (11.9 g, 46.7 mmol), tris(dibenzylideneacetone) dipalladium (0.4278 g, 0.467 mmol), 2-dicyclohexylphosphorus-2',4',6'-triisopropylbiphenyl (0.444 g, 0.934 mmol) and potassium acetate (9.17 g, 655 mmol) were added to 1,4-dioxane (160 mL), the mixture was heated to 80° C. under nitrogen atmosphere, and stirred for 3 h; then the reaction solution was cooled to room temperature and washed with water, magnesium sulfate was added for drying, filtration was carried out, and the solvent was removed from the filtrate under reduced pressure; the crude product was purified by recrystallization using toluene to obtain intermediate II-A-2 as a white solid (18 g, yield 79%).

The intermediate II-A-2 (18 g, 36.8 mmol), 10-bromoanthracene-9-boronic acid (11 g, 36.8 mmol), palladium acetate (0.16 g, 0.736 mmol), 2-dicyclohexylphosphorus-2', 4',6'-triisopropylbiphenyl (0.175 g, 0.368 mmol) and potassium carbonate (10.16 g, 73.6 mmol) were added into a mixture of toluene (80 mL), absolute ethanol (40 mL) and deionized water (20 mL), the resulting mixture was heated to 80° C. under nitrogen atmosphere, and stirred for 2 h; then the reaction solution was cooled to room temperature and washed with water, magnesium sulfate was added for drying, filtration was carried out, and the solvent was removed from the filtrate under reduced pressure; the crude product was purified by recrystallization using the mixture of dichloromethane and n-heptane to obtain intermediate II-A as a white solid (16 g, yield 72%).

Synthesis of Compound 81

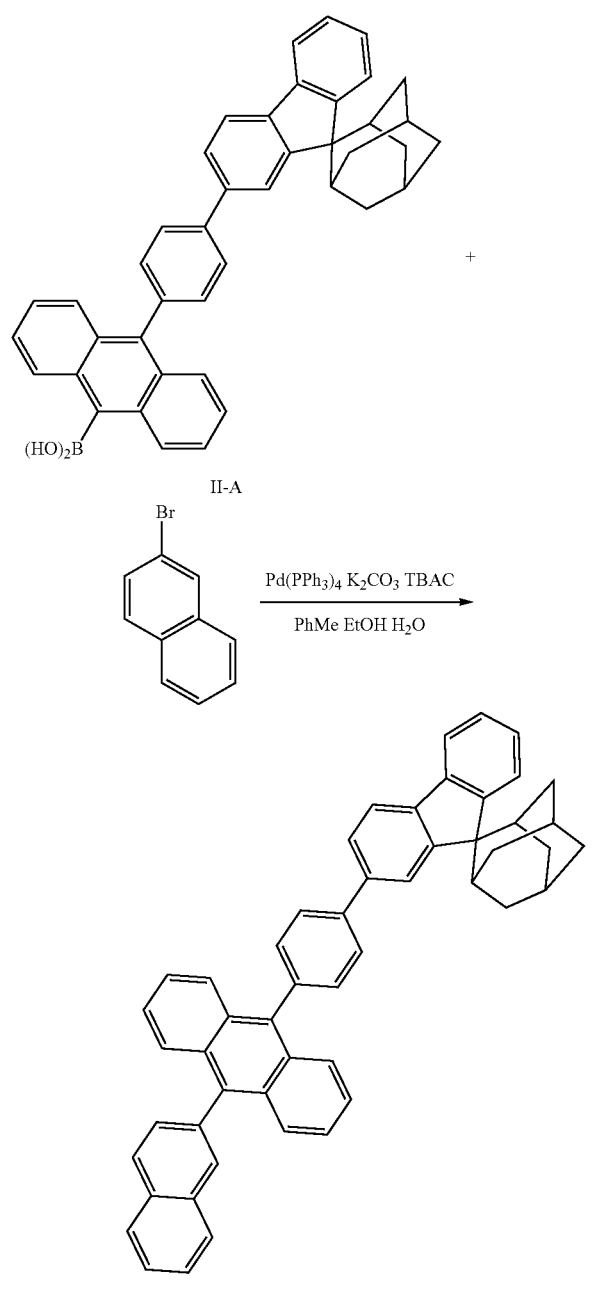

The intermediate II-A (9 g, 15.8 mmol), 2-bromonaphthalene (3.27 g, 15.8 mmol), tetrakis(triphenylphosphine)palladium (0.365 g, 0.316 mmol), potassium carbonate (4.8 g, 3.5 mmol), and tetrabutylammonium bromide (0.25 g, 0.79 mmol) were added into a three-necked flask respectively, toluene (40 mL), ethanol (20 mL) and water (10 mL) were added into the flask, the mixture was heated to reflux at 80° C. for 12 h, extraction was carried out using $CH_2Cl_2$ and water when the reaction was over. The separated organic phase was dried over anhydrous $MgSO_4$ and filtered, the filtrate was concentrated in vacuo to obtain a crude product, and the crude product was purified by silica column chromatography to obtain compound 81 as a white solid (5.2 g, yield 50%).

LC-MS(ESI, pos.ion) m/z: 665.01[M+H]$^+$

Synthesis of Compound 82

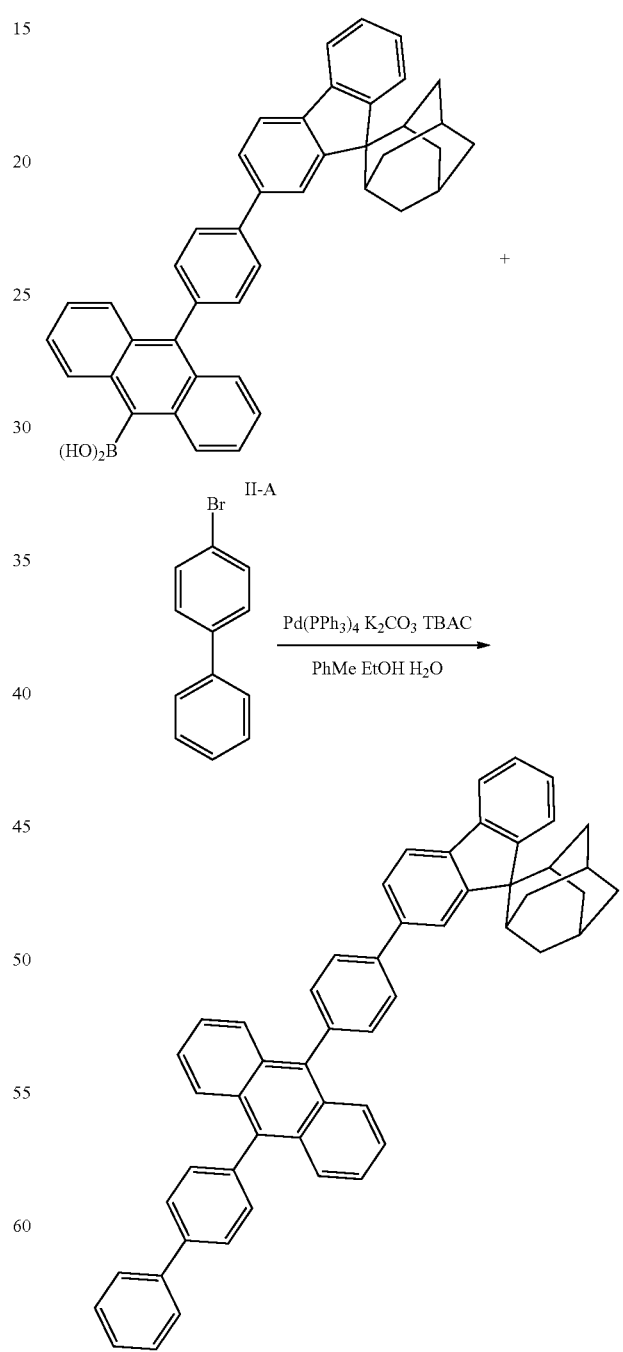

The intermediate II-A (9 g, 15.8 mmol), 4-bromobiphenyl (3.68 g, 15.8 mmol), tetrakis(triphenylphosphine)palladium (0.365 g, 0.316 mmol), potassium carbonate (4.8 g, 3.5 mmol), and tetrabutylammonium bromide (0.25 g, 0.79 mmol) were added into a three-necked flask respectively, toluene (40 mL), ethanol (20 mL) and water (10 mL) were added into the flask, the mixture was heated to reflux at 80° C. for 12 h, extraction was carried out using $CH_2Cl_2$ and water when the reaction was over. The separated organic phase was dried with anhydrous $MgSO_4$ and filtered, the filtrate was concentrated in vacuo to obtain a crude product, and the crude product was purified by silica column chromatography to obtain compound 82 as a white solid (6.65 g, yield 61%).

LC-MS(ESI, pos.ion) m/z:691.03[M+H]$^+$

Synthesis of Compounds 119, 123, 141, and 157

Synthesis of Intermediate III-A-1

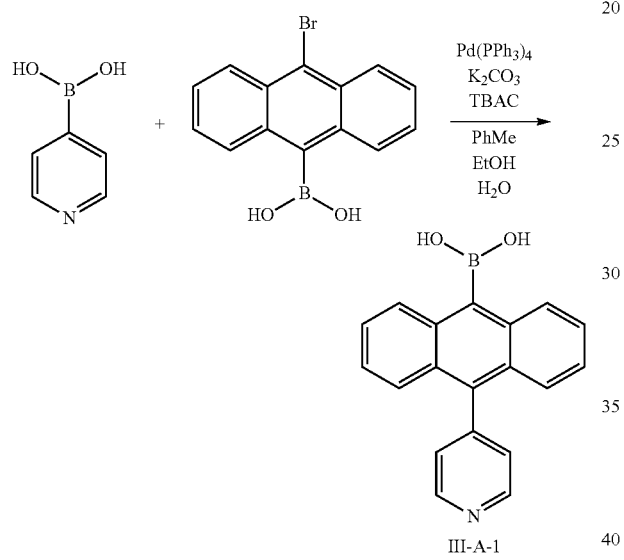

III-A-1

Pyridine-2-boronic acid (6.146 g, 50 mmol), 10-bromoanthracene-9-boronic acid (15 g, 50 mmol), tetrakis(triphenylphosphine)palladium(0.58 g, 0.5 mmol), potassium carbonate (7.35 g, 75 mmol), tetrabutylammonium chloride (0.278 g, 1 mmol), toluene (80 mL), ethanol (20 mL) and deionized water (20 mL) were added into a round bottom flask, the mixture was heated to 78° C. under nitrogen atmosphere, and stirred for 8 hours. The reaction solution was cooled to room temperature, toluene (50 mL) was added for extraction, the organic phases were combined and dried with anhydrous magnesium sulfate, filtration was carried out, and the solvent was removed from filtrate under reduced pressure to obtain a crude product; the obtained crude product was purified by silica column chromatography using n-heptane as a mobile phase, and then purified by recrystallization using a mixture of dichloromethane and ethyl acetate to obtain intermediate III-A-1 as a white solid (11.2 g, 75%).

Intermediates IV-A-1, V-A-1 and VI-A-1 were prepared by referring to the method of synthesizing the intermediate III-A-1 and using the raw material 1 in Table 2 instead of pyridine-2-boronic acid. Wherein the number, structure, raw material, synthesis yield, etc. of the intermediates IV-A-1, V-A-1 and VI-A-1 were shown in Table 2:

TABLE 2

Structure, preparation and characterization data of compounds

| Intermediate | Raw material 1 | Raw material 2 | Structure of compound | Yield (%) |
|---|---|---|---|---|
| Intermediate IV-A-1 | ![HO-B(OH)-C6H4-OCH3] | ![9-Br-10-B(OH)2-anthracene] | ![10-(4-methoxyphenyl)anthracene-9-boronic acid] | 64 |

TABLE 2-continued

Structure, preparation and characterization data of compounds

| Intermediate | Raw material 1 | Raw material 2 | Structure of compound | Yield (%) |
|---|---|---|---|---|
| Intermediate V-A-1 | (dibenzothiophene-2-boronic acid) | | (10-(dibenzothiophen-2-yl)anthracen-9-yl)boronic acid | 72 |
| Intermediate VI-A-1 | (4-cyclohexylphenylboronic acid) | | (10-(4-cyclohexylphenyl)anthracen-9-yl)boronic acid | 80 |

Synthesis of Intermediate III-A-2

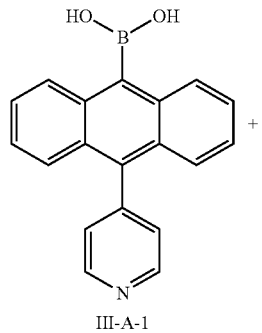

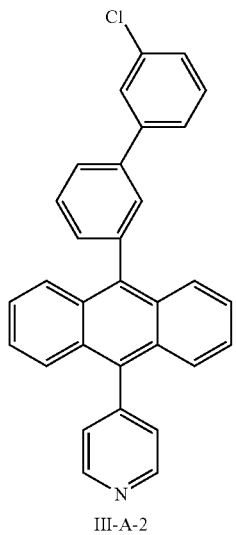

The intermediate III-A-1 (11.2 g, 50 mmol), 3-bromo-3'-chloro-1,1'-biphenyl (13.4 g, 50 mmol), tetrakis(triphenylphosphine)palladium(0.58 g, 0.5 mmol), potassium carbonate (7.35 g, 75 mmol), tetrabutylammonium chloride (0.278 g, 1 mmol), toluene (80 mL), ethanol (20 mL) and deionized water (20 mL) were added into a round bottom flask, the mixture was heated to 78° C. under nitrogen atmosphere, and stirred for 8 hours; then the reaction solution was cooled to room temperature, toluene (50 mL) was added for extraction. The organic phases were combined and dried with anhydrous magnesium sulfate, filtration was carried out, and the solvent was removed from filtrate under reduced pressure to obtain a crude product; the obtained crude product was purified by silica column chromatography using n-heptane as a mobile phase, and then purified by recrystallization using a mixture of dichloromethane and ethyl acetate to obtain intermediate III-A-2 as a white solid (15.9 g, 72%).

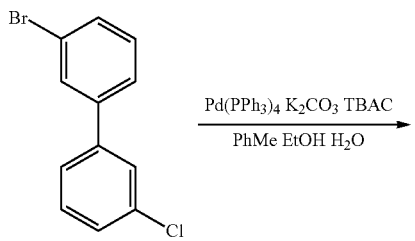

Intermediates IV-A-2, V-A-2, and VI-A-2 were prepared by referring to the method of synthesizing the intermediate III-A-2, using the raw material 1 in Table 3 instead of the intermediate III-A-1 and using the raw material 2 in Table 3 instead of the 3-bromo-3'-chloro-1,1'-biphenyl. The number, structure, raw material, synthesis yield, etc. of the intermediates IV-A-2, V-A-2, and VI-A-2 were shown in Table 3:

TABLE 3
Structure, preparation and characterization data of compounds
| Intermediate | Raw material 1 | Raw material 2 | Structure of compound | Yield (%) |
|---|---|---|---|---|
| Intermediate IV-A-2 | 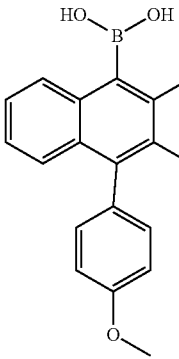 | 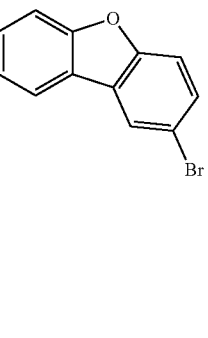 | 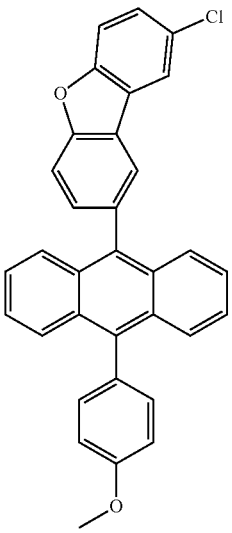 [SMILES: COc1ccc(-c2c3ccccc3c(-c3ccc4oc5ccc(Cl)cc5c4c3)c3ccccc23)cc1] | 68 |
| Intermediate V-A-2 | 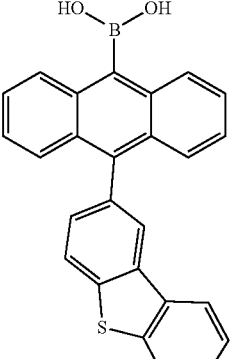 | 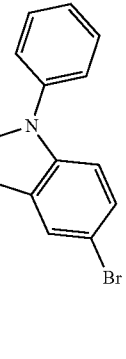 | 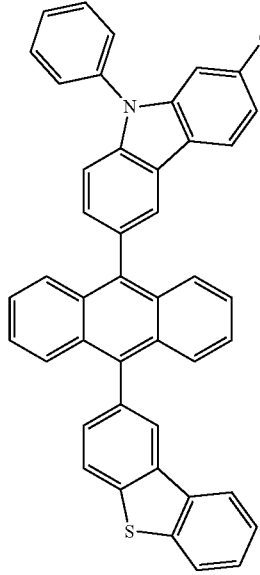 | 71 |

TABLE 3-continued
Structure, preparation and characterization data of compounds
| Intermediate | Raw material 1 | Raw material 2 | Structure of compound | Yield (%) |
|---|---|---|---|---|
| Intermediate VI-A-2 | (HO)₂B-anthracene-phenyl-cyclohexyl | 2,7-dibromo-9,9-diphenylfluorene | Br-fluorene-anthracene-phenyl-cyclohexyl | 69 |
Synthesis of intermediate III-A-3
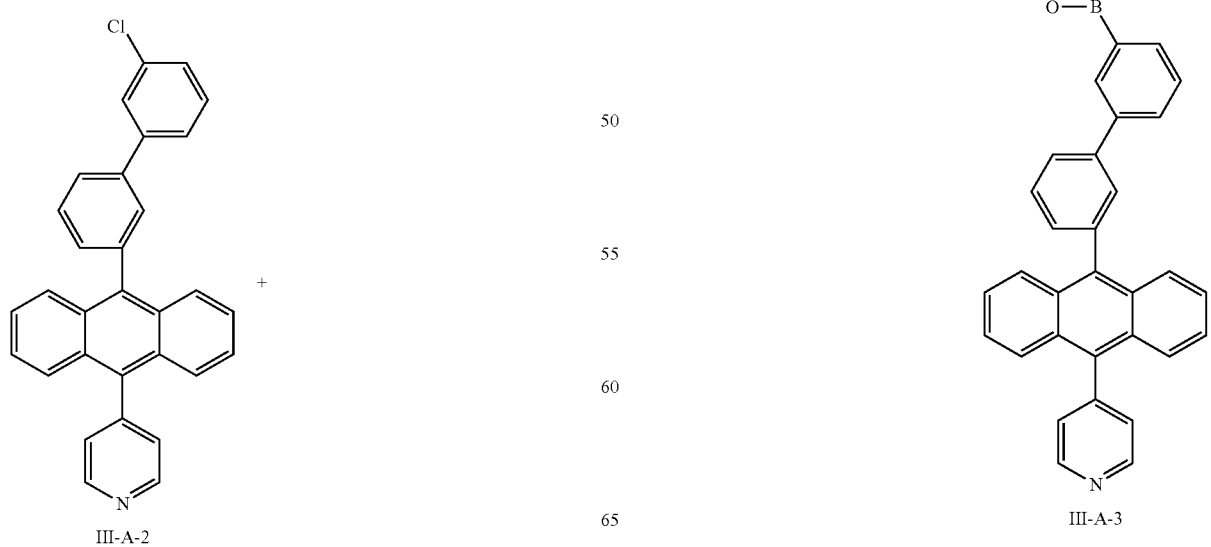
III-A-2 + B₂pin₂ →[Pd₂(dba)₃ KOAc X-Phos, 1,4 Dioxane]→ III-A-3

The intermediate III-A-2 (15.9 g, 36.5 mmol), pinacol diborate (9.16 g, 36.5 mmol), tris(dibenzylideneacetone)dipalladium (0.3346 g, 0.365 mmol), 2-dicyclohexylphosphorus-2',4',6'-triisopropylbiphenyl (0.3468 g, 0.73 mmol) and potassium acetate (9.8 g, 100 mmol) were added to 1,4-dioxane (150 mL), the mixture was heated to 80° C. under nitrogen atmosphere, and stirred for 3 h; then the reaction solution was cooled to room temperature and washed with water, magnesium sulfate was added for drying, filtration was carried out. The solvent was removed from the filtrate under reduced pressure to obtain a crude product; the crude product was purified by recrystallization using toluene to obtain intermediate III-A-3 as a white solid (15.56 g, yield 80%). Intermediates IV-A-3, V-A-3, and VI-A-3 were prepared by referring to the method of synthesizing the intermediate III-A-3 and using the raw material 1 in Table 4 instead of the intermediate III-A-2. The number, structure, raw material, synthesis yield, etc. of the intermediates IV-A-3, V-A-3, and VI-A-3 were shown in Table 4:

TABLE 4

Structure, preparation and characterization data of compounds

| Intermediate | Raw material 1 | Raw material 2 | Structure of compound | Yield (%) |
|---|---|---|---|---|
| Intermediate IV-A-3 | | | | 68 |

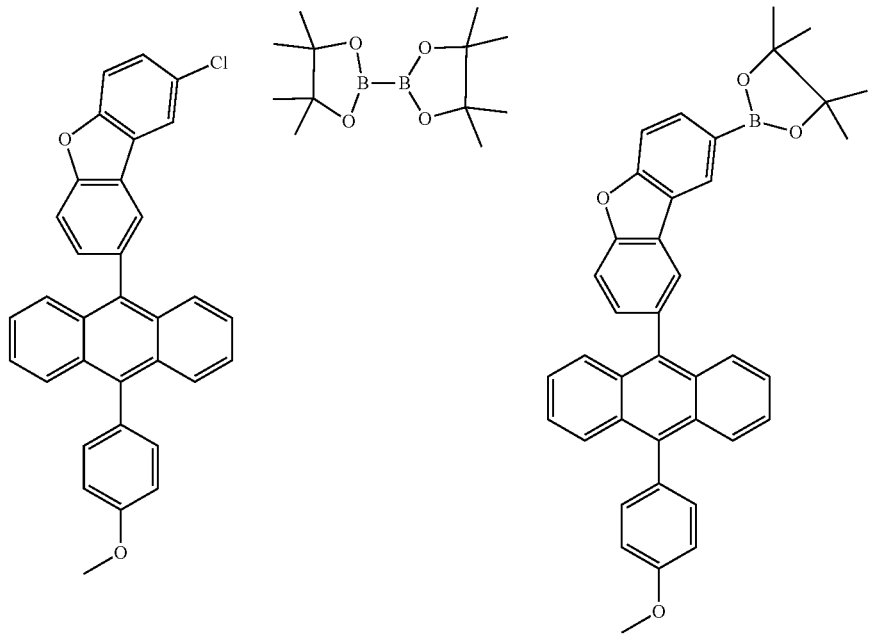

TABLE 4-continued
Structure, preparation and characterization data of compounds
| Intermediate | Raw material 1 | Raw material 2 | Structure of compound | Yield (%) |
|---|---|---|---|---|
| Intermediate V-A-3 | 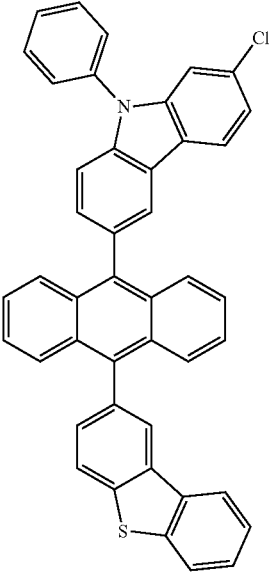 [SMILES: Clc1ccc2c3cc(-c4c5ccccc5c(-c5ccc6sc7ccccc7c6c5)c5ccccc45)ccc3n(-c3ccccc3)c2c1] | | 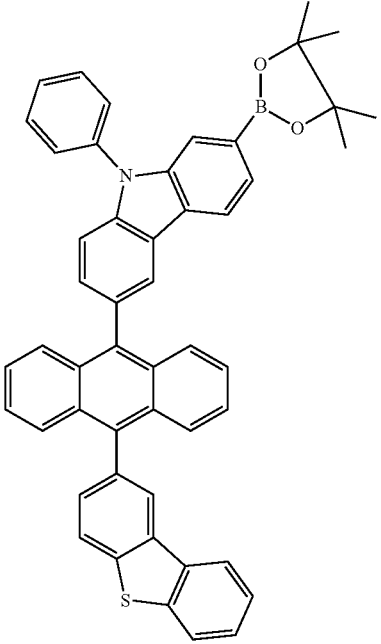 [SMILES: CC1(C)OB(c2ccc3c4cc(-c5c6ccccc6c(-c6ccc7sc8ccccc8c7c6)c6ccccc56)ccc4n(-c4ccccc4)c3c2)OC1(C)C] | 71 |
| Intermediate VI-A-3 | 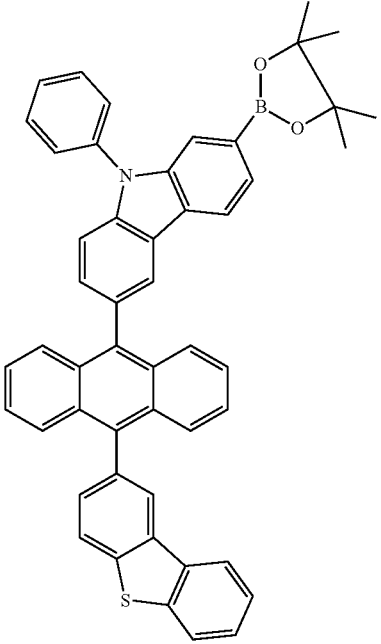 [SMILES: CC1(C)OB(c2ccc3c4cc(-c5c6ccccc6c(-c6ccc7sc8ccccc8c7c6)c6ccccc56)ccc4n(-c4ccccc4)c3c2)OC1(C)C] | | 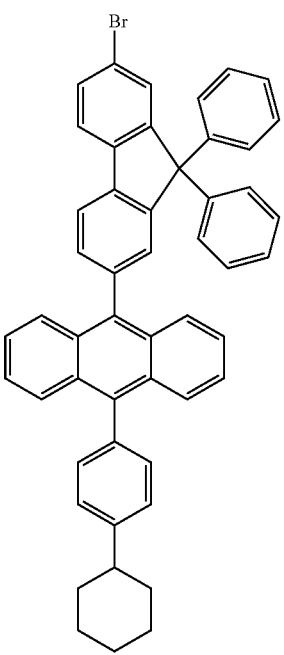 [SMILES: Brc1ccc2c(c1)C(c1ccccc1)(c1ccccc1)c1cc(-c3c4ccccc4c(-c4ccc(C5CCCCC5)cc4)c4ccccc34)ccc1-2] | 69 |

Synthesis of Compound 119

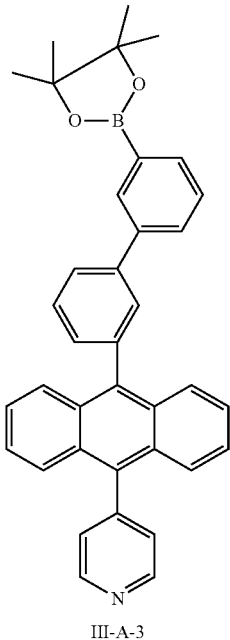

III-A-3

+

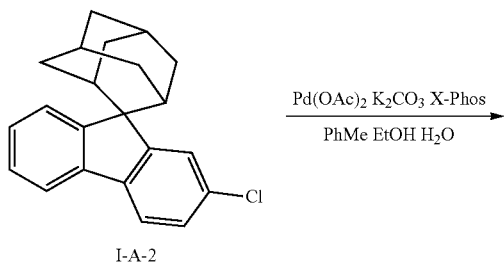

I-A-2

Pd(OAc)₂ K₂CO₃ X-Phos
PhMe EtOH H₂O
→

-continued

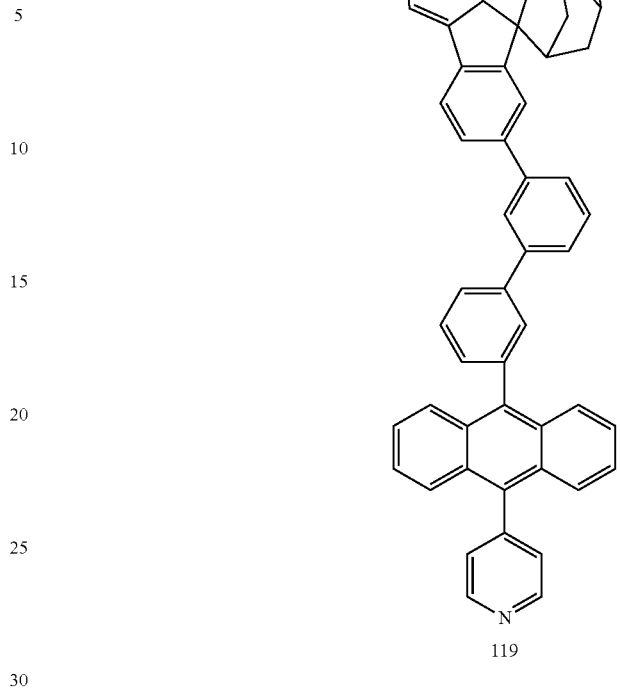

119

The intermediate III-A-3 (15.56 g, 28.1 mmol), the intermediate I-A-2 (8.992 g, 28.1 mmol), palladium acetate (0.0629 g, 0.281 mmol), 2-dicyclohexylphosphorus-2',4',6'-triisopropylbiphenyl (0.267 g, 0.56 mmol) and potassium carbonate (4.5 g, 42 mmol) were added into a mixture of toluene (40 mL), absolute ethanol (20 mL) and deionized water (10 mL), the mixture was heated to 80° C. under nitrogen atmosphere, and stirred for 2 h; then the reaction solution was cooled to room temperature and washed with water, magnesium sulfate was added for drying, filtration was carried out, and the solvent was removed from the filtrate under reduced pressure; the crude product was purified by recrystallization using a mixture of toluene and n-heptane to obtain compound 119 as a white solid (14.56 g, yield 75%).

LC-MS(ESI, pos.ion) m/z:692.32[M+H]⁺

Compounds 123, 141, and 157 were prepared by referring to the method of synthesizing compound 119 and using the raw material 1 in Table 5 instead of the intermediate III-A-3, and the intermediate I-A-2. The number, structure, raw material, synthesis yield, characterization data, etc. of compounds 123, 141, and 157 were shown in Table 5:

TABLE 5
Structure, preparation and characterization data of compounds
| Compound | Raw material 1 | Raw material 2 | Structure of compound | Yield (%) | Mass spectrum (m/z) (M + H)+ |
|---|---|---|---|---|---|
| Compound 123 | 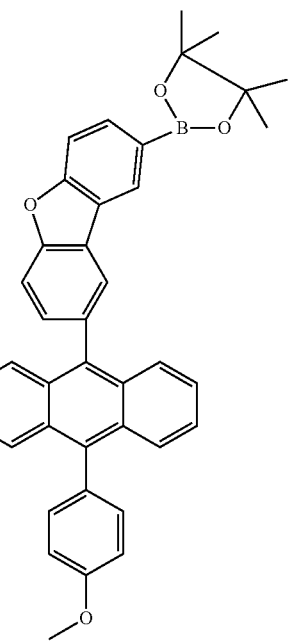 | 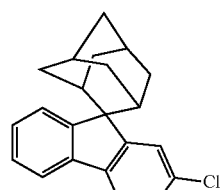 | 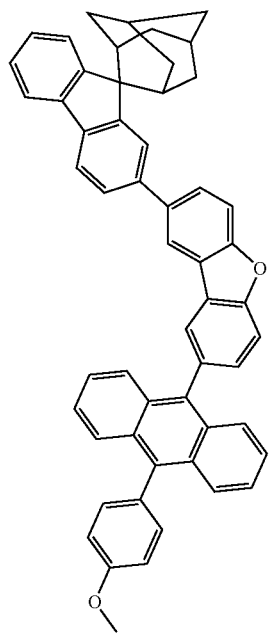 [SMILES: COc1ccc(-c2c3ccccc3c(-c3ccc4oc5ccc(-c6ccc7c(c6)C6(c8ccccc8-7)C7CC8CC9CC6C9(C8)C7)cc5c4c3)c3ccccc23)cc1] | 68 | 735.32 |
| Compound 141 | 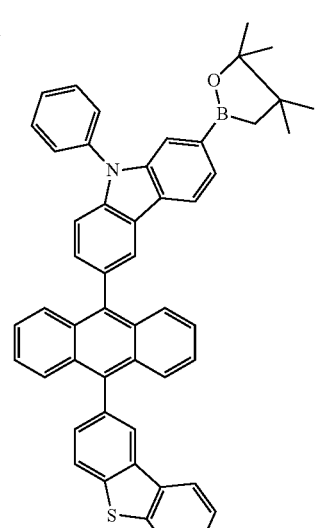 | | 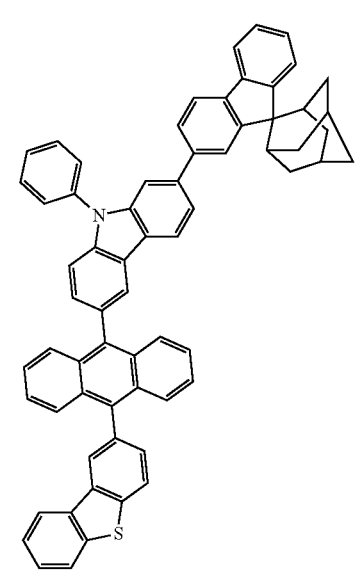 [SMILES: c1ccc(-n2c3ccc(-c4c5ccccc5c(-c5ccc6sc7ccccc7c6c5)c5ccccc45)cc3c3ccc(-c4ccc5c(c4)C4(c6ccccc6-5)C5CC6CC(C5)CC4C6)cc32)cc1] | 70 | 886.34 |

TABLE 5-continued

Structure, preparation and characterization data of compounds

| Compound | Raw material 1 | Raw material 2 | Structure of compound | Yield (%) | Mass spectrum (m/z) (M + H)+ |
|---|---|---|---|---|---|
| Compound 157 | | | | 69 | 937.47 |

Synthesis of Compound 112

Synthesis of Intermediate IV-A-1

(10-(4-(tert-butyl)phenyl)anthracen-9-yl) boronic acid (17.713 g, 50 mmol), 2-bromochlorobenzene (9.57 g, 50 mmol), tetrakis(triphenylphosphine)palladium(0.58 g, 0.5 mmol), potassium carbonate (7.35 g, 75 mmol), tetrabutylammonium chloride (0.278 g, 1 mmol), toluene (80 mL), ethanol (20 mL) and deionized water (20 mL) were added to a round bottom flask, the mixture was heated to 78° C. under nitrogen protection, and stirred for 8 hours; the reaction solution was cooled to room temperature, toluene (50 mL) was added for extraction, the organic phases were combined and dried with anhydrous magnesium sulfate, filtration was carried out, and the solvent was removed from the filtrate under reduced pressure; the obtained crude product was purified by silica column chromatography using n-heptane as a mobile phase, and then purified by recrystallization using a mixture of toluene and n-heptane to obtain intermediate IV-A-1 as a white solid (16.8 g, 80%).

Synthesis of Intermediate IV-A-2

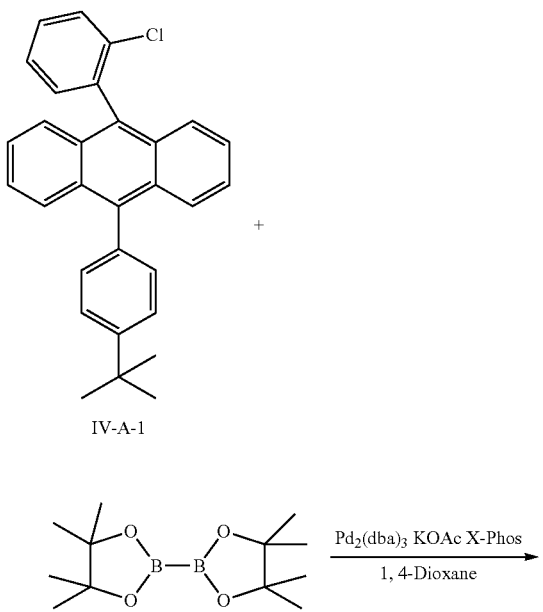

-continued

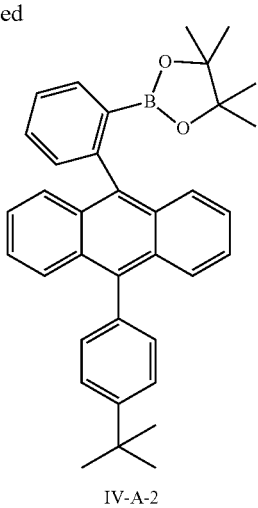

IV-A-2

The intermediate IV-A-1 (16.8 g, 40 mmol), pinacol diborate (9.92 g, 40 mmol), tris(dibenzylideneacetone)dipalladium (0.3663 g, 0.4 mmol), 2-dicyclohexylphosphorus-2',4',6'-triisopropylbiphenyl (0.38 g, 0.8 mmol) and potassium acetate (5.8 g, 60 mmol) were added into 1,4-dioxane (150 mL), the mixture was heated to 80° C. under nitrogen atmosphere, and stirred for 3 h; then the reaction solution was cooled to room temperature and washed with water, magnesium sulfate was added for drying, filtration was carried out, and the solvent was removed from the filtrate under reduced pressure; the obtained crude product was purified by recrystallization using toluene to obtain intermediate IV-A-2 as a white solid (15.56 g, yield 76%).

Synthesis of Intermediate IV-A-3

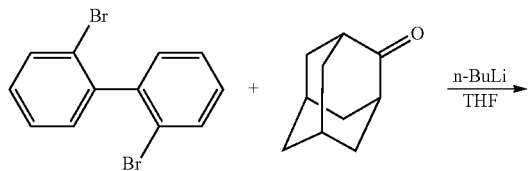

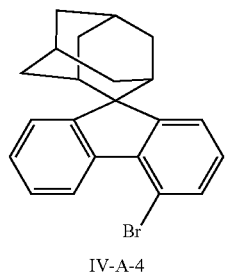

IV-A-3

Under the nitrogen atmosphere, 2-bromo-2-bromobiphenyl (14.2 g, 53 mmol) and THF (85.2 mL) were added into a 250 L three-necked round bottom flask and dissolved at −80° C. to −90° C. until clarification, n-BuLi (25.48 mL) was added dropwise slowly to the reaction system, the system reacted at the constant temperature of −80° C. to −90° C. for 50 min, then a mixture of adamantanone (6.378 g, 42.45 mmol) in THF (26 mL) was slowly added dropwise to the reaction system, and the resulting mixture reacted at the constant temperature of −80° C. to −90° C. for 1 h. After the reaction was completed, the temperature of reaction mixture was naturally raised to room temperature, 5% hydrochloric acid was poured into the reaction solution until pH<7, thorough stirring was carried out, then DCM was added for extraction. The organic phases were combined, washed with water until neutral and dried with anhydrous magnesium sulfate, the solvent was removed under reduced pressure after filtration, the obtained oily substance was added to a flask with n-heptane and heated for reflux to obtain a clear solution, and the clear solution was placed at −20° C. for recrystallization to obtain intermediate IV-A-3 as a white solid (12 g, 68%).

Synthesis of Intermediate IV-A-4

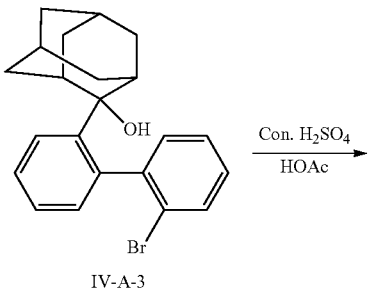

IV-A-4

Under the nitrogen atmosphere, the intermediate IV-A-3 (12.2 g, 36 mmol) was added to glacial acetic acid (150 mL) and the mixture was stirred at 50° C. to 60° C. After the reaction solution was completely clear, concentrated sulfuric acid (0.308 mL) was added dropwise, the reaction solution was continuously heated to 70° C. to 80° C. and stirred for 30 min, then the reaction solution was naturally cooled to room temperature, deionized water (200 L) was added, thorough stirring and filtration were carried out. The filter cake was washed with deionized water to be neutral, put into a vacuum drying oven for baking for 1 h and dissolved in DCM, anhydrous sodium sulfate was added for drying for 30 min, filtration was carried out, the solvent was removed under reduced pressure to obtain the crude product. n-heptane and anhydrous DCM was added to dissolve the crude product, and then the solution of crude product was placed at −20° C. for recrystallization, and the crystal was filtered and then dried in the vacuum drying oven to obtain intermediate IV-A-4 as a white solid (9.2 g, 80%).

Synthesis of Compound 112

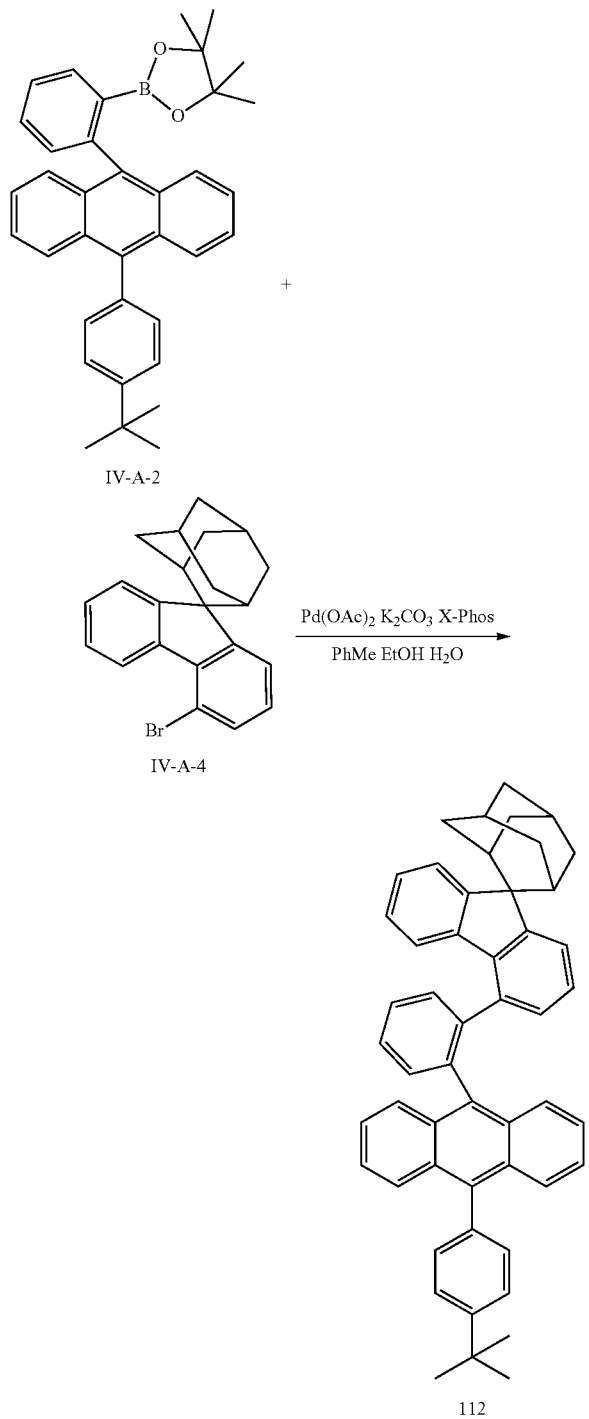

The intermediate IV-A-2 (15.56 g, 30.4 mmol), the intermediate IV-A-4 (11.1 g, 30.4 mmol), palladium acetate (0.068 g, 0.304 mmol), 2-dicyclohexylphosphorus-2',4',6'-triisopropylbiphenyl (0.288 g, 0.608 mmol) and potassium carbonate (4.38 g, 45.6 mmol) were added into a mixture of toluene (40 mL), absolute ethanol (20 mL) and deionized water (10 mL), the mixture was heated to 80° C. under nitrogen atmosphere, and stirred for 2 h; then the reaction solution was cooled to room temperature and washed with water, magnesium sulfate was added for drying, filtration was carried out, and the solvent was removed from the filtrate under reduced pressure; the crude product was recrystallized and purified using a toluene/n-heptane system to obtain compound 112 as a white solid (8.14 g, yield 40%).

LC-MS(ESI,pos.ion) m/z:671.36[M+H]$^+$

Synthesis of Compound 46

Synthesis of Intermediate V-A-1

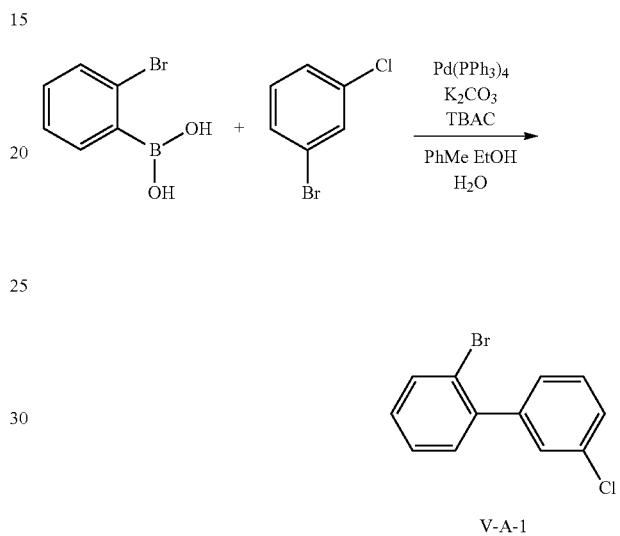

2-bromophenylboronic acid (10 g, 50 mmol), m-chlorobromobenzene (9.57 g, 50 mmol), tetrakis(triphenylphosphine)palladium(0.58 g, 0.5 mmol), potassium carbonate (7.35 g, 75 mmol), tetrabutylammonium chloride (0.278 g, 1 mmol), toluene (80 mL), ethanol (20 mL) and deionized water (20 mL) were added into a round bottom flask, heated to 78° C. under nitrogen atmosphere, and stirred for 8 hours; the reaction solution was cooled to room temperature, toluene (50 mL) was added for extraction, the organic phases were combined and dried with anhydrous magnesium sulfate, filtration was carried out, and the solvent was removed under reduced pressure; the obtained crude product was purified by silica column chromatography using n-heptane as a mobile phase, and then purified by recrystallization using a mixture of toluene and n-heptane to obtain intermediate V-A-1 as a white solid (16.8 g, 80%).

Synthesis of intermediate V-A-2

-continued

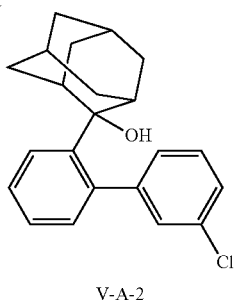

V-A-2

Under the nitrogen atmosphere, the intermediate V-A-1 (16.8 g, 62.8 mmol) and THF (852 mL) were added into a 2 L three-necked round bottom flask and dissolved at −80° C. to −90° C. until clarification, n-BuLi (5.26 mL) was added dropwise slowly to the reaction system, the system reacted at the constant temperature of −80° C. to −90° C. for 50 min, then a solution of adamantanone (9.43 g, 62.8 mmol) THF (160 mL) was slowly added dropwise to the reaction system, and the system reacted at the constant temperature of −80° C. to −90° C. for 1 h. After the reaction was over, the temperature of reaction mixture was naturally raised to room temperature, 5% hydrochloric acid was poured into the reaction solution until pH<7, thorough stirring was carried out, DCM was added for extraction. The organic phases were combined, washed with water until neutral and dried with anhydrous magnesium sulfate, the solvent was removed from the filtrate under reduced pressure after filtration, the obtained oily substance was added to a flask with n-heptane and heated for reflux to obtain a clear solution, and the clear solution was placed at −20° C. for recrystallization to obtain intermediate V-A-2 as a white solid (14.9 g, yield 70%).

Synthesis of Intermediate V-A-3

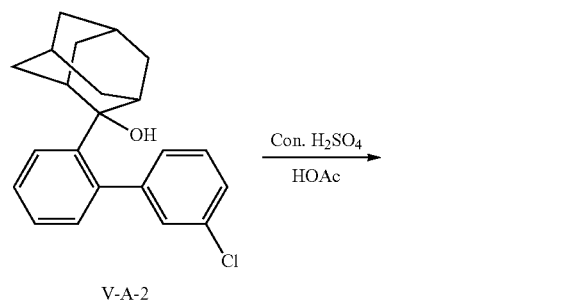

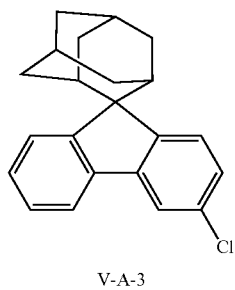

V-A-3

Under the nitrogen atmosphere, the intermediate V-A-2 (14.9 g, 43.9 mmol) was added to glacial acetic acid (150 L), and the mixture was stirred at 50° C. to 60° C. After the reaction solution was completely clear, concentrated sulfuric acid (0.5 mL) was added dropwise, the reaction solution was continuously heated to 70° C. to 80° C. and stirred for 30 min, then the reaction solution was naturally cooled to room temperature, deionized water (200 mL) was added, thorough stirring and filtration were carried out. The filter cake was washed with deionized water to be neutral, put into a vacuum drying oven for baking for 1 h and dissolved in DCM, anhydrous sodium sulfate was added for drying for 30 min, filtration was carried out, the solvent was removed under reduced pressure to obtain the crude product. n-heptane and anhydrous was added to dissolve the crude product, and then the solution of crude product was placed at −20° C. for recrystallization, and the crystal was filtered and then dried in the vacuum drying oven to obtain intermediate V-A-3 as a white solid (14 g, yield 90%).

Synthesis of Intermediate V-A-4

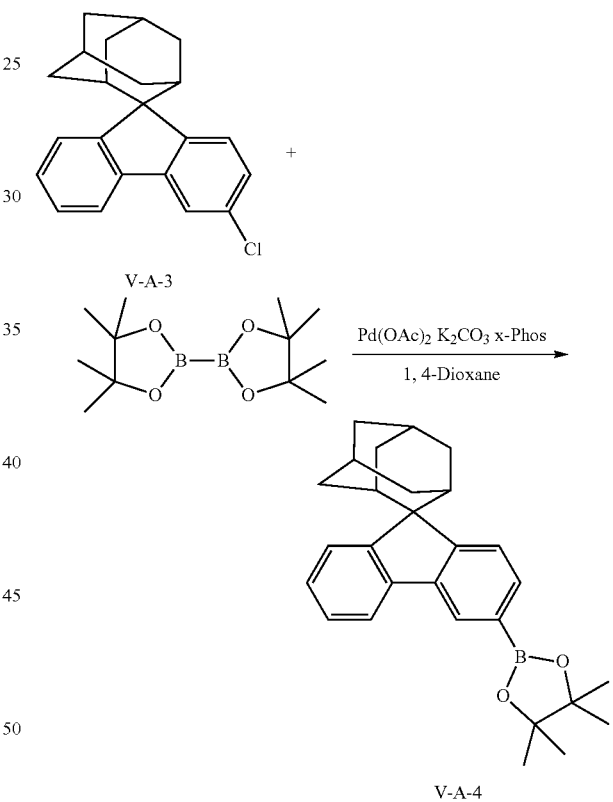

The intermediate V-A-3 (14 g, 44 mmol), pinacol diborate (11.2 g, 44 mmol), tris(dibenzylideneacetone)dipalladium (0.403 g, 0.44 mmol), 2-dicyclohexylphosphorus-2',4',6'-triisopropylbiphenyl (0.418 g, 0.88 mmol) and potassium acetate (8.624 g, 88 mmol) were added into 1,4-dioxane (140 mL), the mixture was heated to 80° C. under nitrogen atmosphere, and stirred for 3 h; then the reaction solution was cooled to room temperature and washed with water, anhydrous magnesium sulfate was added for drying, filtration was carried out, and the solvent was removed from the filtrate under reduced pressure; the crude product was purified by recrystallization using toluene to obtain intermediate V-A-4 as a white solid (14.13 g, yield 78%).

Synthesis of Intermediate V-A

Synthesis of Compound 46

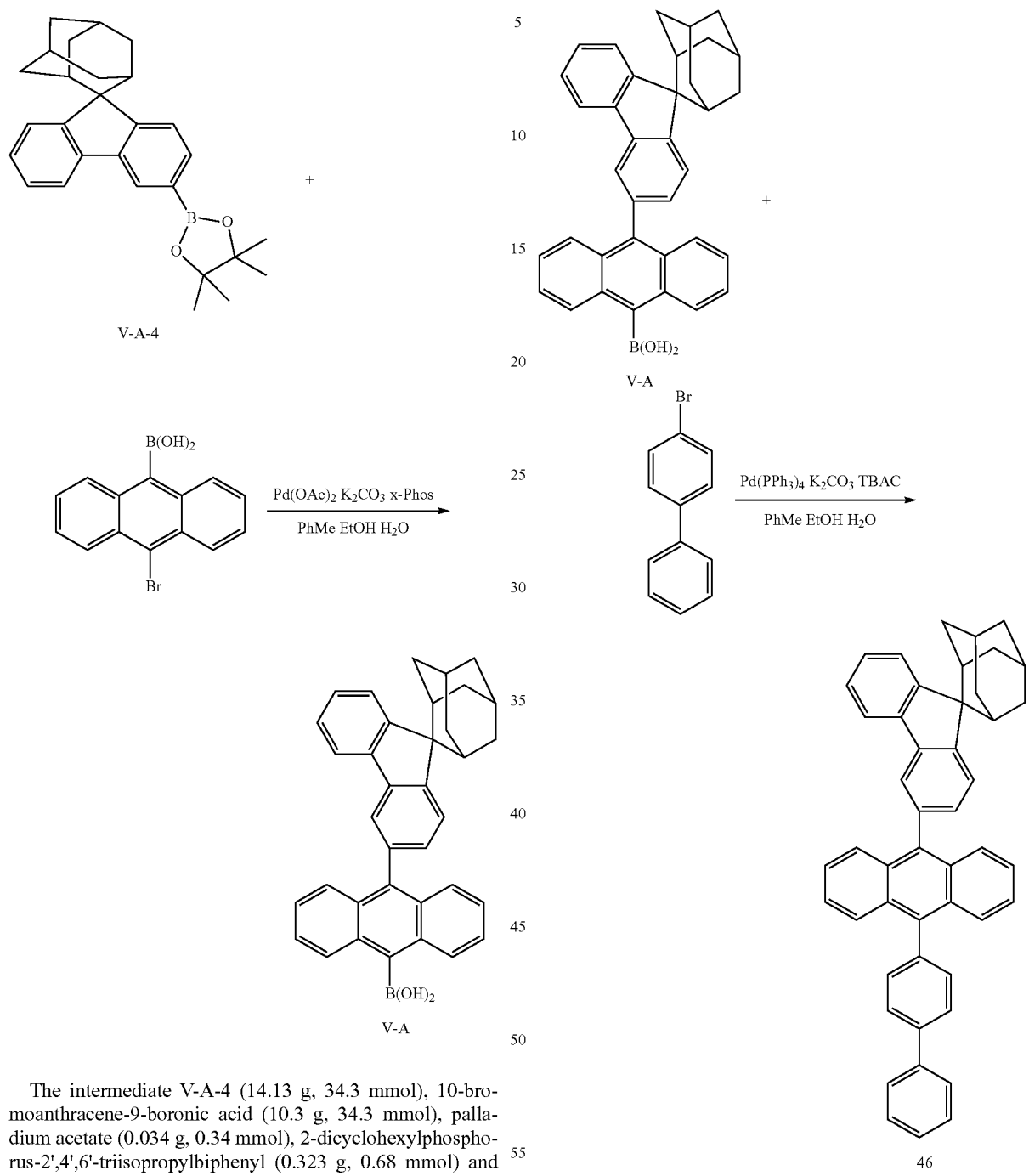

The intermediate V-A-4 (14.13 g, 34.3 mmol), 10-bromoanthracene-9-boronic acid (10.3 g, 34.3 mmol), palladium acetate (0.034 g, 0.34 mmol), 2-dicyclohexylphosphorus-2',4',6'-triisopropylbiphenyl (0.323 g, 0.68 mmol) and potassium carbonate (6.7 g, 68.6 mmol) were added into a mixture of toluene (40 mL), absolute ethanol (20 mL) and deionized water (10 mL), the reaction mixture was heated to 80° C. under nitrogen atmosphere, and stirred for 2 h; then the reaction solution was cooled to room temperature and washed with water, magnesium sulfate was added for drying, filtration was carried out, and the solvent was removed from the filtrate under reduced pressure; the obtained crude product was purified by recrystallization using the mixture of dichloromethane and n-heptane to obtain intermediate V-A as a white solid (16.8 g, yield 85%).

The intermediate V-A (8 g, 15.8 mmol), 4-bromobiphenyl (3.68 g, 15.8 mmol), tetrakis(triphenylphosphine)palladium (0.365 g, 0.316 mmol), potassium carbonate (4.8 g, 3.5 mmol), and tetrabutylammonium bromide (0.25 g, 0.79 mmol) were added to a three-necked flask respectively, toluene (40 mL), ethanol (20 mL) and water (10 mL) were added into the flask, the resulting mixture was heated to reflux at 80° C. and stirred for 12 h, extraction was carried out using $CH_2Cl_2$ and water when the reaction was over. The organic phase was dried with anhydrous $MgSO_4$ and filtered, the organic layer was concentrated, and the obtained crude product was purified by silica column chromatography to obtain compound 46 as a white solid (6.79 g, yield 70%).

LC-MS(ESI, pos.ion) m/z:615.3[M+H]$^+$

Compounds 47 and 48 were prepared by referring to the method of synthesizing compound 46 and using the raw material 2 instead of 4-bromobiphenyl. Wherein the number, structure, raw material, synthesis yield of the last step, mass spectrum data, etc. of compounds 47 and 48 were shown in Table 6:

Preparation and Evaluation of Organic Electroluminescent Device

Example 1

An anode is prepared by the following process: an ITO substrate (manufactured by Corning) with a thickness of 1500 Å was cut into a size of 40 mm×40 mm×0.7 mm, and prepared by photolithography into an experimental substrate with cathode, anode and insulating layer patterns, and sur-

TABLE 6

Structure, preparation and characterization data of compounds

| Compound | Intermediate V-A | Raw material 2 | Structure of compound | Yield (%) | Mass spectrum (m/z) (M + H)$^+$ |
|---|---|---|---|---|---|
| 47 | | 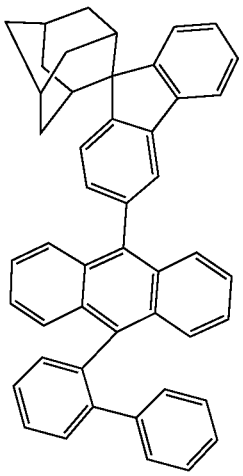 | 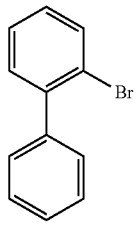 [SMILES: Brc1ccccc1-c1ccccc1] | 68% | 615.30 |
| 48 | 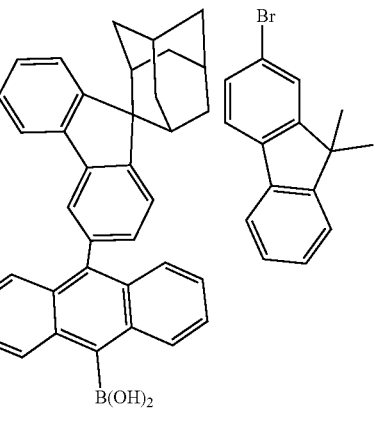 B(OH)$_2$ V-A | 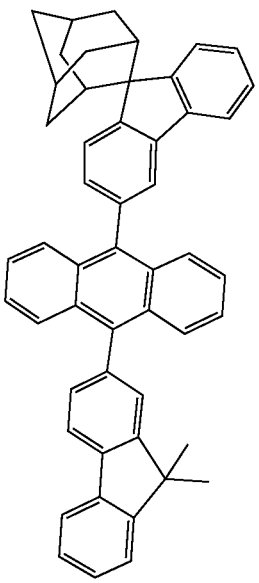 [SMILES: CC1(C)c2ccccc2-c2ccc(-c3c4ccccc4c(-c4ccc5c(c4)-c4ccccc4C54C5CC6CC(C5)CC4C6)c4ccccc34)cc21] Br | | 65% | 655.33 | face treatment was carried out using ultraviolet ozone and $O_2:N_2$ plasma to increase the work function of the anode (experimental substrate) and remove scum.

$F_4$-TCNQ was vacuum-evaporated on the experimental substrate (anode) to form a hole injection layer (HIL) with a thickness of 100 Å, and compound NPB was vacuum-evaporated on the hole injection layer to form a hole transport layer with a thickness of 850 Å (HTL).

Compound PAPB was evaporated on the HTL as an electron blocking layer (EBL) with a thickness of 100 Å.

Compound 1 was used as the host on the EBL, and doped with BD-1 according to a film thickness ratio of 100:3 to form electroluminescent layer (EML) with a thickness of 200 Å.

Compound ET-06 and LiQ were evaporated on the EML as an electron transport layer (ETL) according to a film thickness ratio of 1:1, with a thickness of 350 Å.

Metal Yb is evaporated on the ETL as an electron injection layer (EIL) with a thickness of 10 Å.

A silver (Ag) and magnesium (Mg) doped film layer with a film thickness ratio of 10:1 was evaporated on the EIL as a cathode with a thickness of 110 Å.

Compound CP-5 was evaporated on the cathode as a light extraction layer (CPL) with a thickness of 630 Å to form an organic capping layer (CPL), thereby completing the manufacture of an organic electroluminescent device.

Example 2-Example 30

The organic electroluminescent devices were manufactured by the same method as that in Example 1, except that compounds shown in Table 7 below were used instead of compound 1 when the electroluminescent layer was formed.

Comparative Example 1

The organic electroluminescent device was manufactured by the same method as that in Example 1, except that compound A shown in Table 7 below was used instead of compound 1 when the electroluminescent layer was formed.

Comparative Example 2

The organic electroluminescent device was manufactured by the same method as that in Example 1, except that compound B shown in Table 7 below was used instead of compound 1 when the electroluminescent layer was formed.

Comparative Example 3

The organic electroluminescent device was manufactured by the same method as that in Example 1, except that compound C shown in Table 7 below was used instead of compound 1 when the electroluminescent layer was formed.

Comparative Example 4

The organic electroluminescent device was manufactured by the same method as that in Example 1, except that compound D shown in Table 7 below was used instead of compound 1 when the electroluminescent layer was formed.

The material structures used in the above examples and comparative examples are shown in the following table:

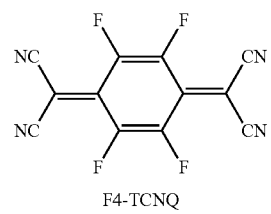

F4-TCNQ

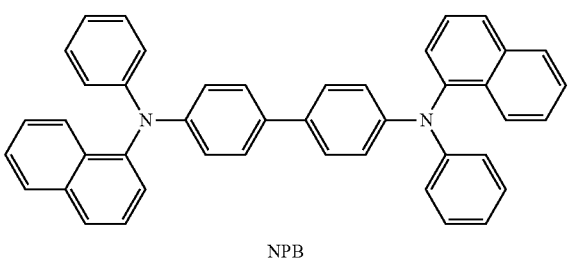

NPB

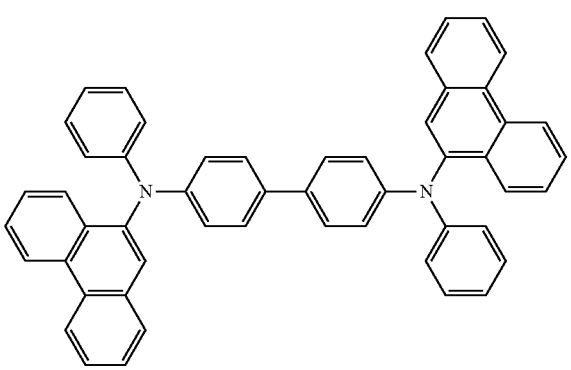

PAPB

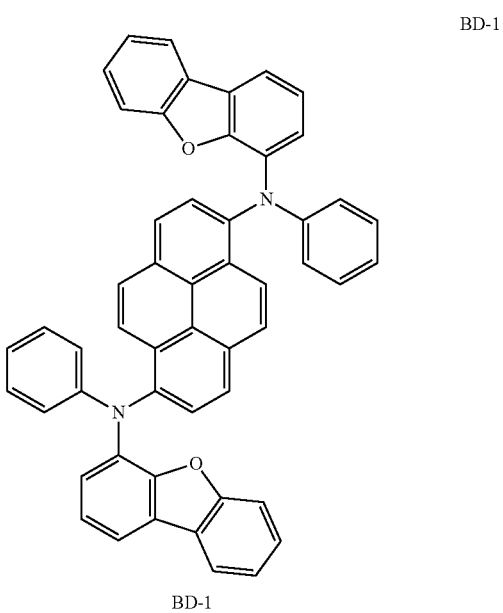

BD-1

ET-06
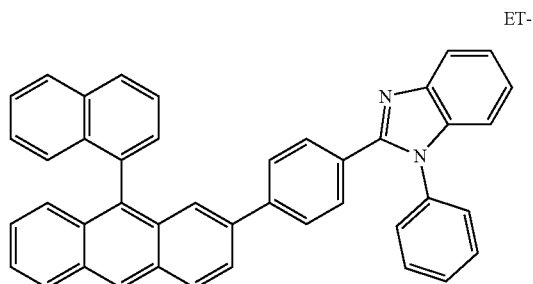
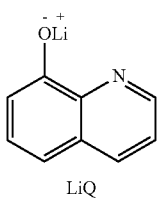
LiQ
CP-5
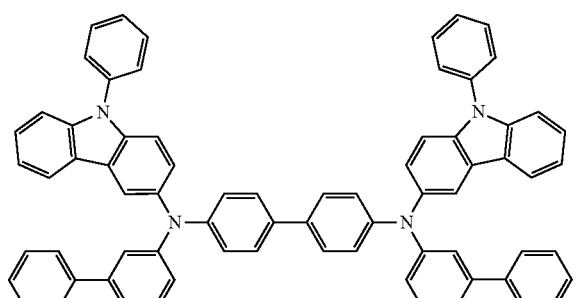
Compound A
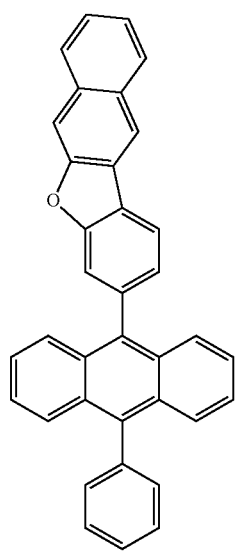
Compound B
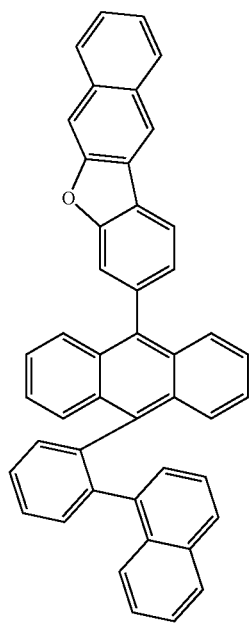
Compound C
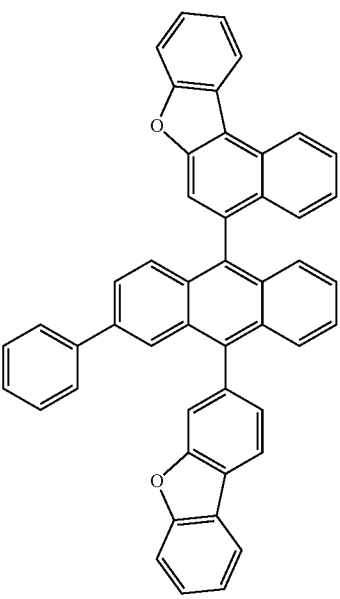
Compound D
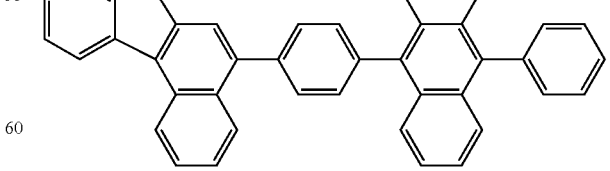
The performances of the organic electroluminescent devices manufactured as above were analyzed under the condition of 20 mA/cm², and the results were shown in Table 7.

TABLE 7

Performance test results of organic electroluminescent devices

| Example | Compound | Driving voltage (V) | Current efficiency (Cd/A) | Power efficiency (1 m/W) | Color coordinates CIEx | Color coordinates CIEy | External quantum efficiency EQE (%) | T95 life (h) |
|---|---|---|---|---|---|---|---|---|
| Example 1 | Compound 1 | 4.02 | 6.70 | 5.11 | 0.140 | 0.050 | 13.45 | 189 |
| Example 2 | Compound 2 | 4.00 | 6.69 | 5.21 | 0.140 | 0.050 | 13.64 | 183 |
| Example 3 | Compound 3 | 3.96 | 6.67 | 5.13 | 0.140 | 0.050 | 13.31 | 184 |
| Example 4 | Compound 4 | 4.02 | 6.66 | 5.24 | 0.140 | 0.050 | 13.78 | 189 |
| Example 5 | Compound 5 | 3.93 | 6.65 | 5.21 | 0.140 | 0.050 | 13.41 | 187 |
| Example 6 | Compound 6 | 4.02 | 6.65 | 5.23 | 0.140 | 0.050 | 13.76 | 182 |
| Example 7 | Compound 7 | 4.04 | 6.64 | 5.26 | 0.140 | 0.050 | 13.39 | 202 |
| Example 8 | Compound 8 | 4.00 | 6.63 | 5.21 | 0.140 | 0.050 | 13.64 | 202 |
| Example 9 | Compound 9 | 3.97 | 6.63 | 5.26 | 0.140 | 0.050 | 13.41 | 207 |
| Example 10 | Compound 10 | 3.95 | 6.62 | 5.28 | 0.140 | 0.050 | 13.39 | 213 |
| Example 11 | Compound 11 | 3.91 | 6.69 | 5.32 | 0.140 | 0.050 | 13.62 | 223 |
| Example 12 | Compound 12 | 4.00 | 6.54 | 5.17 | 0.140 | 0.050 | 13.02 | 158 |
| Example 13 | Compound 13 | 4.04 | 6.52 | 5.11 | 0.140 | 0.050 | 12.98 | 185 |
| Example 14 | Compound 14 | 3.93 | 6.52 | 5.11 | 0.140 | 0.050 | 13.14 | 184 |
| Example 15 | Compound 15 | 4.02 | 6.52 | 5.26 | 0.140 | 0.050 | 13.31 | 220 |
| Example 16 | Compound 16 | 3.94 | 6.51 | 5.29 | 0.140 | 0.050 | 13.14 | 215 |
| Example 17 | Compound 17 | 3.98 | 6.51 | 5.25 | 0.140 | 0.050 | 13.68 | 182 |
| Example 18 | Compound 18 | 3.95 | 6.50 | 5.17 | 0.140 | 0.050 | 13.37 | 189 |
| Example 19 | Compound 81 | 3.95 | 6.47 | 5.24 | 0.140 | 0.050 | 13.56 | 186 |
| Example 20 | Compound 82 | 3.96 | 6.47 | 5.17 | 0.140 | 0.050 | 13.41 | 187 |
| Example 21 | Compound 119 | 3.99 | 6.39 | 5.08 | 0.140 | 0.050 | 13.27 | 168 |
| Example 22 | Compound 123 | 3.98 | 6.47 | 5.11 | 0.140 | 0.050 | 13.31 | 180 |
| Example 23 | Compound 141 | 4.00 | 6.45 | 5.23 | 0.140 | 0.050 | 13.70 | 208 |
| Example 24 | Compound 157 | 4.01 | 6.49 | 5.20 | 0.140 | 0.050 | 13.66 | 181 |
| Example 25 | Compound 112 | 4.05 | 6.49 | 5.17 | 0.140 | 0.050 | 13.72 | 188 |
| Example 26 | Compound 46 | 4.01 | 6.49 | 5.21 | 0.140 | 0.050 | 13.68 | 188 |
| Example 27 | Compound 47 | 3.91 | 6.53 | 5.13 | 0.140 | 0.050 | 13.14 | 188 |
| Example 28 | Compound 48 | 3.95 | 6.49 | 5.15 | 0.140 | 0.050 | 13.31 | 182 |
| Example 29 | Compound 168 | 3.99 | 6.31 | 4.80 | 0.140 | 0.050 | 13.27 | 168 |
| Example 30 | Compound 201 | 3.99 | 6.33 | 5.08 | 0.140 | 0.050 | 13.27 | 170 |
| Comparative Example 1 | Compound A | 4.16 | 5.57 | 4.21 | 0.14 | 0.05 | 11.46 | 116 |
| Comparative Example 2 | Compound B | 4.17 | 5.57 | 4.19 | 0.14 | 0.05 | 11.47 | 115 |
| Comparative Example 3 | Compound C | 4.18 | 5.31 | 3.99 | 0.14 | 0.05 | 10.92 | 108 |
| Comparative Example 4 | Compound D | 4.19 | 5.46 | 4.09 | 0.14 | 0.05 | 11.23 | 128 |

According to the results in Table 7 above, it can be seen that, the compounds 1-18, 81, 82, 119, 123, 141, 157, 112, 46 to 48, 168, and 201 as host materials for blue electroluminescent layer (EML), are compared with the compounds A, B, C, and D used in of comparative example 1 to comparative example 4, the compounds 1 to 18, 81 and 82, compounds 119, 123, 141, 157, 112, 46 to 48, 168 and 201 used in the disclosure as the host material for the blue electroluminescent layer, the driving voltage of the above organic electroluminescent device is reduced by at least 0.11 V, the current efficiency (Cd/A) is increased by at least 13.29%, and the power efficiency (1 m/W) is increased by at least 16.63%, the external quantum efficiency is increased by at least 13.16%, and the lifetime is increased by at least 30%.

In the disclosure, the adamantane spirofluorenyl and the anthryl are linked and combined to obtain a novel compound for organic electroluminescent devices; in the compound, both the adamantane spirofluorene and the anthryl have high hole mobility, when the two are linked, the overall hole mobility of the molecule is further improved, which is beneficial to reduce the working voltage of the device and improve the luminous efficiency; the adamantane spirofluoren is introduced into the anthracene compound light-emitting host to improve the overall molecular weight. The electron density, thereby increasing the carrier transmission rate, the introduction of another aromatic group on the central anthryl enhances the molecular asymmetry, making the material difficult to crystallize and improving device stability. When this type of material is used as the host material of an organic electroluminescent device, the device can have a higher luminous efficiency and a long life.

The invention claimed is:

1. An organic compound, wherein the structure of the organic compound is as shown in chemical formula 1:

Formula 1

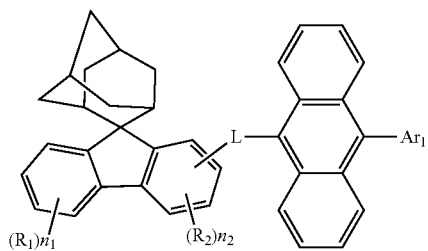

wherein L is selected from single bond, substituted or unsubstituted alkylene with 1 to 20 carbon atoms, substituted or unsubstituted arylene with 6 to 30 carbon atoms, substituted or unsubstituted heteroarylene with 3 to 30 carbon atoms, and substituted or unsubstituted cycloalkylene with 3 to 20 carbon atoms;

$Ar_1$ is selected from substituted or unsubstituted cycloalkyl with 3 to 20 carbon atoms, substituted or unsubstituted aryl with 6 to 40 carbon atoms, and substituted or unsubstituted heteroaryl with 3 to 30 carbon atoms;

each $R_1$ is the same or different, each $R_2$ is the same or different, and $R_1$ and $R_2$ are each independently selected from deuterium; fluorine; chlorine; bromine; cyano; aryl with 6 to 20 carbon atoms, which are optionally substituted by 0, 1, 2, 3, 4 or 5 substituents selected from deuterium, fluorine, cyano, methyl, ethyl, isopropyl, tert-butyl, and trimethylsilyl; heteroaryl with 3 to 18 carbon atoms; alkylsilyl with 3 to 18 carbon atoms; triarylsilyl with 6 to 18 carbon atoms; alkyl with 1 to 12 carbon atoms, alkoxy with 1 to 12 carbon atoms; haloalkyl with 1 to 12 carbon atoms; alkenyl with 2 to 12 carbon atoms; cycloalkyl with 3 to 10 carbon atoms; heterocycloalkyl with 2 to 12 carbon atoms; alkylamino with 1 to 10 carbon atoms; alkylthio with 1 to 10 carbon atoms; aryloxy with 6 to 18 carbon atoms; and arylthio with 6 to 18 carbon atoms;

$n_1$ is the number of substituent $R_1$, $n_1$ is selected from 0, 1, 2, 3 and 4, and when $n_1$ is greater than 1, any two $R_1$ are the same or different; $n_2$ is the number of substituent $R_2$, $n_2$ is selected from 0, 1, 2 and 3, and when $n_2$ is greater than 1, any two $R_2$ are the same or different;

the substituents in $Ar_1$ and L are the same or different from each other, and are each independently selected from deuterium; fluorine; chlorine; bromine; cyano; aryl with 6 to 20 carbon atoms, which are optionally substituted by 0, 1, 2 or 3 substituents selected from deuterium, fluorine, cyano, methyl, and trimethylsilyl; heteroaryl with 3 to 18 carbon atoms; alkylsilyl with 3 to 18 carbon atoms; arylsilyl with 6 to 18 carbon atoms; alkyl with 1 to 12 carbon atoms; alkoxy with 1 to 12 carbon atoms; haloalkyl with 1 to 12 carbon atoms; alkenyl with 2 to 12 carbon atoms; cycloalkyl with 3 to 10 carbon atoms; heterocycloalkyl with 2 to 12 carbon atoms; alkylamino with 1 to 10 carbon atoms; alkylthio with 1 to 10 carbon atoms; aryloxy with 6 to 18 carbon atoms; and an arylthio with 6 to 18 carbon atoms;

the organic compound is not

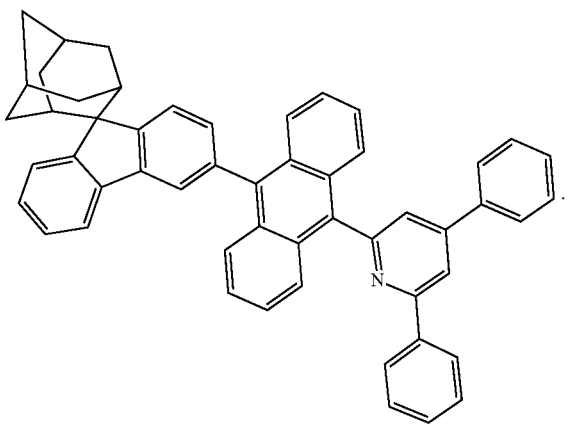 [SMILES: c1ccc(-c2cc(-c3ccccc3)nc(-c3c4ccccc4c(-c4ccc5c(c4)-c4ccccc4C54C5CC6CC(C5)CC4C6)c4ccccc34)c2)cc1]

2. The organic compound according to claim 1, wherein each $R_1$ is the same or different, each $R_2$ is the same or different, and $R_1$ and $R_2$ are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, triarylsilyl with 6 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylamino with 1 to 10 carbon atoms, alkylthio with 1 to 10 carbon atoms, aryloxy with 6 to 18 carbon atoms, and arylthio with 6 to 18 carbon atoms;

the substituents in $Ar_1$ and L are the same or different from each other, and are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, arylsilyl with 6 to 18 carbon atoms, alkyl with 1 to 12 carbon atoms, alkoxy with 1 to 12 carbon atoms, haloalkyl with 1 to 12 carbon atoms, alkenyl with 2 to 12 carbon atoms, cycloalkyl with 3 to 10 carbon atoms, heterocycloalkyl with 2 to 12 carbon atoms, alkylamino with 1 to 10 carbon atoms, alkylthio with 1 to 10 carbon atoms, aryloxy with 6 to 18 carbon atoms, and arylthio with 6 to 18 carbon atoms.

3. The organic compound according to claim 1, wherein each $R_1$ is the same or different, each $R_2$ is the same or different, and $R_1$ and $R_2$ are each independently selected from deuterium, fluorine, chlorine, bromine, cyano, alkyl with 1 to 6 carbon atoms, haloalkyl with 1 to 4 carbon atoms, alkoxy with 1 to 4 carbon atoms, alkylamino with 1 to 4 carbon atoms, alkylthio with 1 to 4 carbon atoms, aryl with 6 to 15 carbon atoms, heteroaryl with 3 to 15 carbon atoms, trialkylsilyl with 3 to 8 carbon atoms, triphenylsilyl, cycloalkyl with 5 to 10 carbon atoms, aryloxy with 6 to 12 carbon atoms, and arylthio with 6 to 12 carbon atoms.

4. The organic compound according to claim 1, wherein L is selected from substituted or unsubstituted arylene with 6 to 25 ring-forming carbon atoms, and substituted or unsubstituted heteroarylene with 3 to 18 ring-forming carbon atoms; the substituents in L are the same or different from each other, and are each independently selected from deuterium, fluorine, chlorine, bromine, cyano, alkyl with 1 to 6 carbon atoms, haloalkyl with 1 to 4 carbon atoms, alkoxy with 1 to 4 carbon atoms, alkylamino with 1 to 4 carbon atoms, alkylthio with 1 to 4 carbon atoms, aryl with 6 to 15 carbon atoms, heteroaryl with 3 to 15 carbon atoms, trialkylsilyl with 3 to 8 carbon atoms, triphenylsilyl, cycloalkyl with 5 to 10 carbon atoms, aryloxy with 6 to 12 carbon atoms, and arylthio with 6 to 12 carbon atoms.

5. The organic compound according to claim 1, wherein L is selected from single bond or the group consisting of groups represented by chemical formula j-1 to chemical formula j-13:

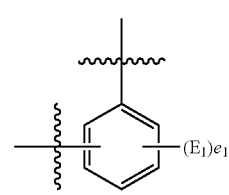

j-1

-continued

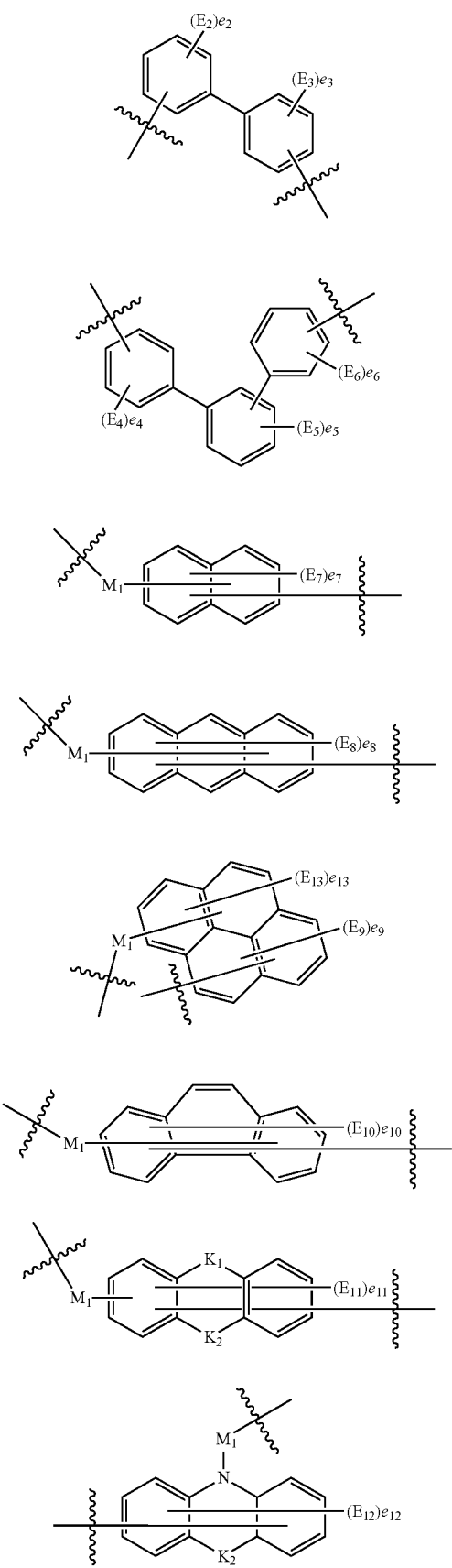

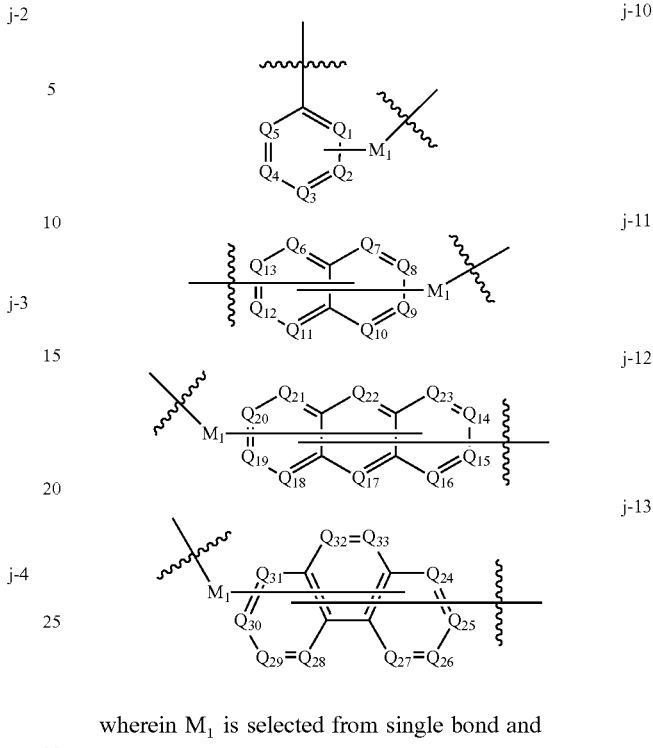

wherein $M_1$ is selected from single bond and

;

$Q_1$ to $Q_5$ are each independently selected from N and $C(F_1)$, and at least one of $Q_1$ to $Q_5$ is selected from N; when two or more of $Q_1$ to $Q_5$ are selected from $C(F_1)$, any two $F_1$ are the same or different;

$Q_6$ to $Q_{13}$ are each independently selected from N and $C(F_2)$, and at least one of $Q_6$ to $Q_{13}$ is selected from N; when two or more of $Q_6$ to $Q_{13}$ are selected from $C(F_2)$, any two $F_2$ are the same or different;

$Q_{14}$ to $Q_{23}$ are each independently selected from N and $C(F_3)$, and at least one of $Q_{14}$ to $Q_{23}$ is selected from N; when two or more of $Q_{14}$ to $Q_{23}$ are selected from $C(F_3)$, any two $F_3$ are the same or different;

$Q_{24}$ to $Q_{33}$ are each independently selected from N and $C(F_4)$, and at least one of $Q_{24}$ to $Q_{33}$ is selected from N; when two or more of $Q_{24}$ to $Q_{33}$ are selected from $C(F_4)$, any two $F_4$ are the same or different;

$E_1$ to $E_{14}$ and $F_1$ to $F_4$ are each independently selected from: hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, a heterocycloalkyl with 2 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms; $e_r$ is the number of substituents $E_r$, and r is any integer from 1 to 14; when r is selected from 1, 2, 3, 4, 5, 6, 9, 13 and 14, $e_r$ is selected from 1, 2, 3 and 4; when r is selected from 7 and 11, $e_r$ is selected from 1, 2, 3, 4, 5 and 6; when r is 12, $e_r$ is selected from 1, 2, 3, 4, 5, 6 and 7; when r is selected from 8 and 10, $e_r$ is selected from 1, 2, 3, 4, 5, 6, 7 and 8; when $e_r$ is greater than 1, any two $E_r$ are the same or different;

$K_1$ is selected from O, S, Se, $N(E_{15})$, $C(E_{16}E_{17})$, and $Si(E_{16}E_{17})$; wherein $E_{15}$, $E_{16}$, and $E_{17}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms, and heterocycloalkyl with 2 to 10 carbon atoms, or $E_{16}$ and $E_{17}$ are connected to each other to form a saturated or unsaturated 5- to 13-membered aliphatic ring together with atoms connected to the both;

$K_2$ is selected from single bond, O, S, Se, $N(E_{18})$, $C(E_{19}E_{20})$, and $Si(E_{19}E_{20})$; wherein $E_{18}$, $E_{19}$, and $E_{20}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms, and heterocycloalkyl with 2 to 10 carbon atoms, or $E_{19}$ and $E_{20}$ are connected to each other to form a saturated or unsaturated 5- to 13-membered aliphatic ring together with atoms connected to the both.

6. The organic compound according to claim 1, wherein L is selected from single bond, and unsubstituted $W_1$ or substituted $W_1$, wherein the unsubstituted $W_1$ is selected from the group consisting of the following substituents:

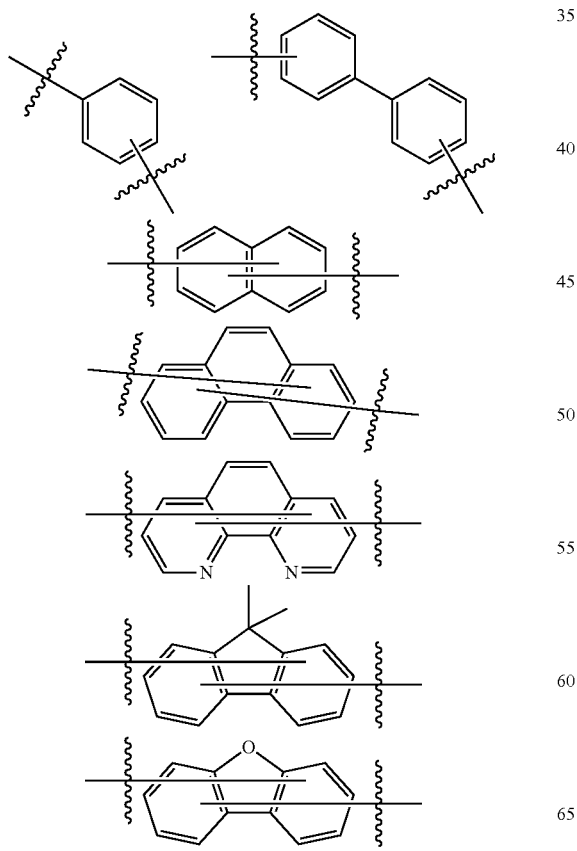

-continued

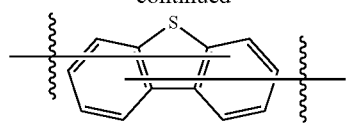

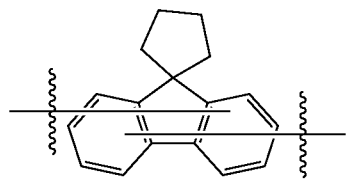

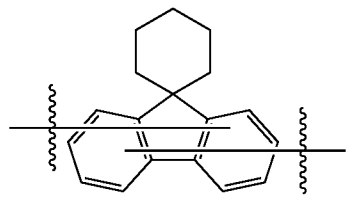

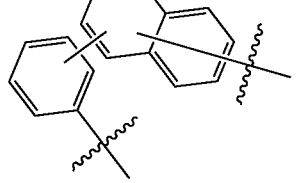

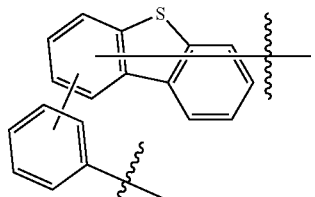

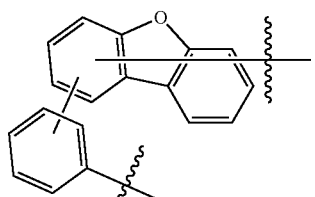

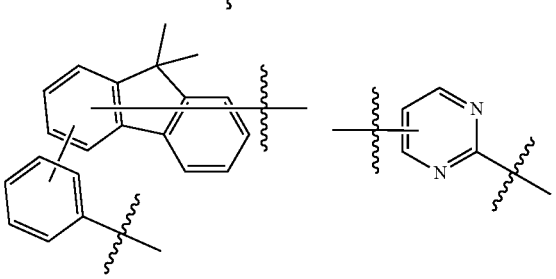

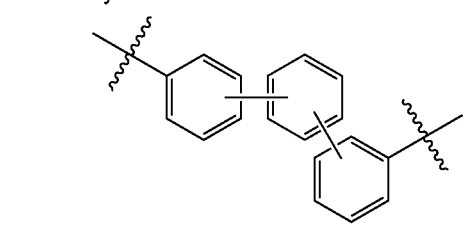

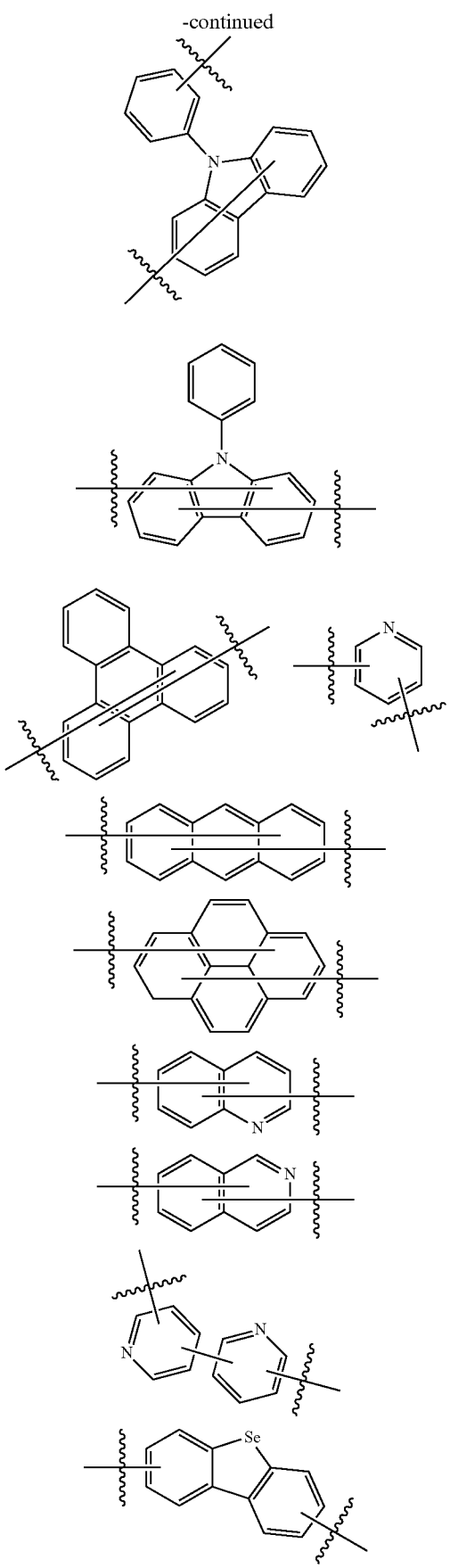

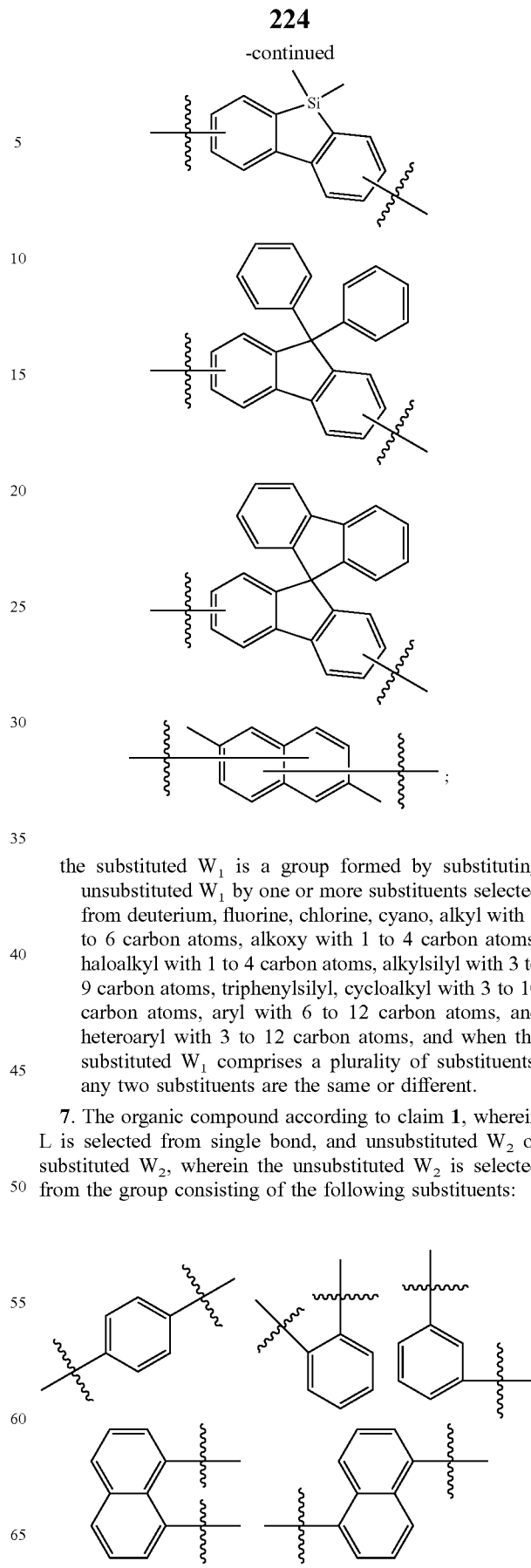

the substituted $W_1$ is a group formed by substituting unsubstituted $W_1$ by one or more substituents selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, triphenylsilyl, cycloalkyl with 3 to 10 carbon atoms, aryl with 6 to 12 carbon atoms, and heteroaryl with 3 to 12 carbon atoms, and when the substituted $W_1$ comprises a plurality of substituents, any two substituents are the same or different.

7. The organic compound according to claim 1, wherein L is selected from single bond, and unsubstituted $W_2$ or substituted $W_2$, wherein the unsubstituted $W_2$ is selected from the group consisting of the following substituents:

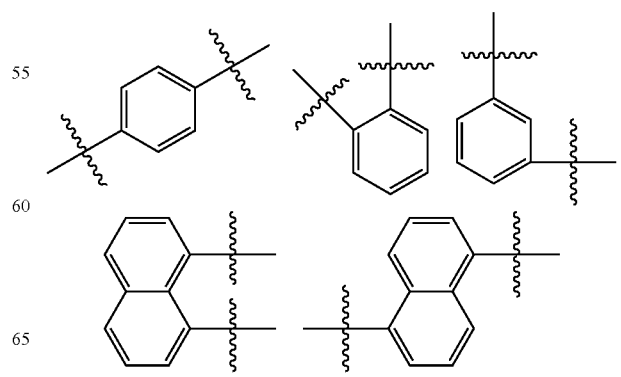

225
-continued
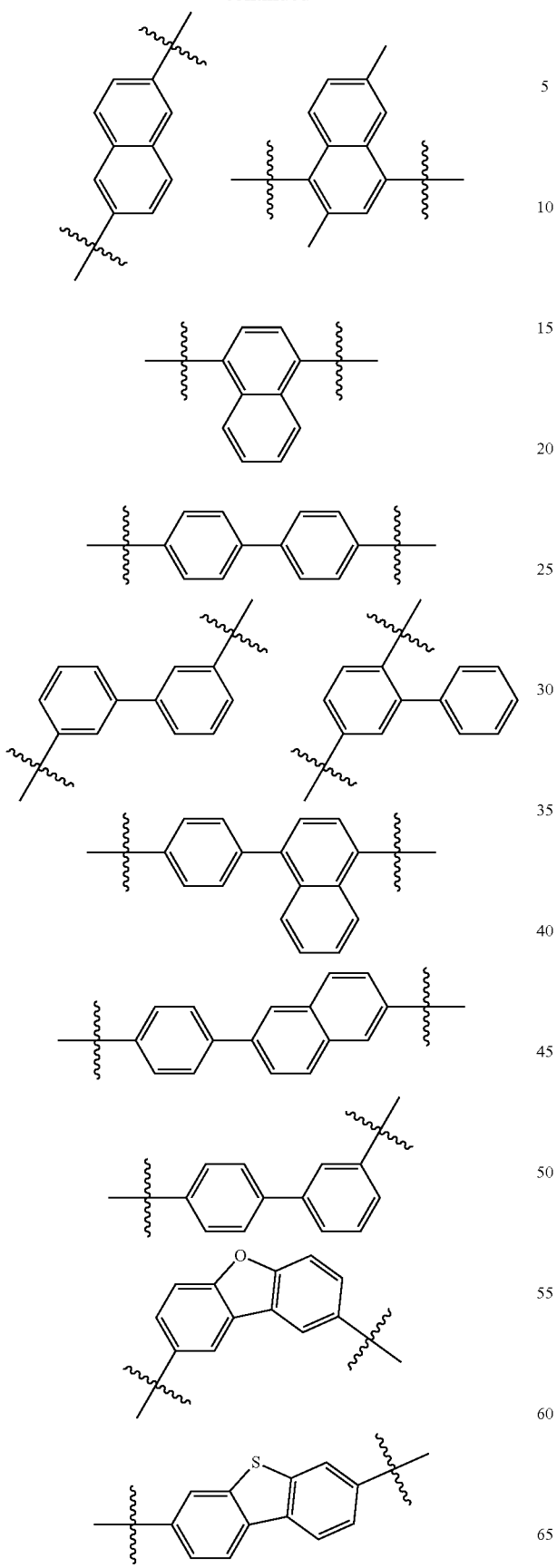
226
-continued
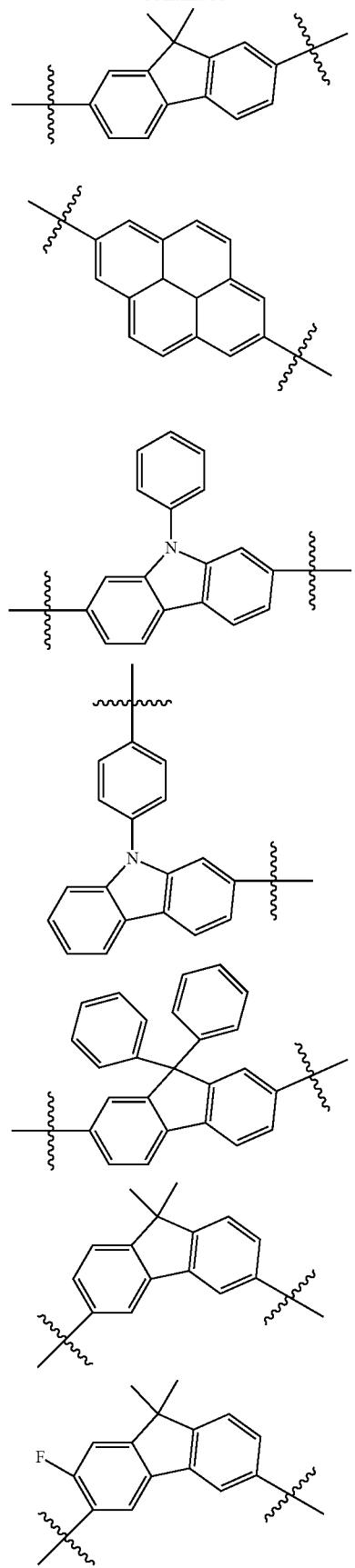

227
-continued
228
-continued
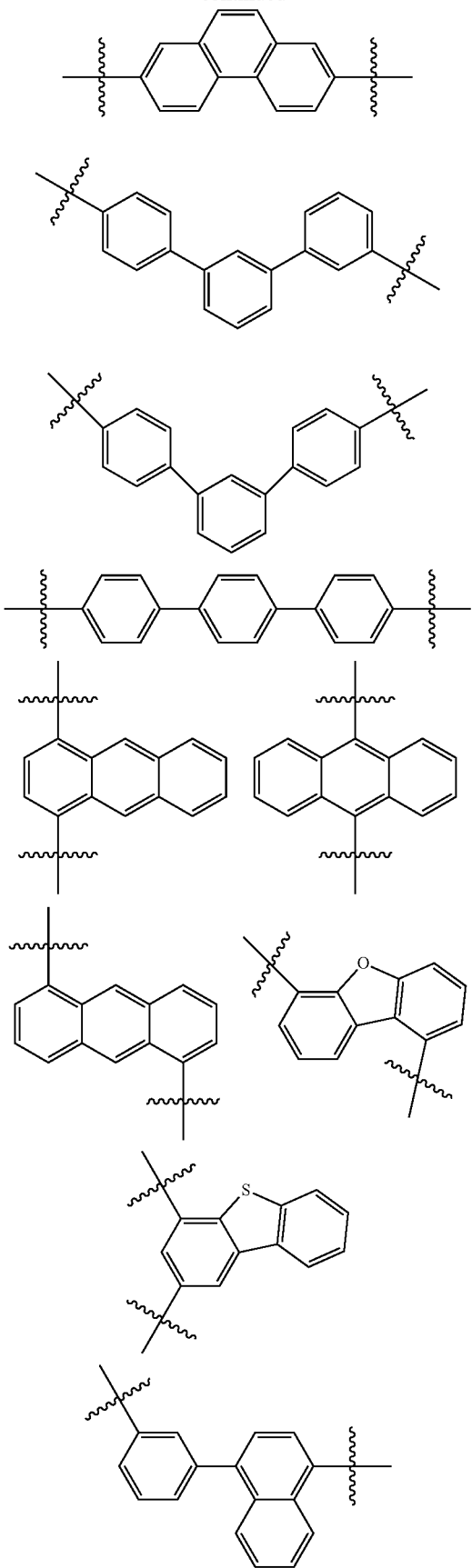
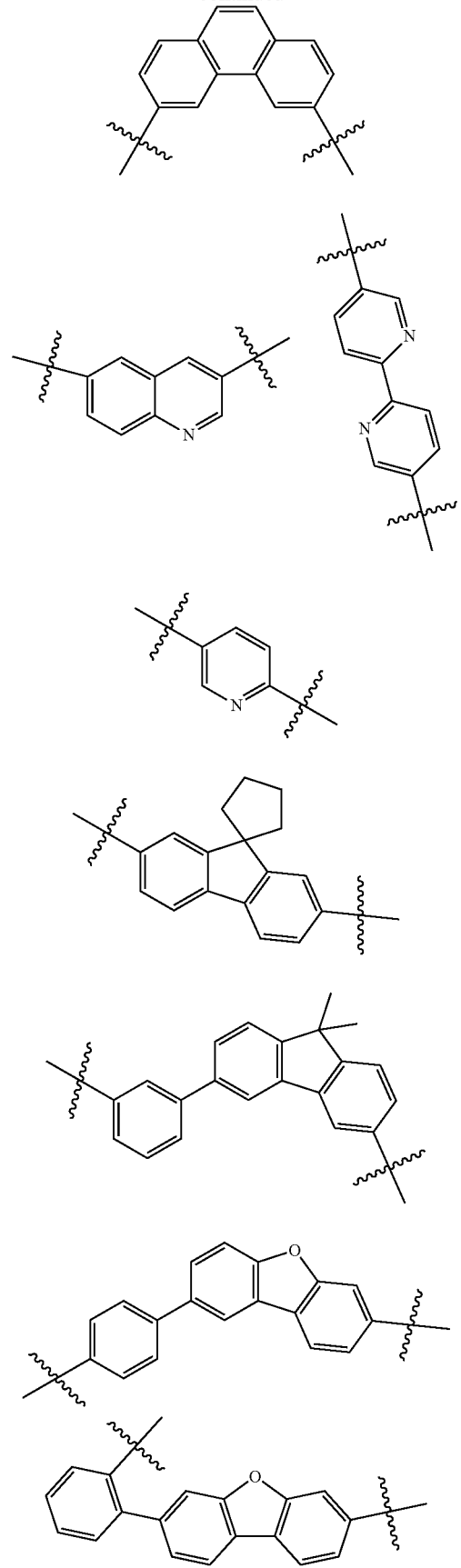

-continued

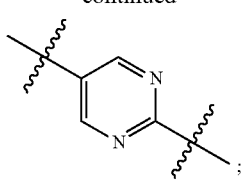

the substituted W₂ is a group formed by substituting unsubstituted W₂ by one or more substituents selected from deuterium, fluorine, chlorine, cyano, methyl, ethyl, isopropyl, tert-butyl, methoxy, ethoxy, isopropoxy, trifluoromethyl, triphenylsilyl, cyclopentyl, cyclohexyl, trifluoromethyl, trimethylsilyl, phenyl, naphthyl, pyridyl, dibenzothienyl, dibenzofuryl, quinolyl, and isoquinolinyl, and when the substituted W₂ comprises a plurality of substituents, any two substituents are the same or different.

8. The organic compound according to claim 1, wherein Ar₁ is selected from substituted or unsubstituted aryl with 6 to 25 ring-forming carbon atoms, or substituted or unsubstituted heteroaryl with 4 to 18 ring-forming carbon atoms.

9. The organic compound according to claim 1, wherein Ar₁ is selected from the group consisting of substituents represented by formula S-1 to formula S-11:

S-5
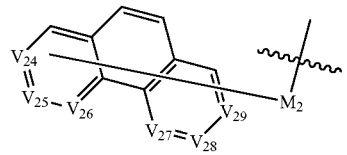

S-6
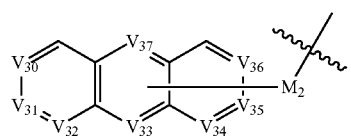

S-7
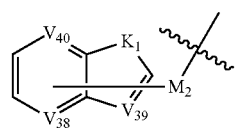

S-8
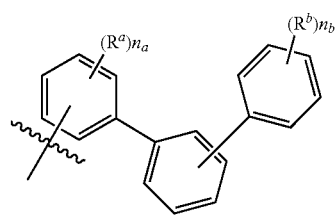

S-9
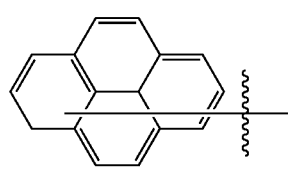

S-10
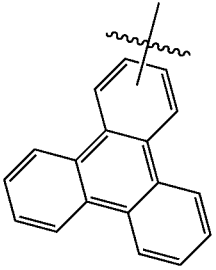

S-11
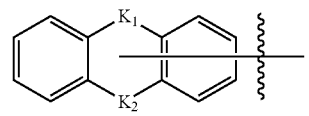

in the above groups, M₂ is selected from single bond and

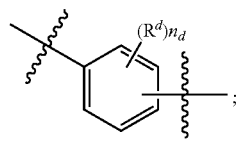

$n_a$ and $n_d$ are each independently 1, 2, 3 or 4; when a group comprises two or more $R^a$, each $R^a$ is the same or different; when a group comprises two or more $R^d$, each $R^d$ is the same or different; $n_b$ is selected from 1, 2, 3, 4 and 5; when a group comprises two or more $R^b$, each $R^b$ is the same or different;

$V_1$ to $V_{40}$ are each independently selected from $C(R^v)$ and N, and when a group comprises two or more $R^v$, any two $R^v$ are the same or different from each other;

V is selected from the group consisting of O, S, Se, $N(R^{v1})$, $C(R^{v2}R^{v3})$ and $Si(R^{v2}R^{v3})$;

$K_1$ and $K_2$ are each independently selected from O, S and $N(R^k)$;

$R^a$, $R^b$, $R^d$, $R^k$, $R^{v1}$, $R^{v2}$, and $R^{v3}$ are each independently hydrogen, aryl with 6 to 18 carbon atoms, heteroaryl with 3 to 18 carbon atoms, alkyl with 1 to 10 carbon atoms, cycloalkyl with 3 to 10 carbon atoms, and heterocycloalkyl with 2 to 10 carbon atoms; or, $R^{v2}$ and $R^{v3}$ connected to the same atom are connected to each other to form a saturated or unsaturated 5- to 13-membered aliphatic ring together with the atom connected to the both;

each $R^v$ is independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 18 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and arylthio with 6 to 18 carbon atoms.

10. The organic compound according to claim 1, wherein Ar₁ is unsubstituted T₁ or substituted T₁, wherein the unsubstituted T₁ is selected from the group consisting of the following substituents:

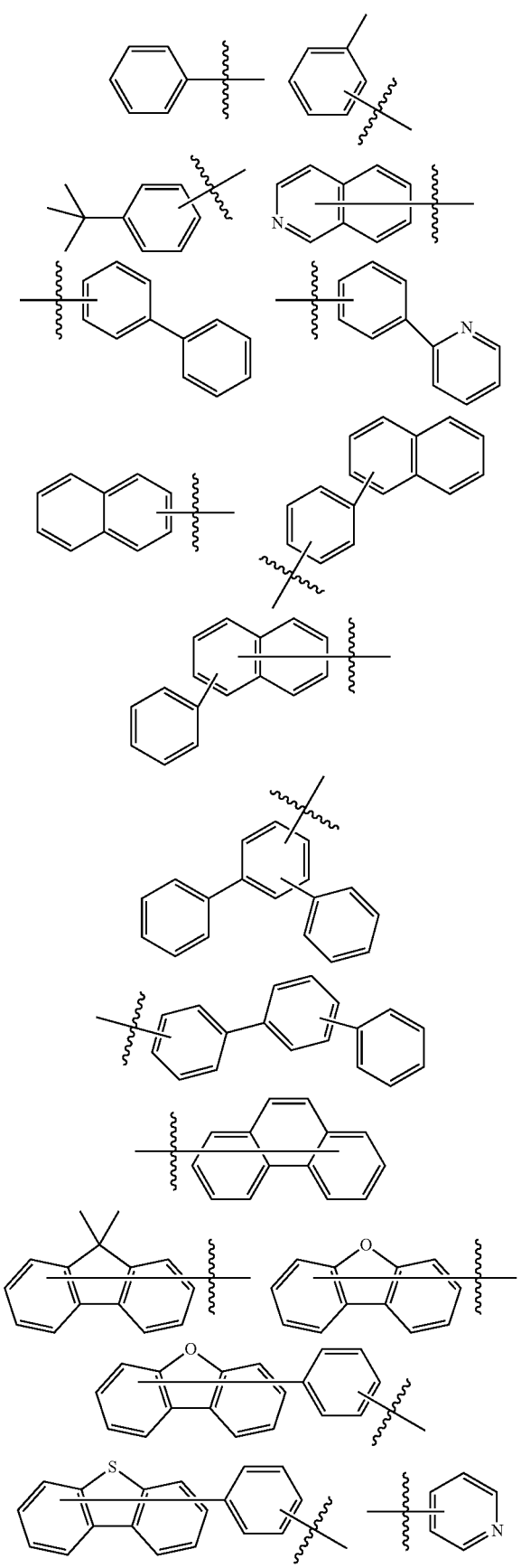
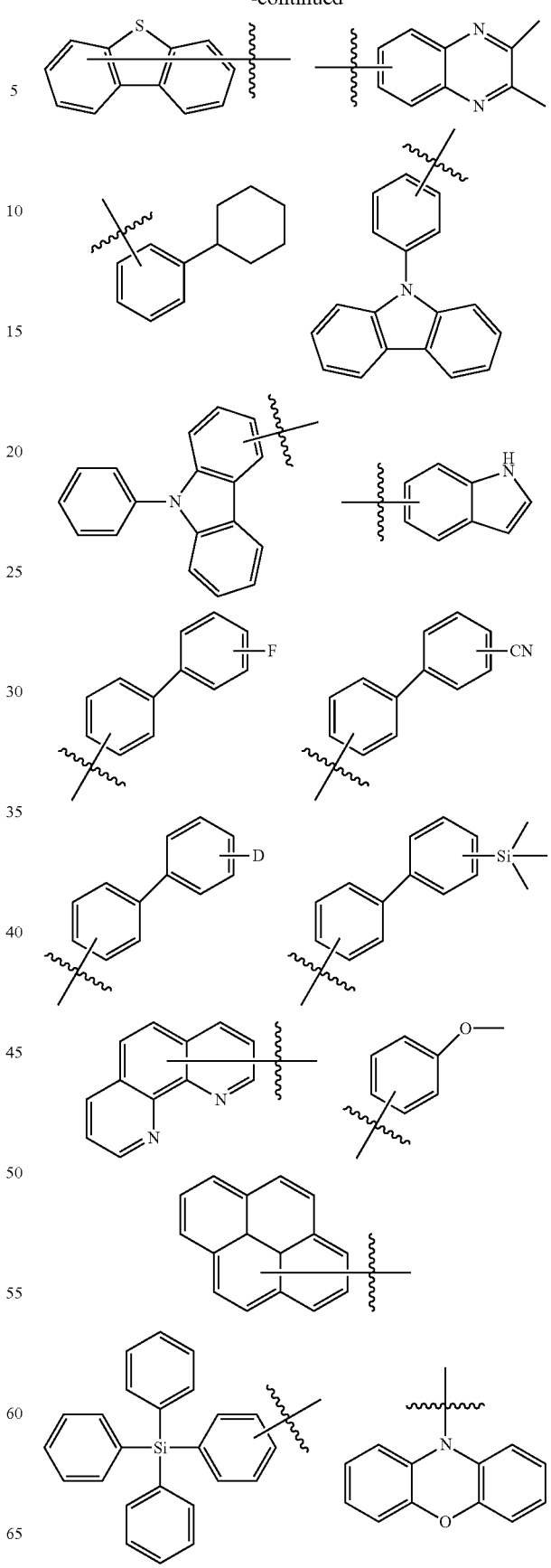

-continued

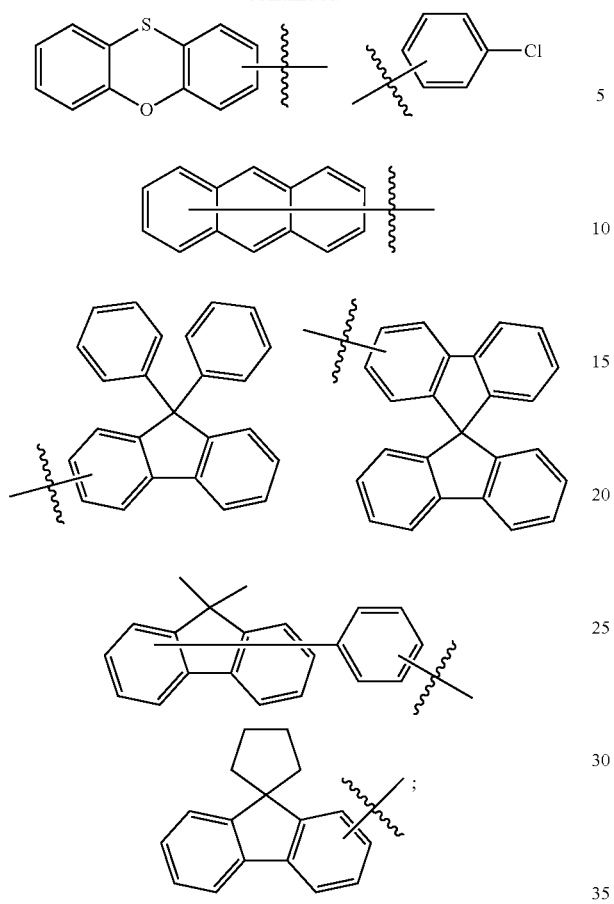

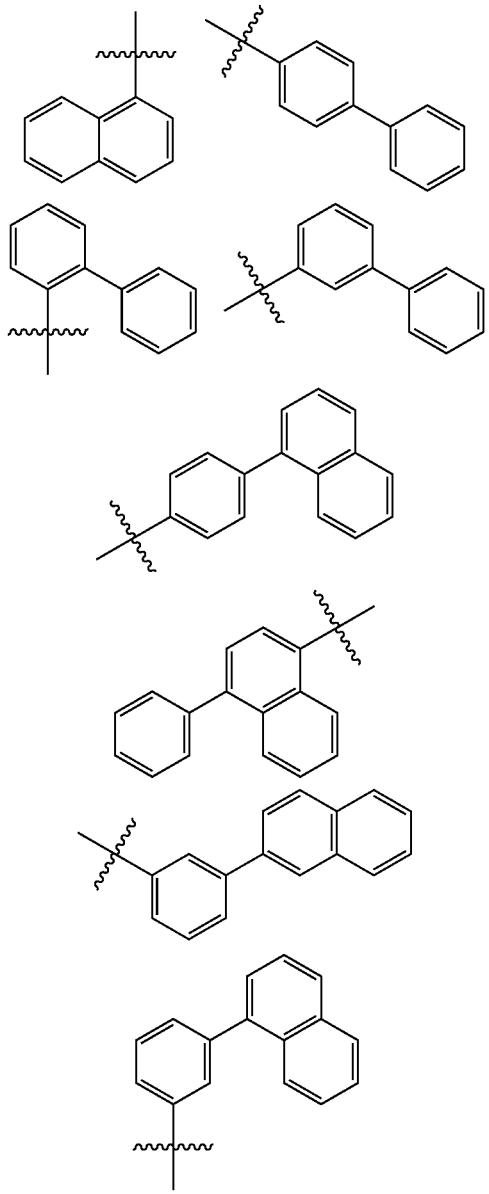

the substituted $T_1$ is a group formed by substituting unsubstituted $T_1$ by one or more substituents selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, triphenylsilyl, cycloalkyl with 5 to 10 carbon atoms, aryl with 6 to 15 carbon atoms, and heteroaryl with 3 to 12 carbon atoms, and when the substituted $T_1$ comprises a plurality of substituents, any two substituents are the same or different.

11. The organic compound according to claim 1, wherein $Ar_1$ is selected from the group consisting of the following substituents:

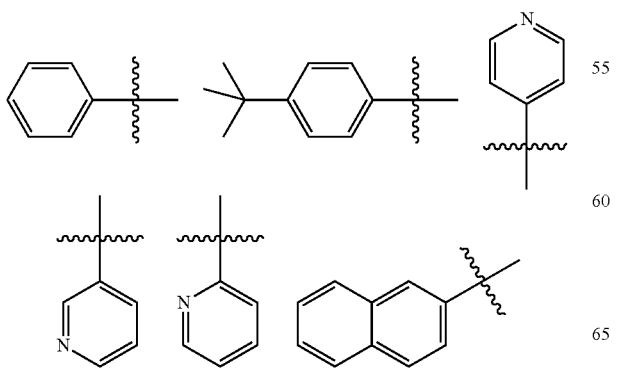

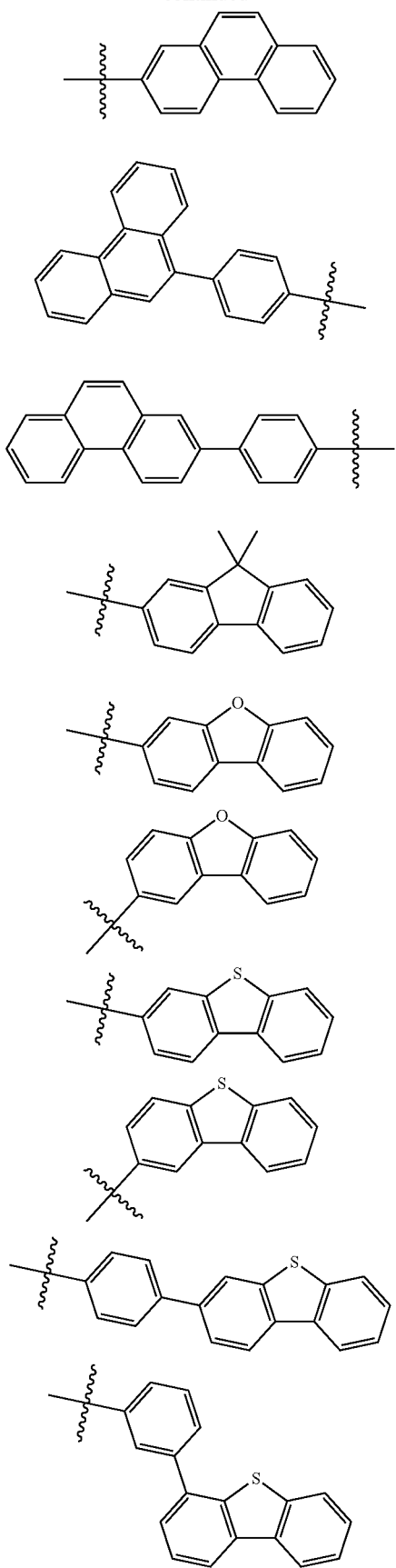
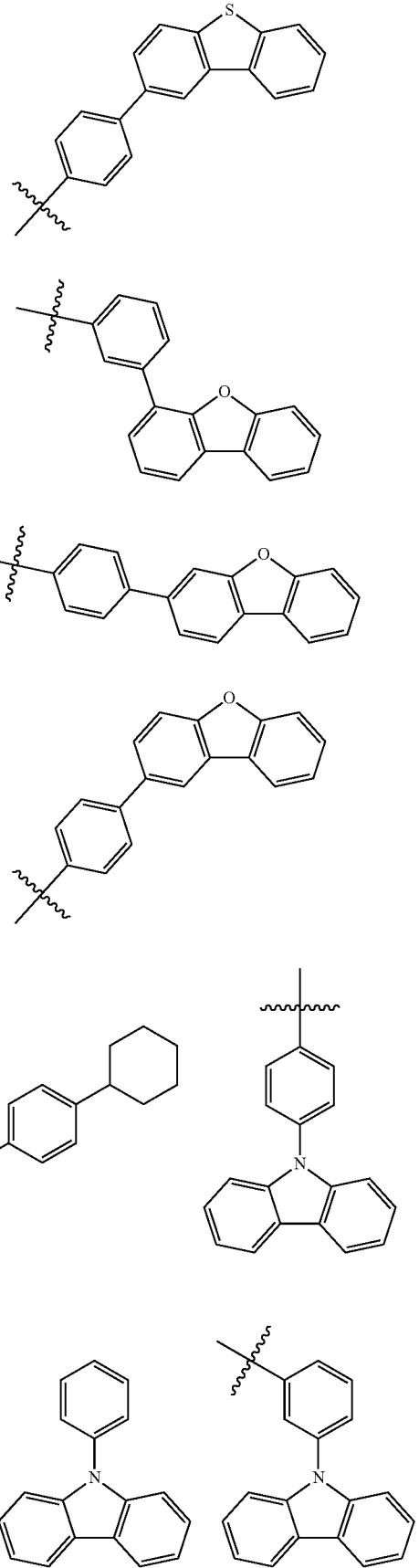

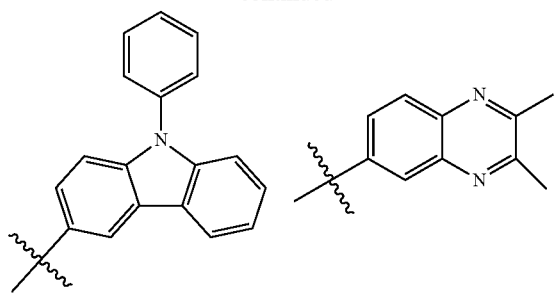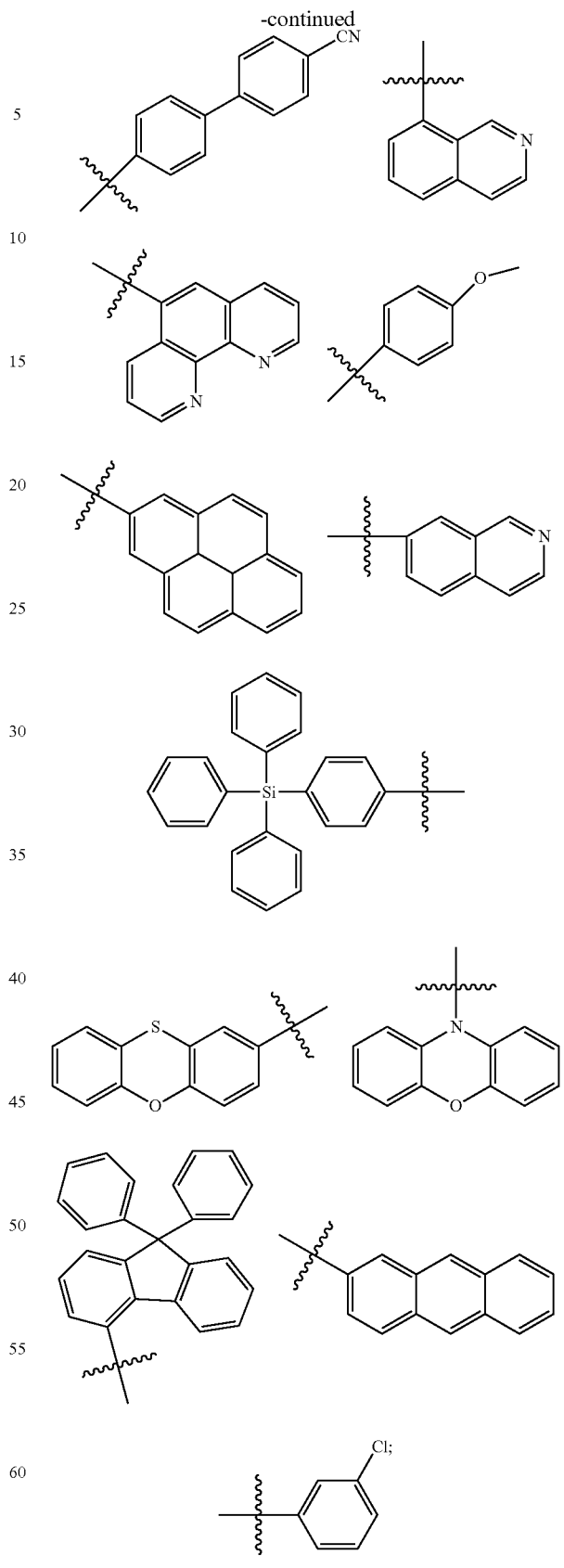
alternatively, $Ar_1$ is independently selected from the following groups:

239
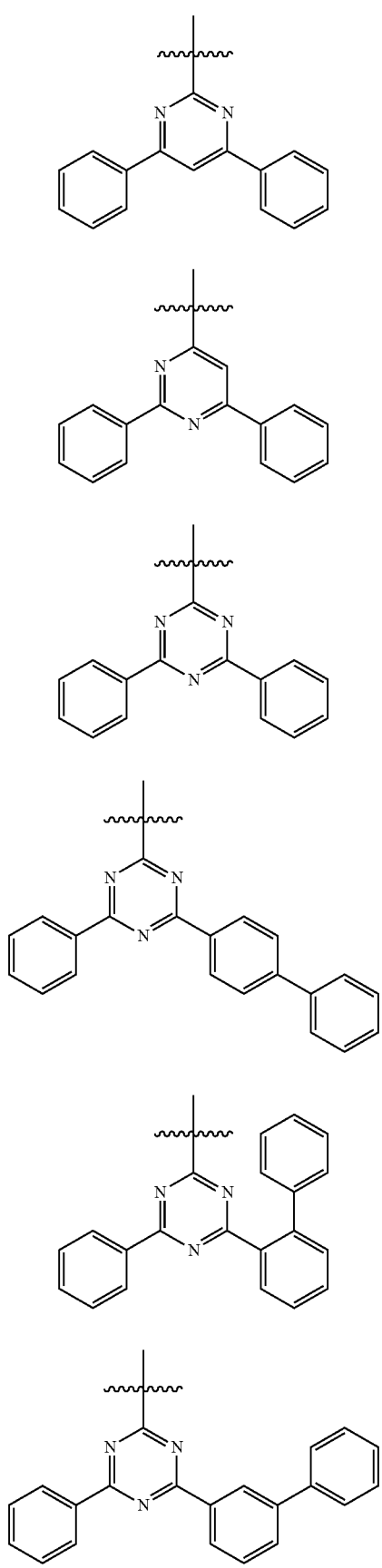
240
-continued
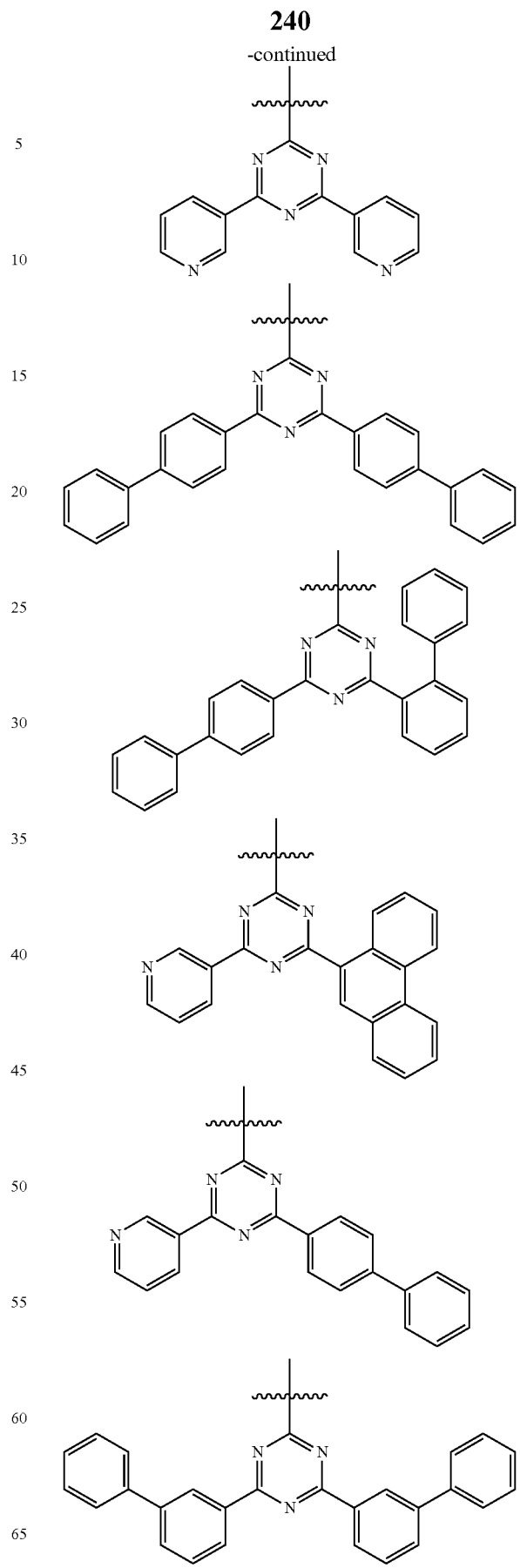

-continued
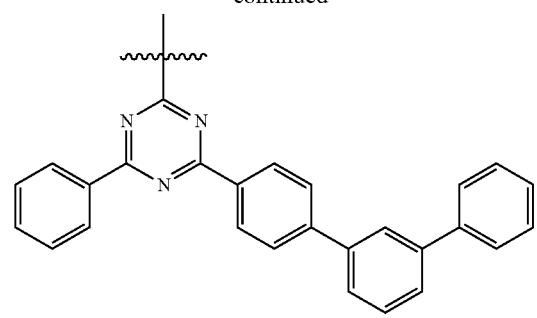
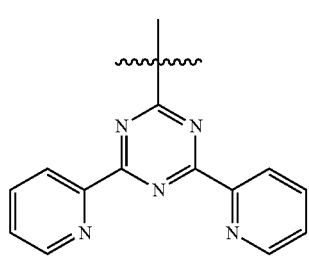
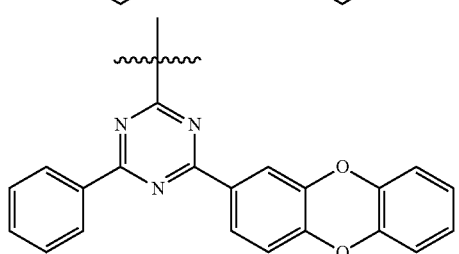
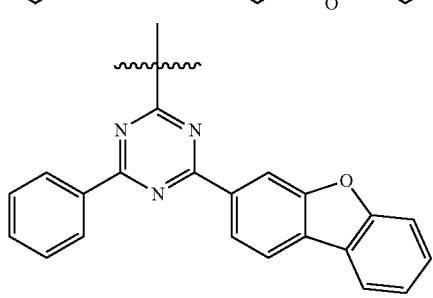
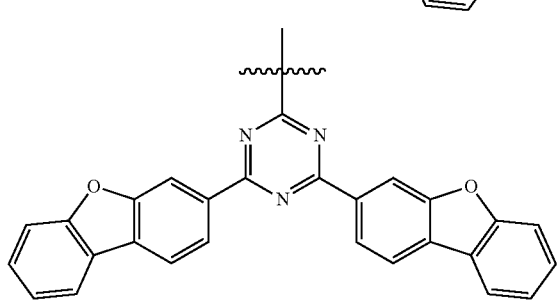
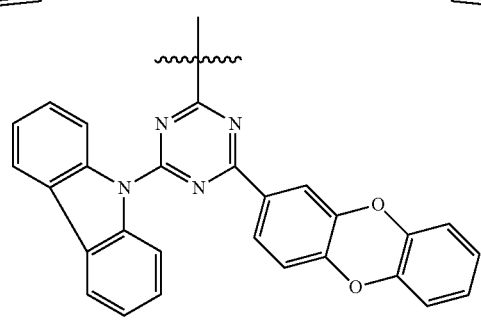
-continued
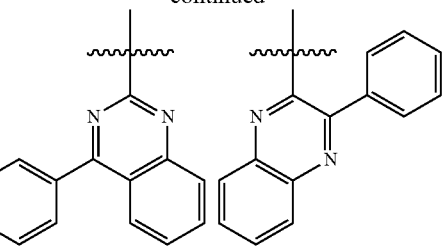
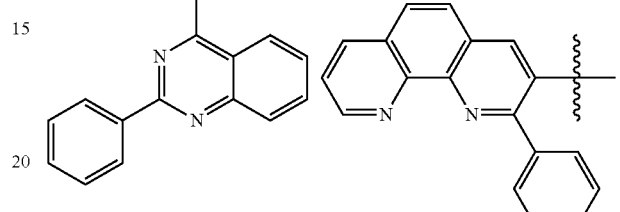
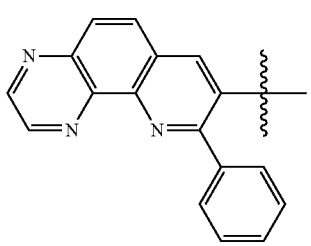
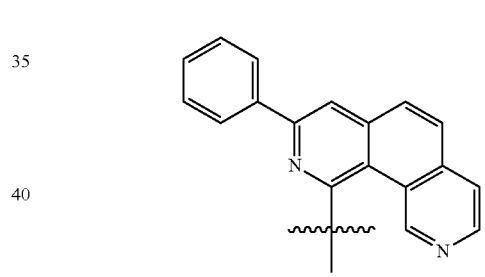
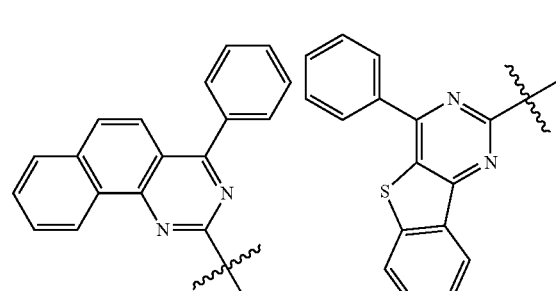
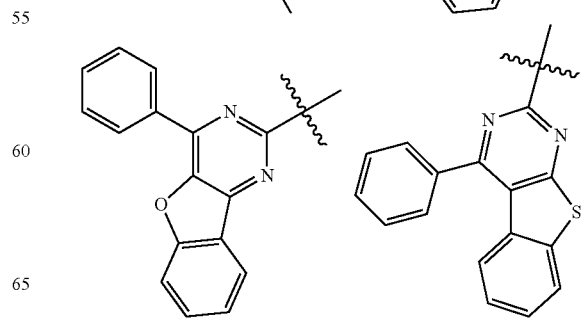

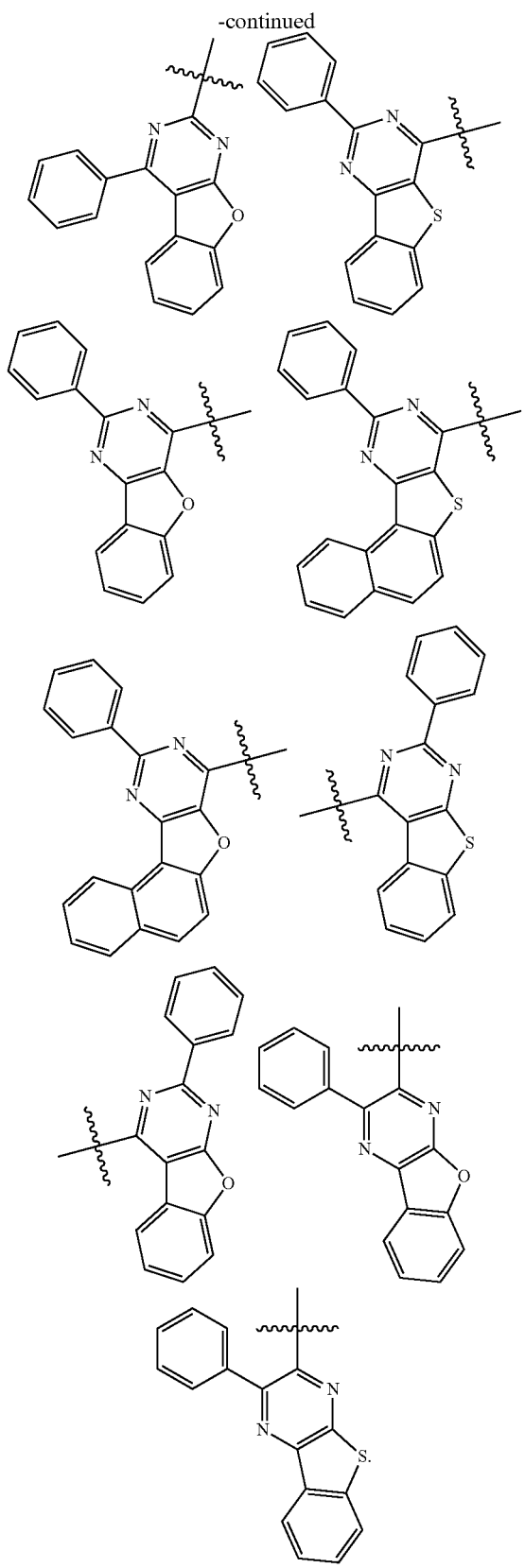

12. The organic compound according to claim 1, wherein $Ar_1$ is selected from the group represented by the following chemical formula S-12 and chemical formula S-13:

S-12

S-13 wherein $V_{41}$ to $V_{55}$ are each independently selected from $C(R^{v4})$ and N, at least one of $V_{48}$ to $V_{55}$ is N, and when the same group comprises a plurality of $R^{v4}$, any two $R^{v4}$ are the same or different from each other;

T is selected from the group consisting of O, S, Se, $N(R^{t1})$, $C(R^{t2}R^{t3})$ and $Si(R^{t2}R^{t3})$;

$R^{t1}$, $R^{t2}$, and $R^{t3}$ are each independently hydrogen, aryl with 6 to 18 carbon atoms, heteroaryl with 3 to 18 carbon atoms, alkyl with 1 to 10 carbon atoms, cycloalkyl with 3 to 10 carbon atoms, or heterocycloalkyl with 2 to 10 carbon atoms; or, $R^{t2}$ and $R^{t3}$ connected to the same atom are connected to each other to form a saturated or unsaturated 5- to 13-membered ring together with the atom connected to the both;

each $R^{v4}$ is independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylamino with 1 to 10 carbon atoms, alkylthio with 1 to 10 carbon atoms, aryloxy with 6 to 18 carbon atoms, and an arylthio with 6 to 18 carbon atoms, or any two adjacent $R^{v4}$ are connected to each other to form a 6- to 10-membered aromatic ring or a 6- to 10-membered heteroaromatic ring.

13. The organic compound according to claim 1, wherein $Ar_1$ is selected from substituted or unsubstituted $T_2$, wherein the unsubstituted $T_2$ is independently selected from the following groups:

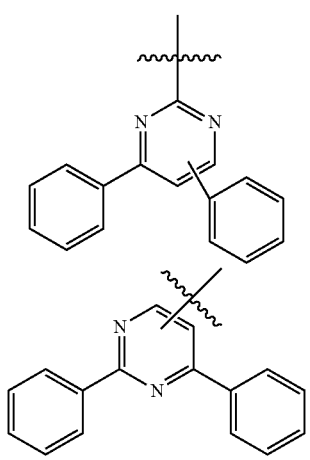

245
-continued
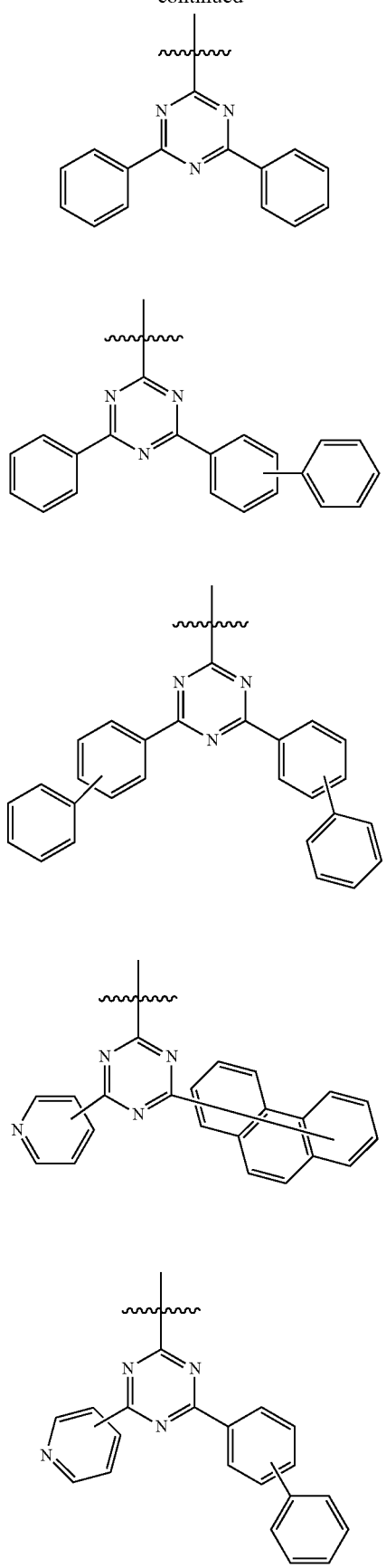
246
-continued
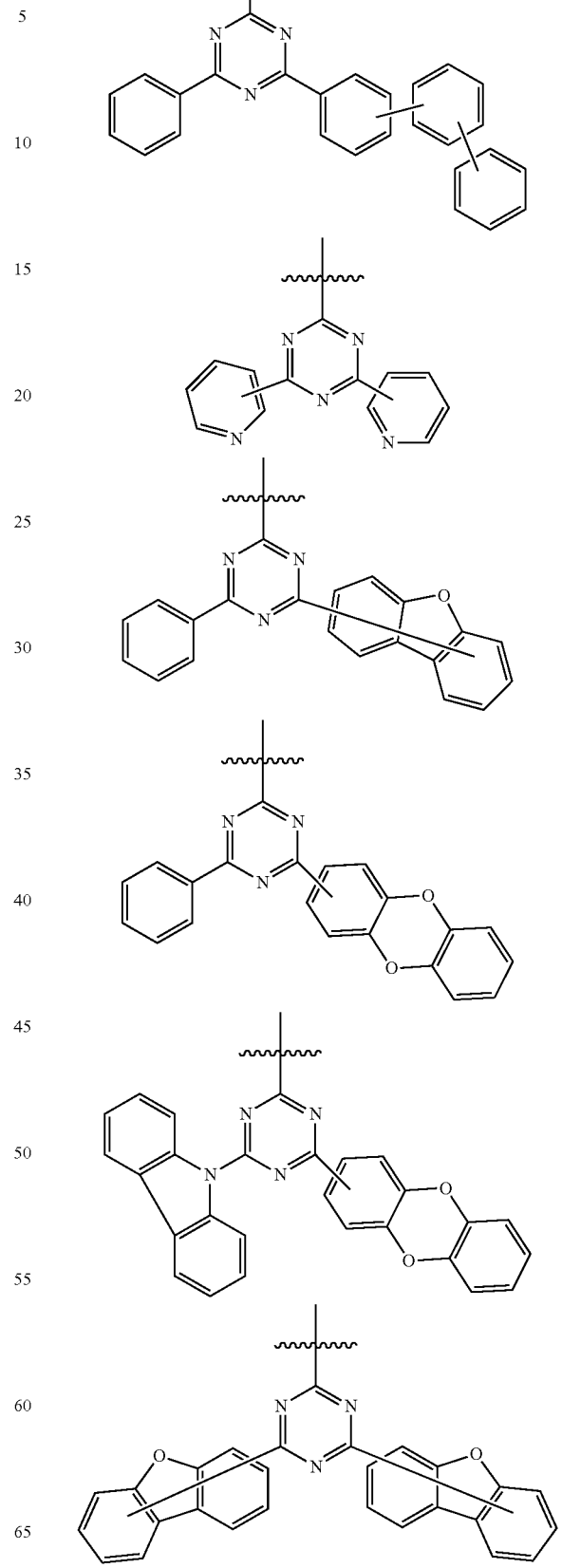

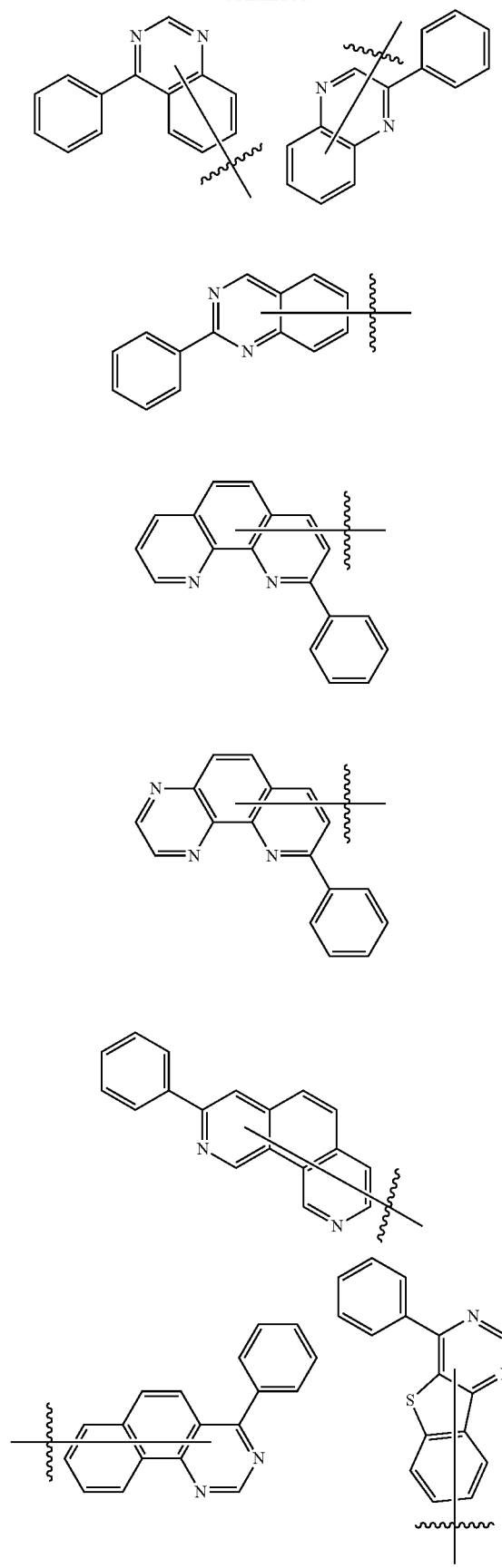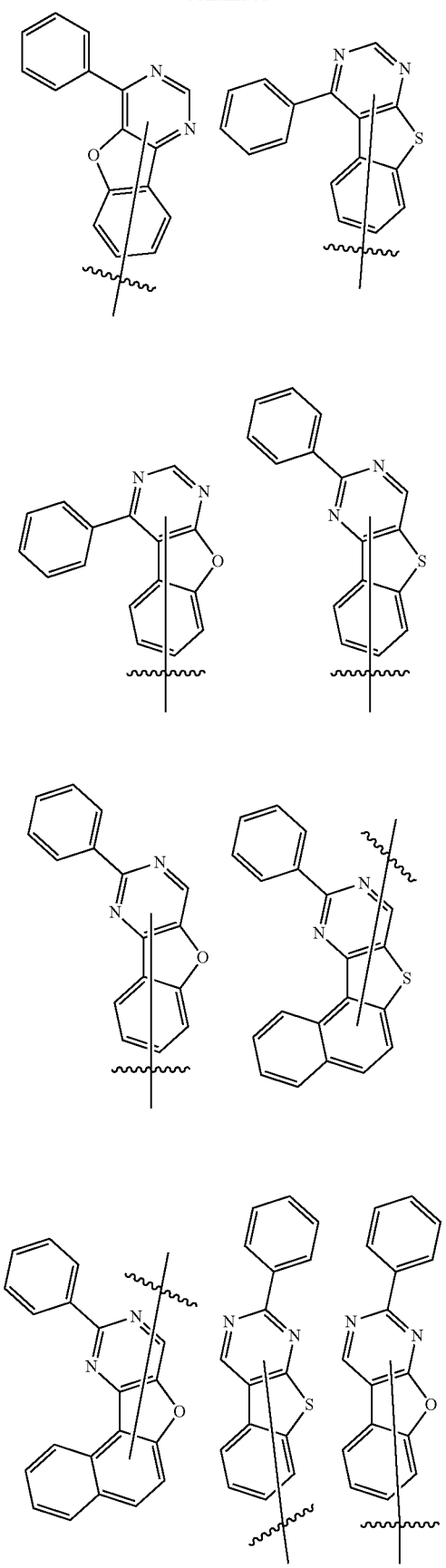

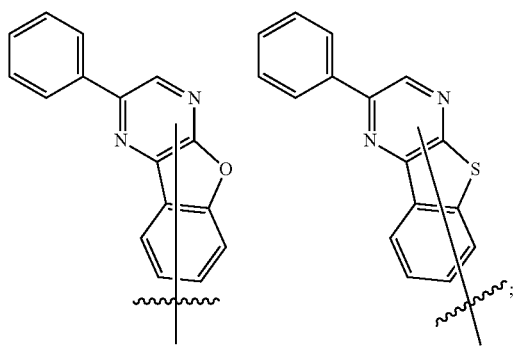

the substituted $T_2$ is a group formed by substituting unsubstituted $T_2$ by one or more substituents selected from deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, arylsilyl with 6 to 18 carbon atoms, cycloalkyl with 5 to 7 carbon atoms, aryl with 6 to 13 carbon atoms, and heteroaryl with 3 to 12 carbon atoms, and when the substituted $T_2$ comprises a plurality of substituents, any two substituents are the same or different.

14. The organic compound according to claim 1, having a structure shown in at least one of the following chemical formulae 1-1 to 1-3:

1-1

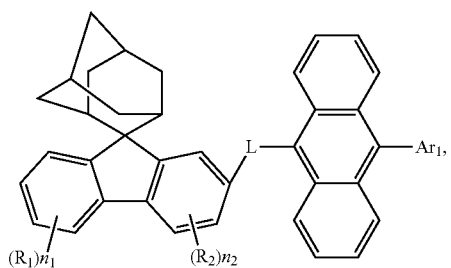

1-2

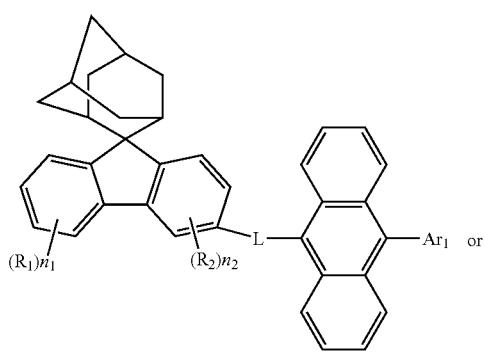

1-3

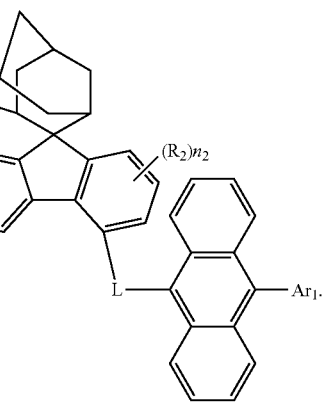

15. The organic compound according to claim 1, wherein $R_1$ and $R_2$ are the same or different from each other, and are each independently selected from deuterium; fluorine; chlorine; bromine; cyano; methyl; ethyl; isopropyl; tert-butyl; methoxy; ethoxy; isopropoxy; n-propoxy; cyclopentyl; cyclohexyl; trifluoromethyl; trimethylsilyl; triphenylsilyl; phenyl, which is optionally substituted by 0, 1, 2, 3, 4 or 5 substituents selected from deuterium, fluorine, chlorine, bromine, cyano, methyl, ethyl, isopropyl, tert-butyl, and trimethylsilyl; naphthyl; pyridyl; pyrimidyl; dibenzothienyl; dibenzofuryl; and quinolyl; and when the numbers of $R_1$ and $R_2$ are more than 1, any two $R_1$ or $R_2$ are the same or different.

16. The organic compound according to claim 1, wherein the organic compound is selected from the group consisting of the following compounds:

1

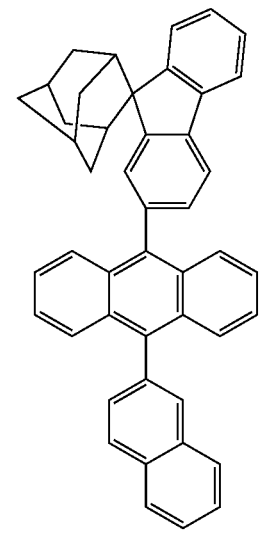

251
-continued
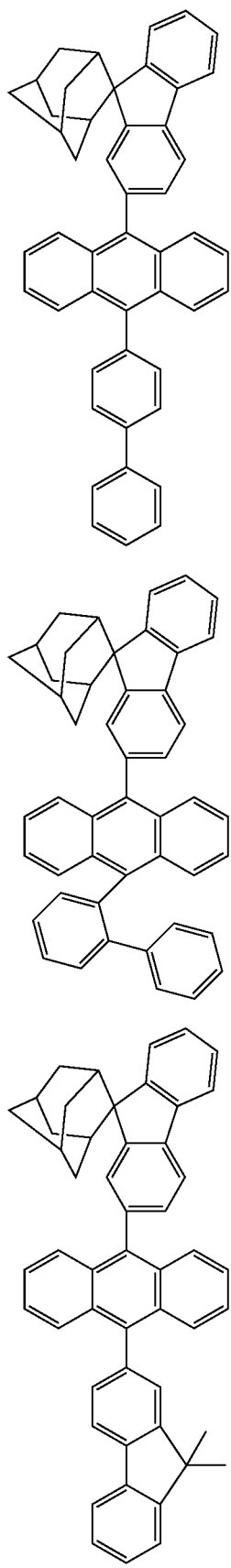
252
-continued
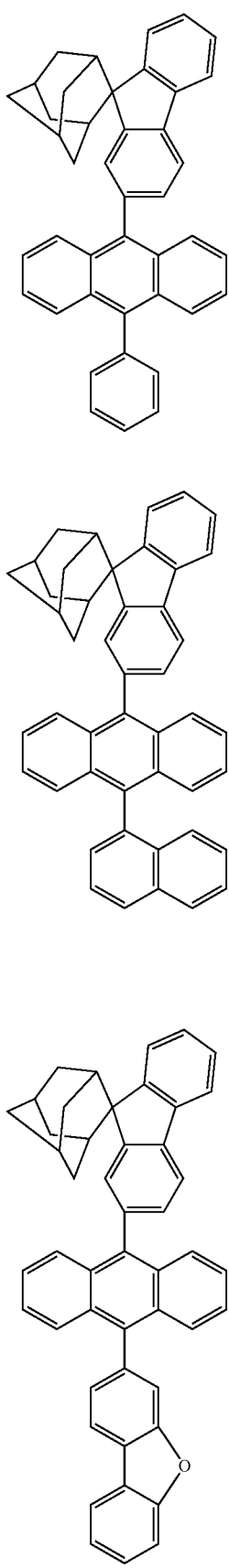

253
-continued
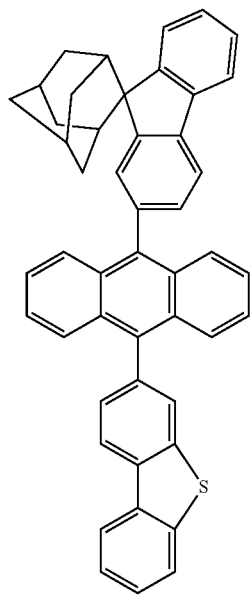
254
-continued
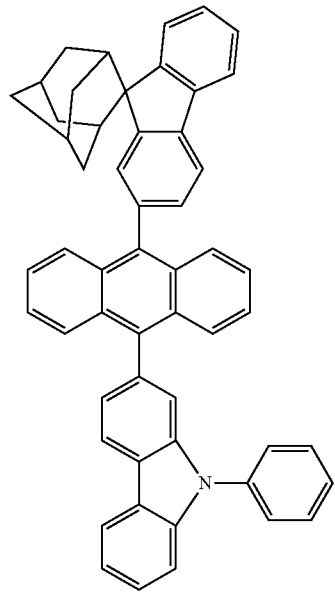
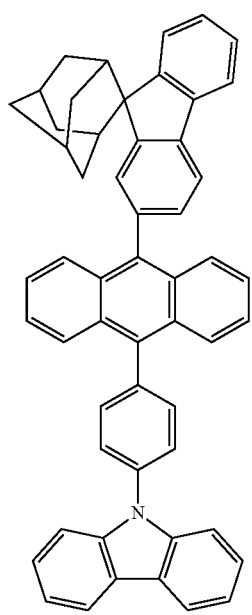
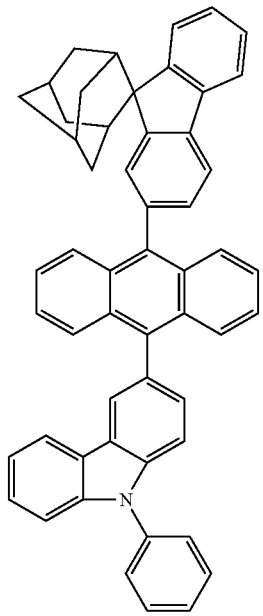

12
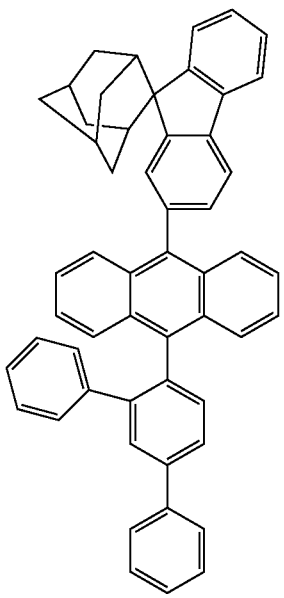
13
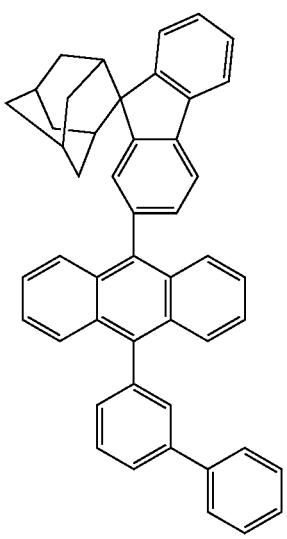
14
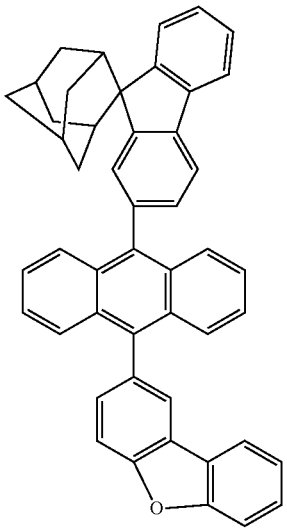
15
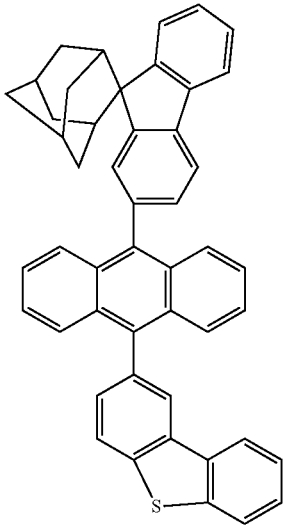
16

257
-continued
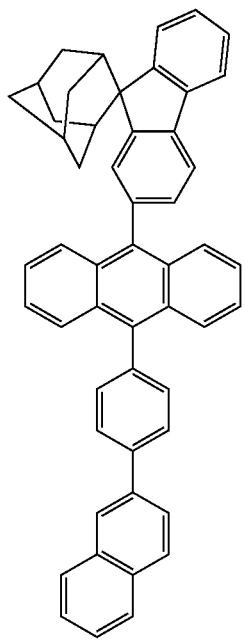
17
258
-continued
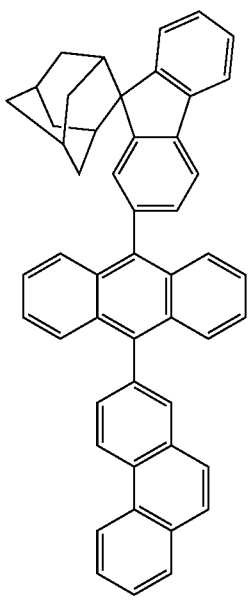
19
18
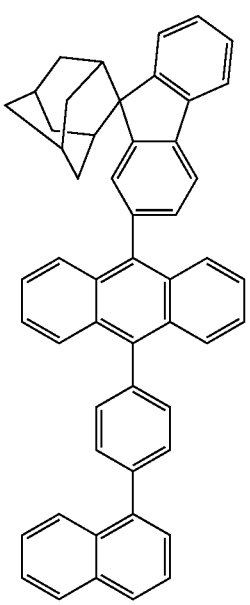
20
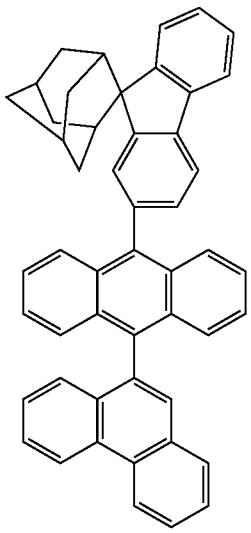

21
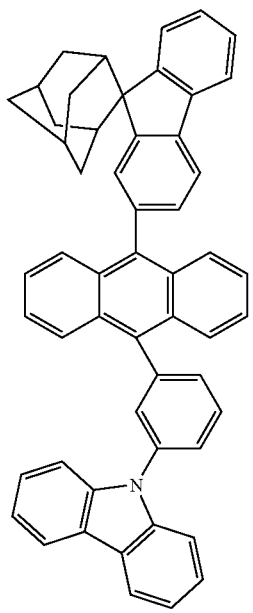
22
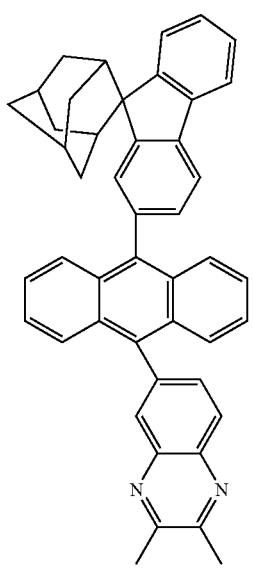
23
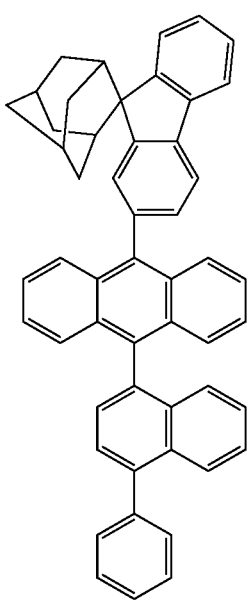
24
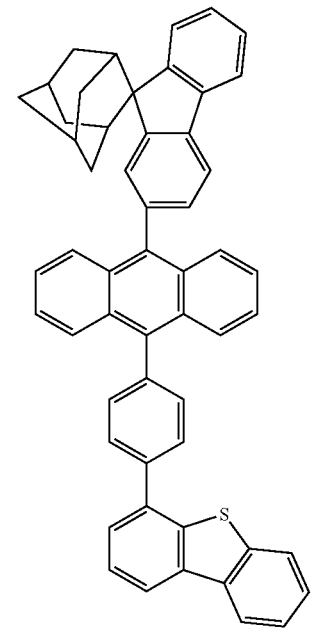

261
-continued
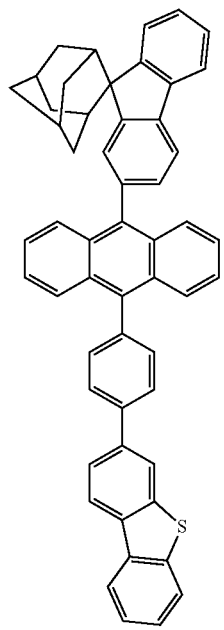
25
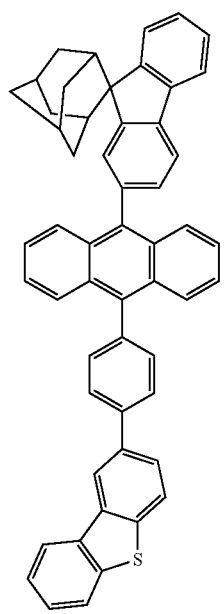
26
262
-continued
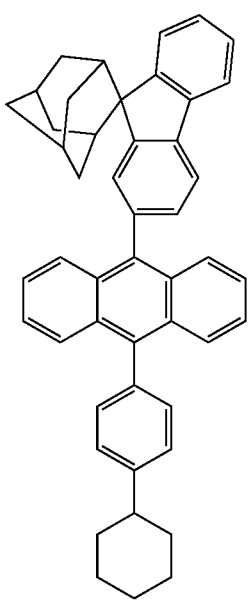
27
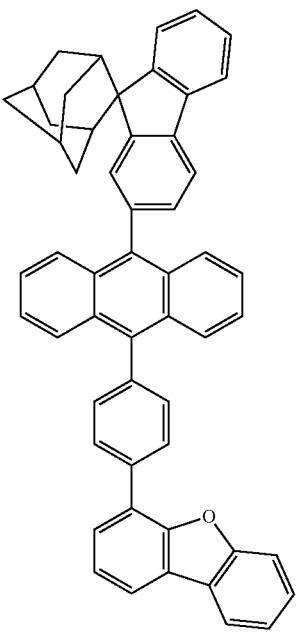
28

263
-continued
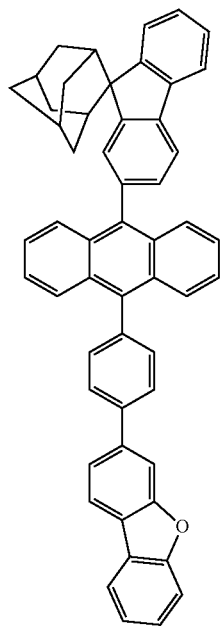
264
-continued
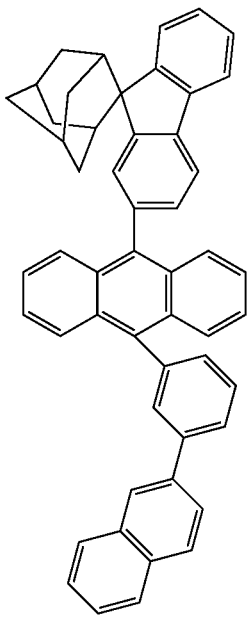
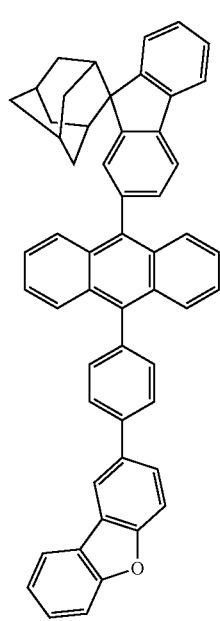
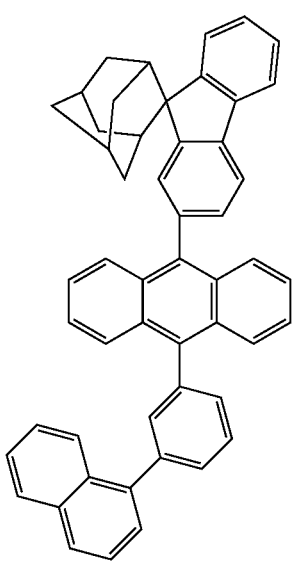

265
-continued
33
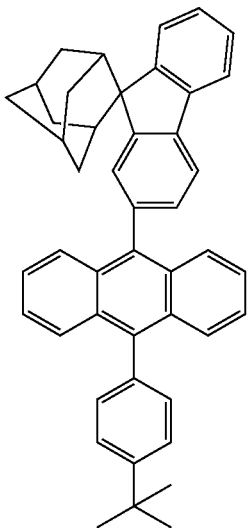
34
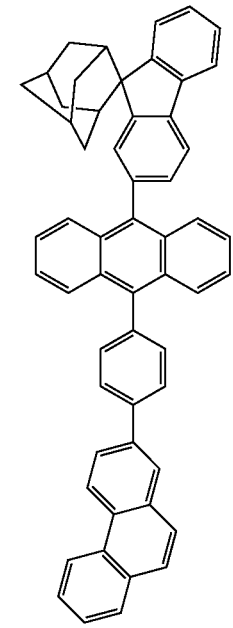
266
-continued
35
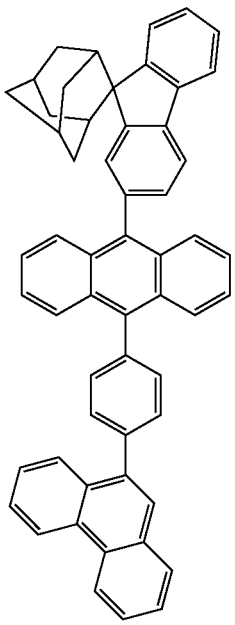
36
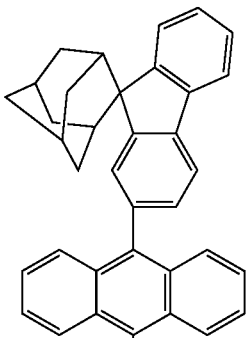
37
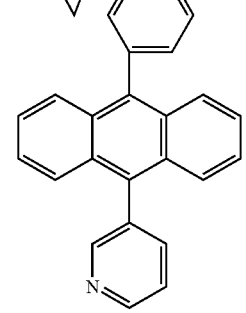

38
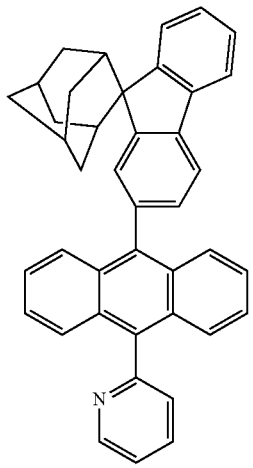
39
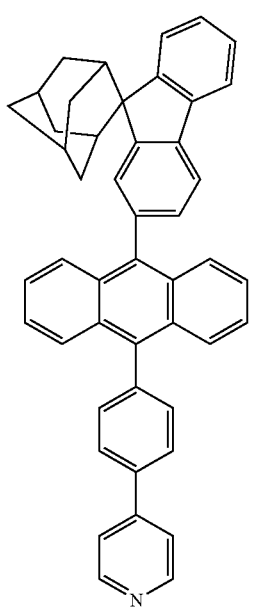
40
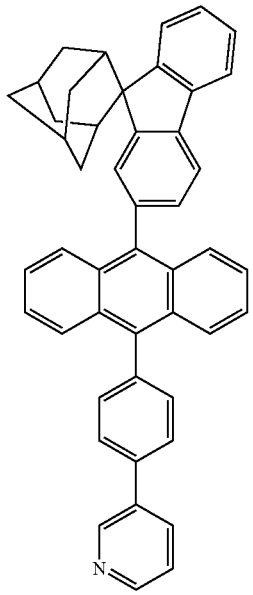
41
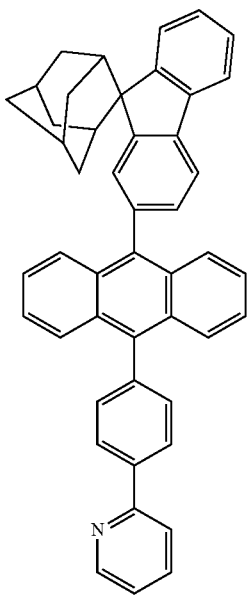
42
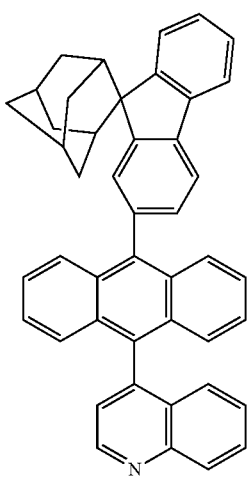
43
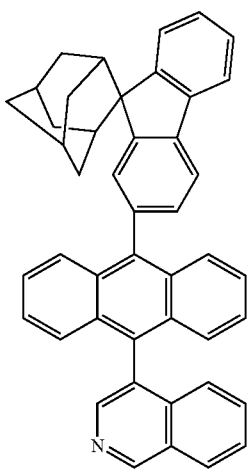

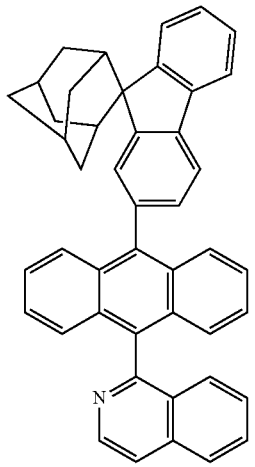
44
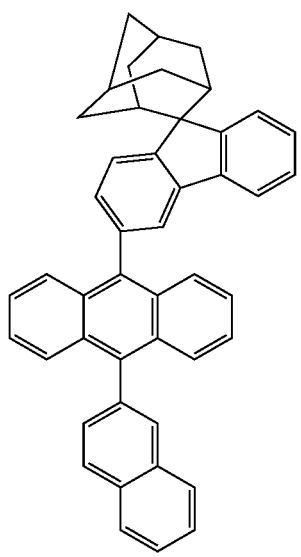
45
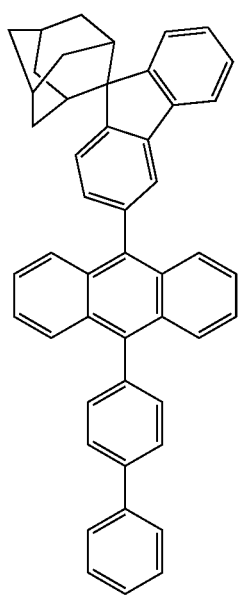
46
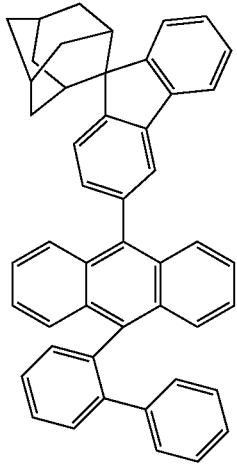
47
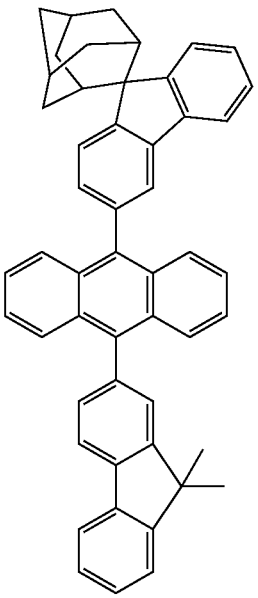
48
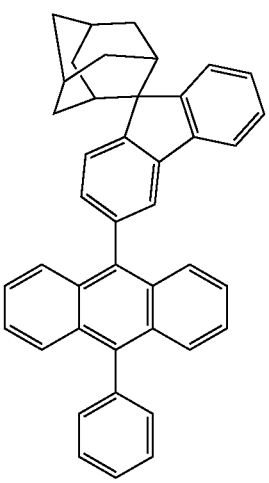
49

271
-continued
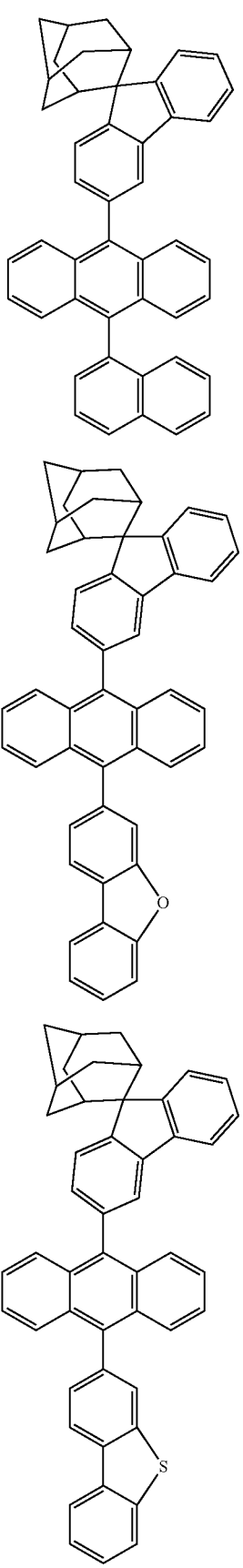
272
-continued

273
-continued
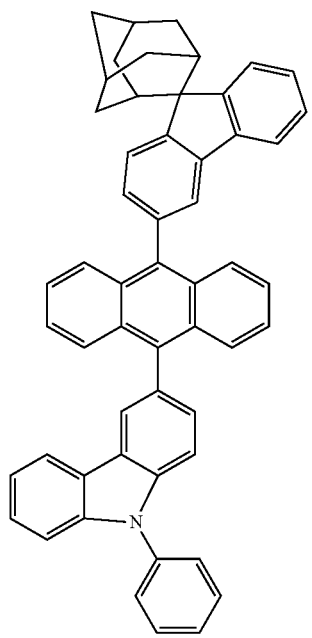
55
56
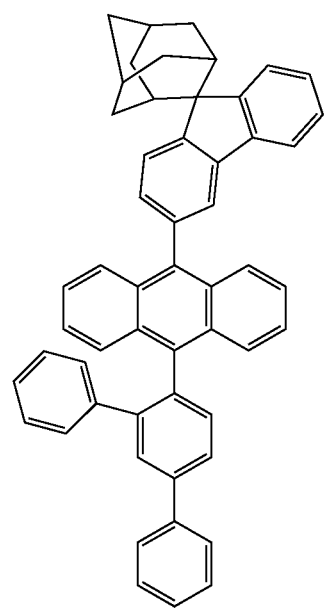
274
-continued
57
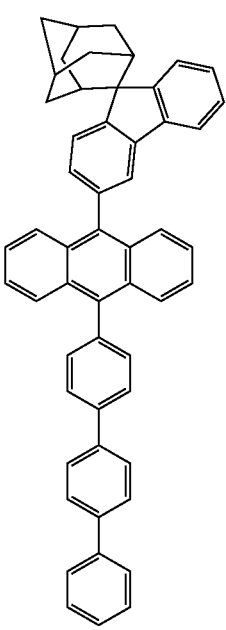
58
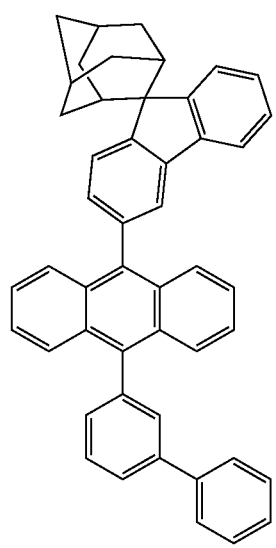

275
-continued
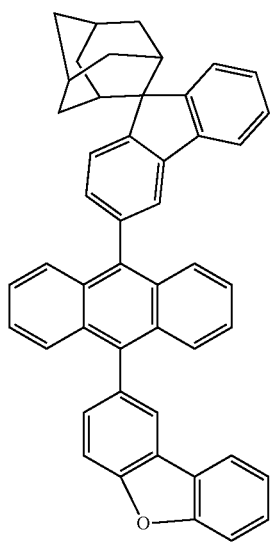
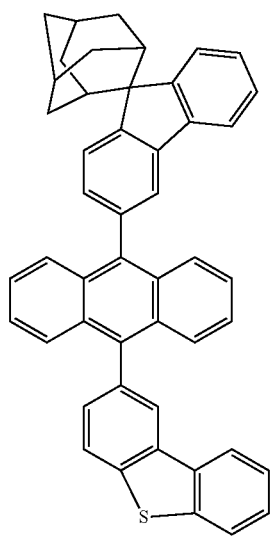
276
-continued
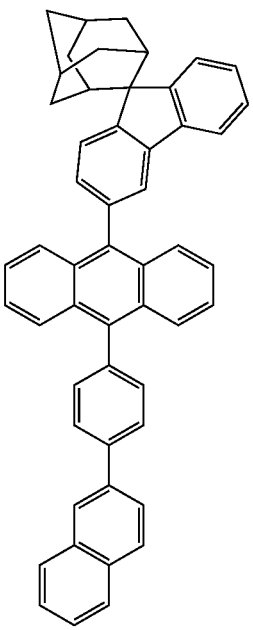
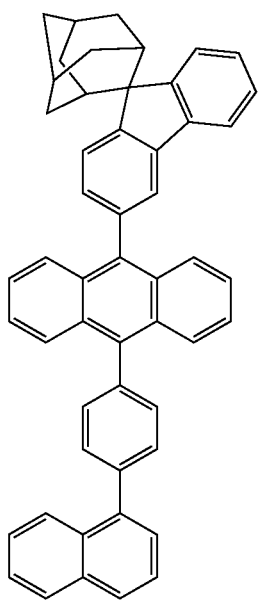

63
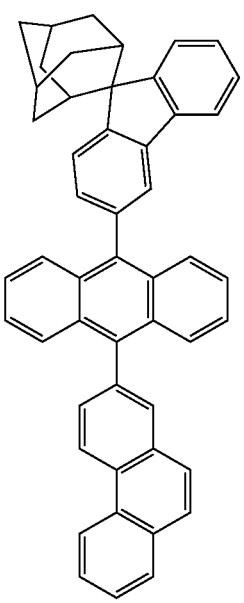
64
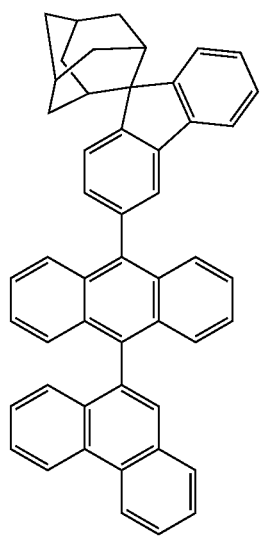
65
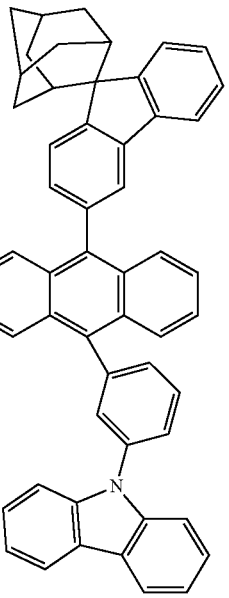
66
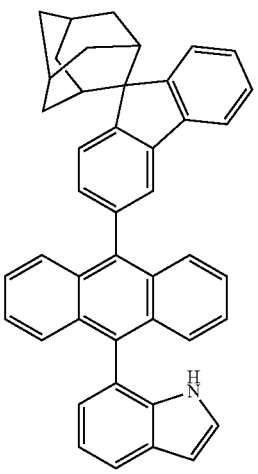
67
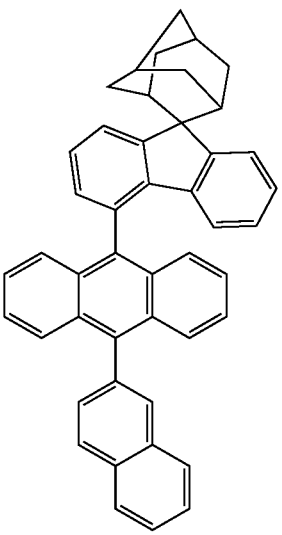

279
-continued
68
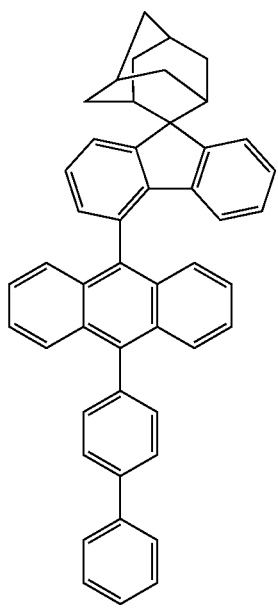
69
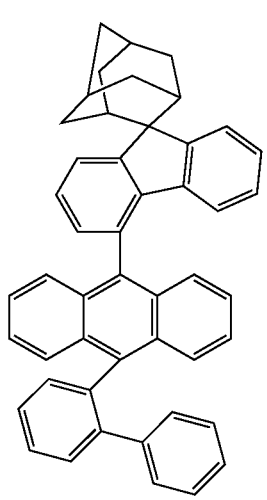
280
-continued
70
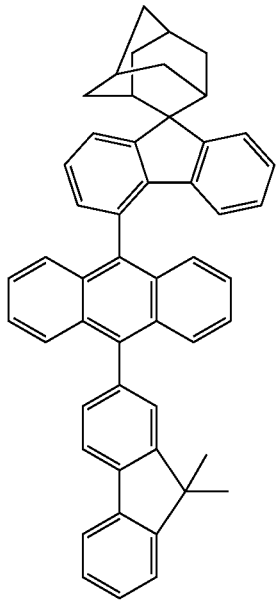
71
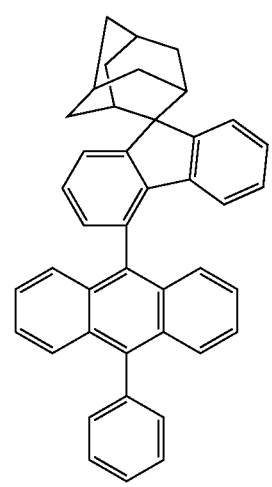
72

281
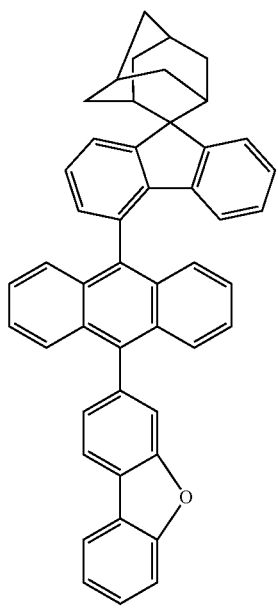
282
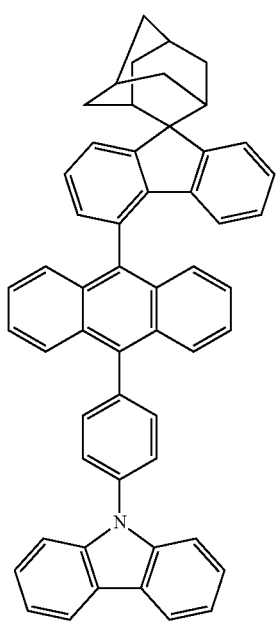
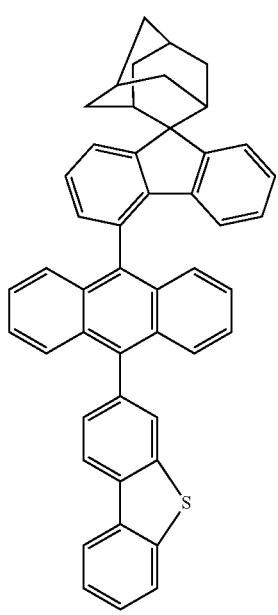
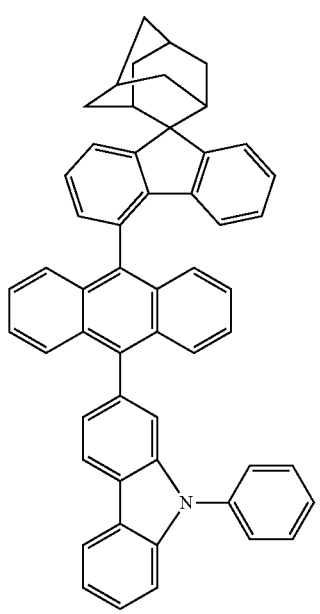

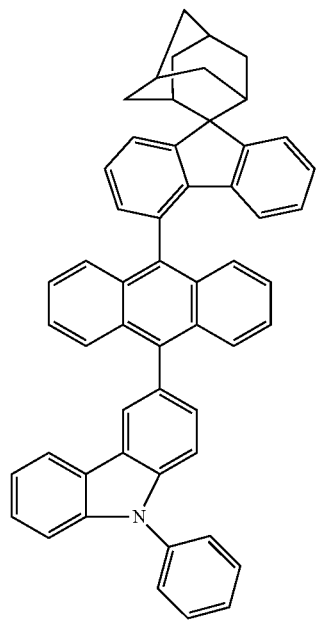
77
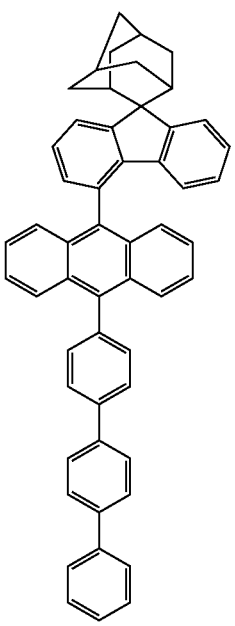
79
78
80

285
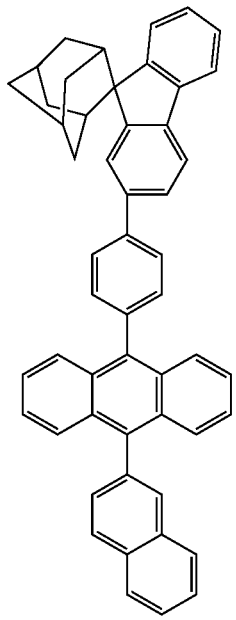
286
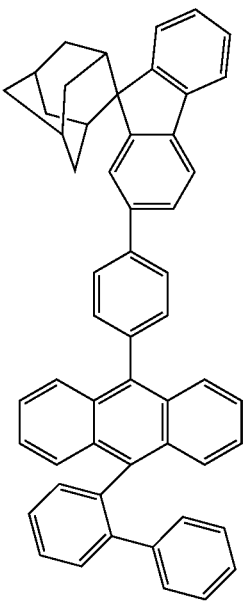
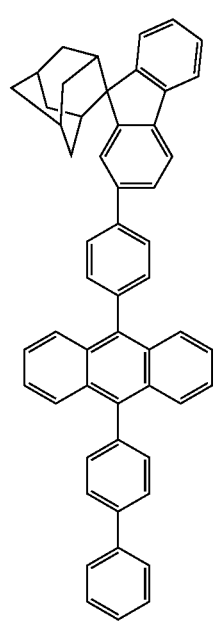
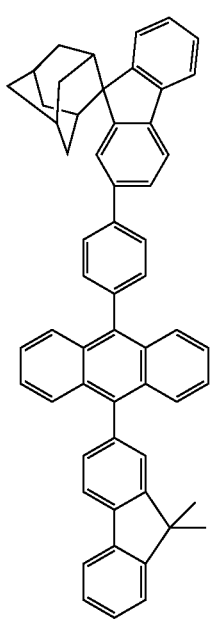

287
-continued
85
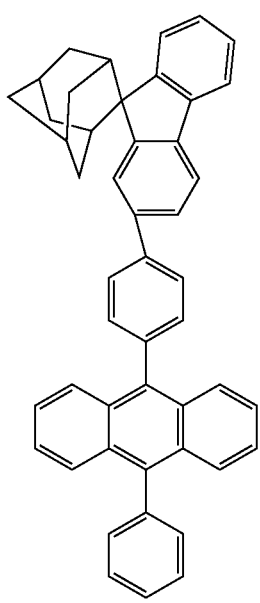
86
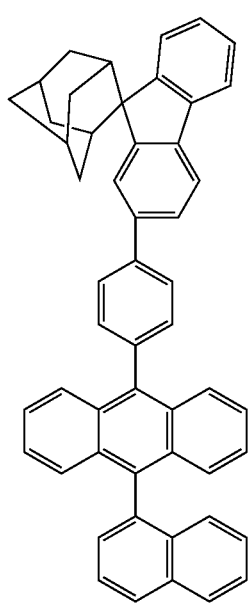
288
-continued
87
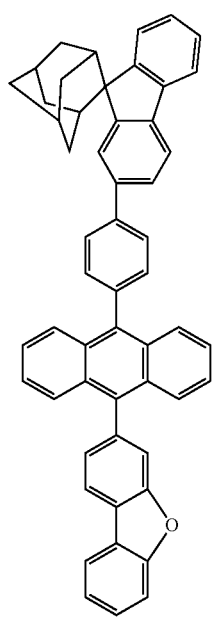
88
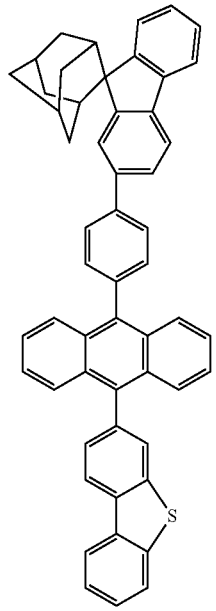

89
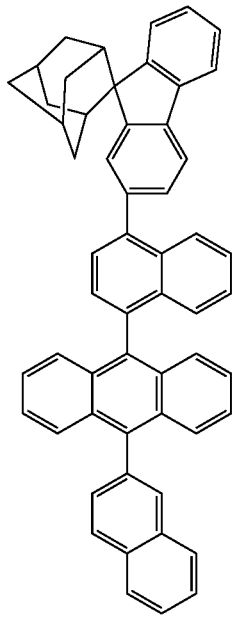
90
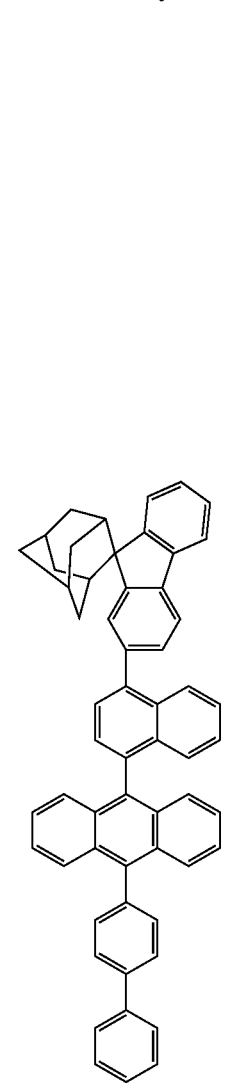
91
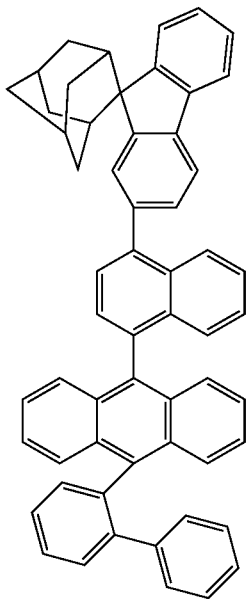
92
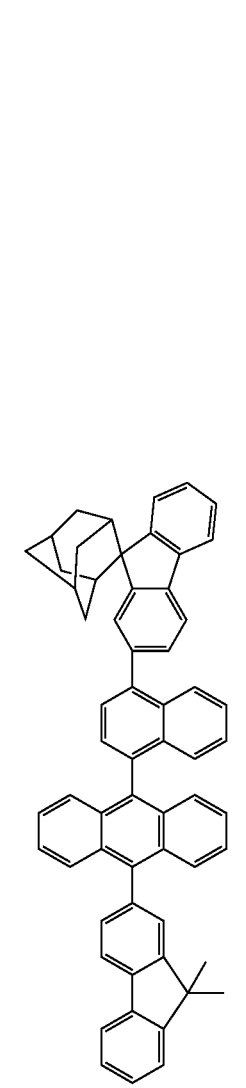

93
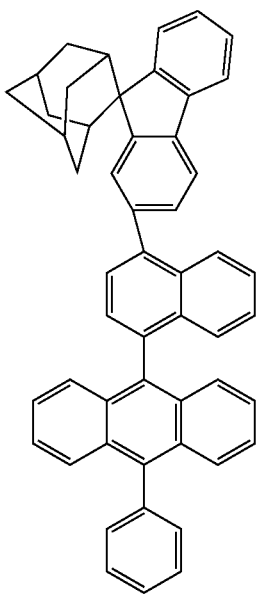
94
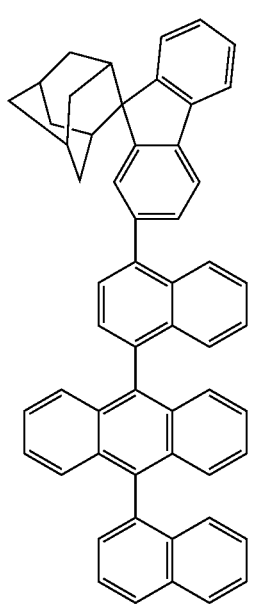
95
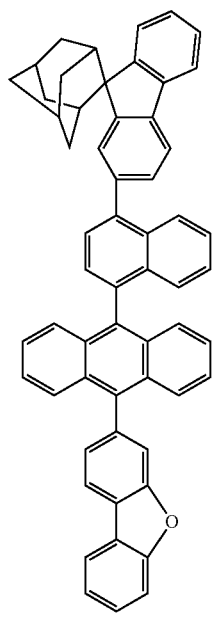
96
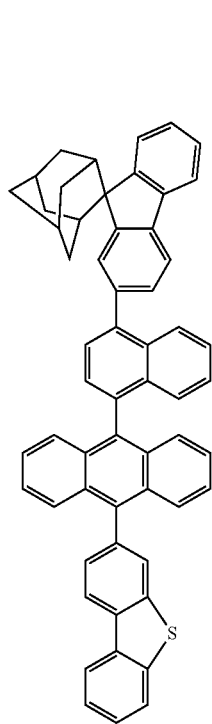

97
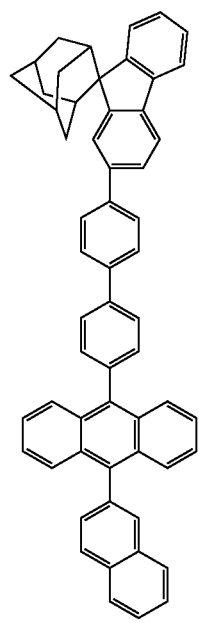
98
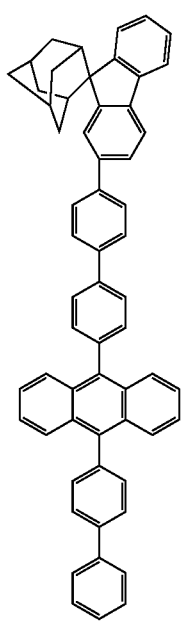
99
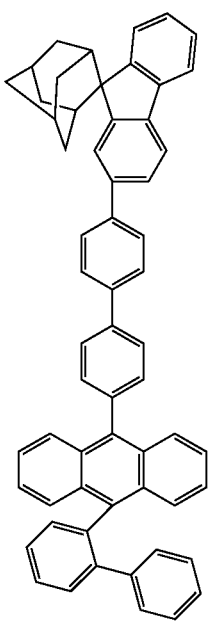
100
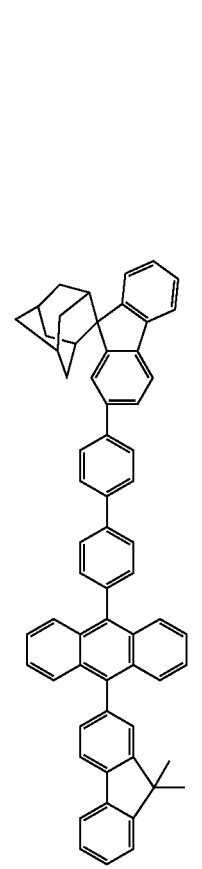

295
-continued
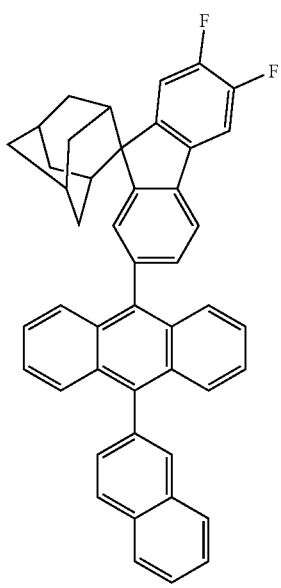
101
296
-continued
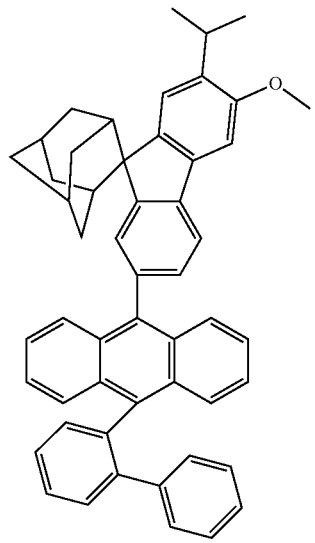
103
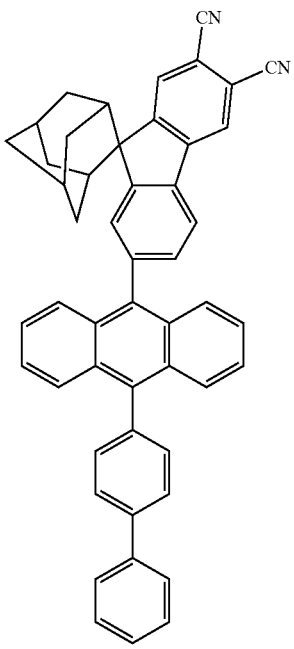
102
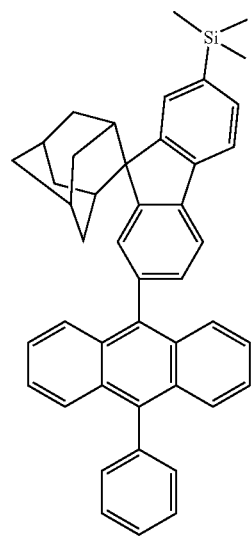
104

297
-continued
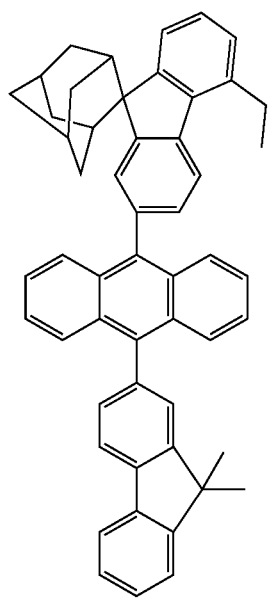
105
106
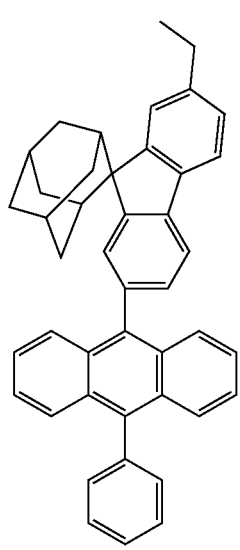
298
-continued
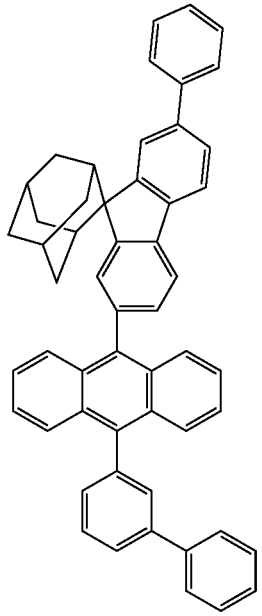
107
108
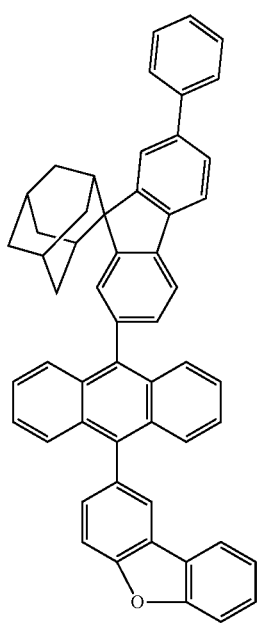

108 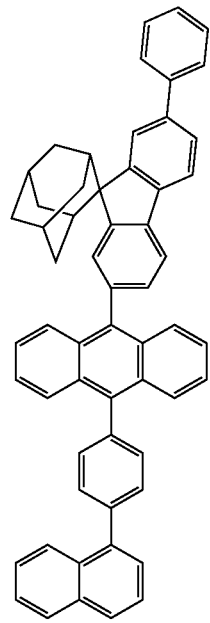
110 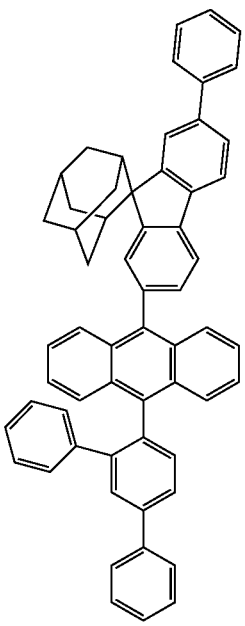
111 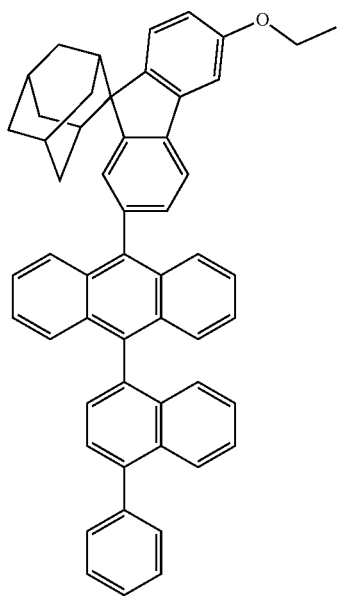
112 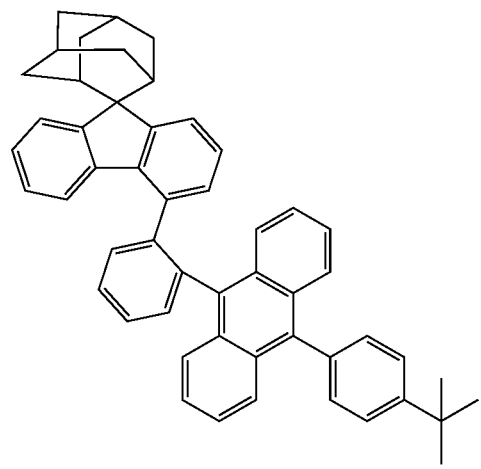
113 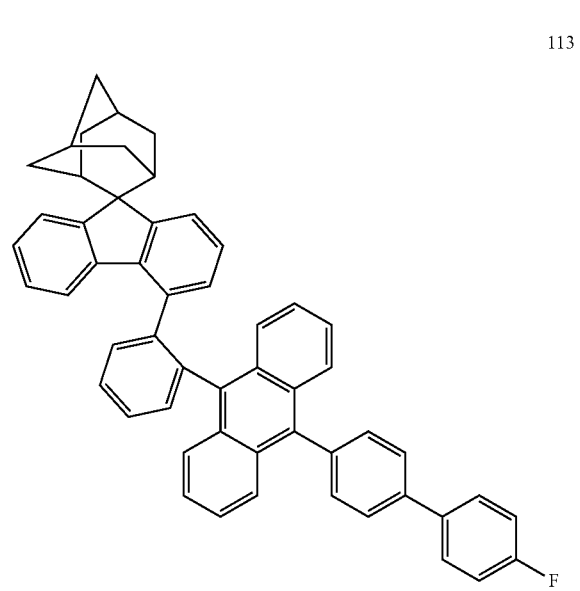

301
-continued
114
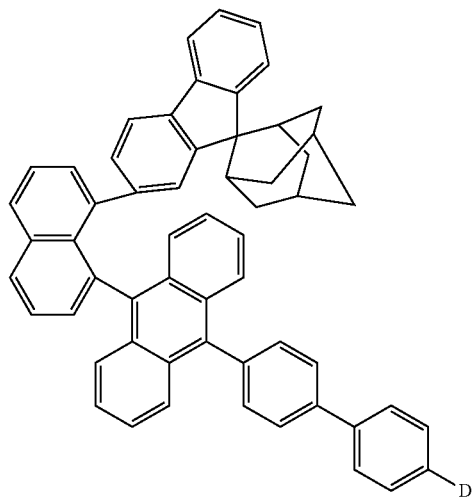
115
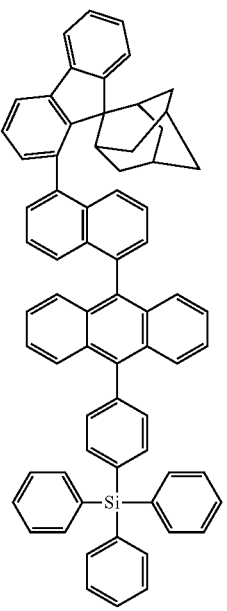
302
-continued
116
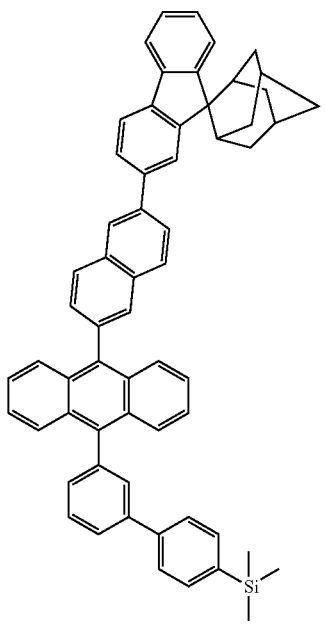
117
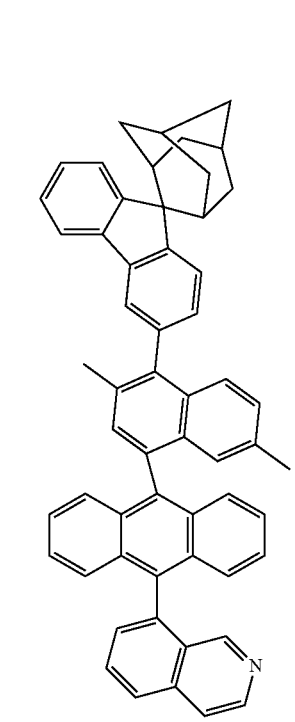

303
-continued
118
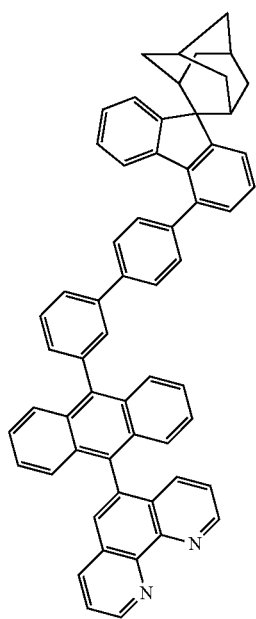
119
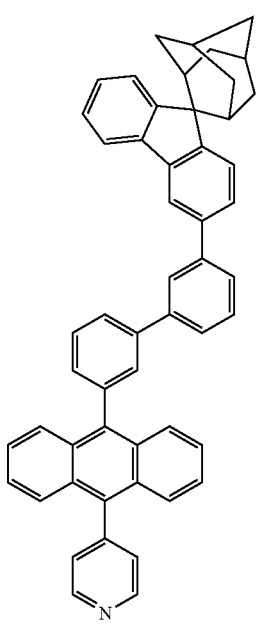
304
-continued
120
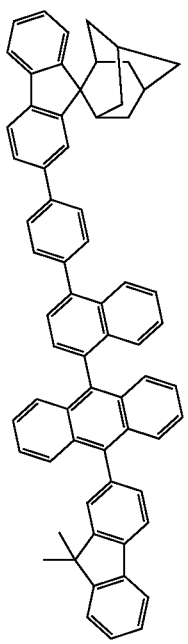
121
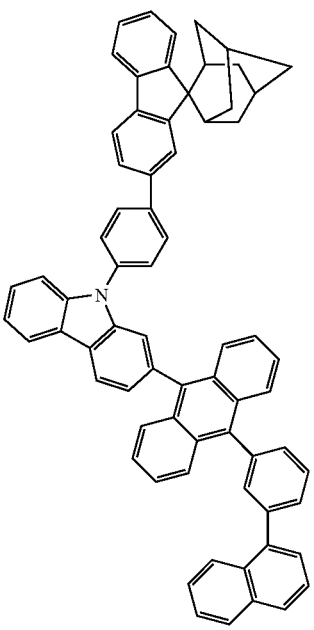

305
-continued
122
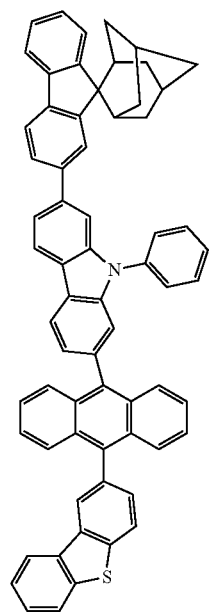
123
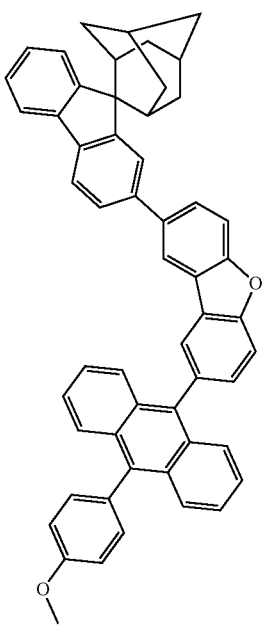
306
-continued
124
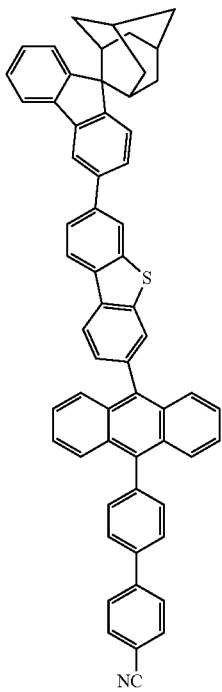
125
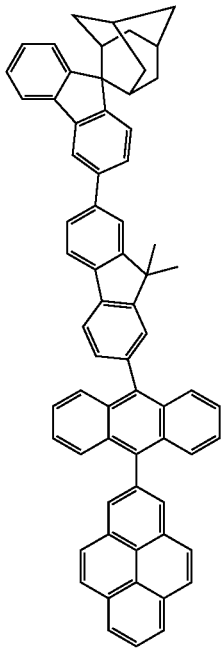

307
-continued
126
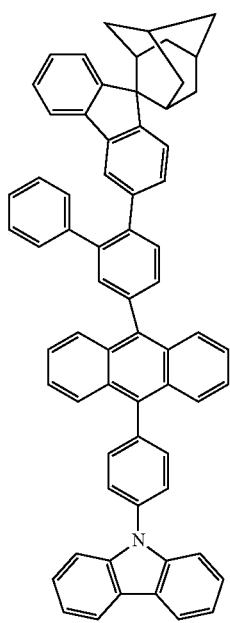
127
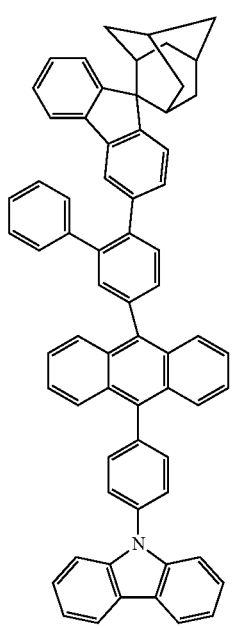
308
-continued
128
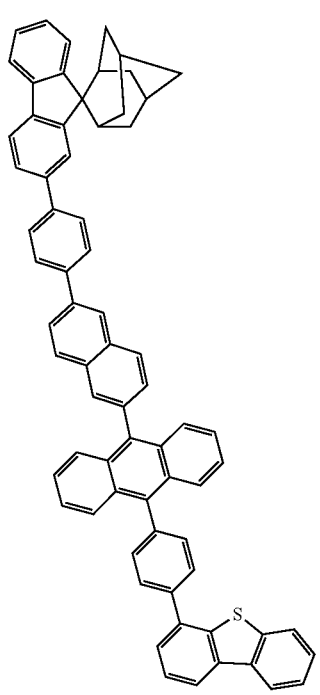
129
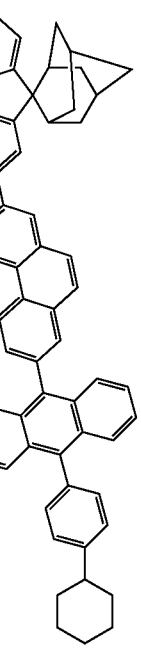

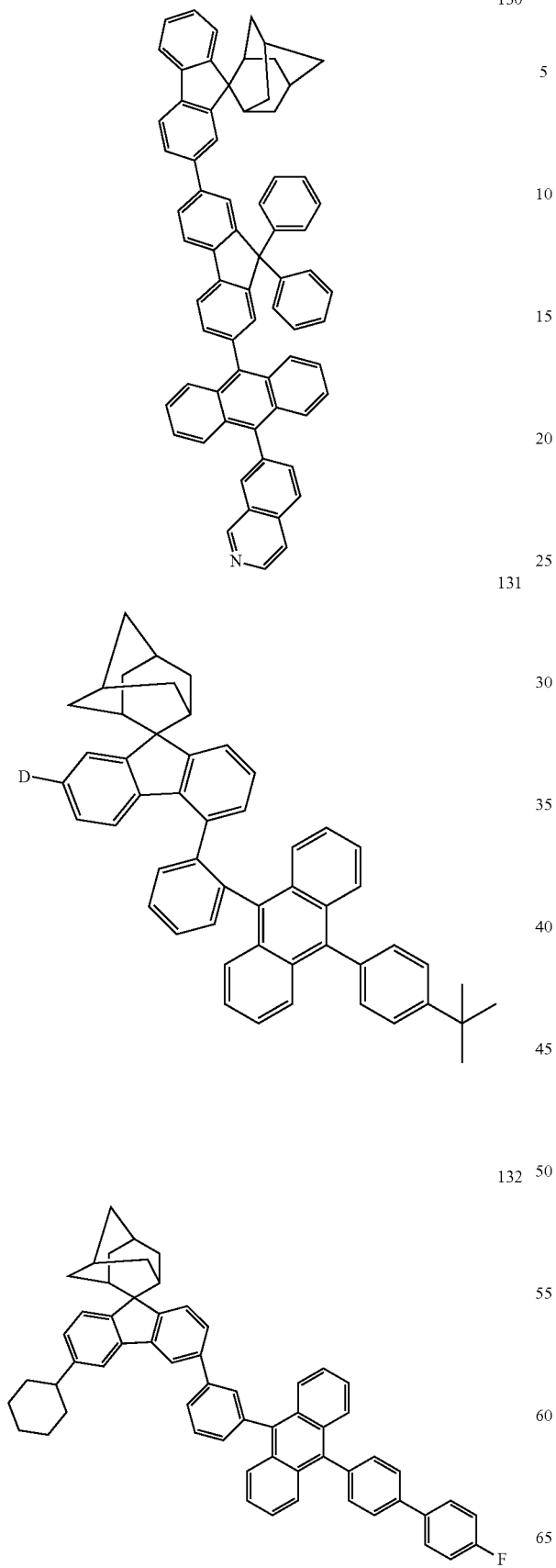

311
-continued
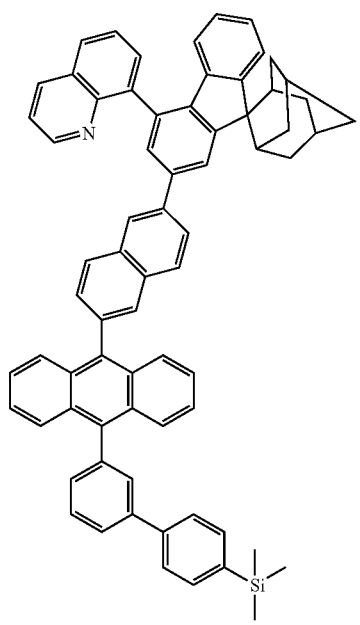
135
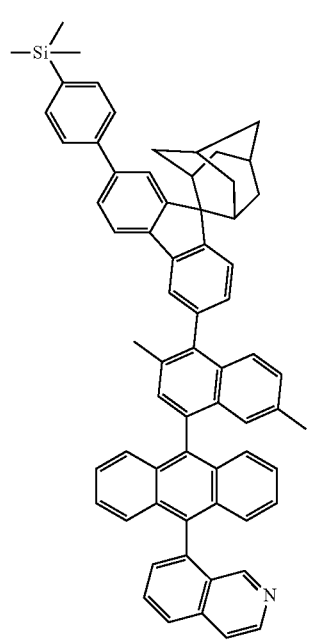
136
312
-continued
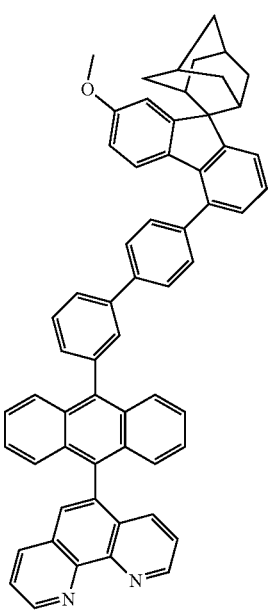
137
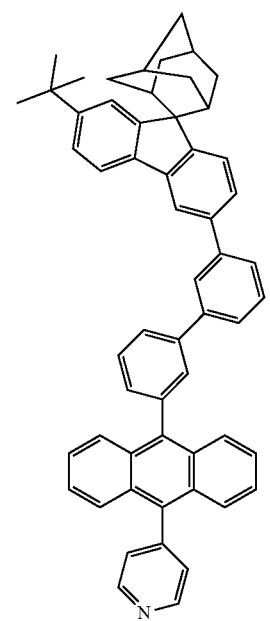
138

313
-continued
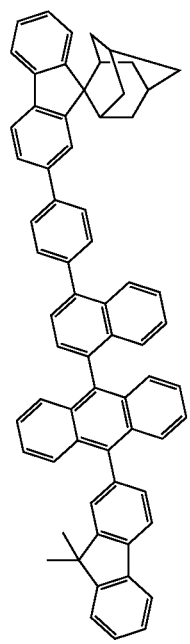
139
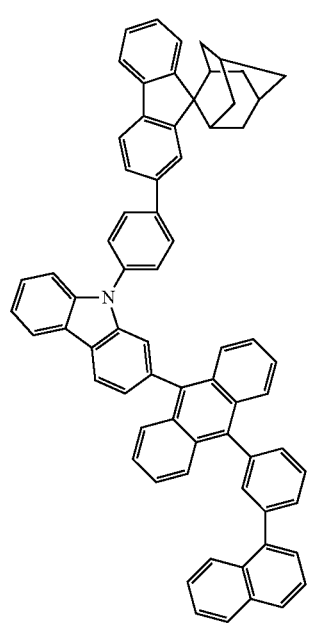
140
314
-continued
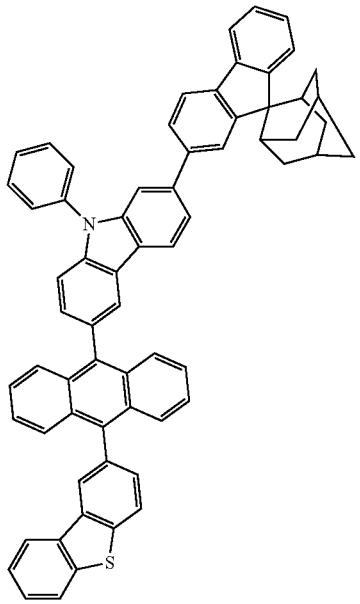
141
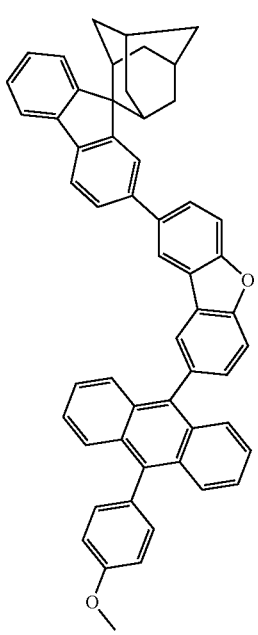
142

315
-continued
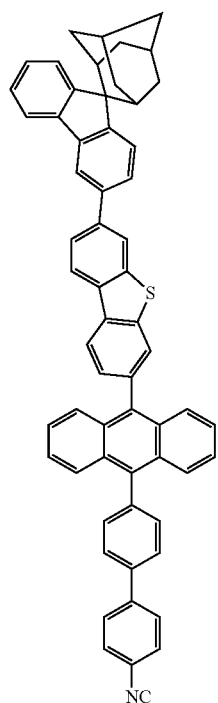
143
316
-continued
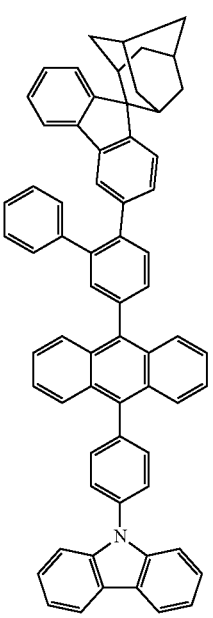
145
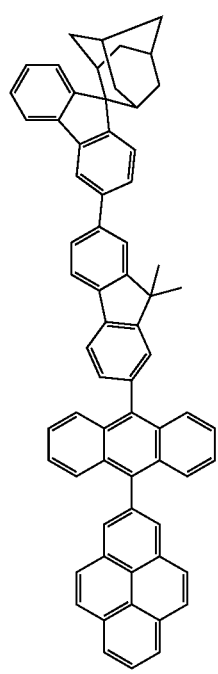
144
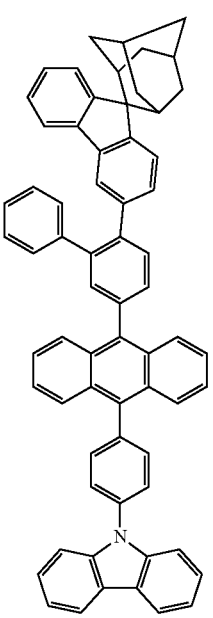
146

317
-continued
148
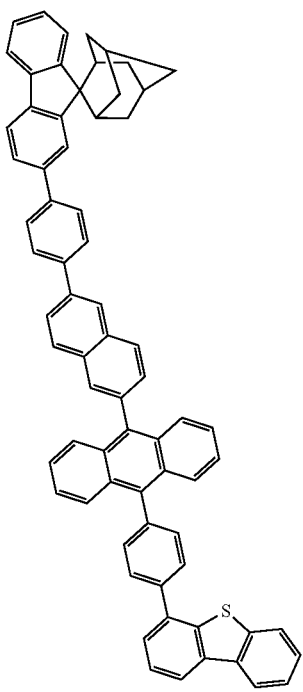
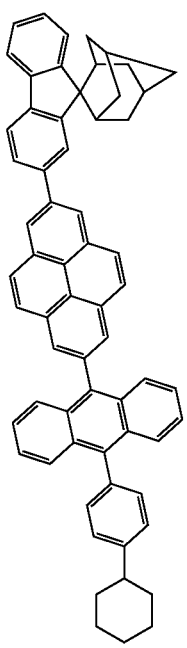
318
-continued
147
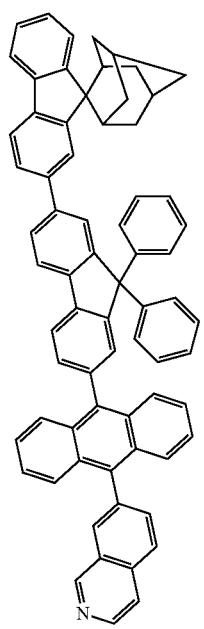
149
150
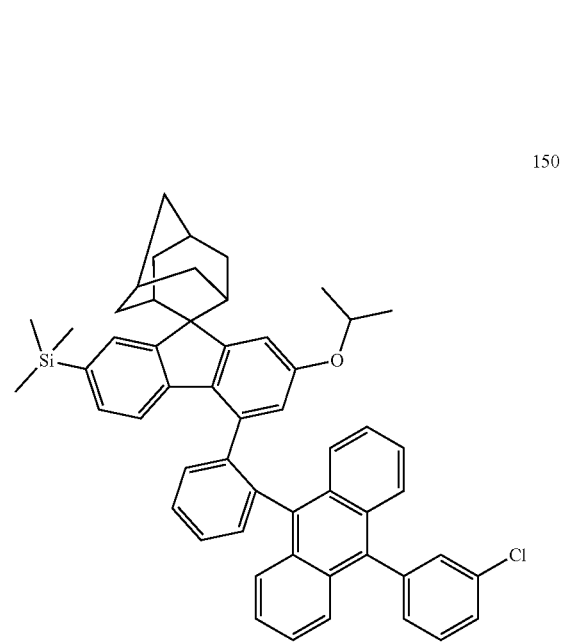

319
-continued
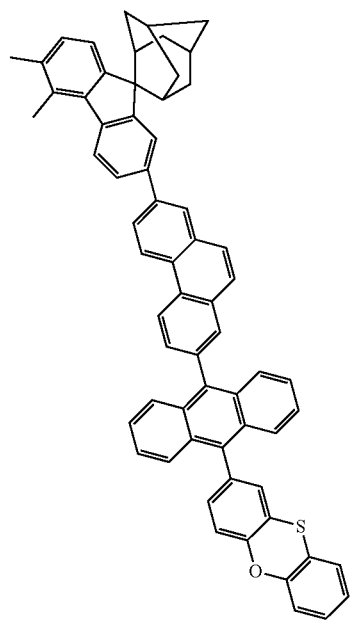
152
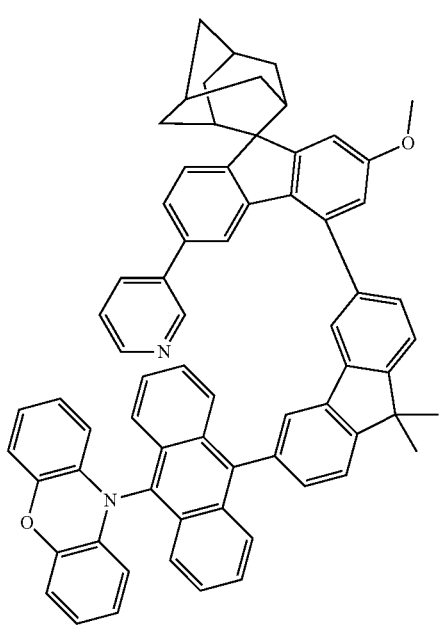
320
-continued
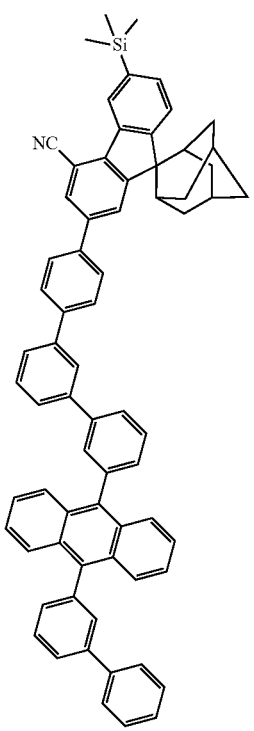
154
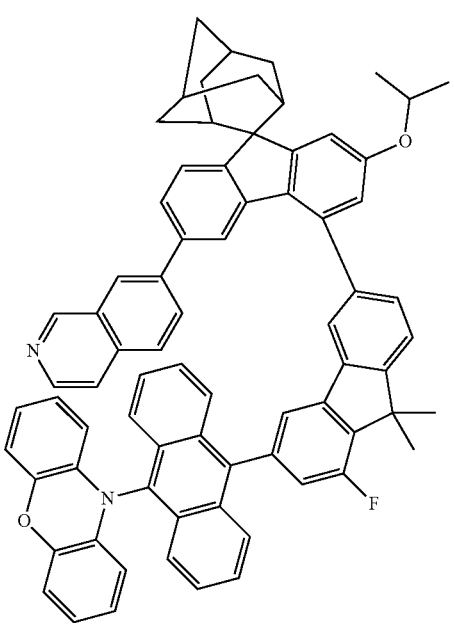

321
-continued
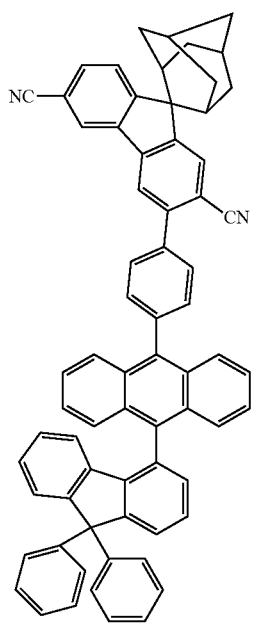
155
322
-continued
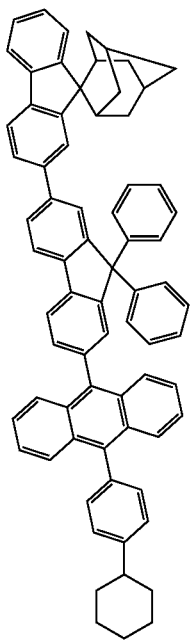
157
156
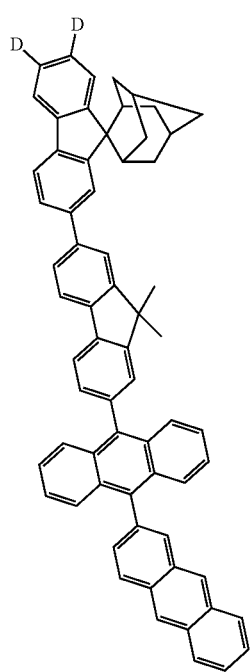
158
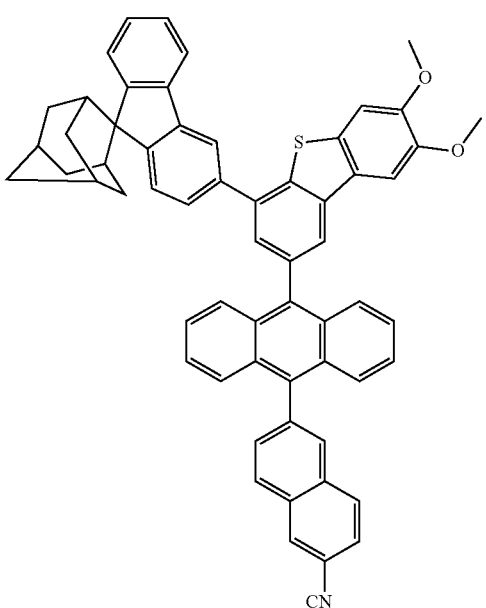

323
-continued
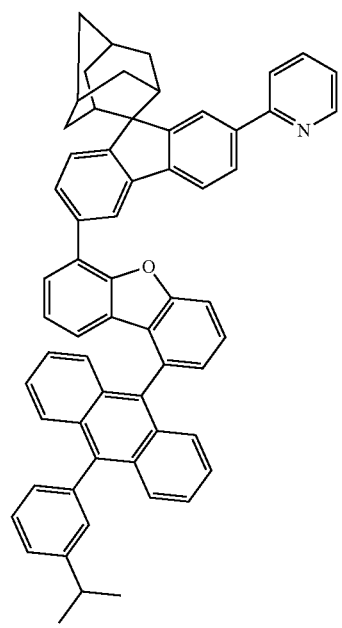
159
324
-continued
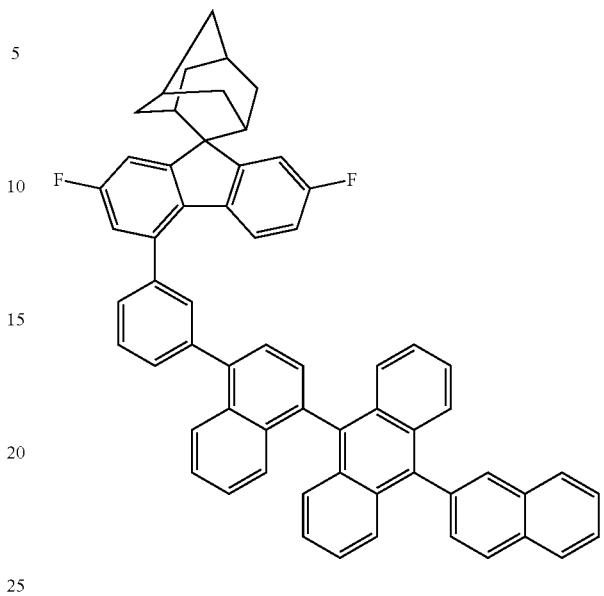
161
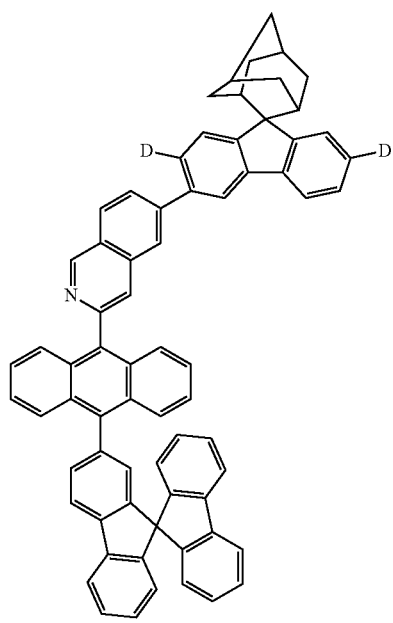
160
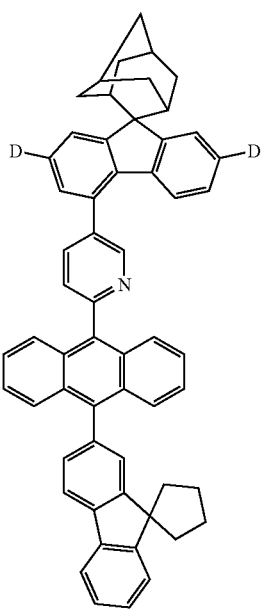
162

325
-continued
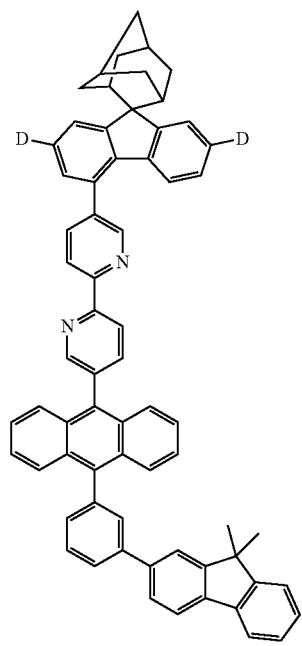
163
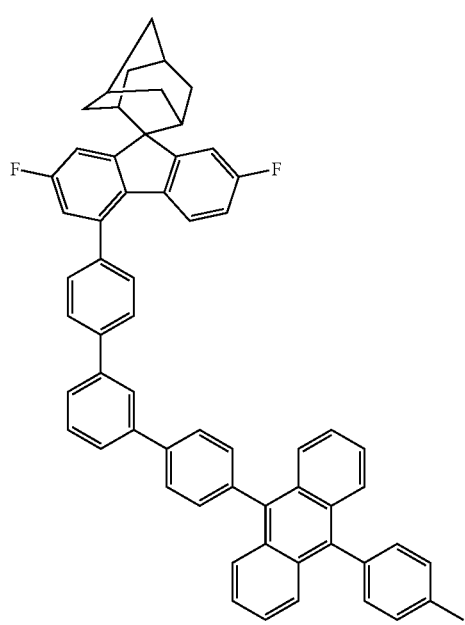
164
326
-continued
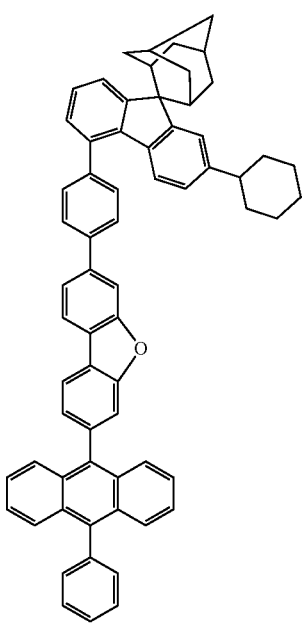
165
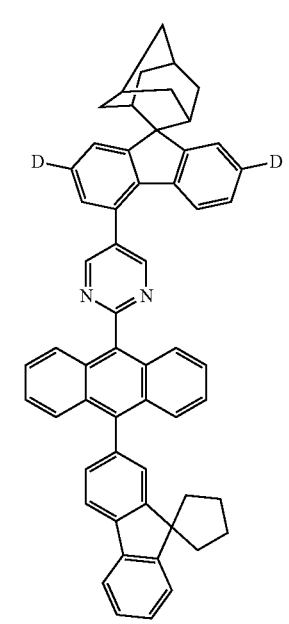
166

327 -continued
167
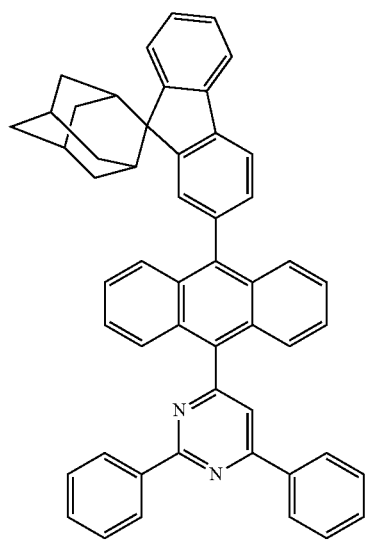
168
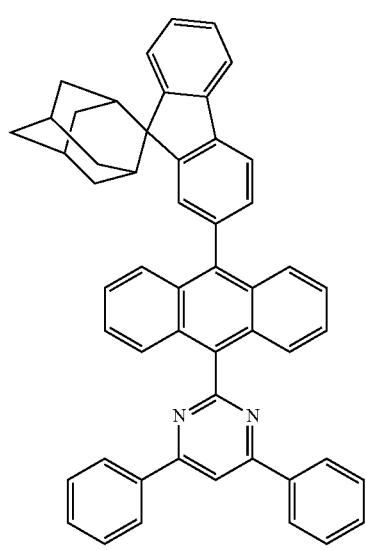
169
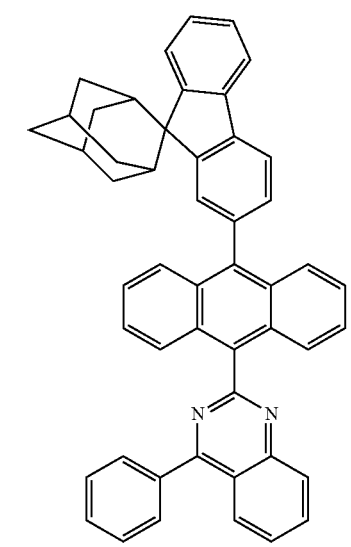
328 -continued
170
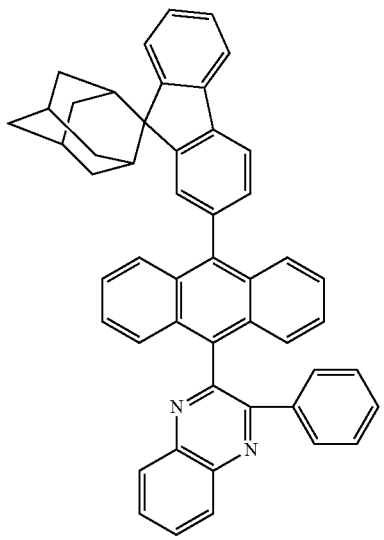
171
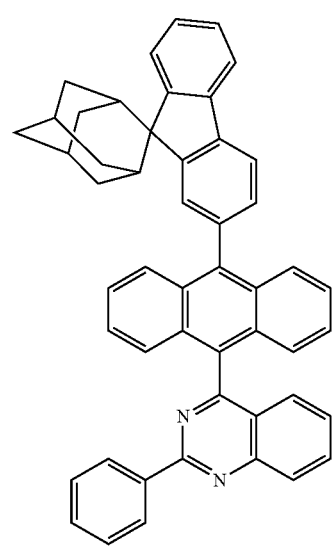

172
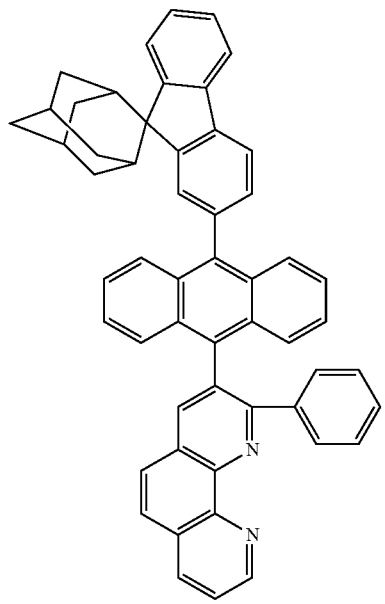
173
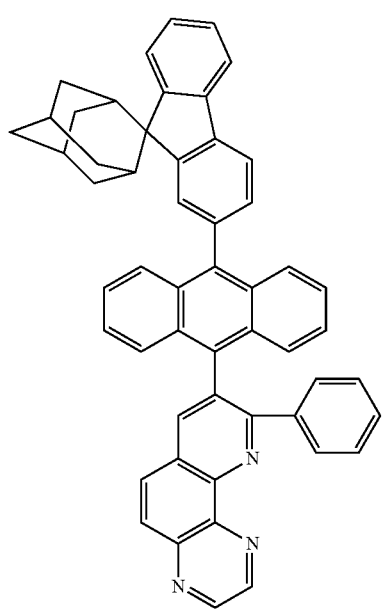
174
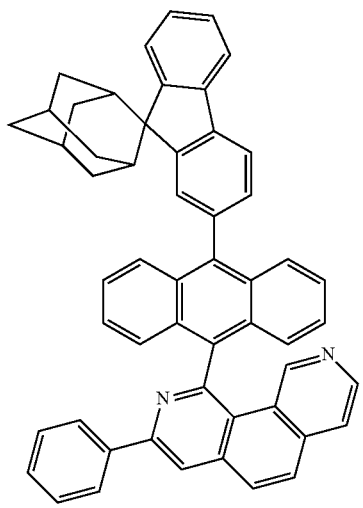
175
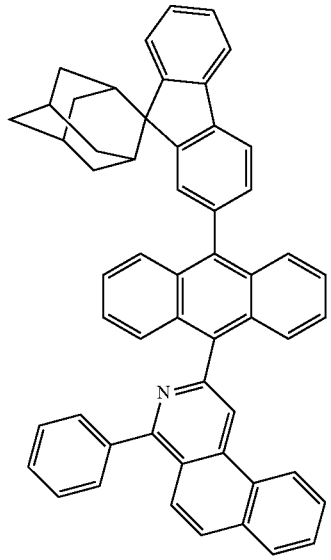
176
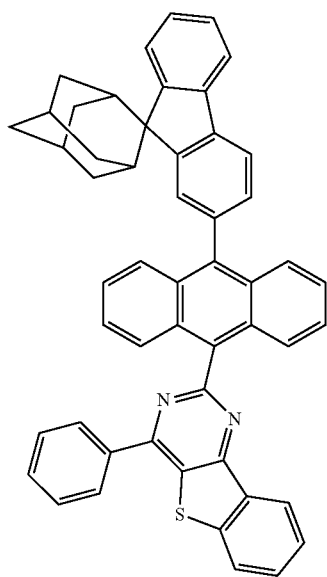

331
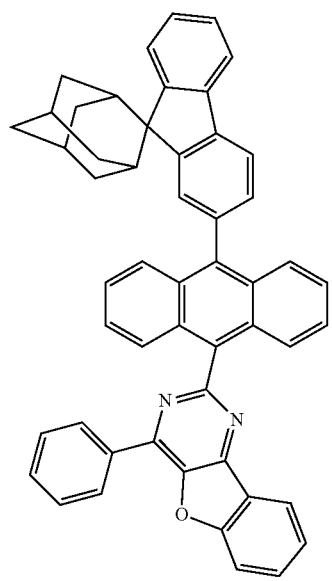
332
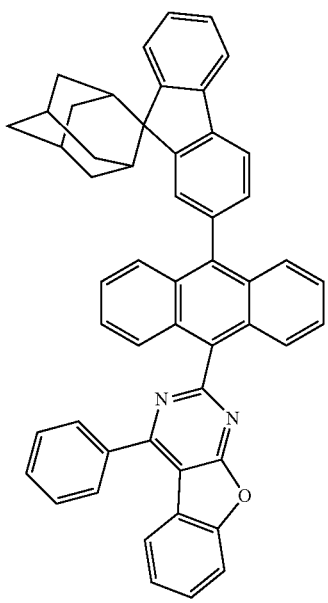
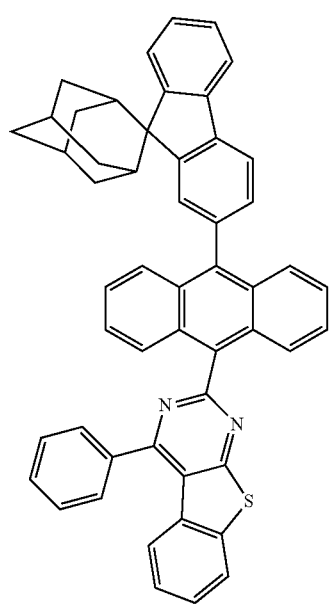
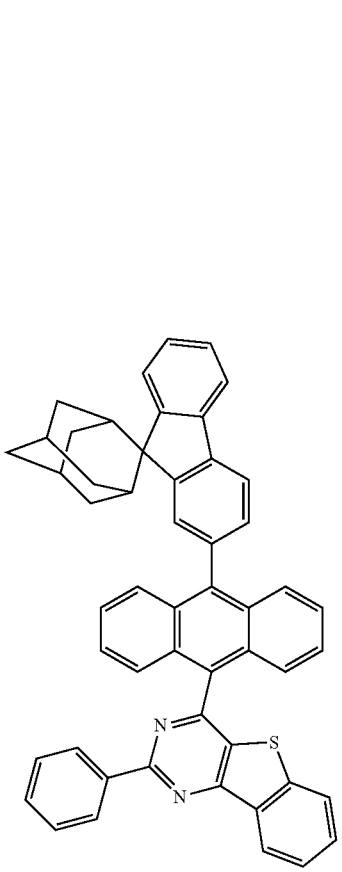

181
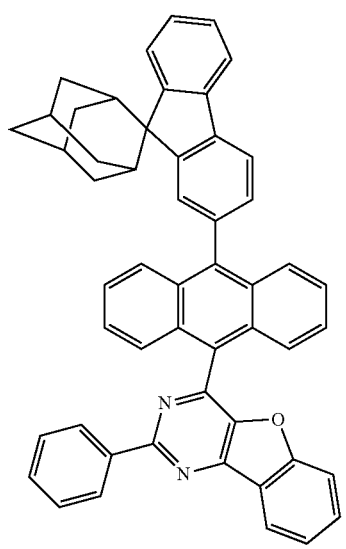
182
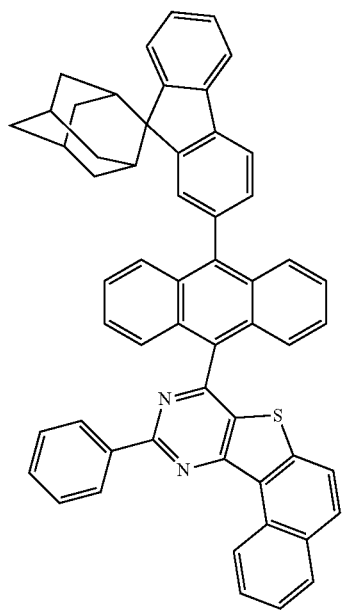
183
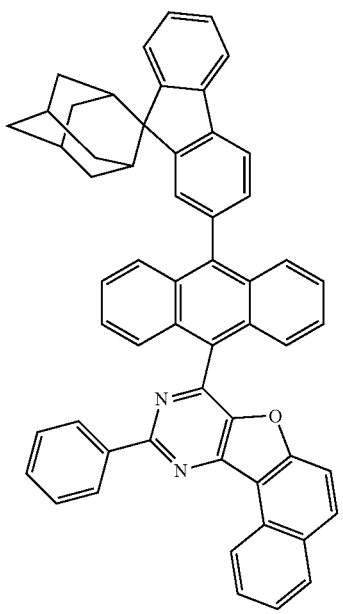
184
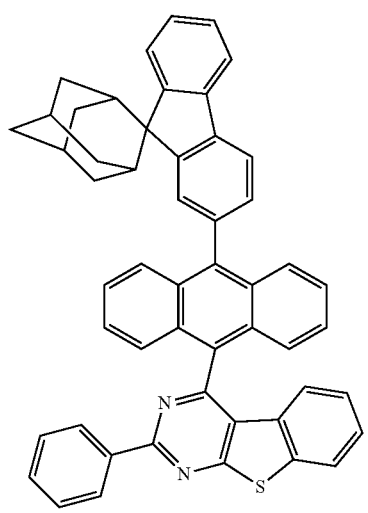
185
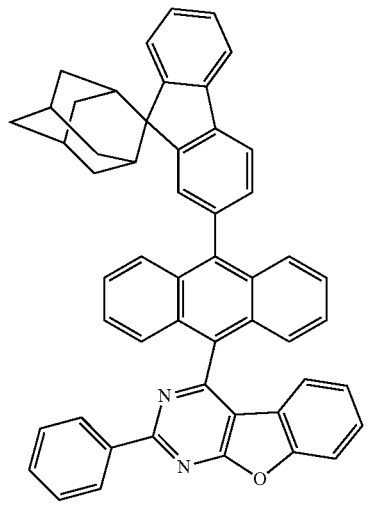

335
-continued
186
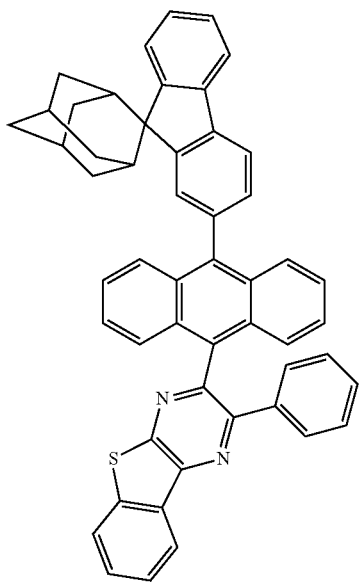
187
336
-continued
188
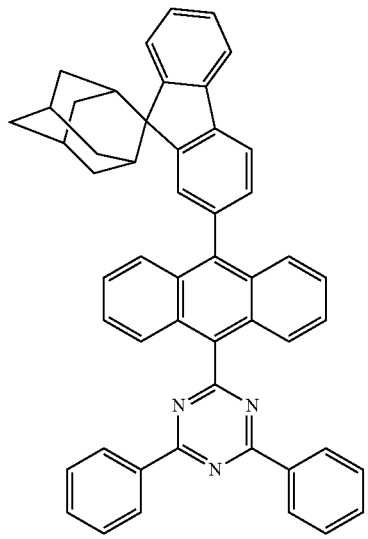
189

337
-continued
190
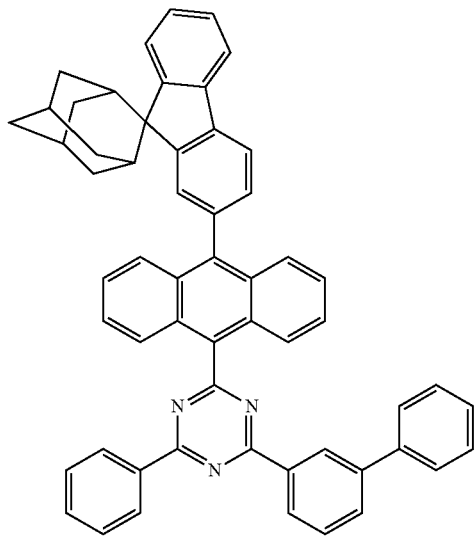
191
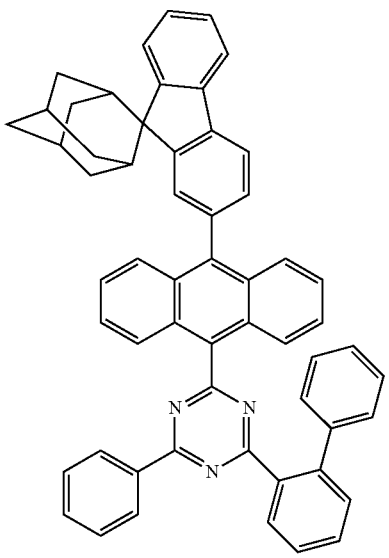
338
-continued
192
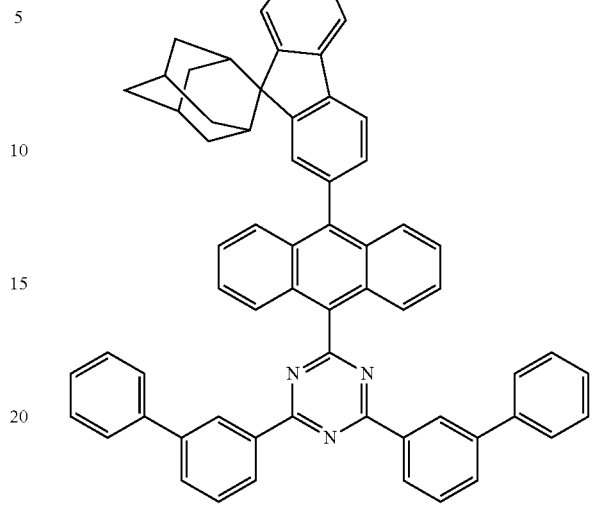
193
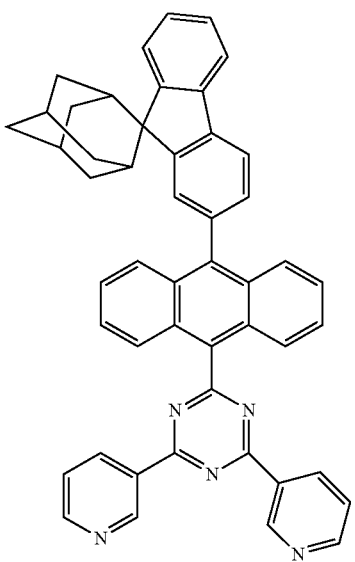

339
-continued
194
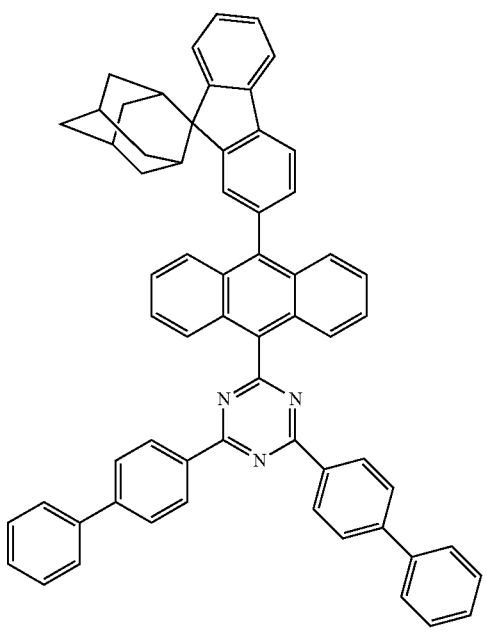
195
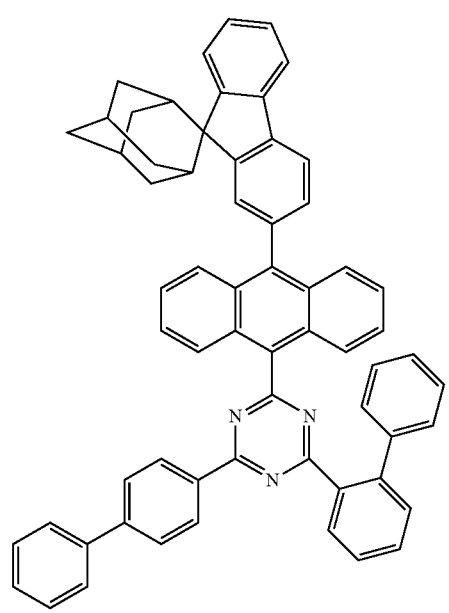
340
-continued
196
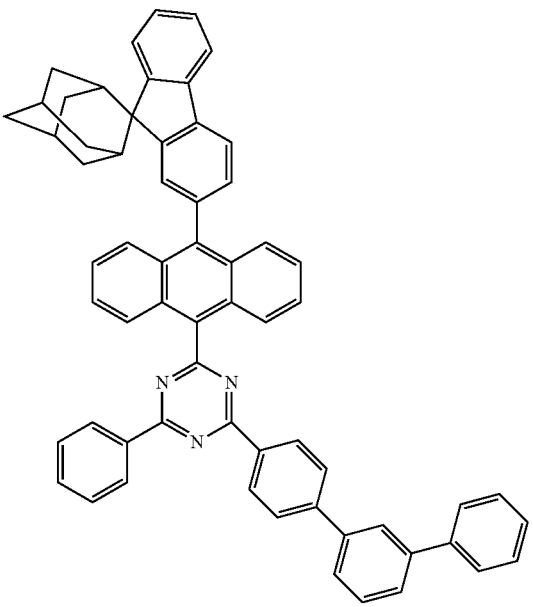
197
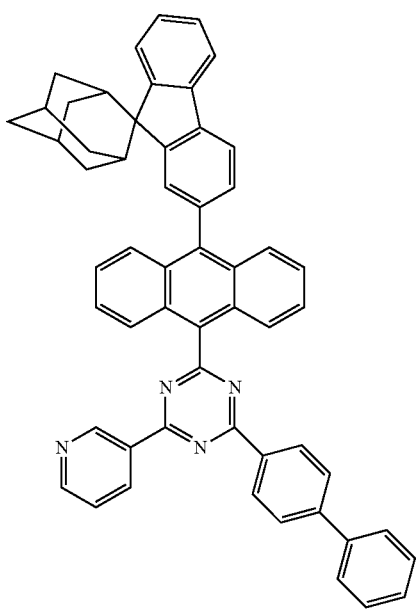

341
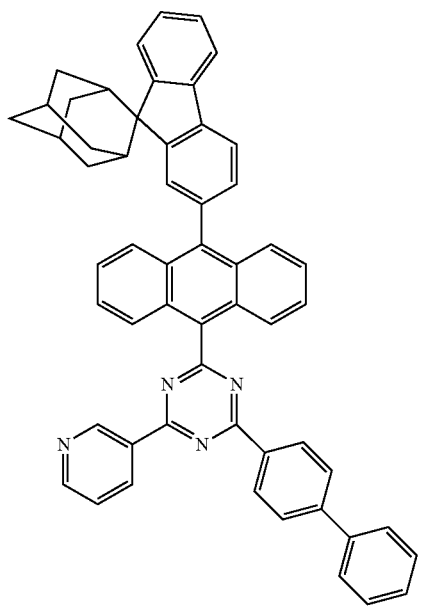
342
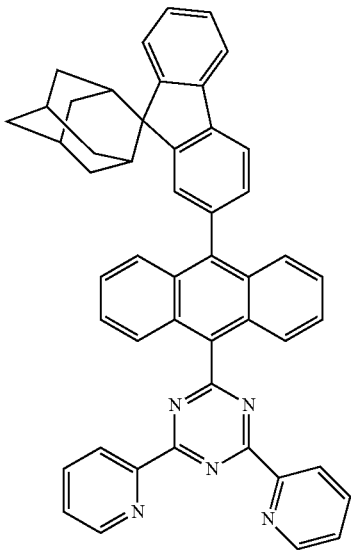
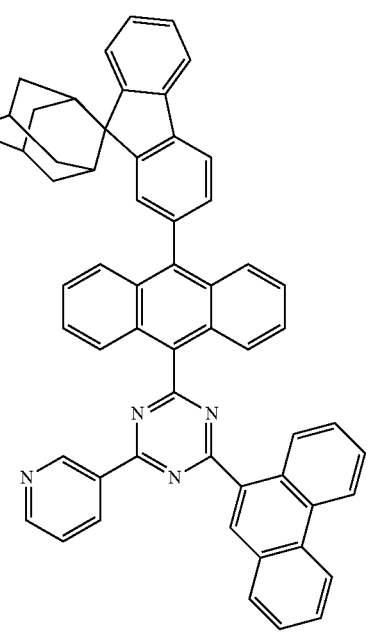
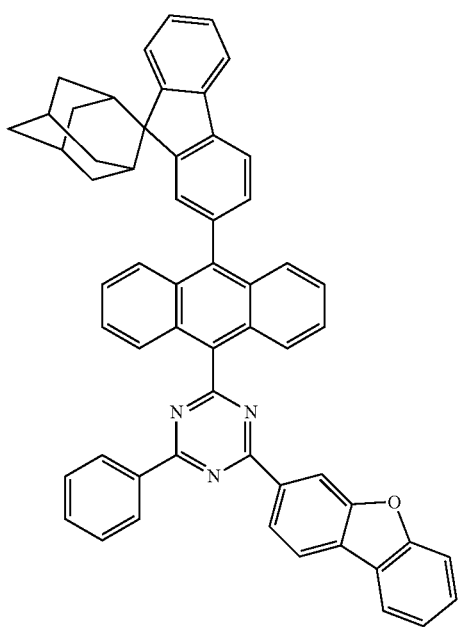

343
-continued

202
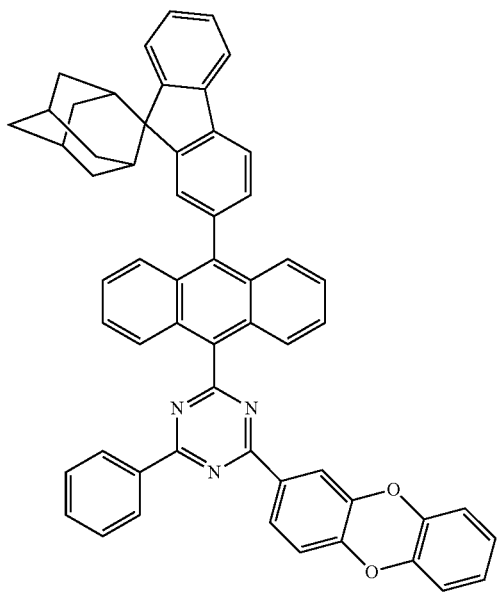

203
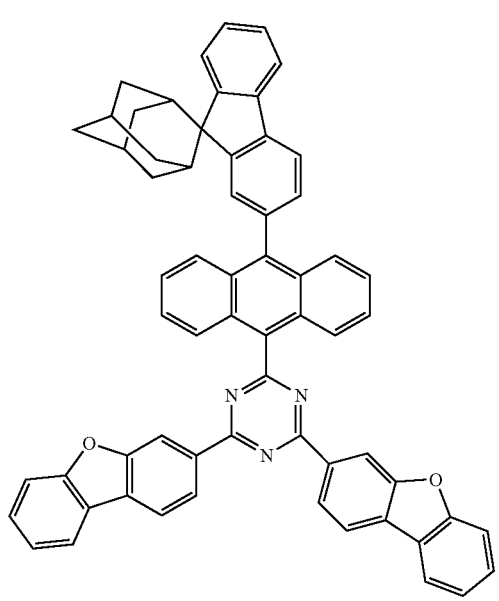

344
-continued

204
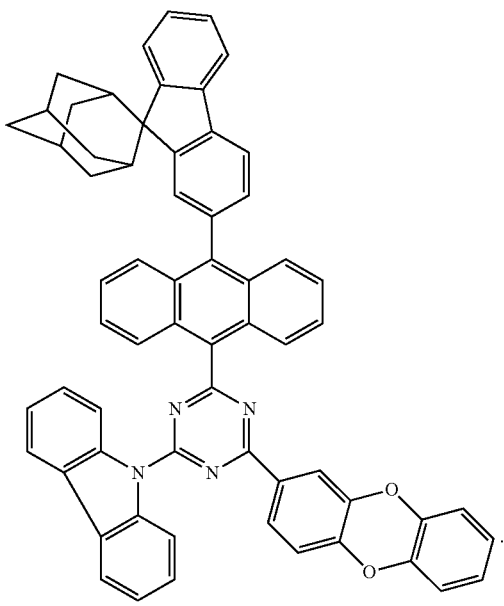

17. An organic electroluminescence device, comprising an anode, a cathode arranged opposite the anode, and a functional layer arranged between the anode and the cathode;

wherein the functional layer comprises the organic compound according to claim 1.

18. The organic electroluminescence device according to claim 17, wherein the functional layer comprises an organic electroluminescence layer, and the organic electroluminescence layer comprises a host material, and the host material comprises the organic compound according to claim 1.

19. An electronic apparatus, comprising the organic electroluminescence device according to claim 17.

* * * * *